(12) United States Patent
Park et al.

(10) Patent No.: US 10,734,588 B2
(45) Date of Patent: *Aug. 4, 2020

(54) COMPOUND FOR ORGANIC ELECTRONIC ELEMENT, AND ORGANIC ELECTRONIC ELEMENT AND ELECTRONIC DEVICE USING SAME

(71) Applicant: Duk San Neolux Co., Ltd., Cheonan-si, Chungcheongnam-do (KR)

(72) Inventors: Jonggwang Park, Ulsan (KR); Ka Young Eom, Icheon-si (KR); Hyoung Keun Park, Chuncheon-si (KR); Hyemin Cho, Goyang-si (KR); Dae Won Lee, Uiwang-si (KR); Jung Hwan Park, Hwaseong-si (KR); Yeon Hee Choi, Cheonan-si (KR); Seung Won Yeo, Daejeon (KR)

(73) Assignee: Duk San Neolux Co., Ltd (KR)

( * ) Notice: Subject to any disclaimer, the term of this patent is extended or adjusted under 35 U.S.C. 154(b) by 444 days.

This patent is subject to a terminal disclaimer.

(21) Appl. No.: 15/313,801

(22) PCT Filed: Apr. 14, 2015

(86) PCT No.: PCT/KR2015/003736
§ 371 (c)(1),
(2) Date: Nov. 23, 2016

(87) PCT Pub. No.: WO2015/182872
PCT Pub. Date: Dec. 3, 2015

(65) Prior Publication Data
US 2017/0200903 A1    Jul. 13, 2017

(30) Foreign Application Priority Data

May 28, 2014    (KR) .................. 10-2014-0064696

(51) Int. Cl.
| | |
|---|---|
| *H01L 51/00* | (2006.01) |
| *C07D 495/04* | (2006.01) |
| *C09K 11/06* | (2006.01) |
| *C07D 519/00* | (2006.01) |
| *C07D 491/048* | (2006.01) |
| *H01L 51/50* | (2006.01) |
| *C09B 57/00* | (2006.01) |
| *C09K 11/02* | (2006.01) |

(52) U.S. Cl.
CPC ...... *H01L 51/0071* (2013.01); *C07D 491/048* (2013.01); *C07D 495/04* (2013.01); *C07D 519/00* (2013.01); *C09B 57/00* (2013.01); *C09K 11/02* (2013.01); *C09K 11/06* (2013.01); *H01L 51/0052* (2013.01); *H01L 51/0054* (2013.01); *H01L 51/0058* (2013.01); *H01L 51/0067* (2013.01); *H01L 51/0072* (2013.01); *H01L 51/0073* (2013.01); *H01L 51/0074* (2013.01); *C09K 2211/1007* (2013.01); *C09K 2211/1011* (2013.01); *C09K 2211/1048* (2013.01); *C09K 2211/1051* (2013.01); *C09K 2211/1059* (2013.01); *C09K 2211/1088* (2013.01); *C09K 2211/1092* (2013.01); *H01L 51/0003* (2013.01); *H01L 51/0085* (2013.01); *H01L 51/5016* (2013.01); *H01L 51/5072* (2013.01)

(58) Field of Classification Search
CPC .............. C07D 491/048; C07D 495/04; C07D 519/00; C09B 57/00; C09K 11/02; C09K 11/06; C09K 2211/1007; C09K 2211/1011; C09K 2211/1048; C09K 2211/1051; C09K 2211/1059; C09K 2211/1088; C09K 2211/1092; H01L 51/0003; H01L 51/0052; H01L 51/0054; H01L 51/0058; H01L 51/0067; H01L 51/0071; H01L 51/0072; H01L 51/0073; H01L 51/0074; H01L 51/0085; H01L 51/5016; H01L 51/5072
See application file for complete search history.

(56) References Cited

U.S. PATENT DOCUMENTS

| | | | |
|---|---|---|---|
| 8,507,904 B2 | 8/2013 | Kim et al. | |
| 9,017,828 B2 | 4/2015 | Kim et al. | |
| 9,331,288 B2* | 5/2016 | Park | ..................... C07D 491/04 |
| 2005/0116659 A1* | 6/2005 | Kim | ..................... H01L 25/048 |
| | | | 315/169.3 |
| 2008/0023724 A1* | 1/2008 | Takeda | ................ H01L 51/5265 |
| | | | 257/103 |
| 2013/0324721 A1 | 12/2013 | Inoue et al. | |
| 2013/0334518 A1 | 12/2013 | Park et al. | |
| 2014/0027747 A1 | 1/2014 | Mun et al. | |

(Continued)

FOREIGN PATENT DOCUMENTS

| | | |
|---|---|---|
| CN | 105899518 A | 8/2016 |
| CN | 105934436 A | 9/2016 |

(Continued)

OTHER PUBLICATIONS

Machine translation for WO 2015/037675 A1 (publication date: Mar. 2015) (Year: 2015).*

(Continued)

*Primary Examiner* — Dawn L Garrett
(74) *Attorney, Agent, or Firm* — Harness, Dickey & Pierce, P.L.C.

(57) ABSTRACT

The present invention provides a compound, and an organic electronic element and an electronic device using the same, the compound capable of improving light-emitting efficiency, lowering drive voltage, and increasing lifespan of an element.

10 Claims, 1 Drawing Sheet

(56) References Cited

U.S. PATENT DOCUMENTS

| | | | | |
|---|---|---|---|---|
| 2014/0291645 | A1* | 10/2014 | Inoue | H01L 51/0074 |
| | | | | 257/40 |
| 2015/0069350 | A1* | 3/2015 | Kim | C09K 11/06 |
| | | | | 257/40 |
| 2015/0266863 | A1* | 9/2015 | Dyatkin | C07D 409/10 |
| | | | | 257/40 |
| 2015/0349272 | A1* | 12/2015 | Park | C07D 491/04 |
| | | | | 257/40 |
| 2016/0005981 | A1 | 1/2016 | Kim et al. | |
| 2016/0308142 | A1* | 10/2016 | Kim | C07D 495/04 |
| 2016/0351826 | A1* | 12/2016 | Kim | C07D 495/04 |

FOREIGN PATENT DOCUMENTS

| | | |
|---|---|---|
| JP | H06220059 A | 8/1994 |
| JP | 2011-084531 A | 4/2011 |
| KR | 10-2013-0135008 A | 12/2013 |
| WO | WO-2006050965 A1 | 5/2006 |
| WO | WO-2010052569 A2 | 5/2010 |
| WO | WO 2013/137572 A1 * | 9/2013 |
| WO | WO 2015/037675 A1 * | 3/2015 |
| WO | WO 2016/140497 A2 * | 9/2016 |

OTHER PUBLICATIONS

Machine translation for WO 2016/140497 A2 (publication date Sep. 2016). (Year: 2016).*

Bo Chao et al., "Copper(I)-Mediated Cascade Reactions: An Efficient Approach to the Sythesis of Functionalized Benzofuro[3,2-d]pyrimidines", Organic Letters, 2012, vol. 14, pp. 2398-2401.

M. Robba et al., "Synthese De Benzo (1) Thieno [2,3-d] Pyrimidines et de (1) [3,2-d] Pyrimidines", Tetrahedron Letters, 1972, vol. 13, pp. 4549-4551.

Chil Won Lee, "High Quantum Efficiency Blue Phosphorescent Organic Light-Emitting Diodes Using 6-Position-Modified Benzofuro [2, 3-b] pyridine Derivatives", Appl. Mater. Interfaces, 2013, vol. 5, pp. 2169-2173.

* cited by examiner

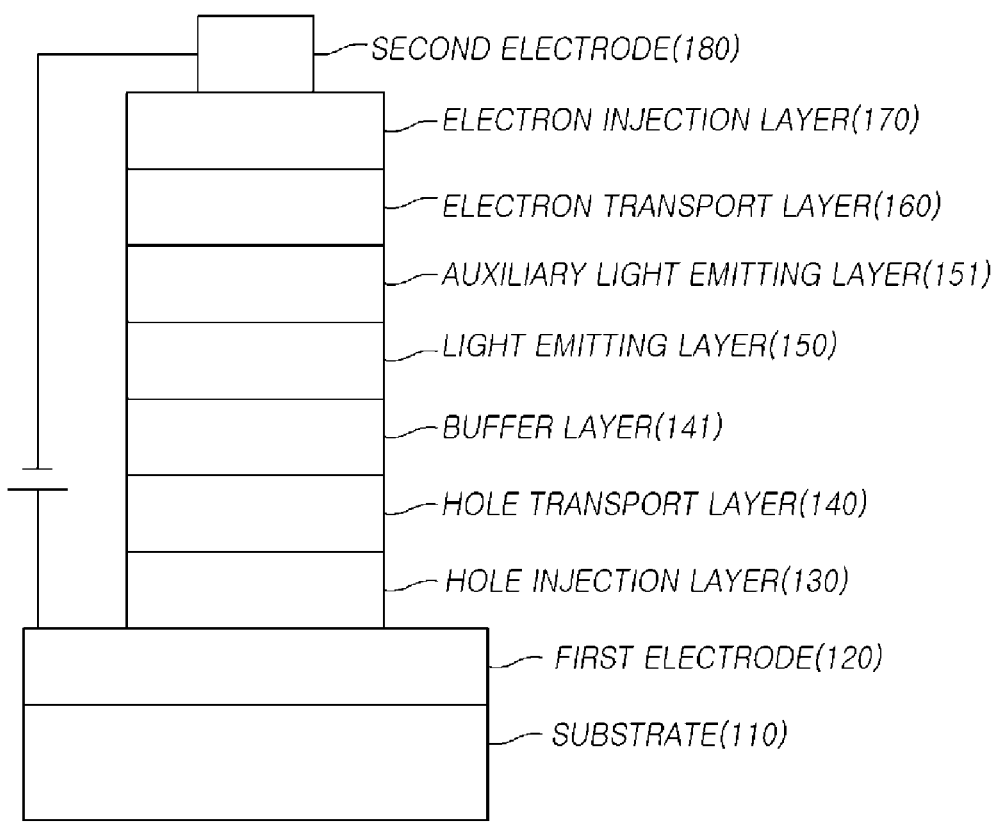

COMPOUND FOR ORGANIC ELECTRONIC ELEMENT, AND ORGANIC ELECTRONIC ELEMENT AND ELECTRONIC DEVICE USING SAME

TECHNICAL FIELD

The present invention relates to a compound for an organic electronic element, an organic electronic element using the same, and an electronic device.

BACKGROUND ART

In general, an organic light emitting phenomenon refers to a phenomenon in which electric energy is converted into light energy of an organic material using an organic material. An organic electronic element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electronic element, and for Embodiment, may include a hole injection layer, a hole transport layer, a light emitting layer, an electron transport layer, an electron injection layer, or the like.

A material used as an organic material layer in an organic electronic element may be classified into a light emitting material and a charge transport material, for Embodiment, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Currently, the power consumption is required more and more as the size of display becomes larger and larger in the portable display market. Therefore, the power consumption is a very important factor in the portable display with a limited power source of the battery, and efficiency and life span issue also is solved.

Efficiency, life span, driving voltage, and the like are correlated with each other. For Embodiment, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

In general, an electron transferred from an electron transport layer to a light emitting layer and a hole transferred from a hole transport layer to the light emitting layer are recombined to form an exciton.

However, the hole moves faster than the electron, and the exciton formed in the light emitting layer moves int the electron transport layer, causing the charge unbalance in the light emitting layer, resulting the emission of light in the interface of the electron transport layer.

When light emission occurs in an interface of the hole transporting layer, the organic electroluminescent device suffers from the disadvantage of a reduction in color purity, and efficiency. Especially, high-temperature stability deteriorates at the time of manufacturing an organic electronic element, resulting in a short lifespan of the organic electronic element. Therefore, the development of an electron transport material having improved hole blocking ability while having high-temperature stability and high electron mobility (within the driving voltage range of a blue element of the electron mobility full device is needed (*Adv. Funct. Mater.* 2013, 23, 1300023).

When only one material is used as a light emitting material, there occur problems of shift of a maximum luminescence wavelength to a longer wavelength due to intermolecular interactions and lowering of the efficiency of a corresponding element due to the deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

However, only the introduction of hosts/dopants cannot maximize efficiency, and the maximal efficiency can be attained by characteristics exhibited from a combination of core and sub-substituents of the light emitting material and an optimal combination of host/dopants.

That is, in order to allow the organic electronic element to sufficiently exhibit excellent characteristics, most of all, materials constituting an organic material layer in the element, for Embodiments, a hole injection material, a hole transport material, a light emitting material, an electron transport material, an electron injection material, and the like need to be supported by stable and efficient materials, but the development of stable and efficient materials for the organic material layer for an organic electronic element is not sufficiently achieved. Therefore, the development of new materials is continuously required, and especially, the development of an electron transport material and a light emitting material is urgently required.

DETAILED DESCRIPTION OF THE INVENTION

Technical Problem

In order to solve the above-mentioned problems occurring in the prior art, an object of the present invention is to provide a compound capable of achieving high luminous efficiency, a low driving voltage, and an improved lifespan of an element, an organic electronic element using the same, and an electronic device.

Technical Solution

In accordance with an aspect of the present invention, there is provided a compound represented by the following formula.

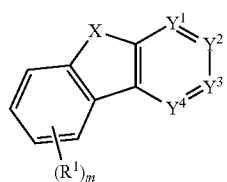

In another aspect of the present invention, there are provided an organic electronic element using the compound represented by the above formula, and an electronic device.

Advantageous Effects

The use of the compound according to the present invention can achieve high luminous efficiency and a low driving voltage of an element and significantly improving an improved lifespan of an element.

Brief Description of the Drawings Drawing

The FIGURE illustrates an Embodiment of an organic electronic light emitting element according to the present invention.

MODE FOR CARRYING OUT THE INVENTION

Hereinafter, some embodiments of the present invention will be described in detail with reference to the accompanying illustrative drawings In designation of reference numerals to components in respective drawings, it should be noted that the same elements would be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b), or the like may be used herein when describing components of the present invention. Each of these terminologies is not used to define an essence, order, or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in the specification and the accompanying claims, unless otherwise stated, the following is the meaning of the term as follows.

Unless otherwise stated, the term "halo" or "halogen" as used herein includes fluorine (F), bromine (Br), chlorine (Cl), and iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "haloalkyl group" or "halogen alkyl group" as used herein means an alkyl group substituted with halogen.

The term "heteroalkyl group" as used herein means an alkyl group of which at least one of carbon atoms is substituted with a hetero atom.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an alkyl group to which oxygen radical is attached, but not limited to, and, unless otherwise stated, has 1 to 60 carbon atoms.

The term "alkenoxyl group", "alkenoxy group", "alkenyloxyl group", or "alkenyloxy group" as used herein means an alkenyl group to which oxygen radical is attached, but not limited to, and, unless otherwise stated, has 2 to 60 carbon atoms.

The term "aryloxyl group" or "aryloxy group" as used herein means an aryl group to which oxygen radical is attached to, but not limited to, and has 6 to 60 carbon atoms.

Unless otherwise stated, the terms "aryl group" and "arylene group" each have 6 to 60 carbon atoms, but not limited thereto. The aryl group or arylene group herein means a monocyclic or polycyclic aromatic group, and includes an aromatic ring that is formed in conjunction with an adjacent substituent linked thereto or participating in the reaction. Embodiments of the aryl group may include a phenyl group, a biphenylyl group, a terphenylyl group, a naphthyl group, an anthracenyl group, a fluorene group, a spirofluorene group, and a spirobifluorene group.

The prefix "aryl" or "ar" means a radical substituted with an aryl group. For Embodiment, an arylalkyl group may be an alkyl group substituted with an aryl group, and an arylalkenyl group may be an alkenyl group substituted with an aryl group, and a radical substituted with an aryl group has a number of carbon atoms defined as herein.

Also, when prefixes are named subsequently, it means that substituents are listed in the order described first. For Embodiment, an arylalkoxy group means an alkoxy group substituted with an aryl group, an alkoxylcarbonyl group means a carbonyl group substituted with an alkoxyl group, and an arylcarbonylalkenyl group also means an alkenyl group substituted with an arylcarbonyl group, wherein the arylcarbonyl group may be a carbonyl group substituted with an aryl group.

Unless otherwise stated, the term "heteroalkyl" as used herein means alkyl containing one or more heteroatoms. Unless otherwise stated, the term "heteroaryl group" or "heteroarylene group" as used herein means, but not limited to, an aryl or arylene group having 2 to 60 carbon atoms and containing one or more heteroatoms, includes at least one of monocyclic and polycyclic rings, and may also be formed in conjunction with an adjacent group.

Unless otherwise stated, the term "heterocyclic group" as used herein contains one or more heteroatoms, has 2 to 60 carbon atoms, includes at least one of homocyclic and heterocyclic rings, and may also be formed in conjunction with an adjacent group.

Unless otherwise stated, the term "heteroatom" as used herein represents N, O, S, P, or Si.

In addition, the "heterocyclic group" also may include a ring containing $SO_2$ instead of carbon forming the ring. For Embodiments, the "heterocyclic group" includes the following compound.

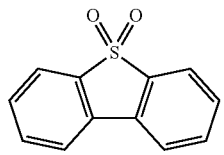 [SMILES: O=S1(=O)c2ccccc2-c2ccccc21]

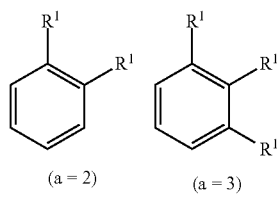

(a = 2)   (a = 3)

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "carbonyl" as used herein is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether" as used herein is represented by —R—O—R', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynl having 2 to 20 carbon atoms, or the combination of these.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the formulas used in the present invention are defined as in the index definition of the substituent of the following Formula.

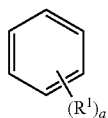

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$'s may be the same and different, and are linked to the benzene ring as follows. When a is an integer of 4 to 6, the substituents $R^1$'s may be the same and different, and are linked to the benzene ring in a similar manner to that when a is an integer of 2 or 3, hydrogen atoms linked to carbon constituents of the benzene ring being not represented as usual.

The FIGURE illustrates an organic electronic element according to an embodiment of the present invention.

Referring to the FIGURE, an organic electronic element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electronic element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electronic element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150. For Embodiment, the inventive compound may be used as the light emitting layer 150, the hole transport layer 140, and/or the emission-auxiliary layer 151.

Since depending on the type and position of a substituent to be attached, a band gap, electrical properties, interfacial properties, and the like may vary even in the same core, it is very important what the types of core and a combination of substituent attached to the core are. Specially, long life span and high efficiency can be simultaneously achieved when an optimal combination of energy levels and T1 values, inherent material properties (mobility, interfacial properties, etc.), and the like among the respective layers included in the organic material layer is given.

Accordingly, in the present invention, a combination of energy levels and T1 values, inherent material properties (mobility, interfacial properties, etc.), and the like among the respective layers included in the organic material layer is optimized by forming a light emitting layer or an emission-auxiliary layer by using the compound represented by Formula 1, and thus the life span and efficiency of the organic electronic element can be improved at the same time.

The organic electronic element according to an embodiment of the present invention may be manufactured using a PVD (physical vapor deposition) method. For Embodiment, the organic electronic element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for Embodiment, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electronic element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a color conversion material (CCM) structure in which electroluminescence from a blue (B) organic light emitting layer, and photoluminescence from an inorganic luminescent using the electroluminescence are combined. The present invention is applicable to these WOLEDs.

Further, the organic electronic element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electronic element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

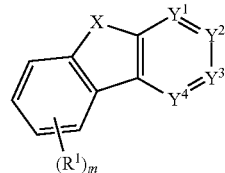

[Formula 1]

In Formula 1, m is an integer of 0-4.

$R^1$ may be selected from the group consisting of deuterium, halogen, a $C_6$-$C_{60}$ aryl group, a fluorenyl group, a $C_2$-$C_{60}$ heterocyclic group containing at least one heteroatom selected from O, N, S, Si, and P, a fused ring group of a $C_3$-$C_{60}$ aliphatic group and a $C_6$-$C_{60}$ aromatic group, $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, wherein, when m is an integer of 2 or greater, a plurality of $R^1$ may be identical to or different from each other.

Alternatively, when m is an integer of 2 or greater, a plurality of $R^1$ may be identical to or different from each other, and may bind to each other to form at least one ring. Here, R1 not forming the ring may be defined as above.

X is O or S.

$Y^1$ and $Y^4$ each are independently $CR^a$ or N.

$Y^2$ and $Y^3$ each are independently $CR^b$ or N.

However, one of $Y^1$ and $Y^4$ is N and one of $Y^2$ and $Y^3$ is N.

$R^a$ may be selected from the group consisting of hydrogen, deuterium, and -$L^1$-$Ar^1$.

$R^b$ may be selected from the group consisting of hydrogen, deuterium, and -$L^2$-$Ar^2$.

$Ar^1$ and $Ar^2$ each may be independently selected from the group consisting of a $C_6$-$C_{60}$ aryl group, a fluorenyl group, a fused ring group of a $C_3$-$C_{60}$ aliphatic group and a $C_6$-$C_{60}$ aromatic group, a $C_2$-$C_{60}$ heterocyclic group containing at least one heteroatom selected from O, N, S, Si, and P, a $C_1$-$C_{50}$ alkyl group, a $C_2$-$C_{20}$ alkenyl group, a $C_2$-$C_{20}$ alkynyl group, $C_1$-$C_{30}$ alkoxyl group, and a $C_6$-$C_{30}$ aryloxy group.

$L^1$ and $L^2$ each may be independently selected from the group consisting of a single bond, a $C_6$-$C_{60}$ arylene group, a fluorenylene group, a $C_2$-$C_{60}$ bivalent heterocyclic group containing at least one heteroatom selected from O, N, S, Si, and P, a bivalent fused ring group of $C_3$-$C_{60}$ aliphatic group and $C_6$-$C_{60}$ aromatic group, and a bivalent aliphatic hydrocarbon group, wherein $L^1$ and $L^2$ (excluding a single bond) each may be substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group. Here, the single bond means a direct linkage due to the absence of $L^1$ and $L^2$, and formulas 1-1, 1-78, and the like, which may be included in chemical formula 1 of the present invention, represent compounds wherein $L^1$ is a single bond, and formulas 1-89, 1-117, and the like, which may be included in chemical formula 1 of the present invention, represent compounds wherein $L^2$ is a single bond.

For Embodiment, when $Ar^1$ and $Ar^2$ are an aryl group, $Ar^1$ and $Ar^2$ each may be independently a phenyl group, a biphenyl group, a terphenyl group, a naphthyl group, an anthryl group, a phenanthryl group, a pyrenyl group, a triphenylenyl group, or the like. In addition, when $L^1$ and $L^2$ are an arylene group, $L^1$ and $L^2$ each may be independently a phenylene group, a biphenylene group, a terphenylene group, a naphthylene group, an anthrylene group, a phenanthrylene group, a pyrenylene group, a triphenylenylene group, or the like.

The aryl group, fluorenyl group, heterocyclic group, fusion group, alkyl group, alkenyl group, alkoxy group, and aryloxy group of $R^1$, $Ar^1$, and $Ar^2$ each may be substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

Here, the aryl group may be an aryl group having 6-60 carbon atoms, preferably 6-40 carbon atoms, and more preferably 6-30 carbon atoms;

the heterocyclic group may be a heterocyclic group having 2-60 carbon atoms, preferably 2-30 carbon atoms, and more preferably 2-20 carbon atoms;

the arylene group may be an arylene group having 6-60 carbon atoms, preferably 6-30 carbon atoms, and more preferably 6-20 carbon atoms; and the alkyl group may be an alkyl group having 1-50 carbon atoms, preferably 1-30 carbon atoms, more preferably 1-20 carbon atoms, and especially preferably 1-10 carbon atoms.

Specially, the compound represented by Formula 1 above may be represented by one of the formulas below.

[Formula 2]

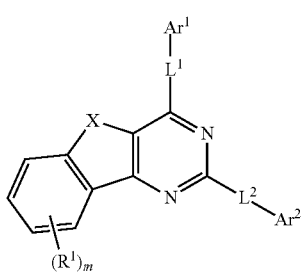

[Formula 3]

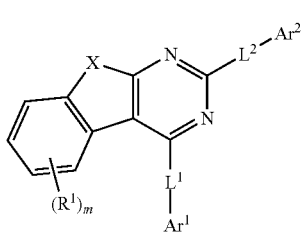

In Formulas 2 and 3 above, X, $R^1$, $Ar^1$, $Ar^2$, $L^1$, $L^2$, and m may be defined as in Formula 1.

Specifically, $Ar^1$ and $Ar^2$ in the compounds represented by Formulas 1 to 3 above may be independently represented by one of Formulas A1 to A8 below.

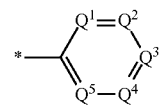

A1

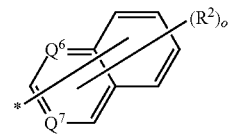

A2

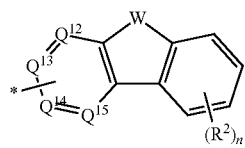

A3

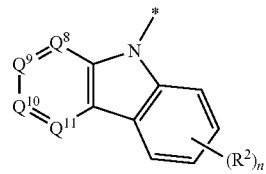

A4

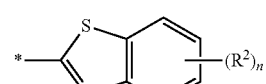

A5

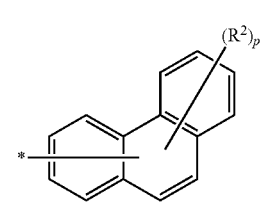

A6

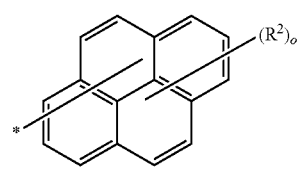

A7

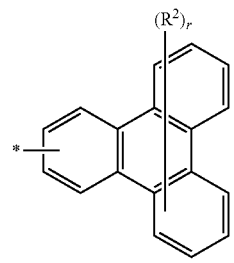

A8

In Formulas A1 to A8, n is an integer of 0-4; o is an integer of 0-5;

p is an integer of 0-6; and r is an integer of 0-8.

$R^1$ to $Q^{11}$ each are independently $CR^c$ or N.

$R^{12}$ to $R^{15}$ each are independently C, $CR^d$, or N.

W is S, O, $NR^e$, or $CR^fR^g$.

$R^2$ may be selected from the group consisting of deuterium, halogen, a $C_6$-$C_{60}$ aryl group, a fluorenyl group, a $C_2$-$C_{60}$ heterocyclic group containing at least one heteroatom selected from O, N, S, Si, and P, a fused ring group of a $C_3$-$C_{60}$ aliphatic group and a $C_6$-$C_{60}$ aromatic group, $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, wherein, when n, o, p, and r each are an integer of 2 or greater, a plurality of $R^2$ may be identical to or different from each other.

Alternatively, when n, o, p, and r each are an integer of 2 or greater, a plurality of $R^2$ may be identical to or different from each other, and may bind to each other to form at least one ring. Here, R2 not forming the ring may be defined as above.

$R^c$ and $R^d$ each may be independently selected from the group consisting of hydrogen, deuterium, a $C_6$-$C_{60}$ aryl group, a fluorenyl group, a fused ring group of a $C_3$-$C_{60}$ aliphatic group and a $C_6$-$C_{60}$ aromatic group, a $C_2$-$C_{60}$ heterocyclic group containing at least one heteroatom selected from O, N, S, Si, and P, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group; and $R^c$ and $R^d$ each may be substituted with at least one selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

$R^e$ to $R^g$ each may be independently selected from the group consisting of a $C_6$-$C_{60}$ aryl group, a $C_2$-$C_{60}$ heterocyclic group containing at least one heteroatom selected from O, N, S, Si, and P, a $C_1$-$C_{50}$ alkyl group, a $C_2$-$C_{20}$ alkenyl group, a $C_1$-$C_{30}$ alkoxy group, and a fluorenyl group.

Mark * represents a linkage with $L^1$ or $L^2$.

More specifically, the compound represented by Formulas 1 to 3 may be one of the following compounds.

1-1

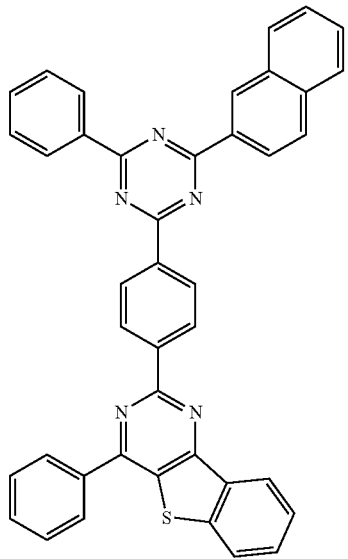

1-2

1-3

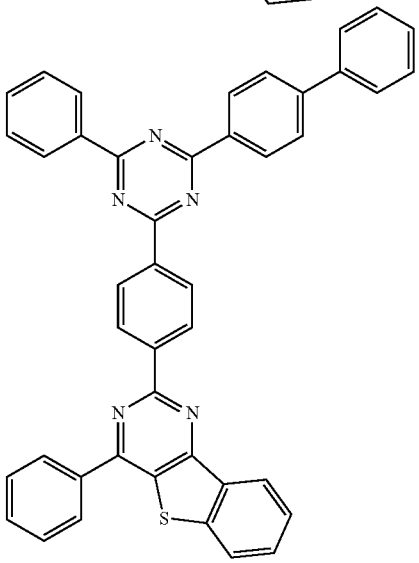

1-4

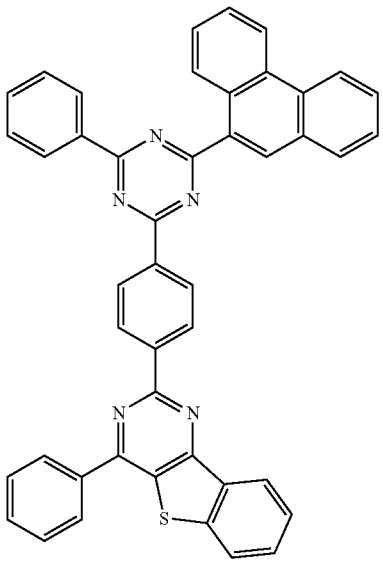

-continued
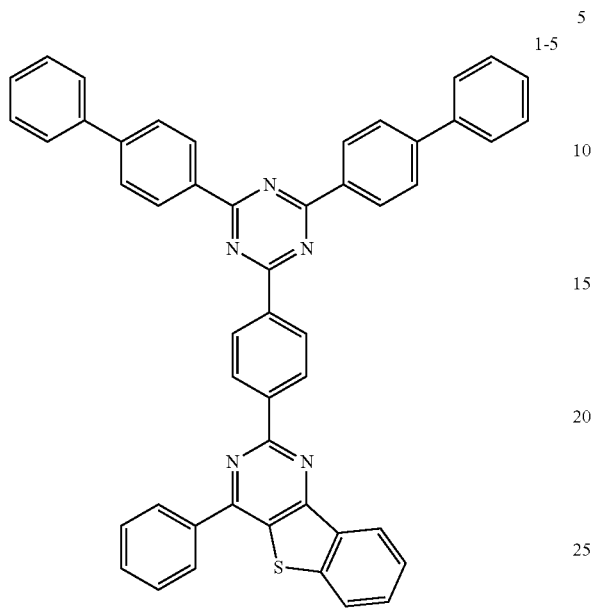
1-5
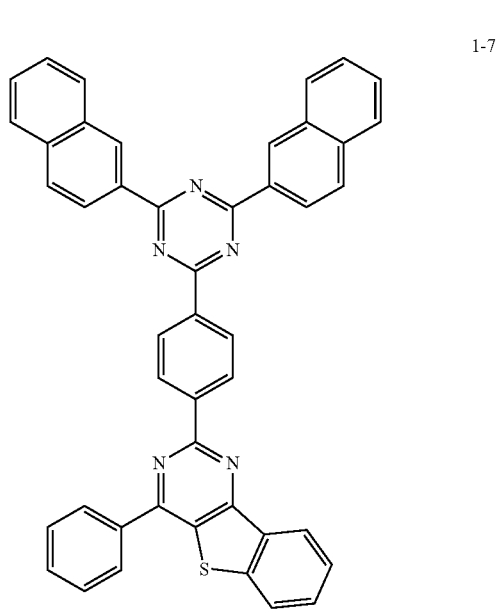
1-7
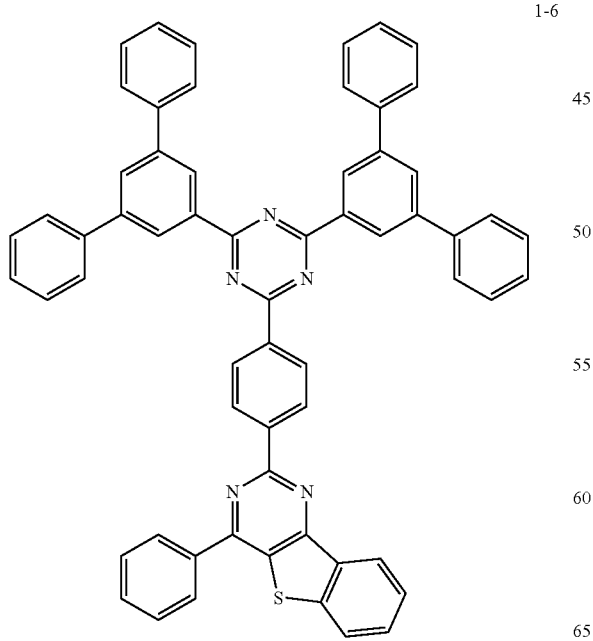
1-6
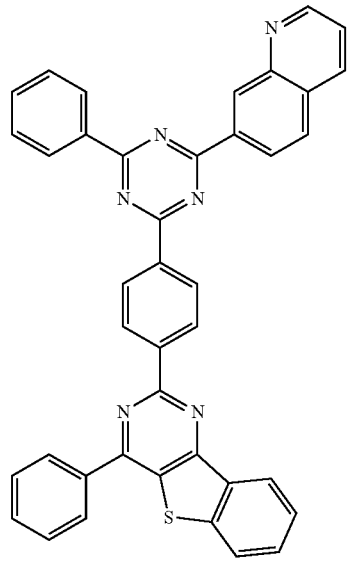
1-8

1-9
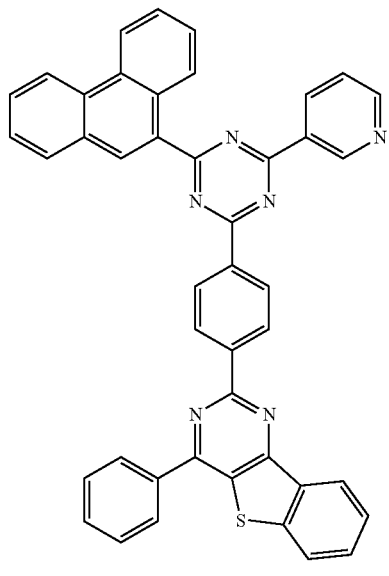
1-10
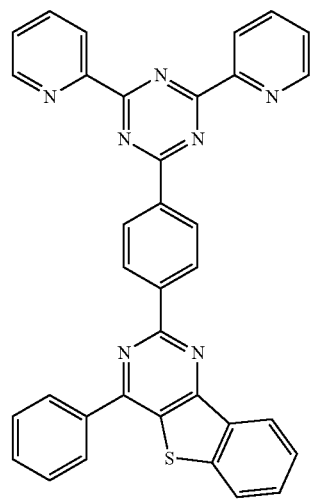
1-11
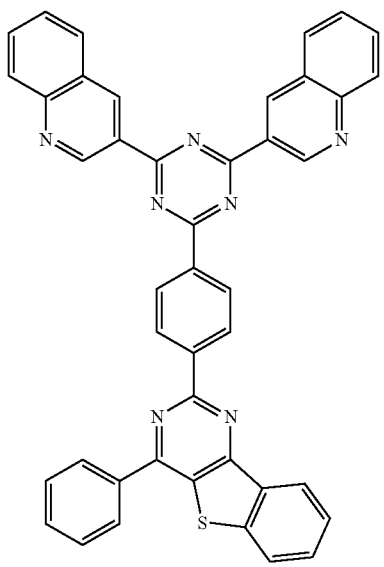
1-12
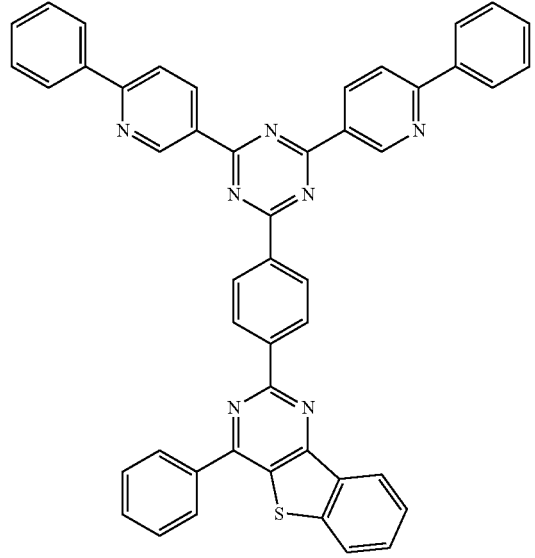
1-13
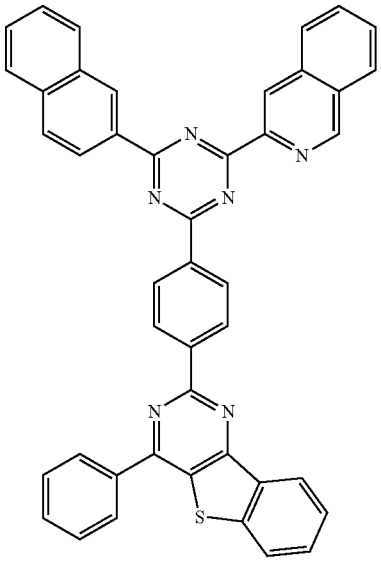
1-14
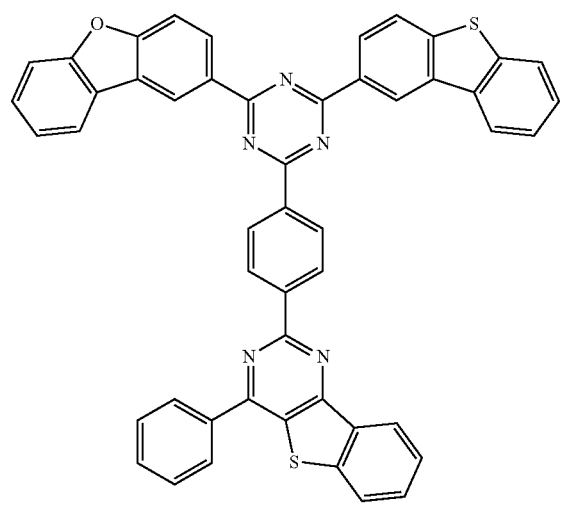

-continued
1-15
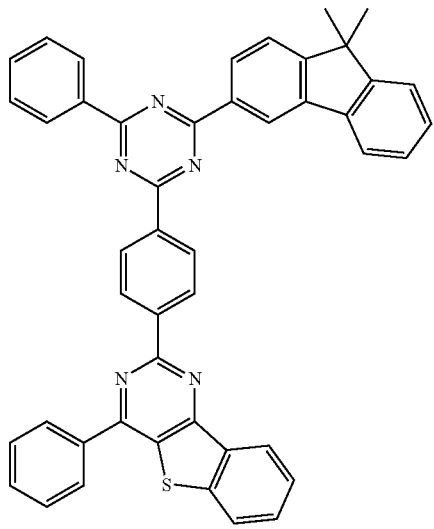
1-16
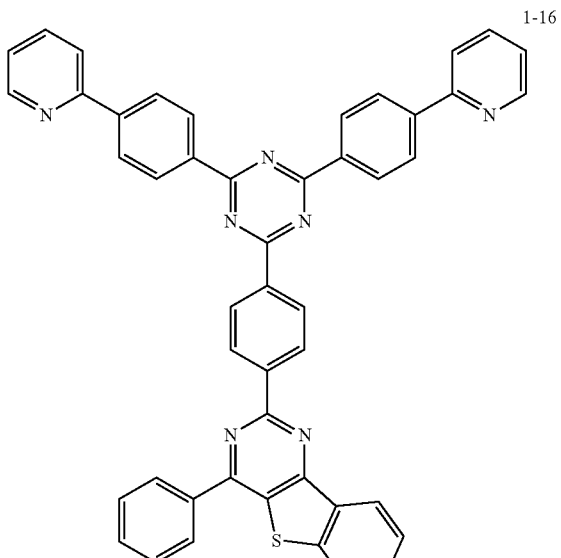
1-17
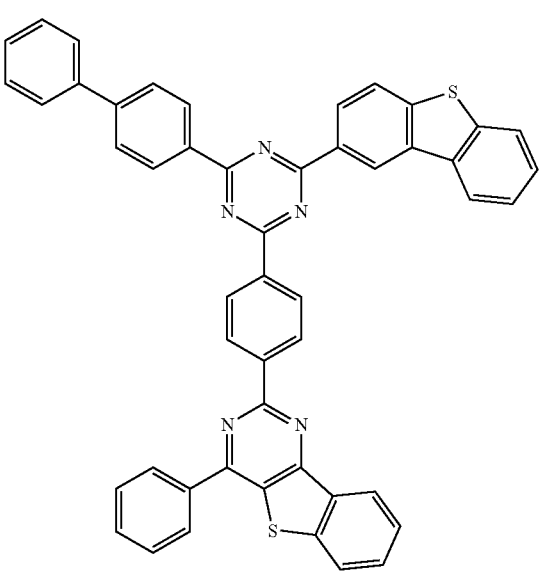
-continued
1-18
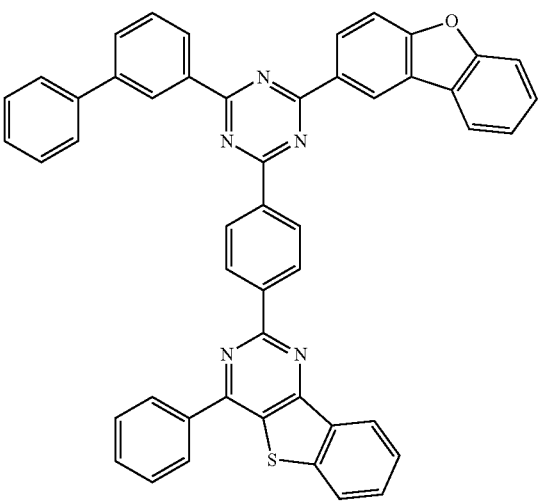
1-19
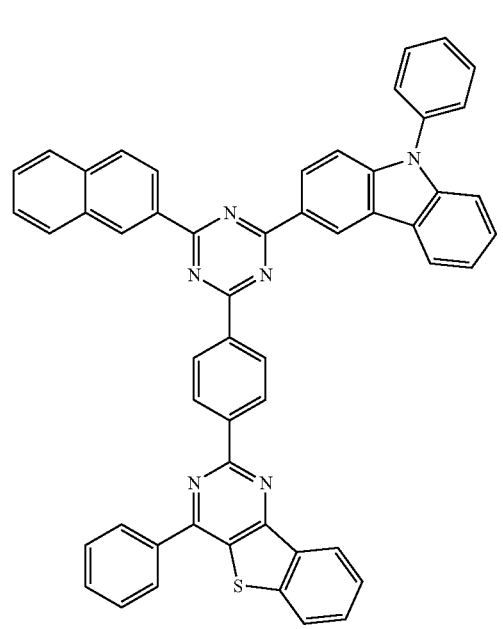
1-20
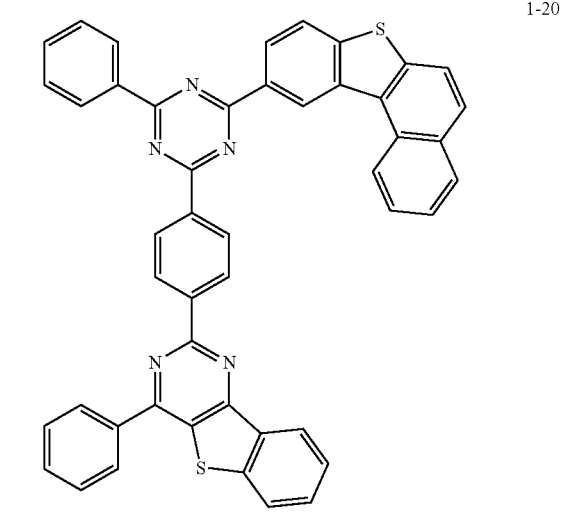

-continued
1-21
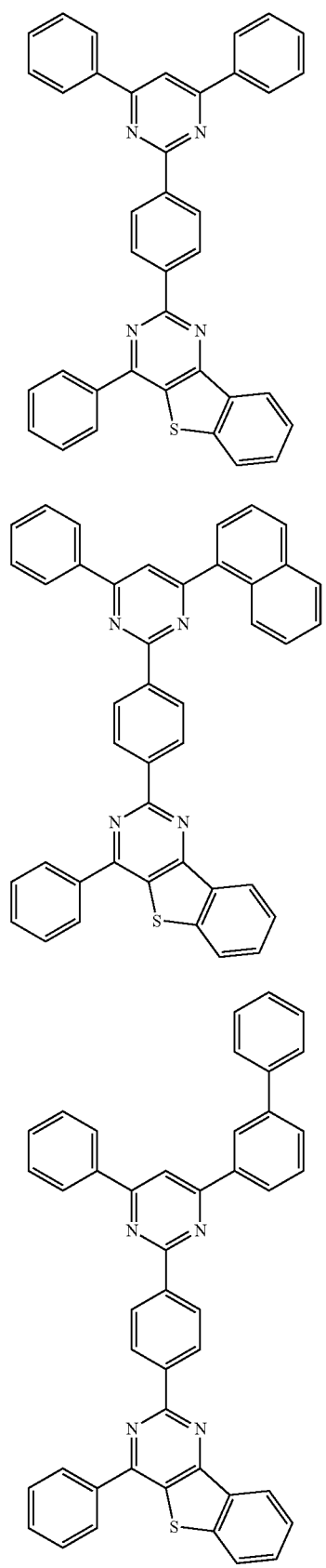
1-22
1-23
1-24
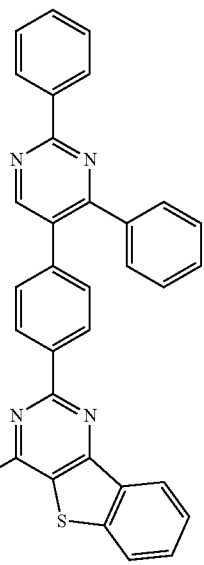
1-25
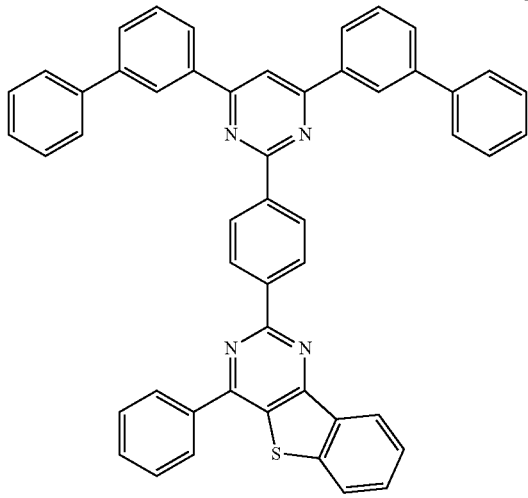
1-26
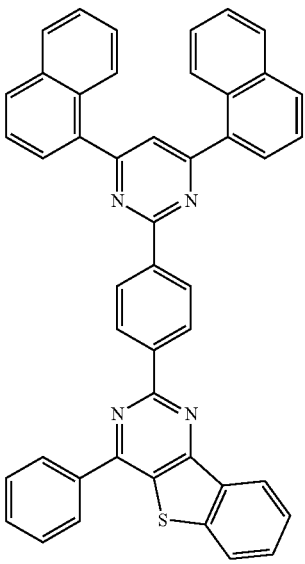

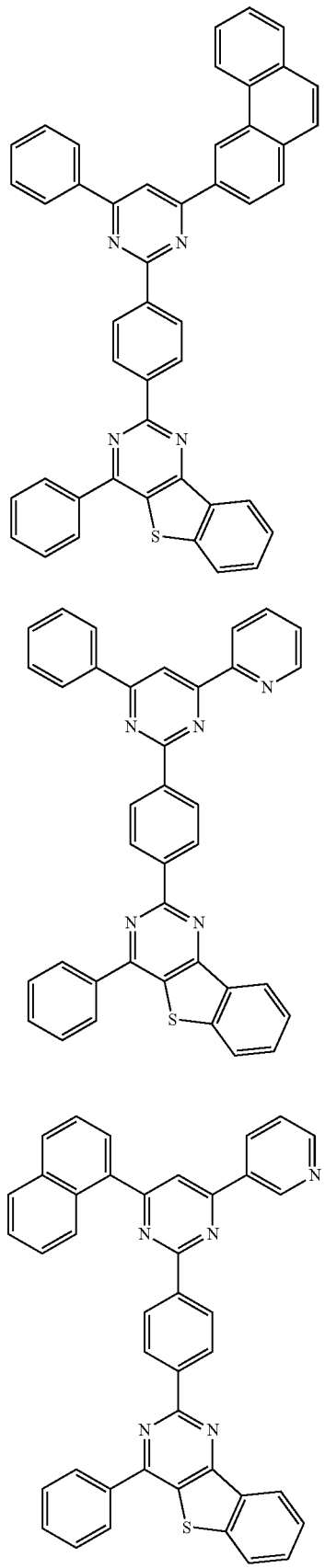
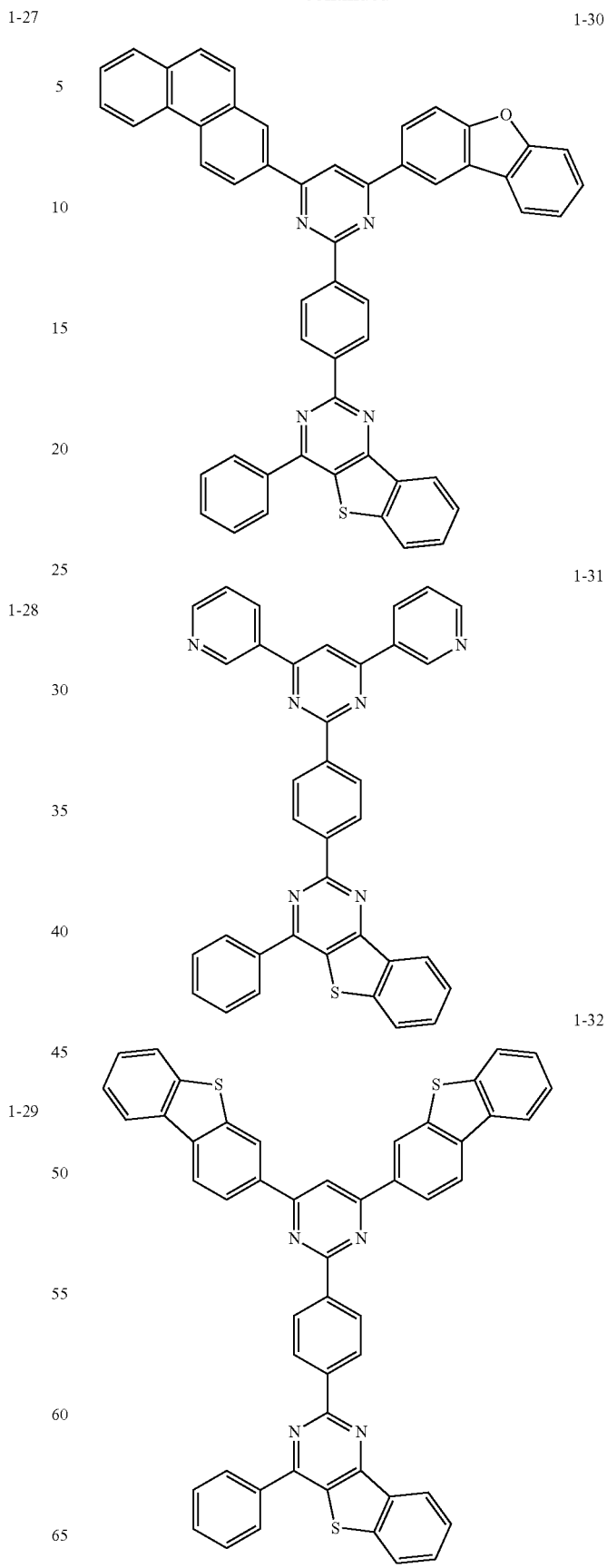

1-33
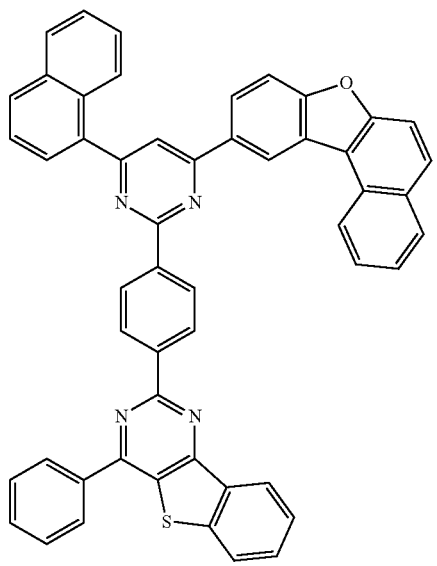
1-34
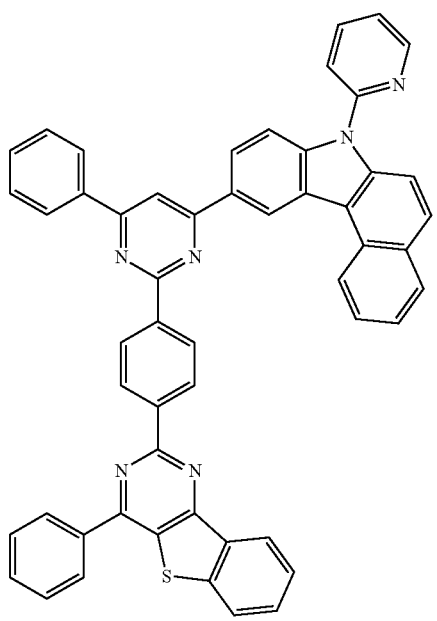
1-35
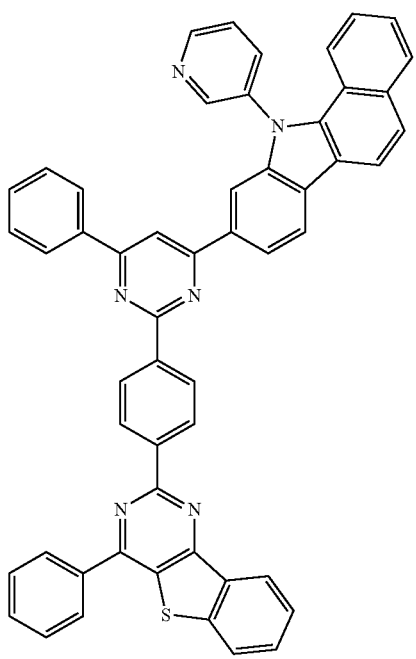
1-36
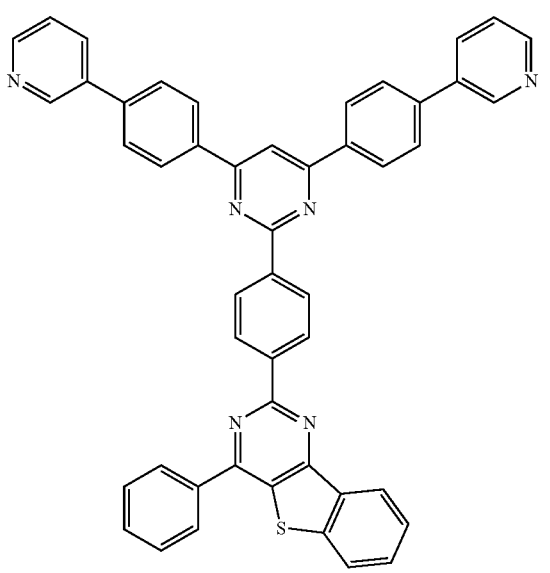

1-37
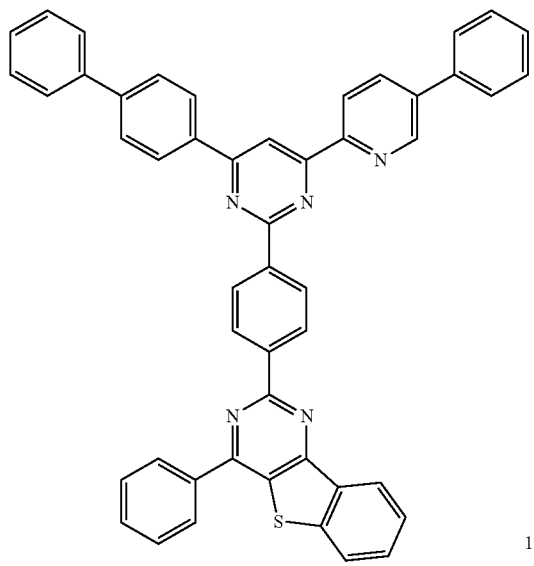
1-38
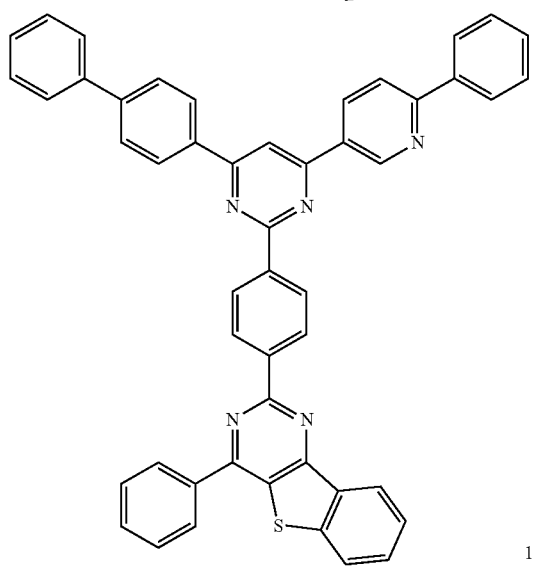
1-39
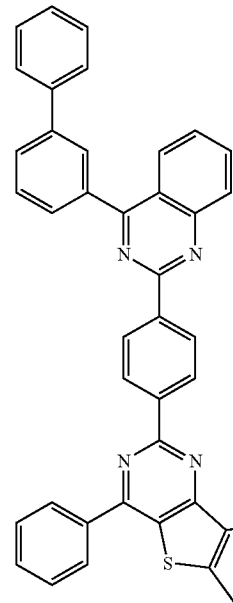
1-40
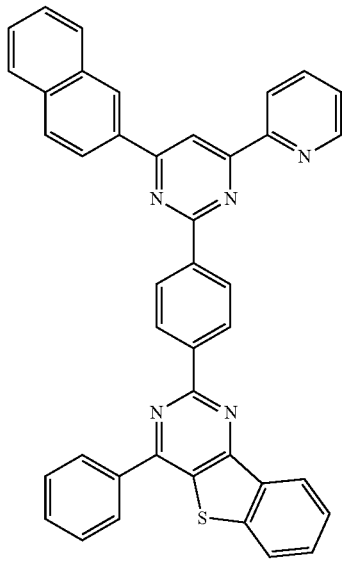
1-41
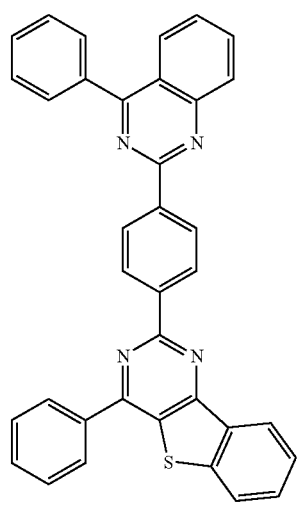
1-42

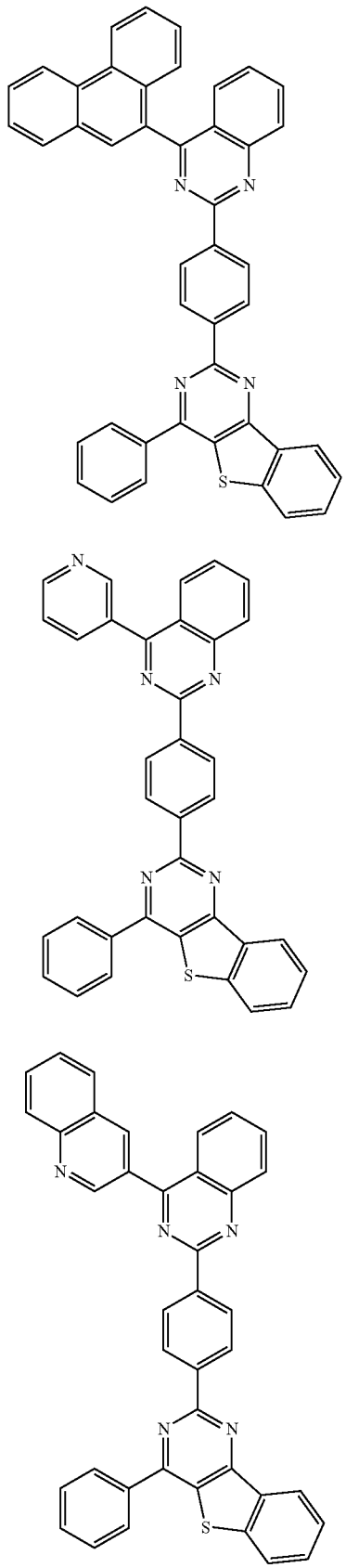
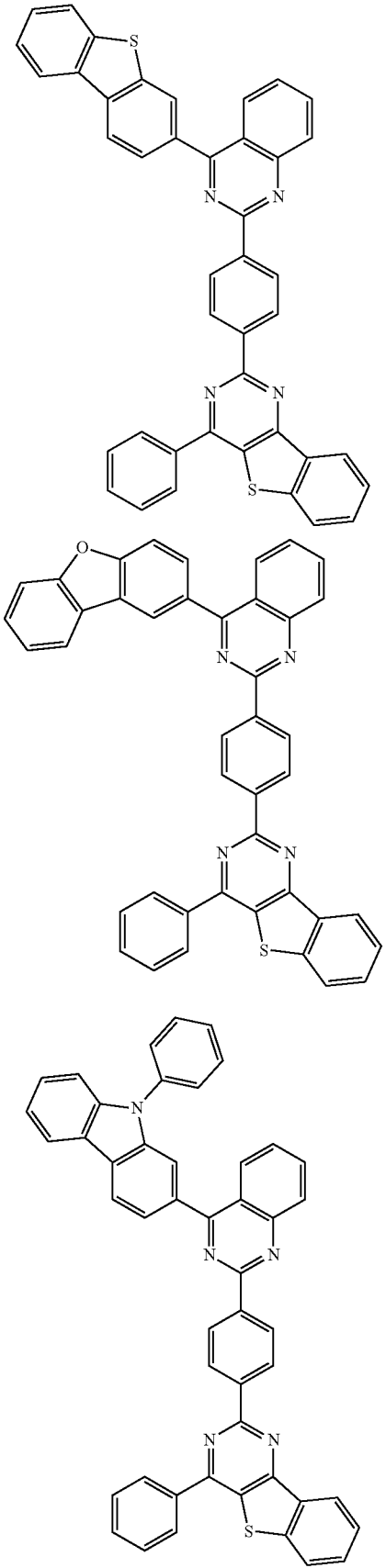

-continued
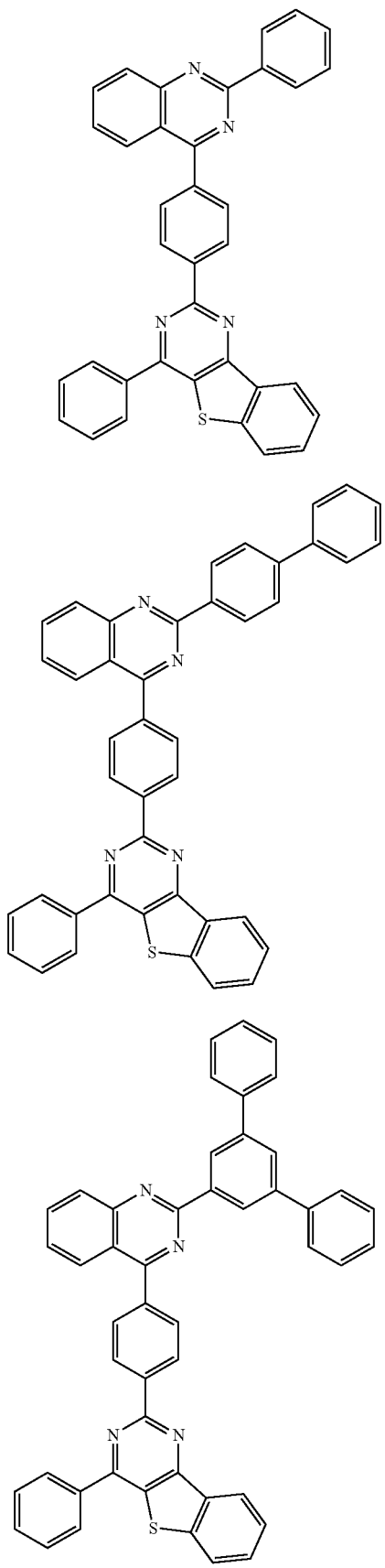
1-49
1-50
1-51
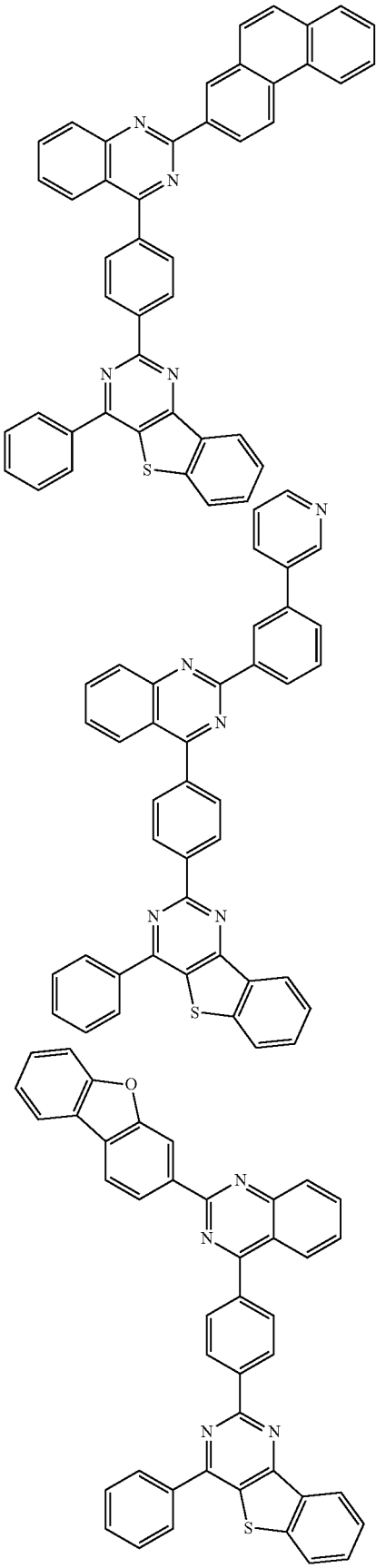
1-52
1-53
1-54

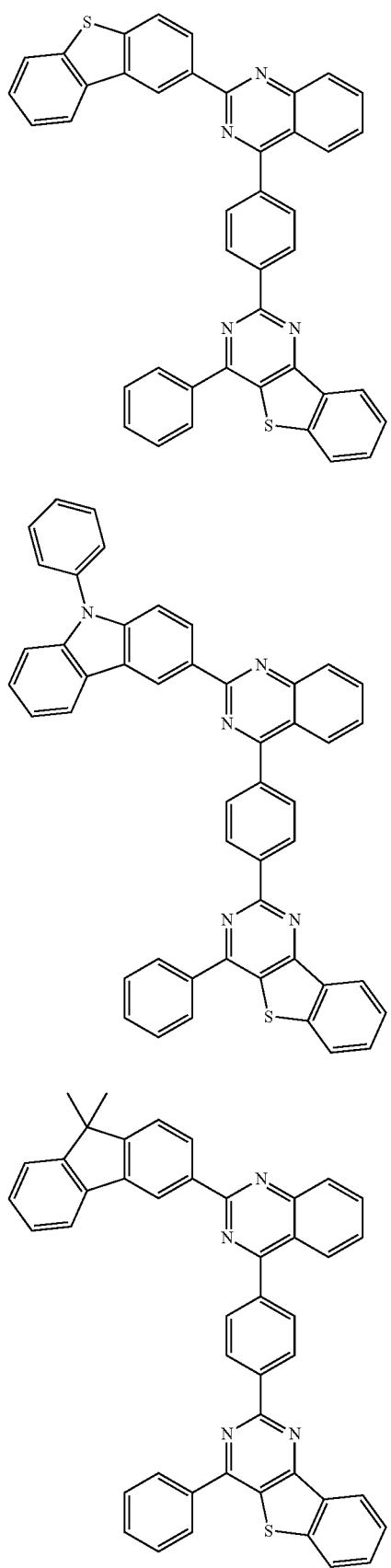
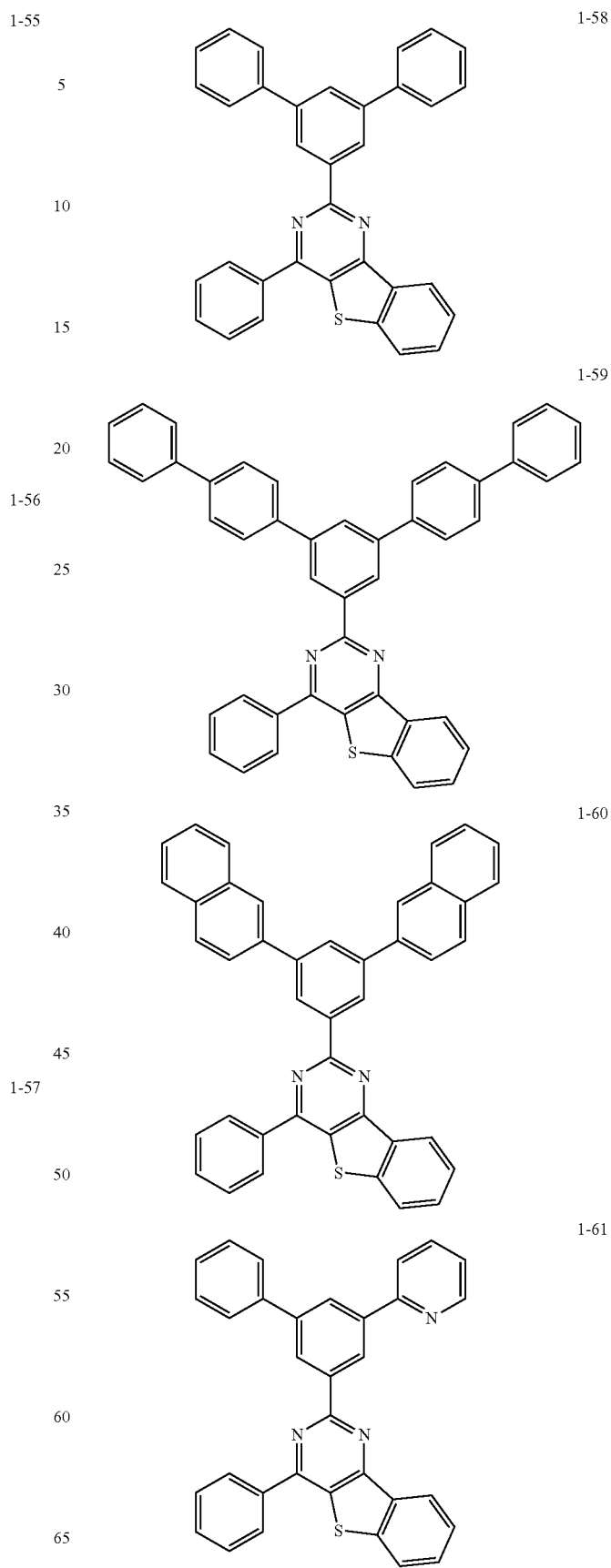

1-62
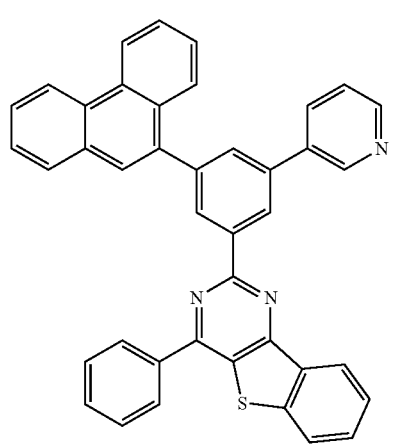
1-63
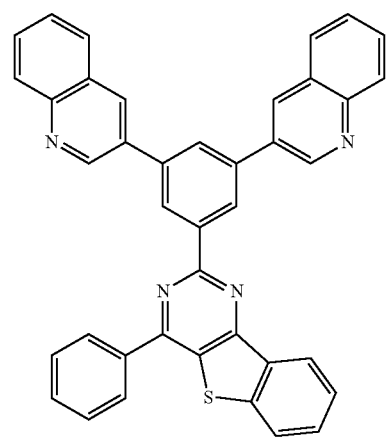
1-64
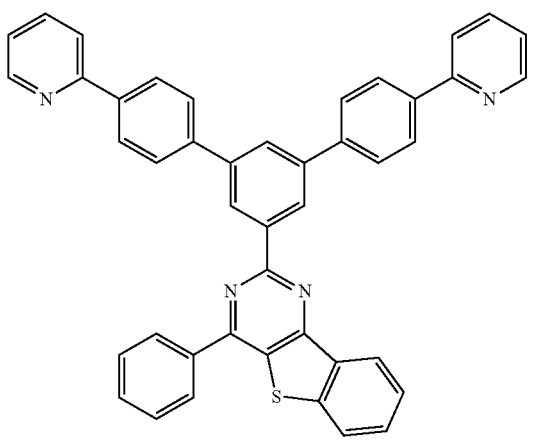
1-65
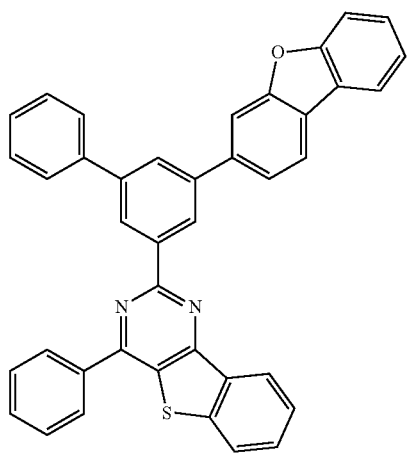
1-66
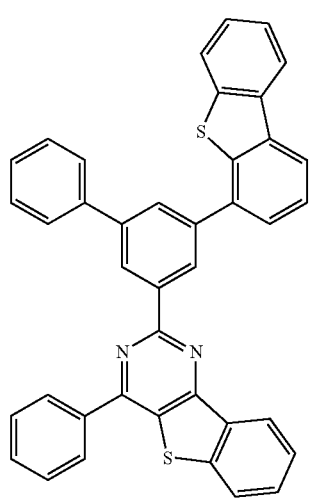
1-67
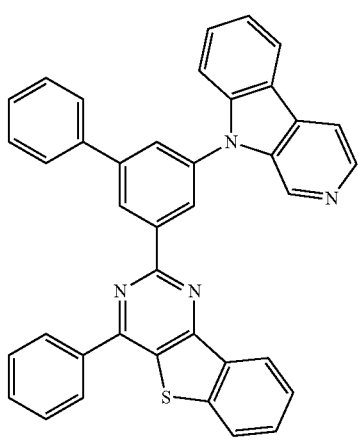

1-68
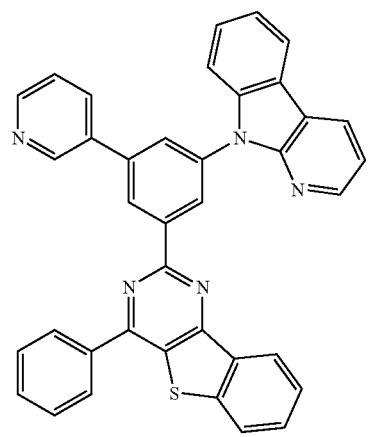
1-69
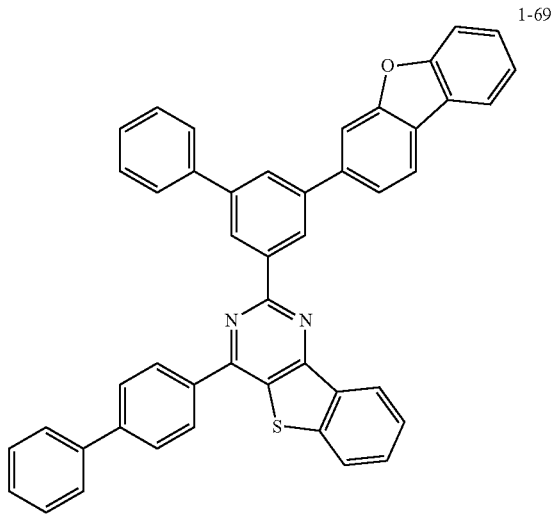
1-70
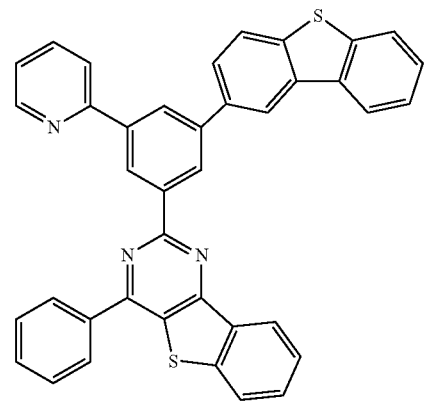
1-71
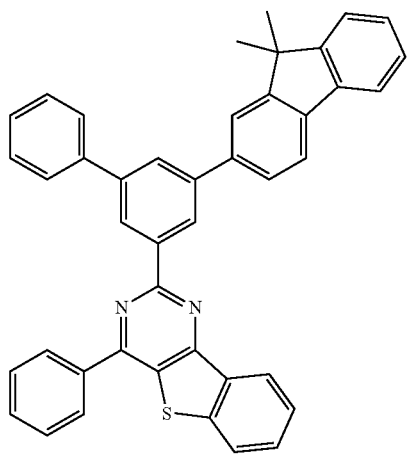
1-72
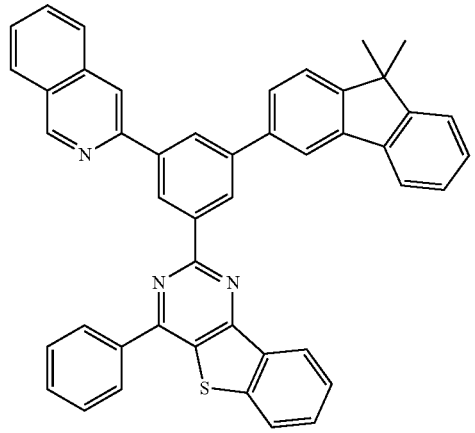
1-73
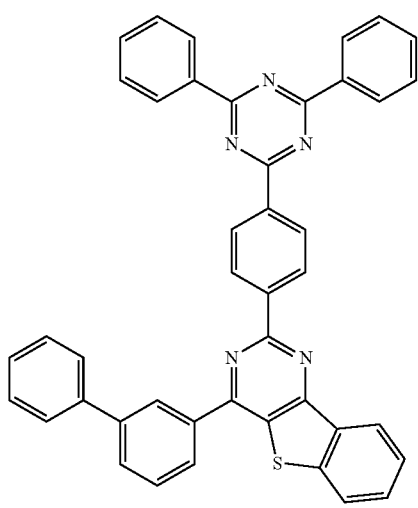

1-74
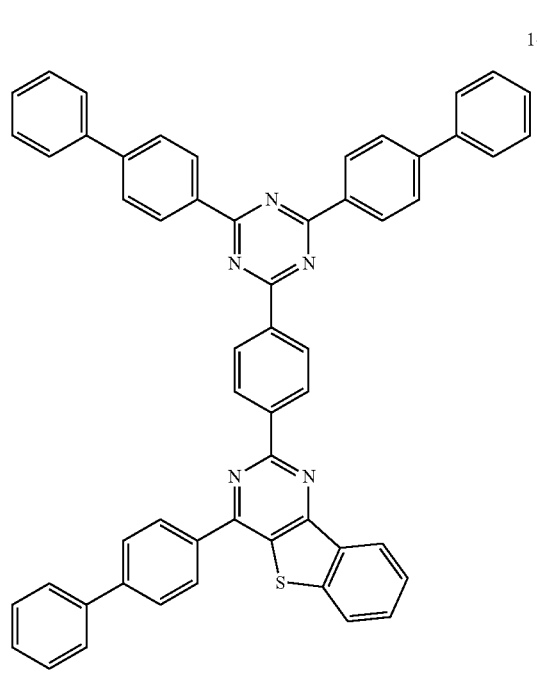
1-75
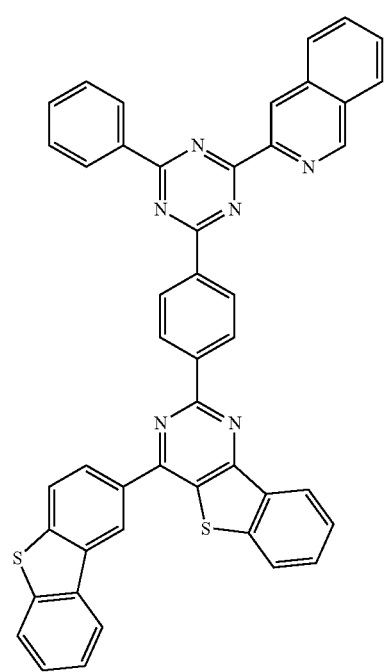
1-76
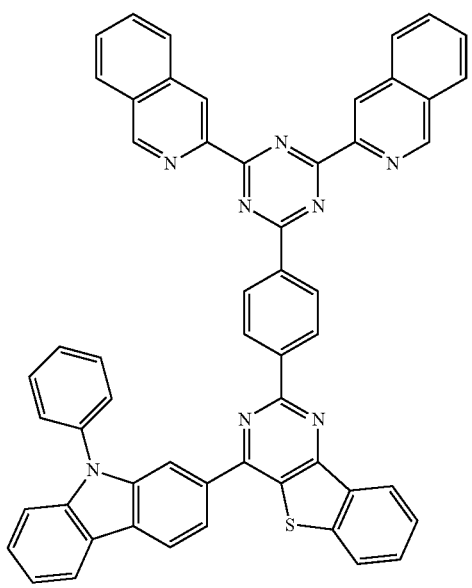
1-77
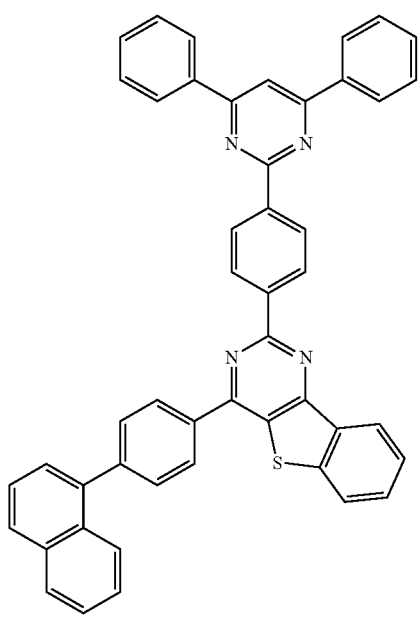

-continued
1-78
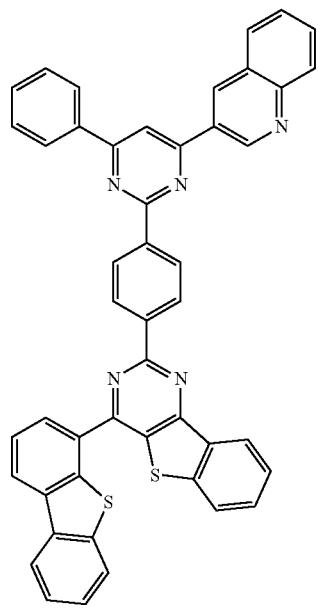
1-80
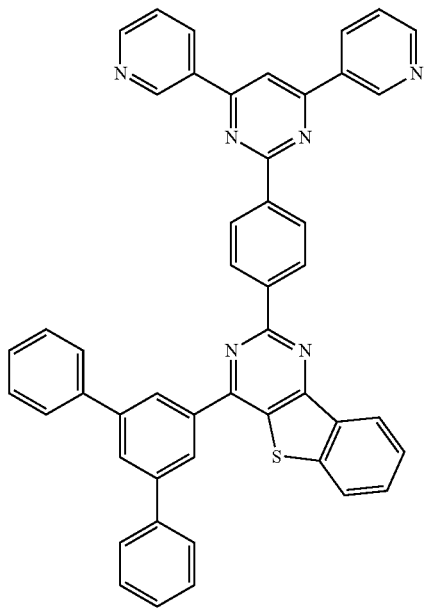
1-79
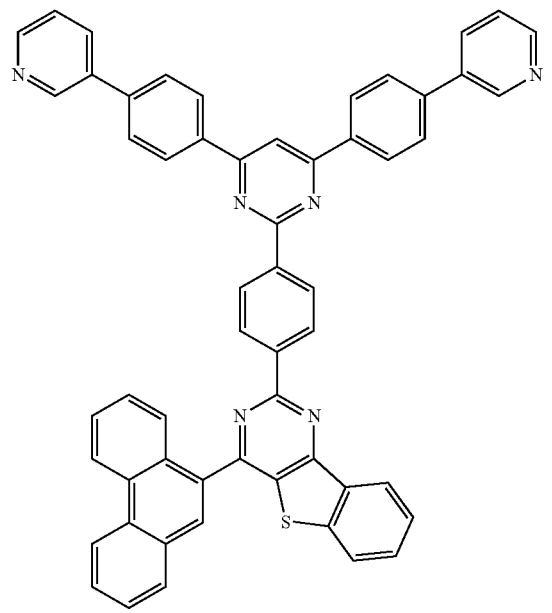
1-81
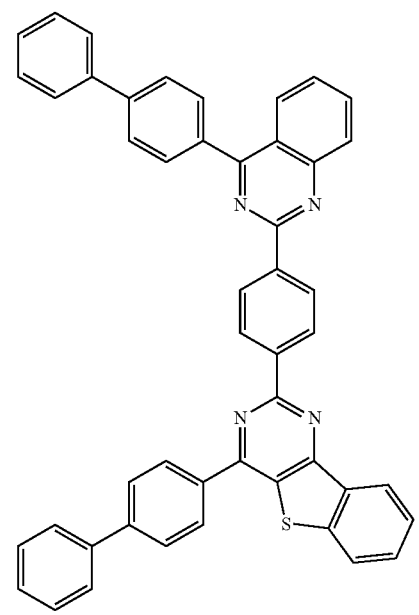

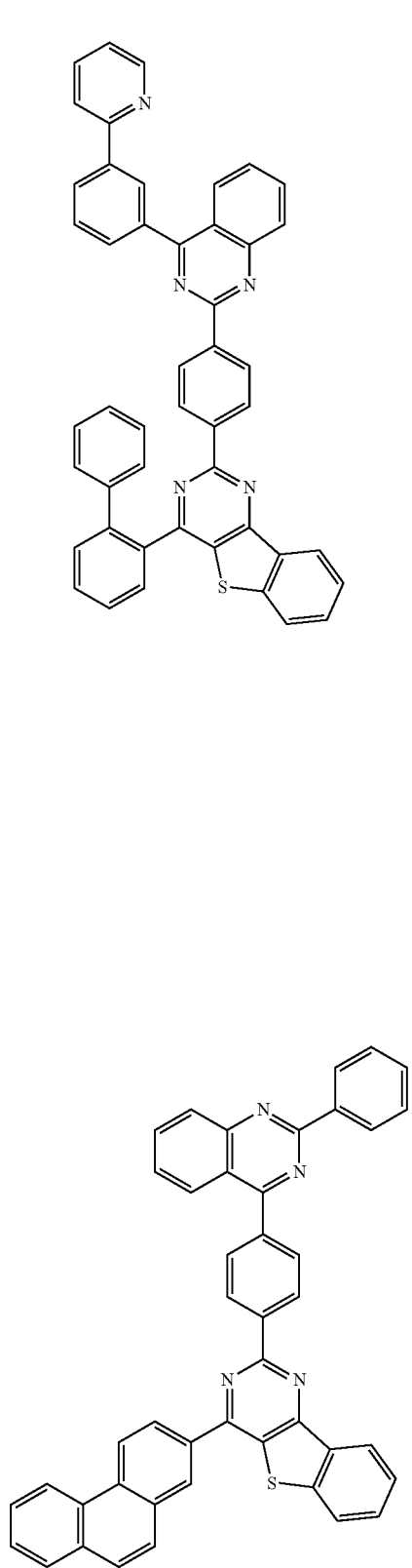
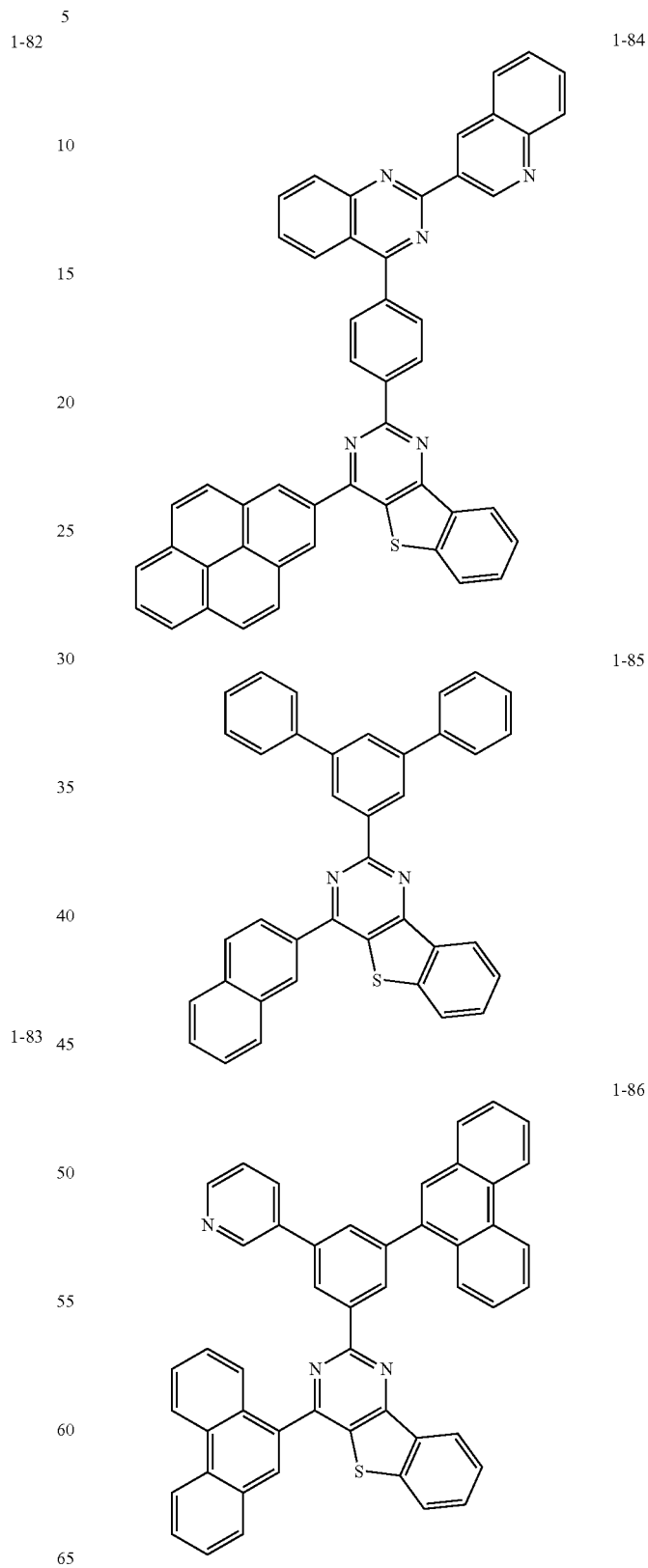

-continued
1-87
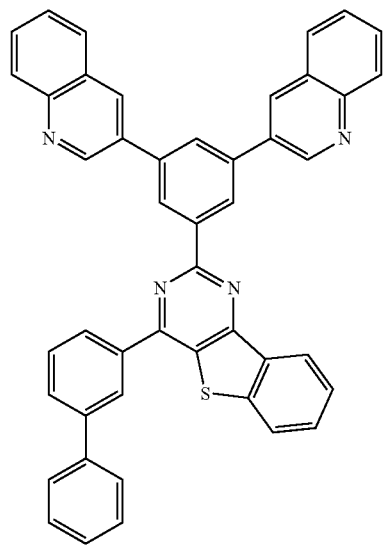
1-88
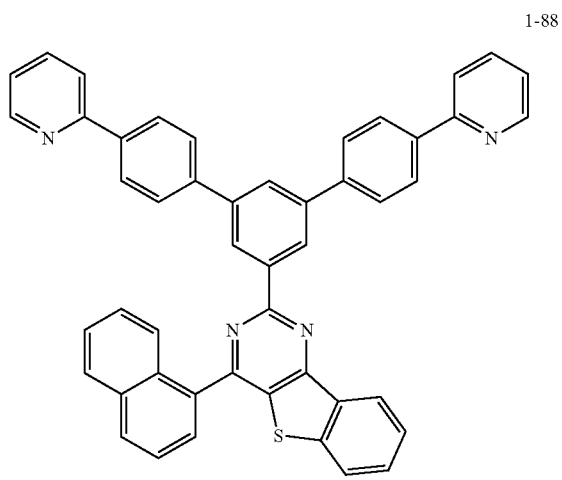
1-89
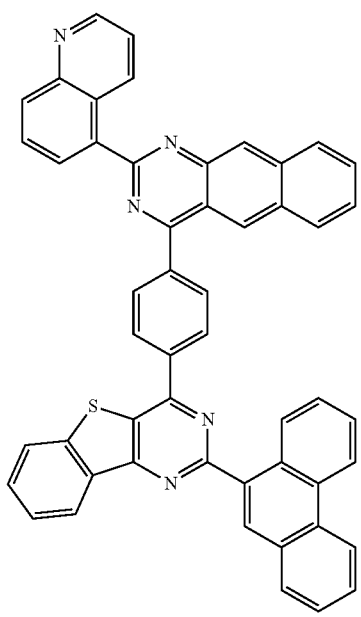
1-90
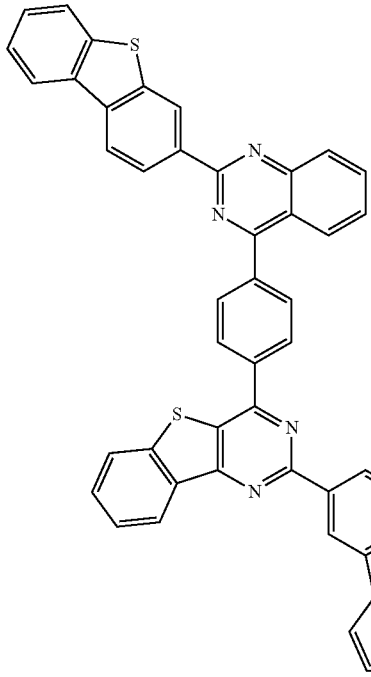
1-91
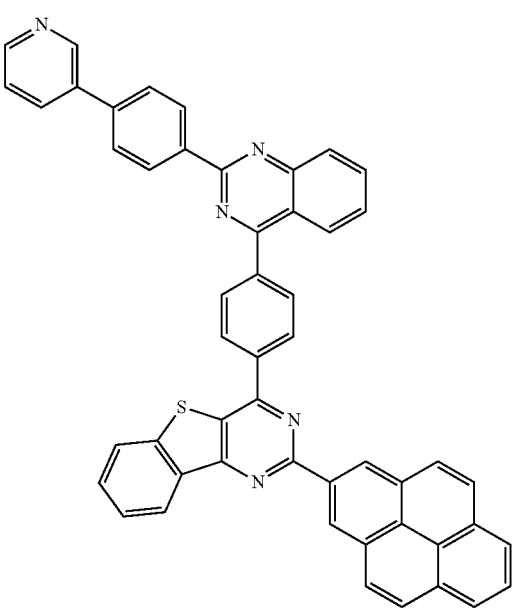

-continued
1-92
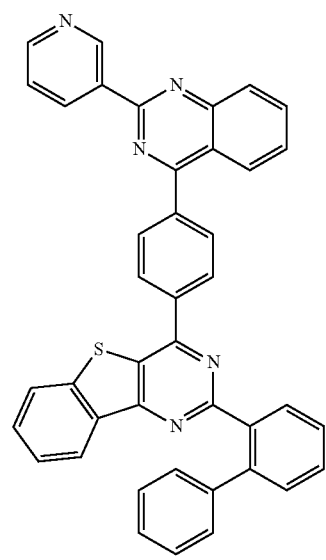
1-93
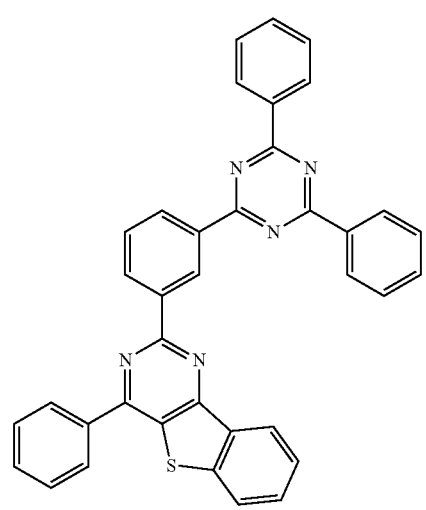
1-94
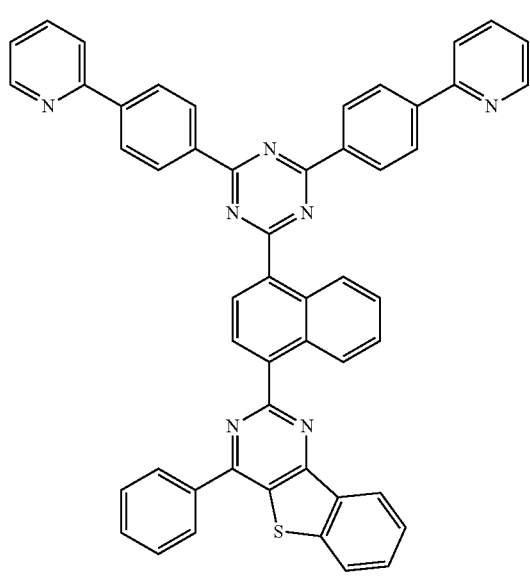
1-95
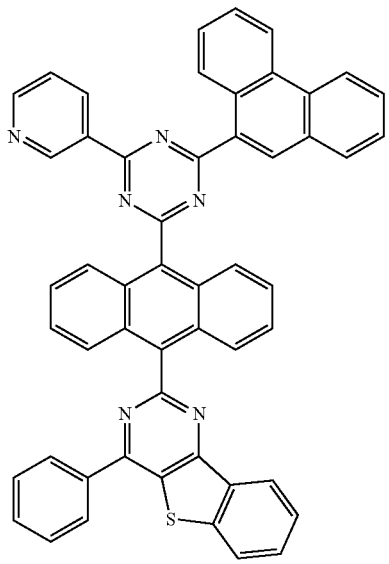
1-96
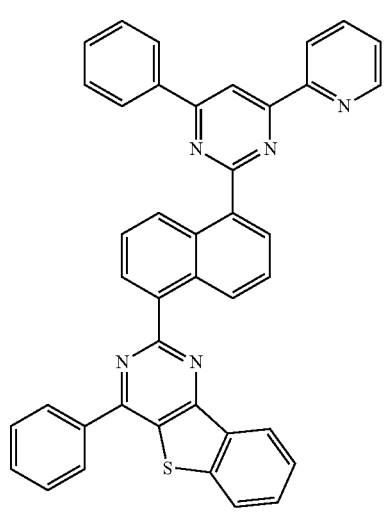
1-97
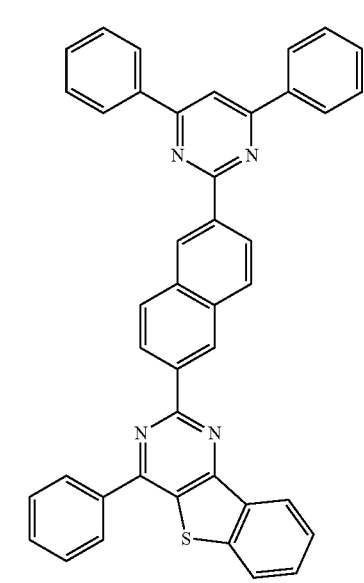

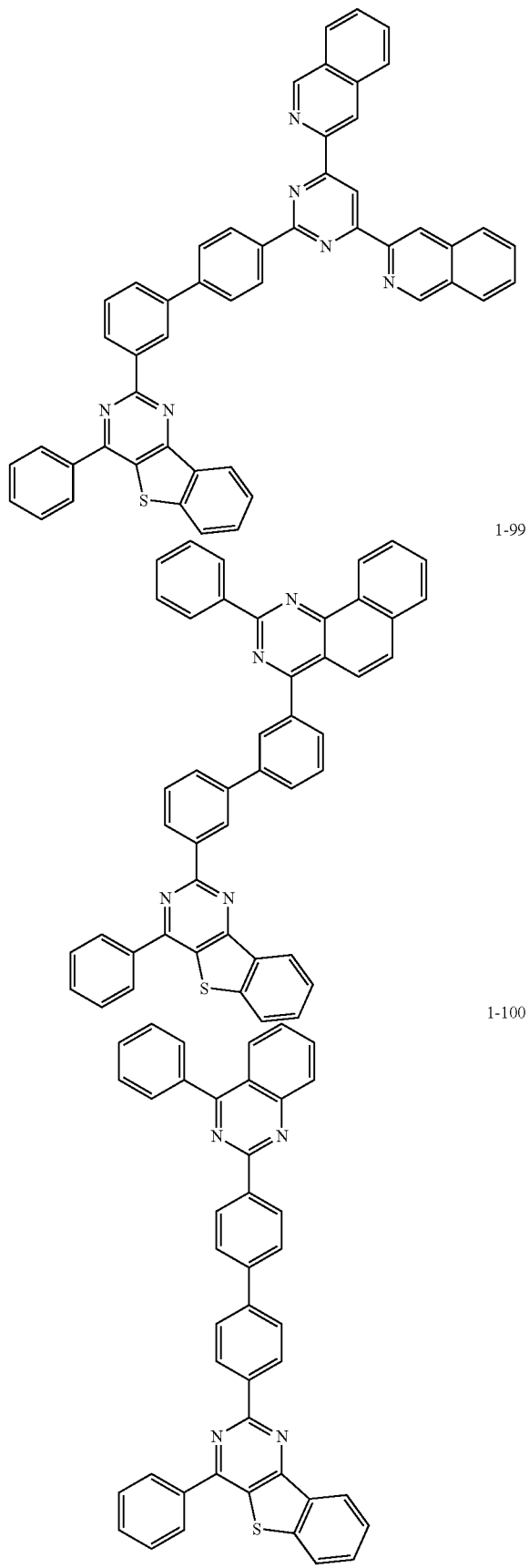
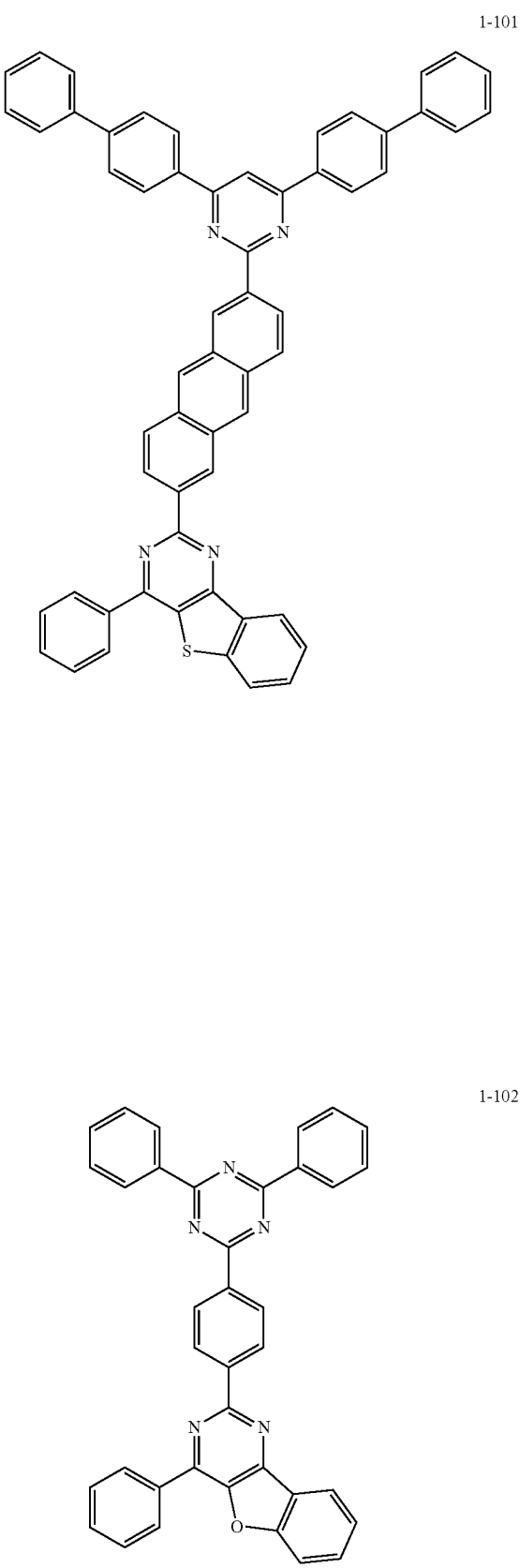

-continued
1-103
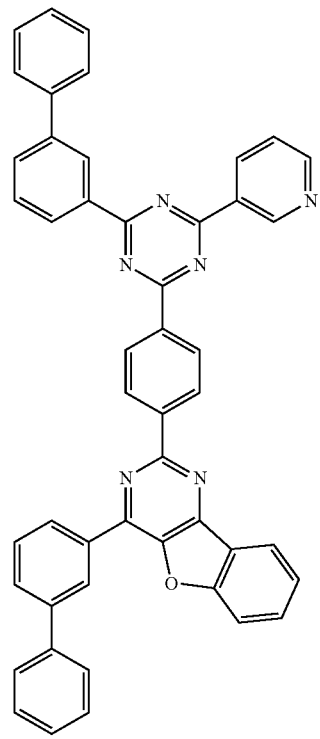
1-104
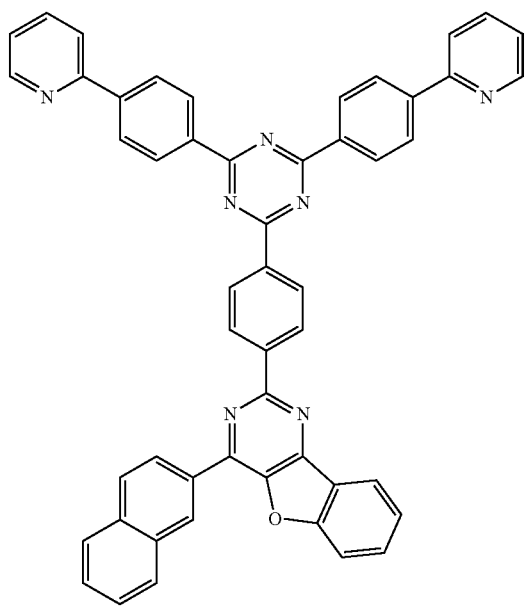
1-105
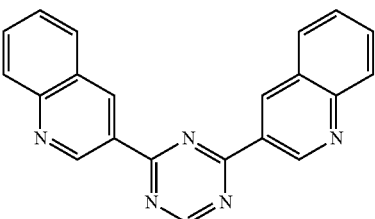
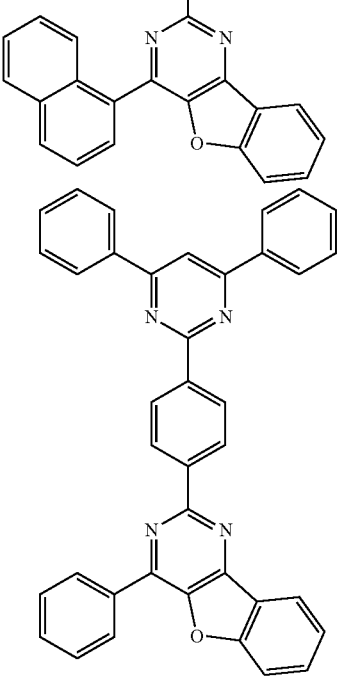
1-106
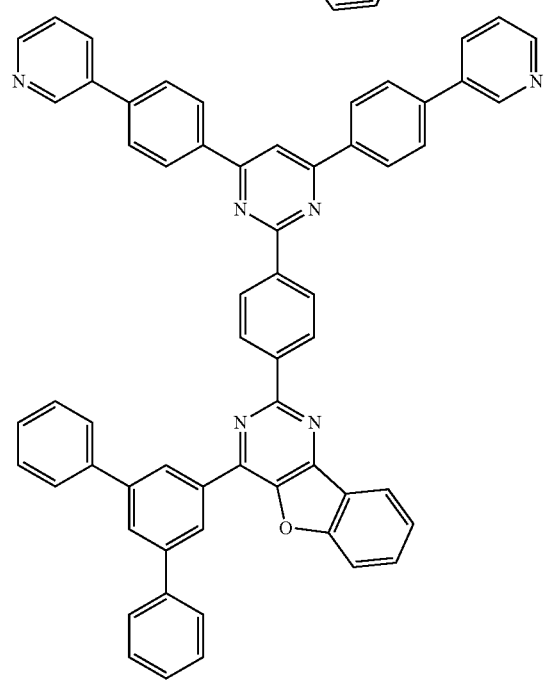
1-107

-continued
1-108
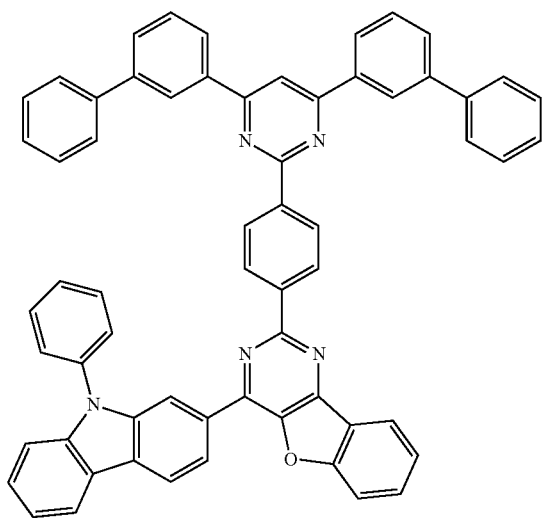
1-109
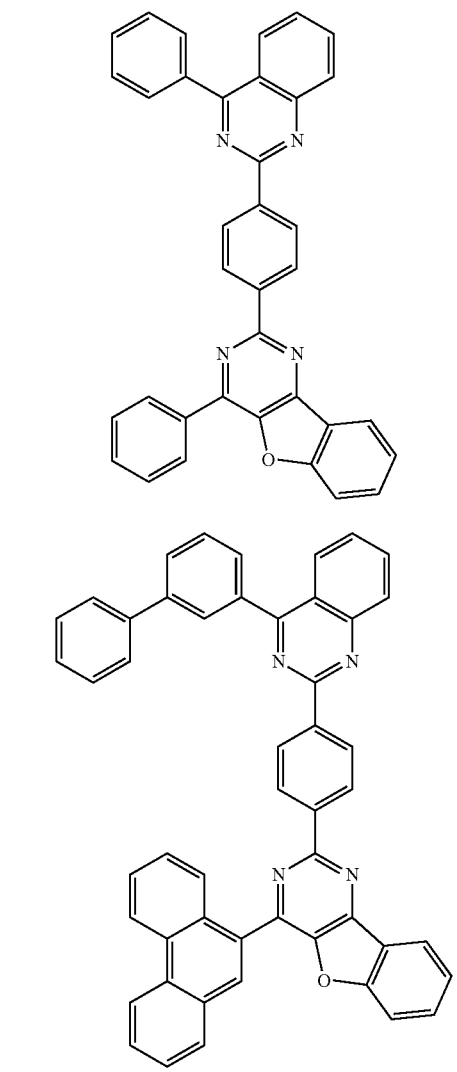
1-111
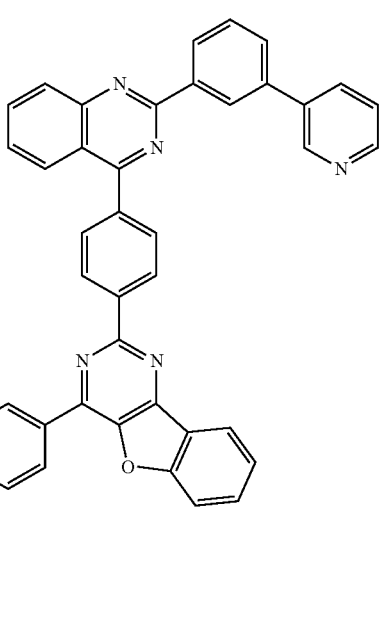
1-112
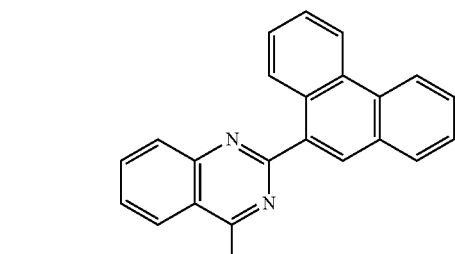
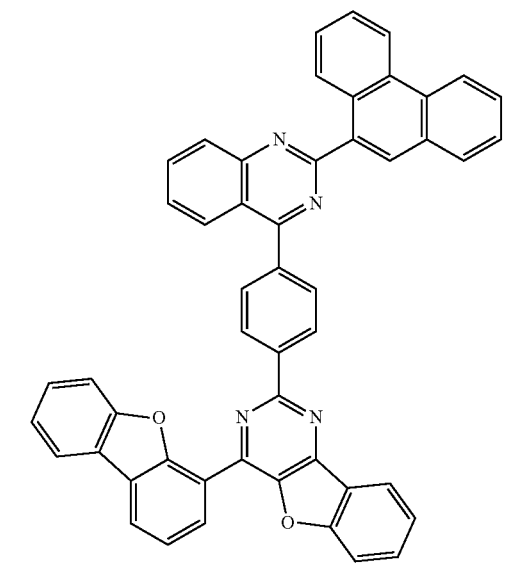
1-113
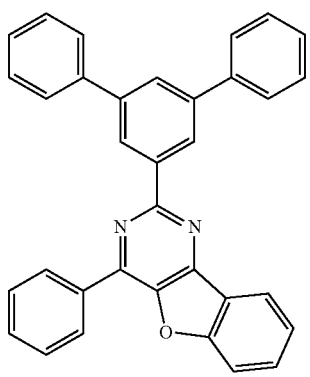

1-114
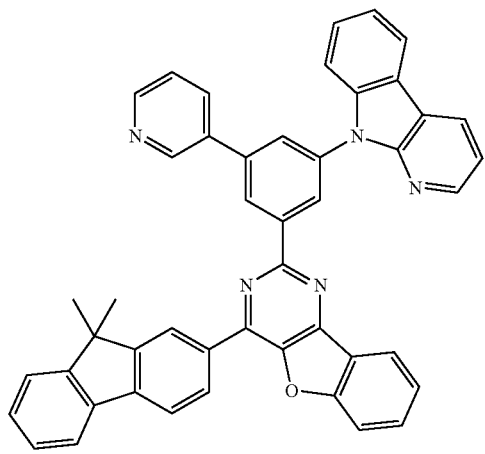
1-115
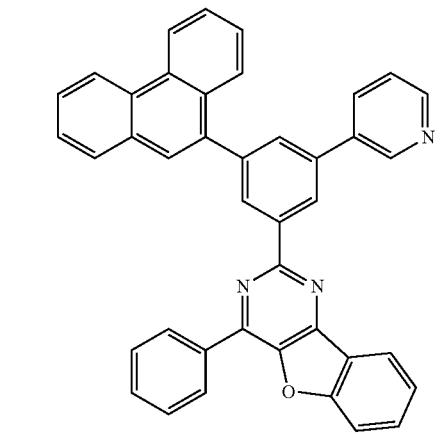
1-116
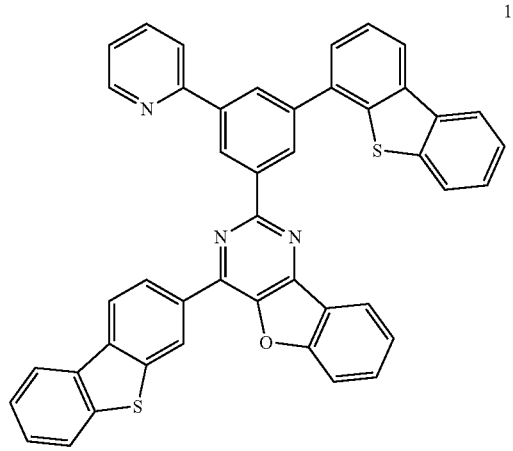
1-117
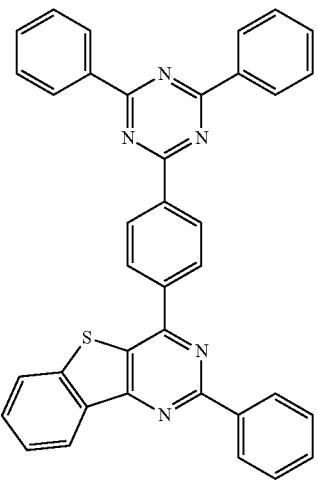
1-118
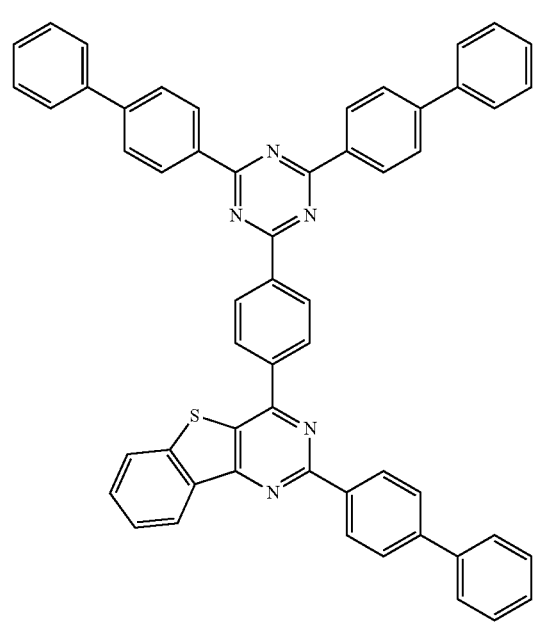
1-119
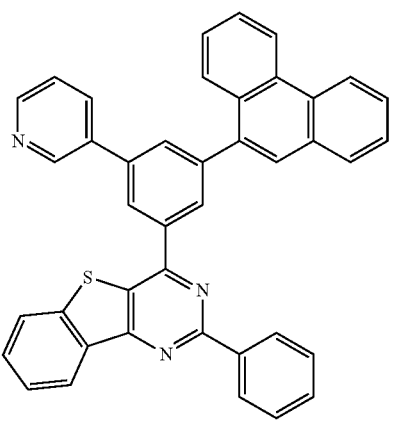

1-120
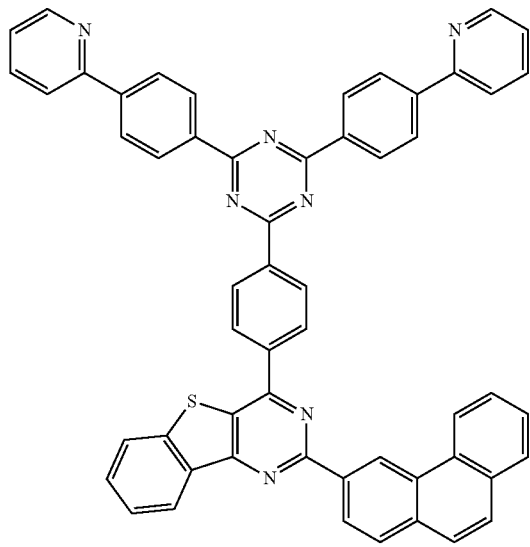
1-121
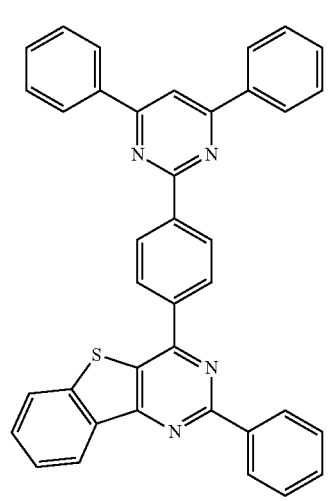
1-122
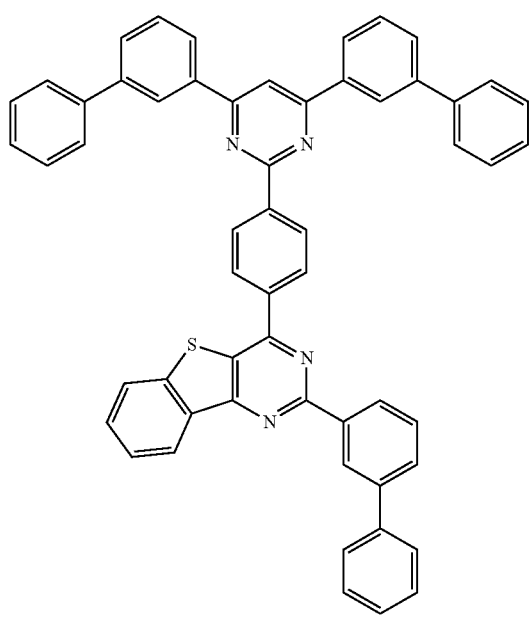
1-123
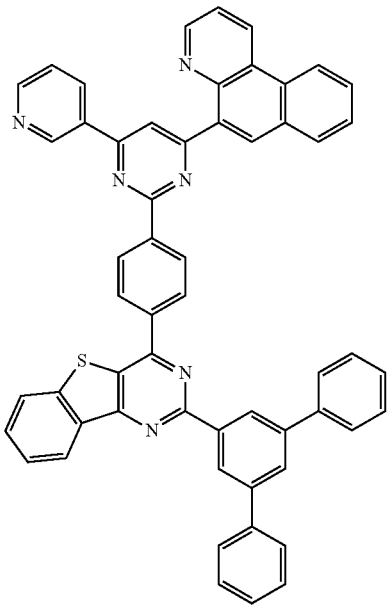
1-124
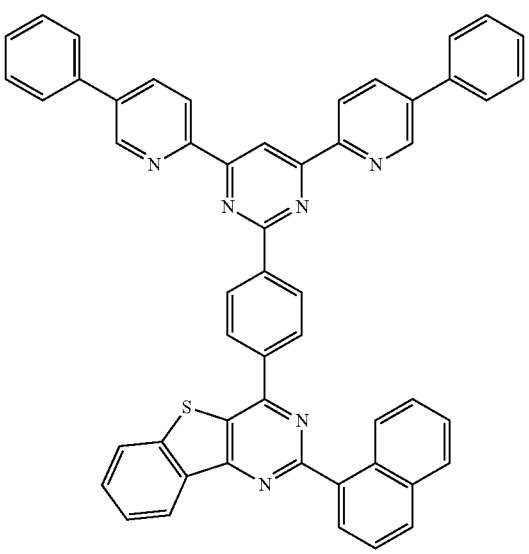
1-125
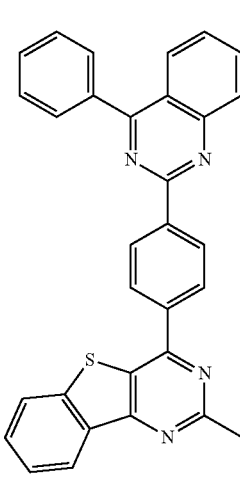

1-126
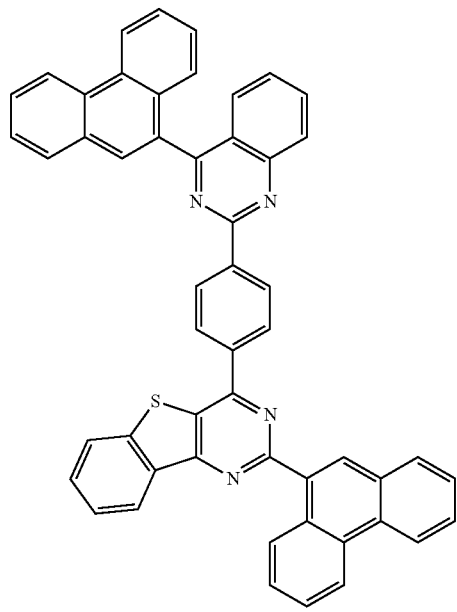
1-127
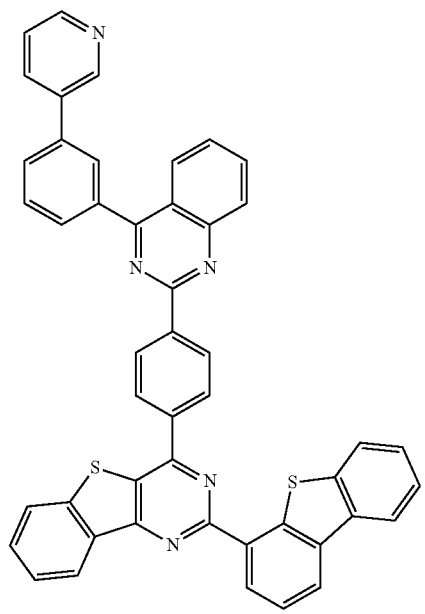
1-128
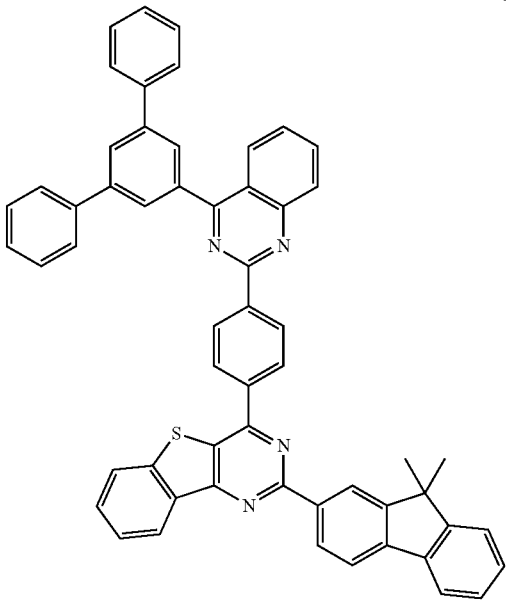
1-129
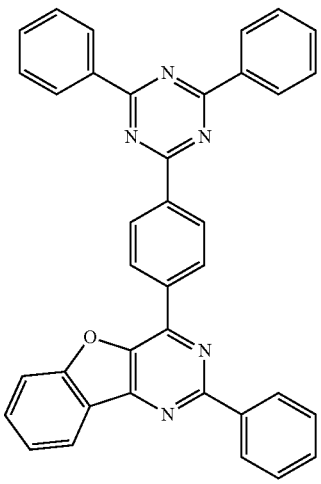
1-130
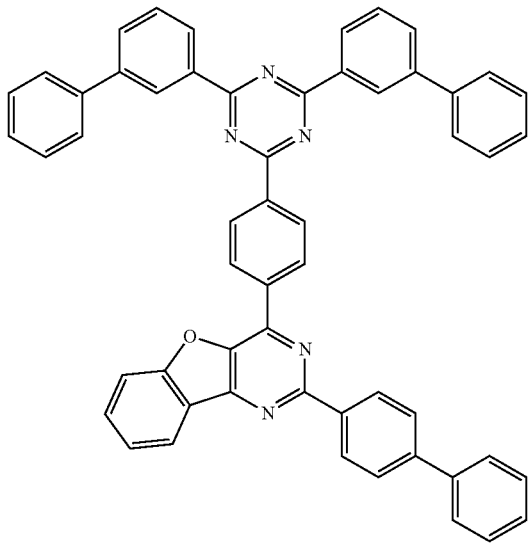

1-131
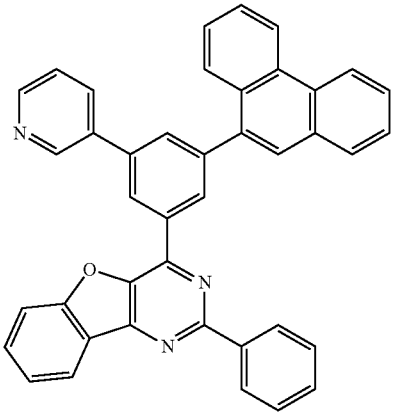
1-132
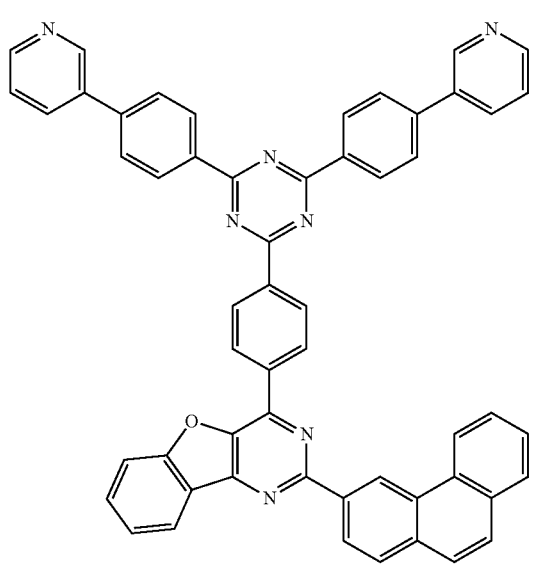
1-133
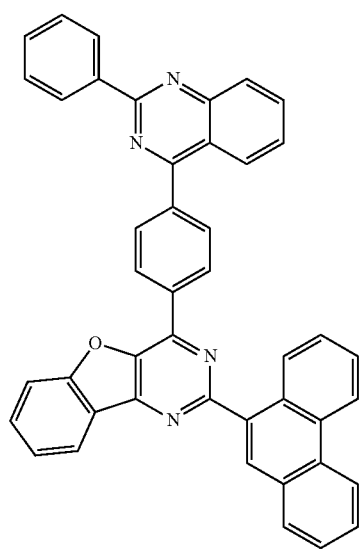
1-134
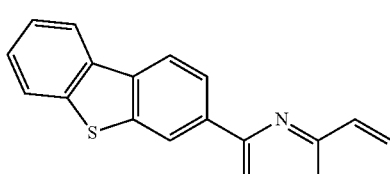
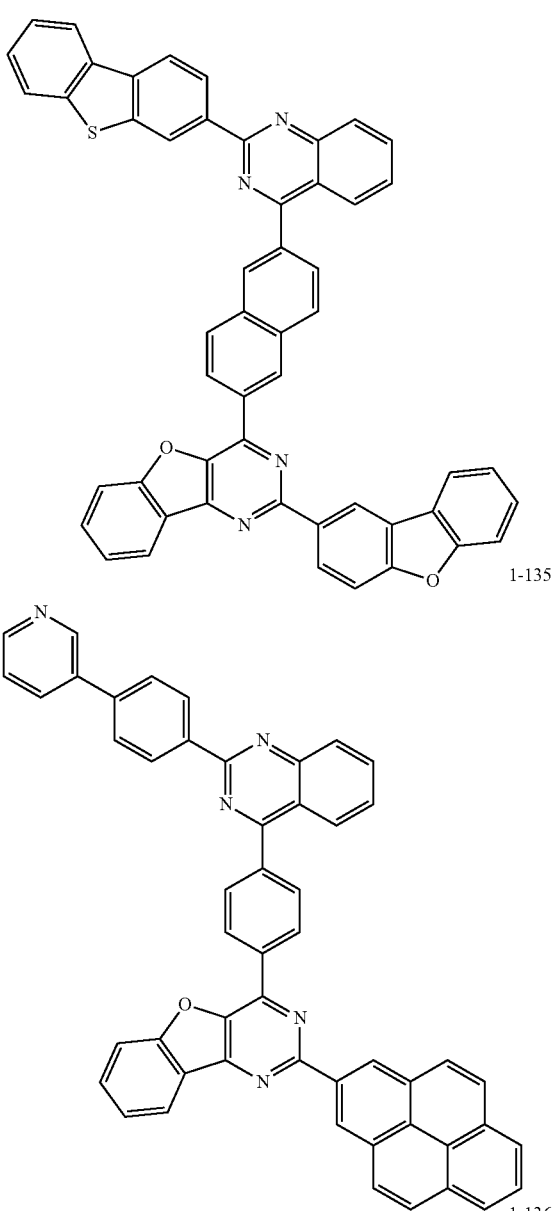
1-135
1-136
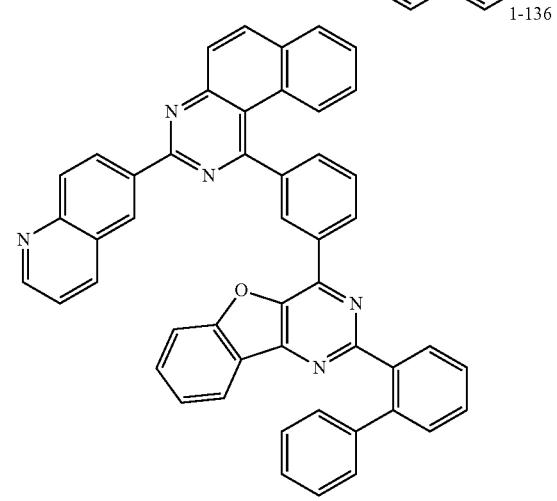

-continued
1-137
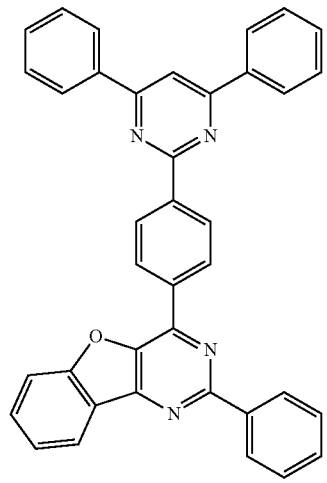
1-138
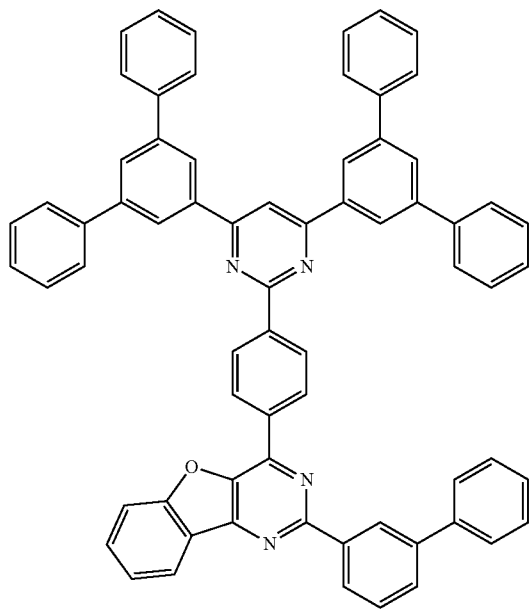
-continued
1-139
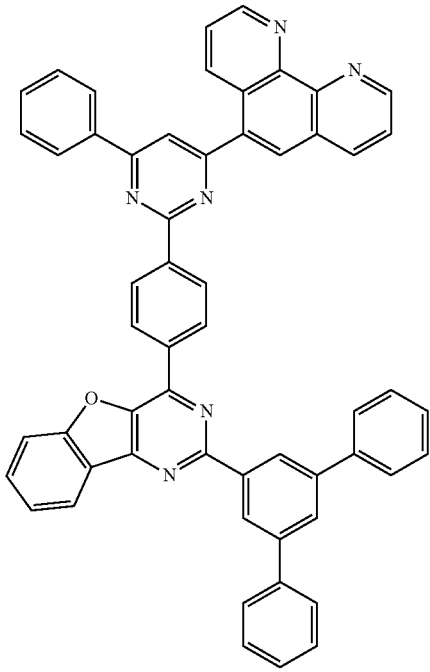
1-140
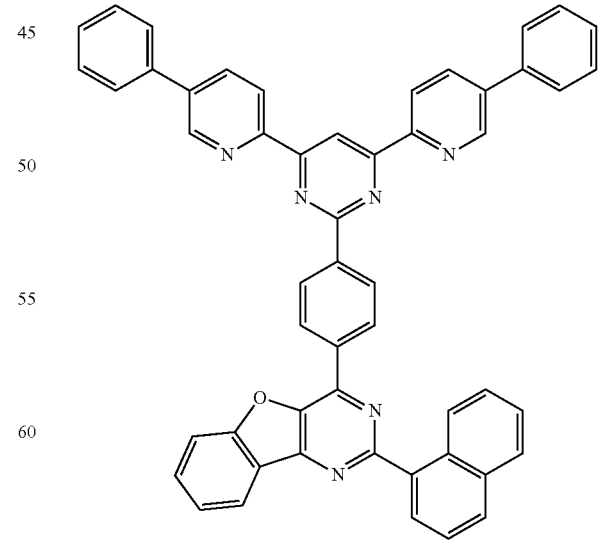

-continued
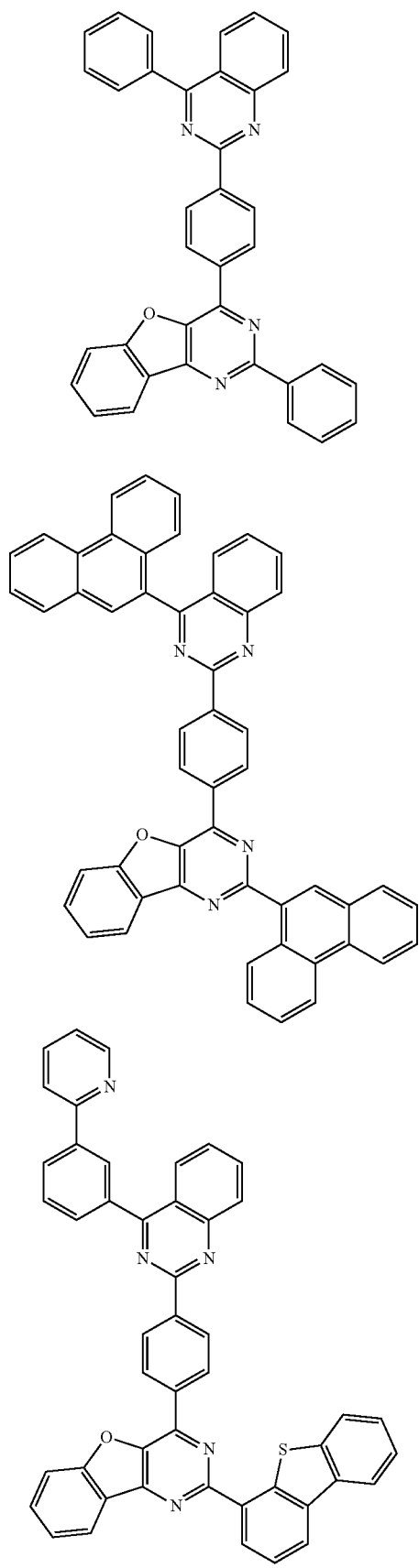
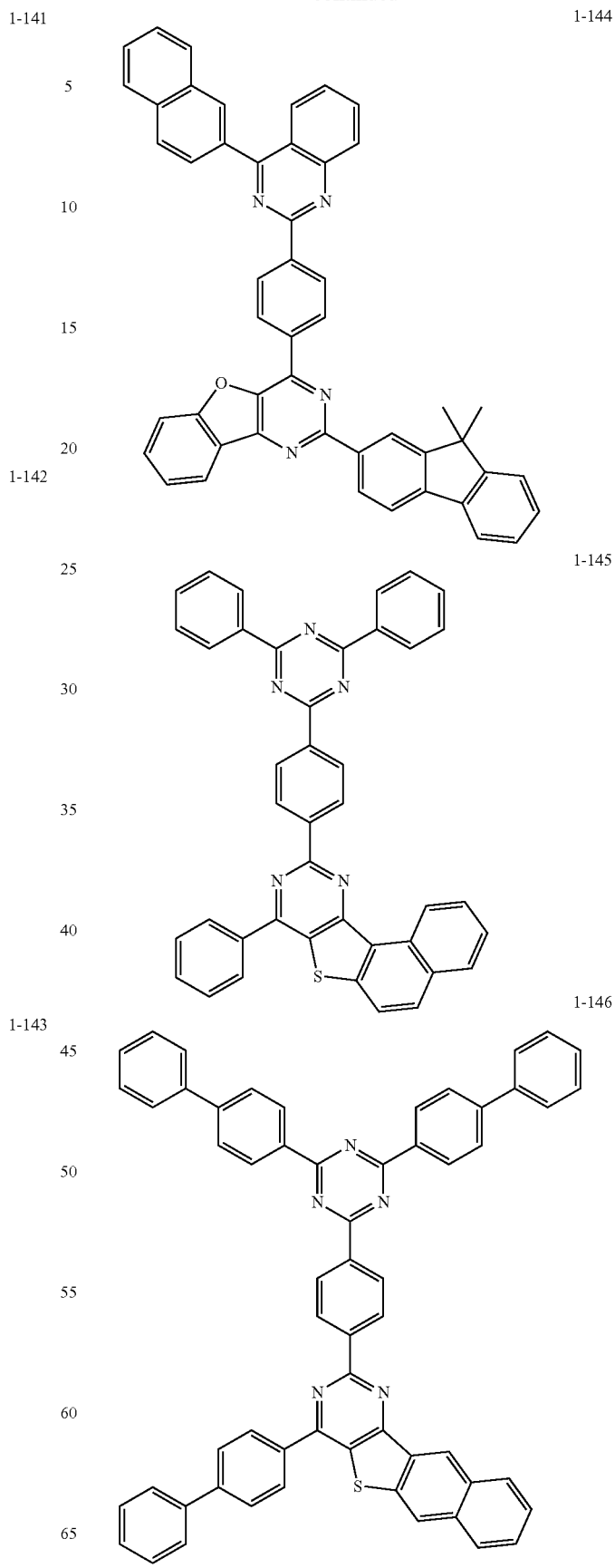

-continued
1-147
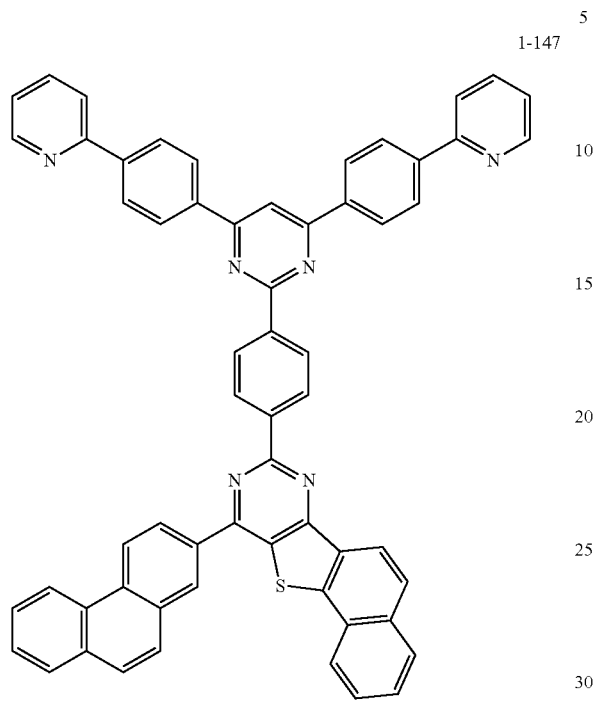
1-149
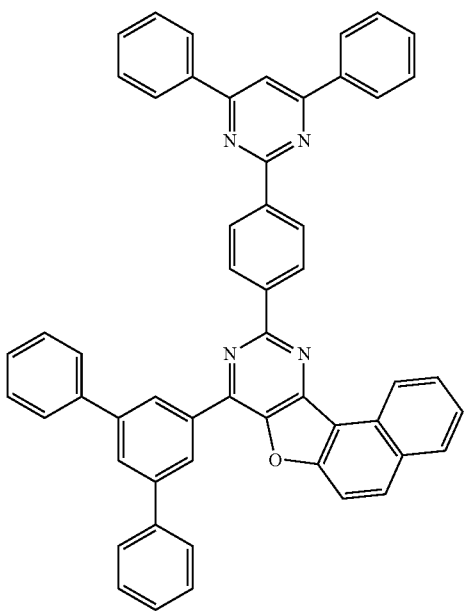
1-148
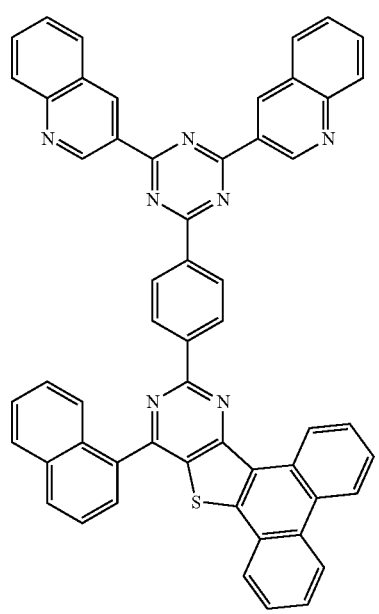
1-150
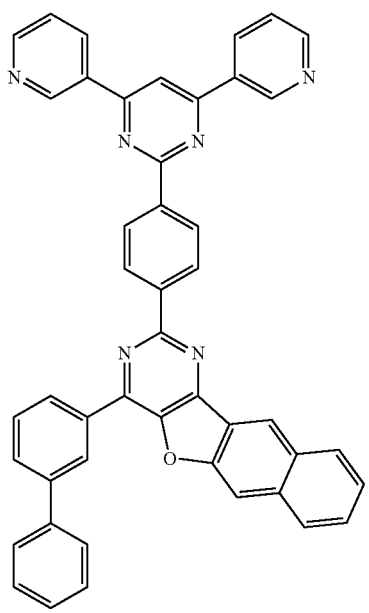

1-151
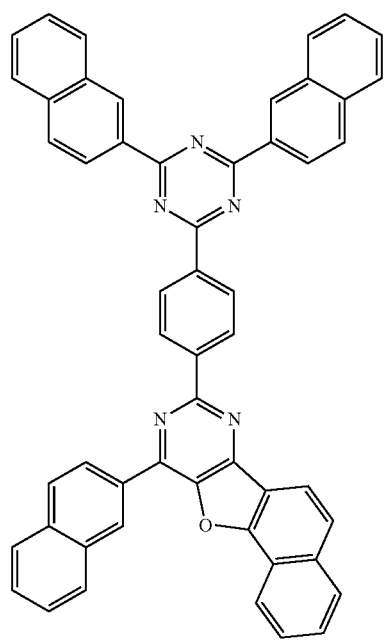
1-153
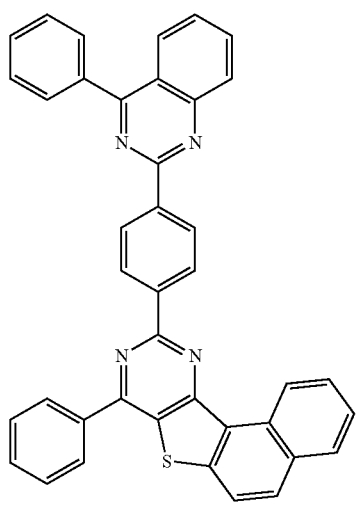
1-152
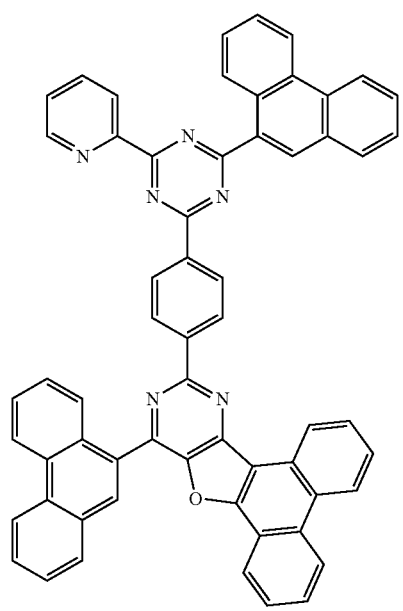
1-154
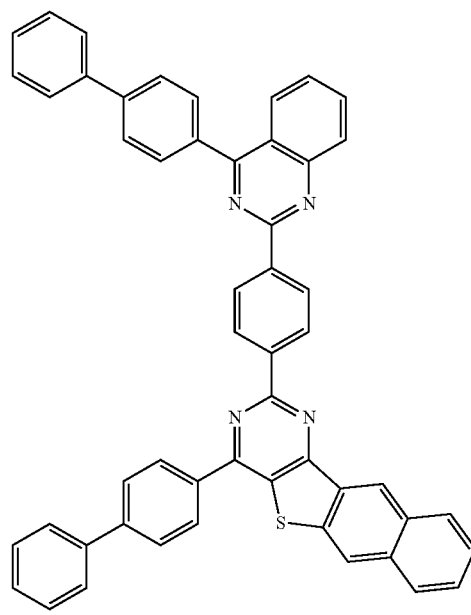

-continued
1-155
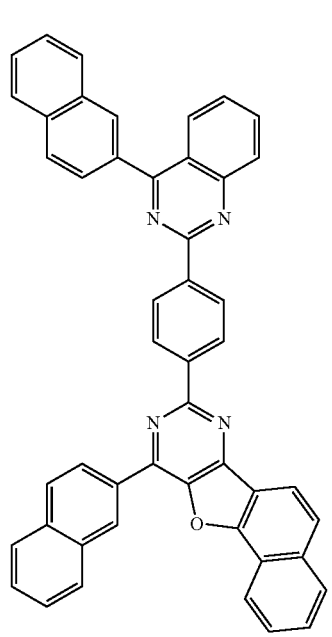
1-156
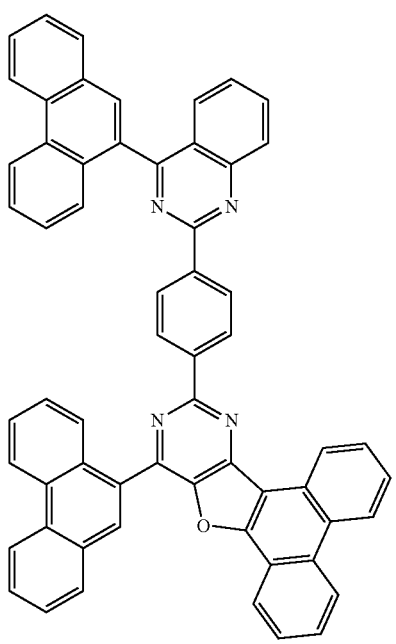
-continued
1-157
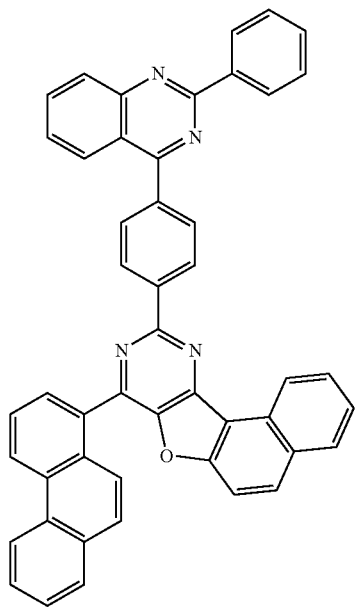
1-158
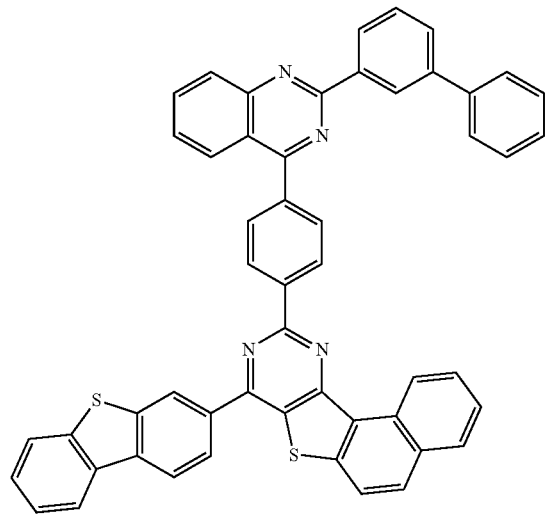

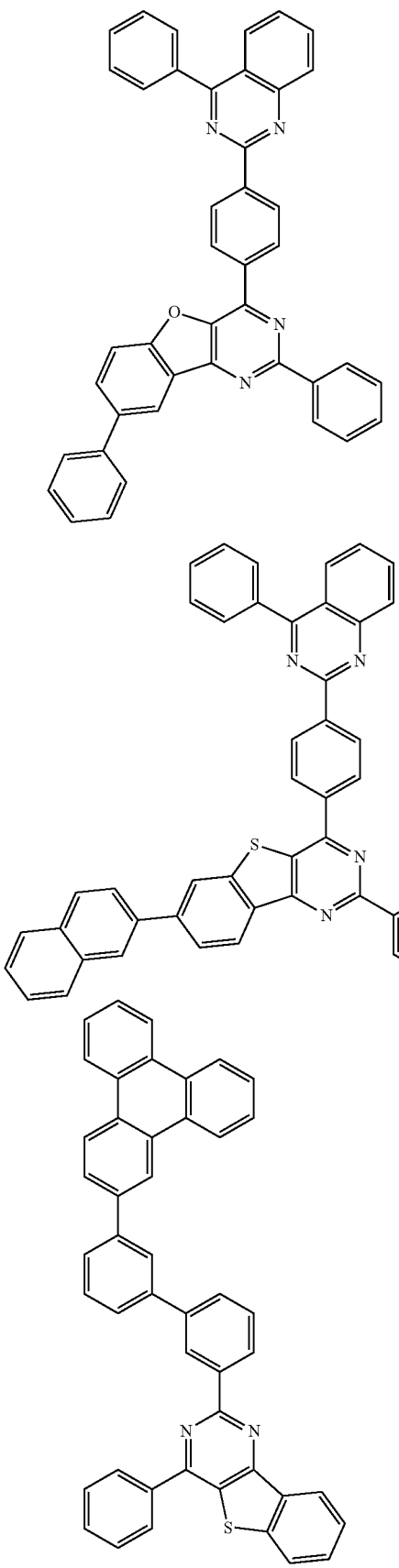
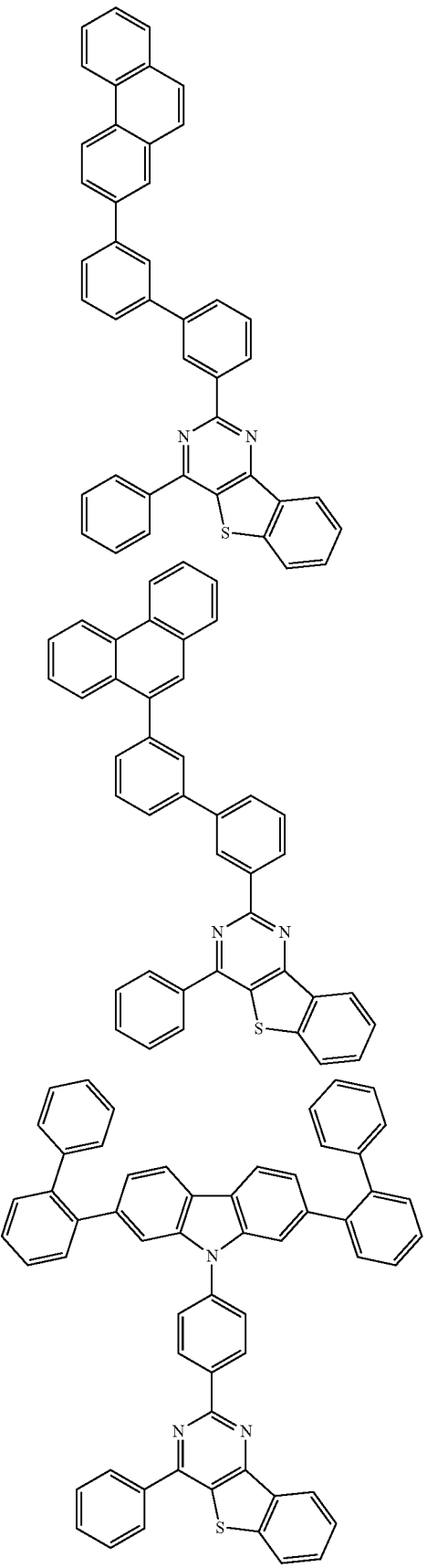

1-165
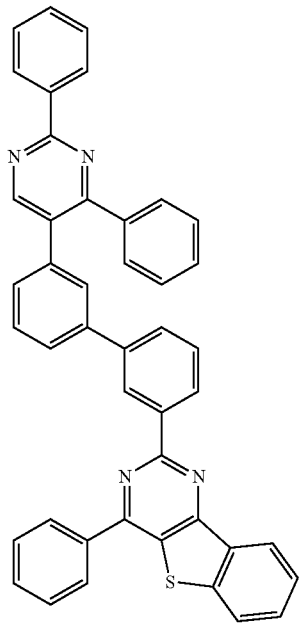
1-166
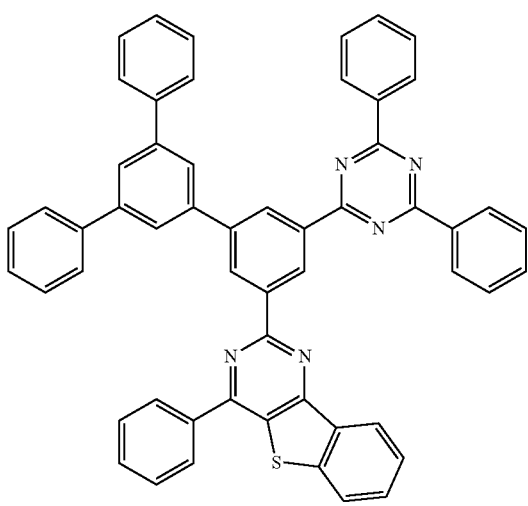
1-167
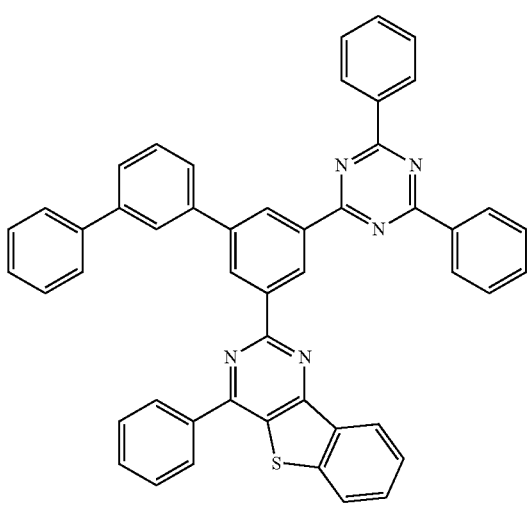
1-168
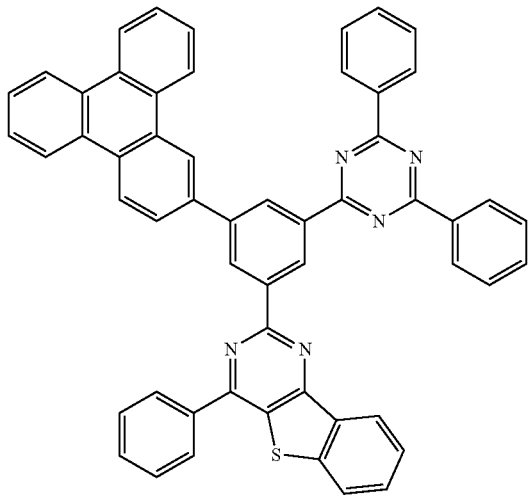
1-169
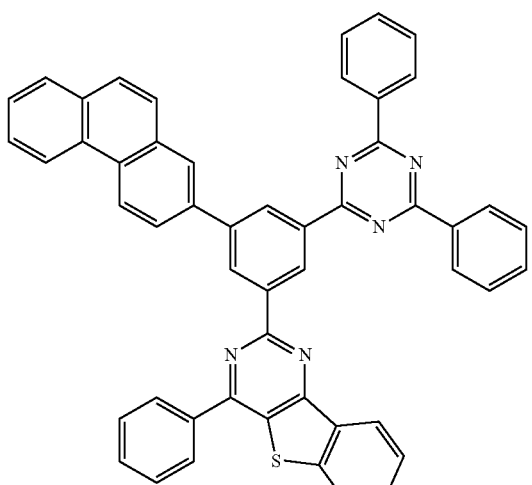
1-170
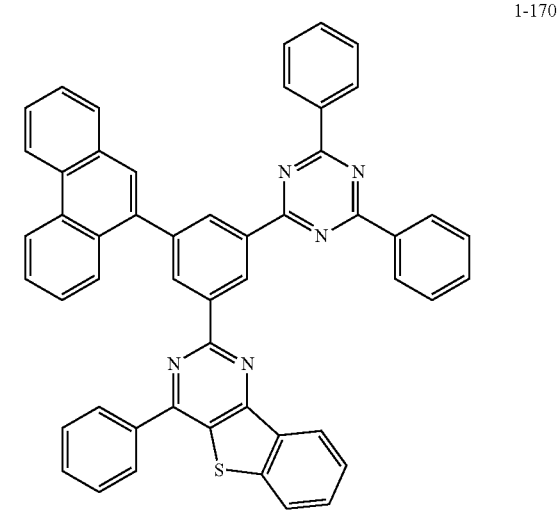

1-171
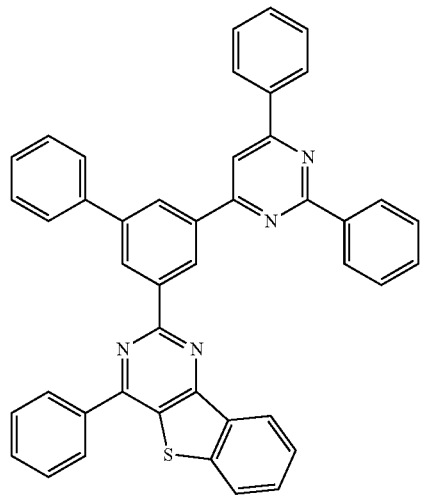
1-172
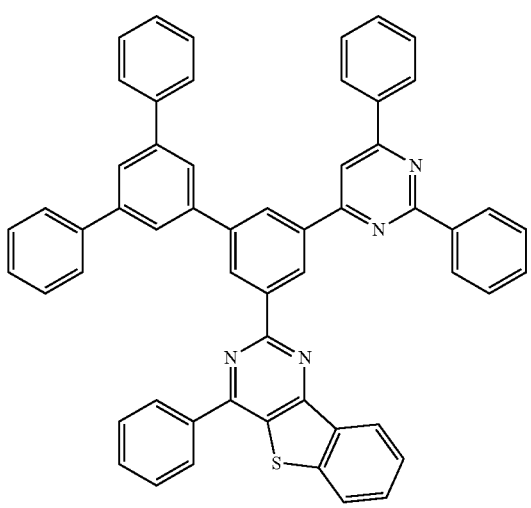
1-173
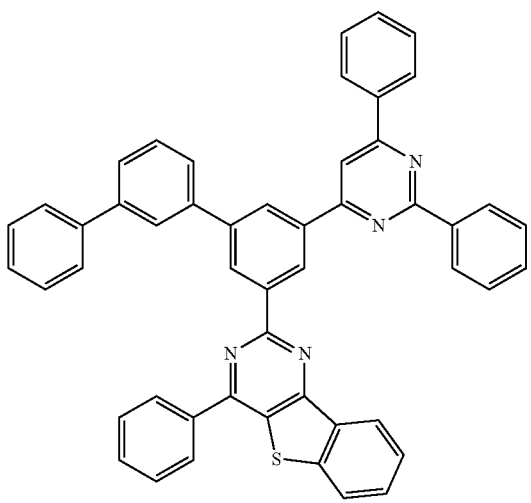
1-174
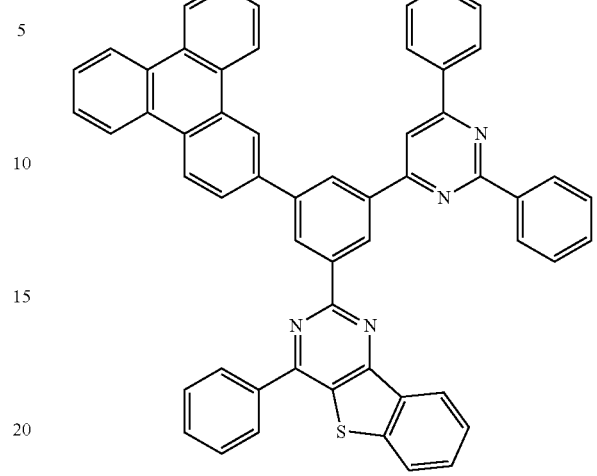
1-175
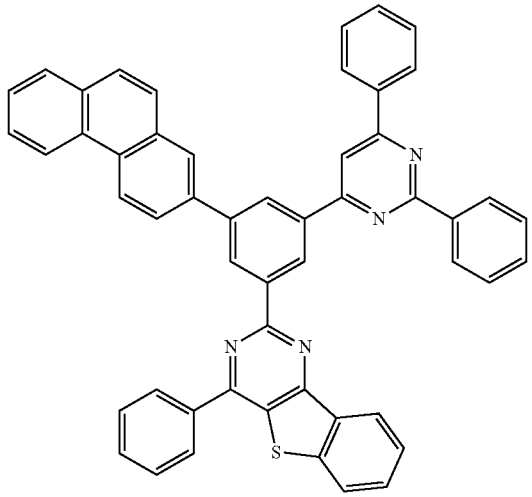
1-176
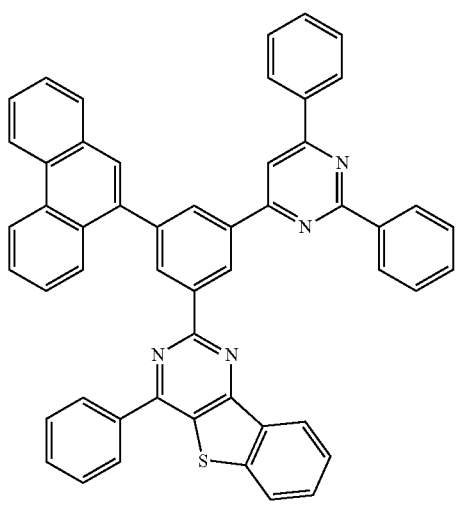

1-177
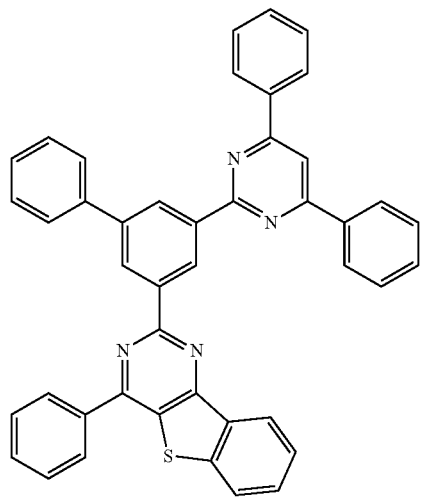
1-180
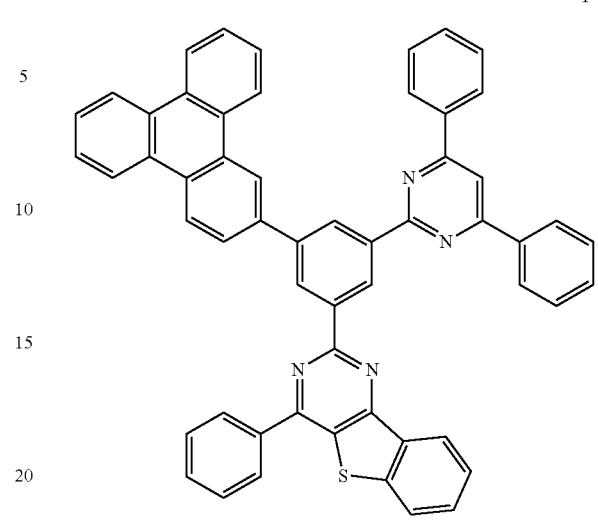
1-178
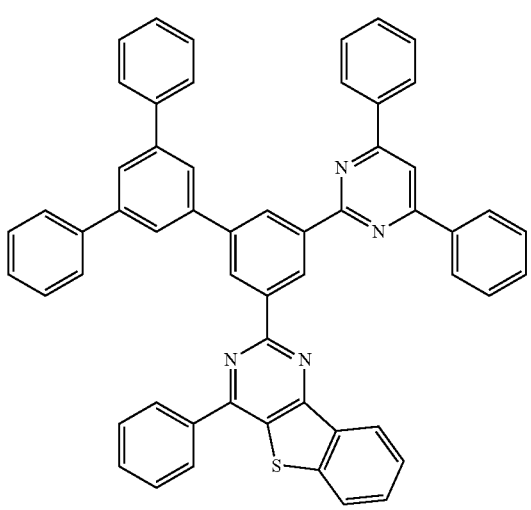
1-181
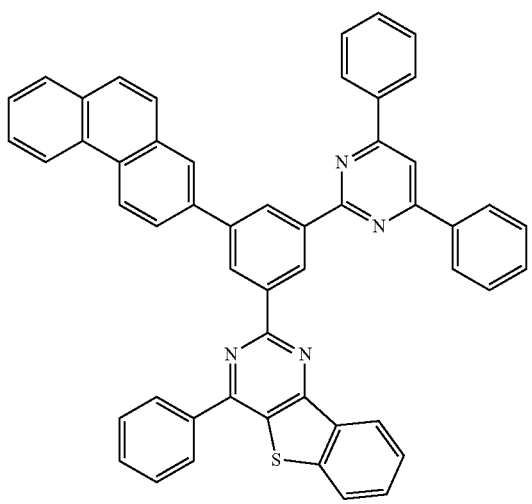
1-179
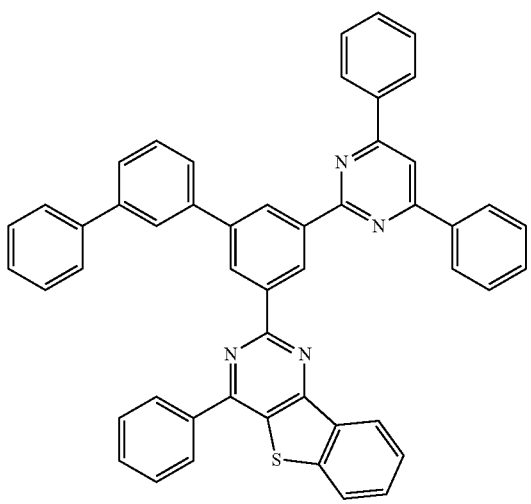
1-182
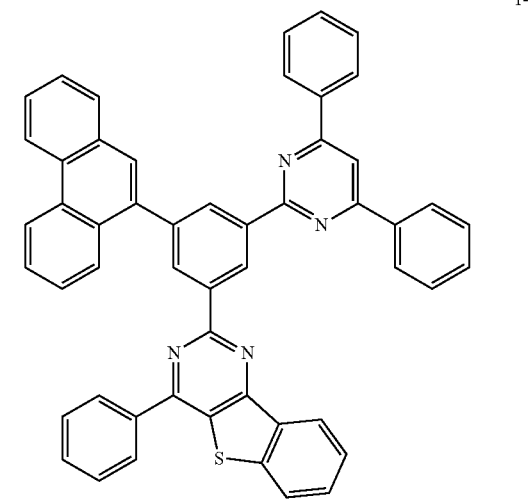

1-183
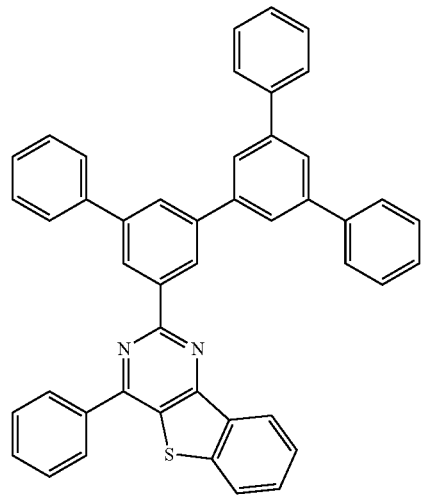
1-186
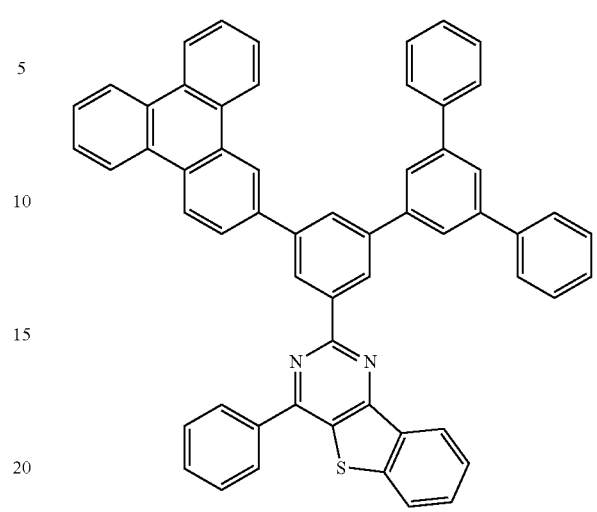
1-184
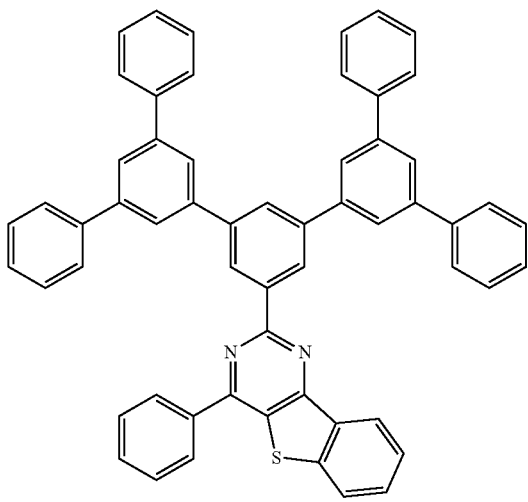
1-187
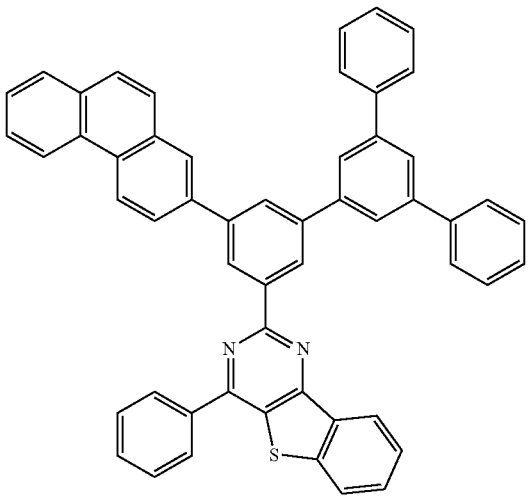
1-185
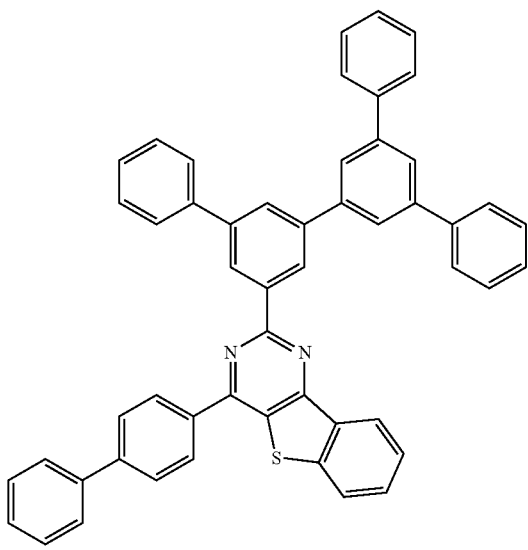
1-188
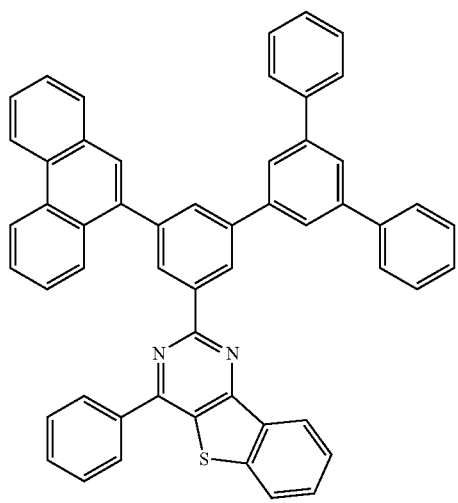

-continued
1-189
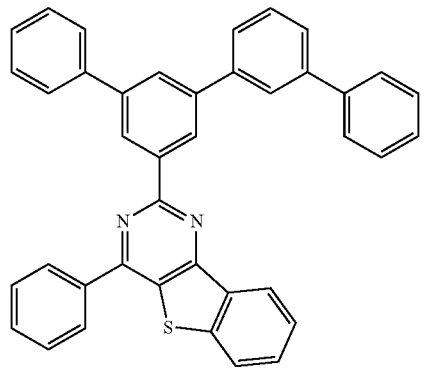
1-190
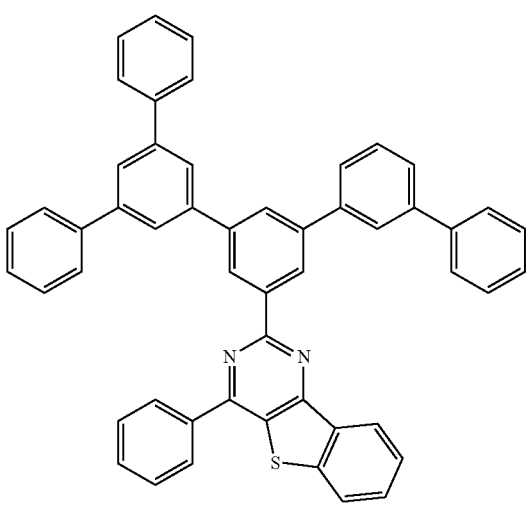
1-191
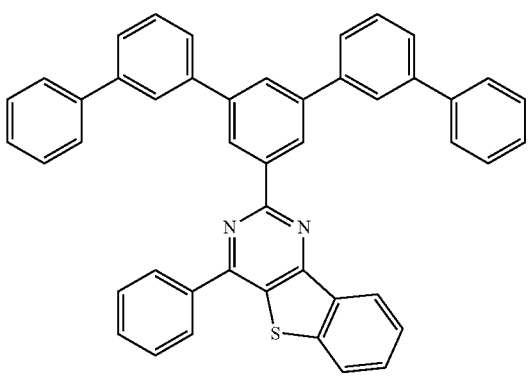
-continued
1-192
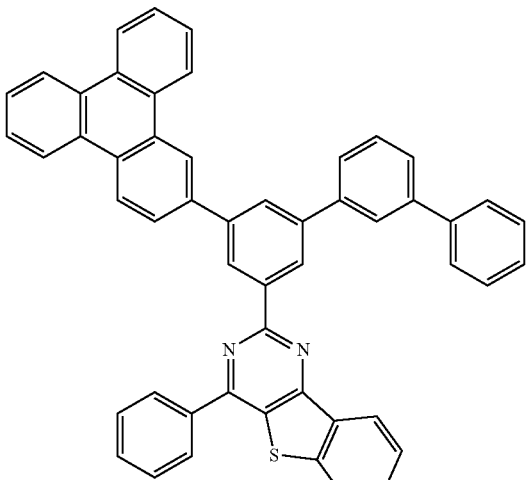
1-193
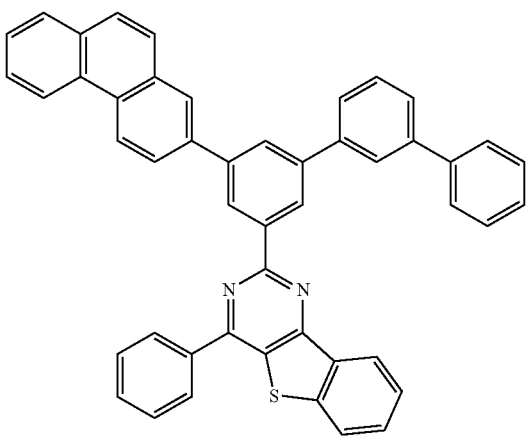
1-194
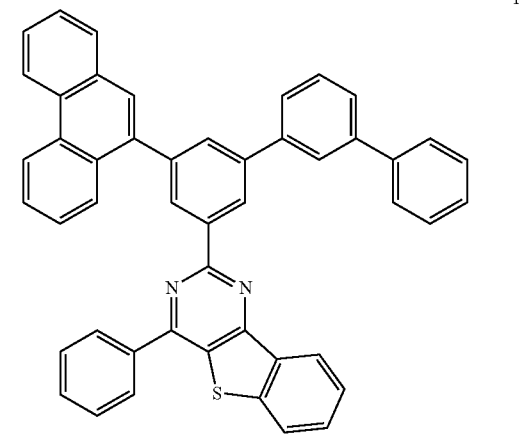

-continued
1-195
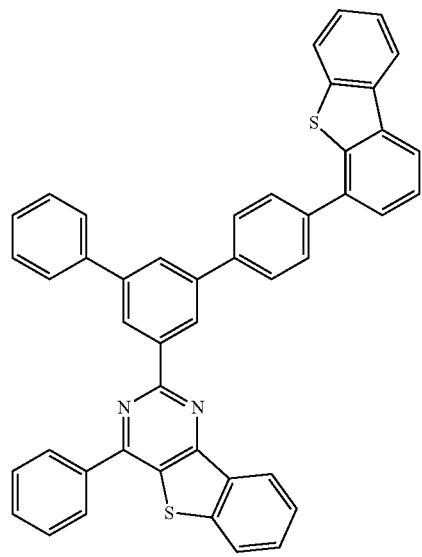
1-196
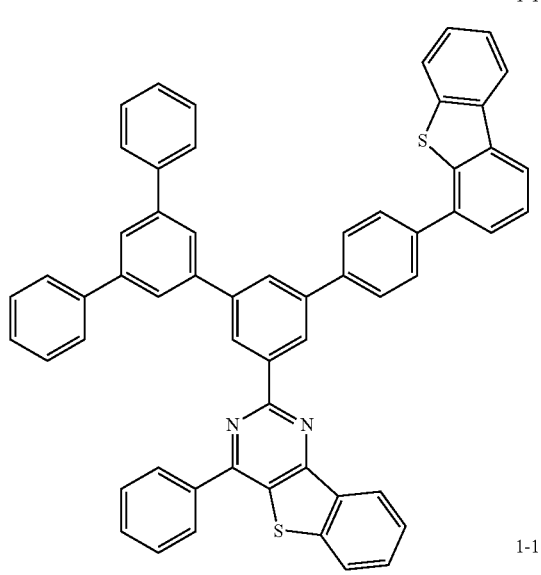
1-197
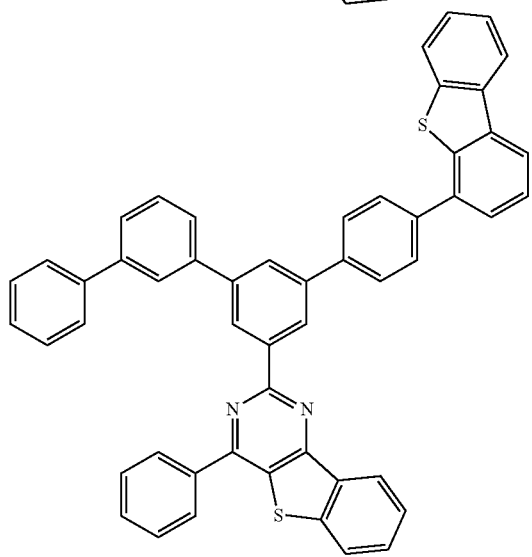
-continued
1-198
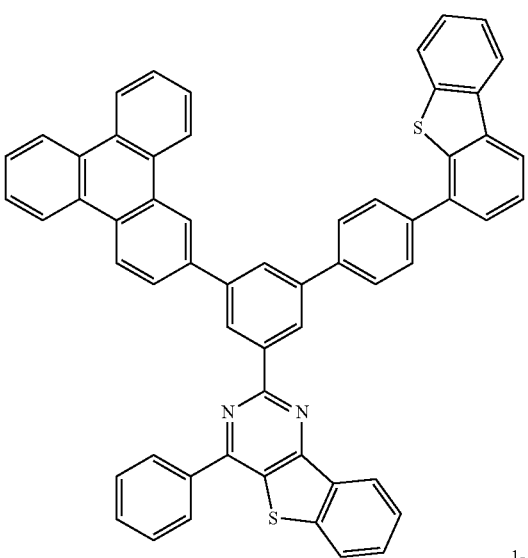
1-199
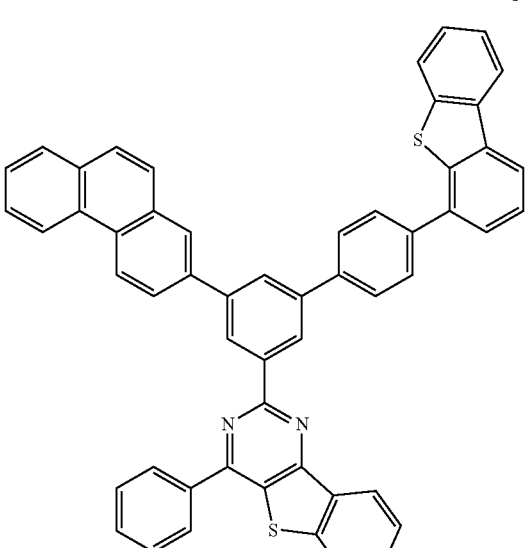
1-200
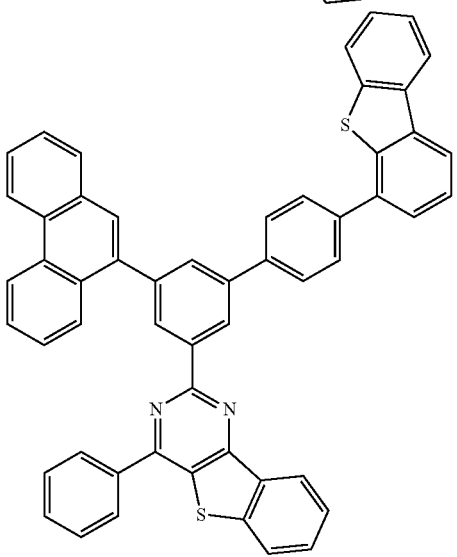

1-201
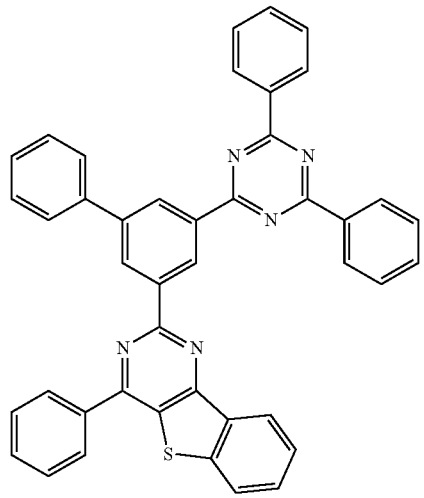
2-1
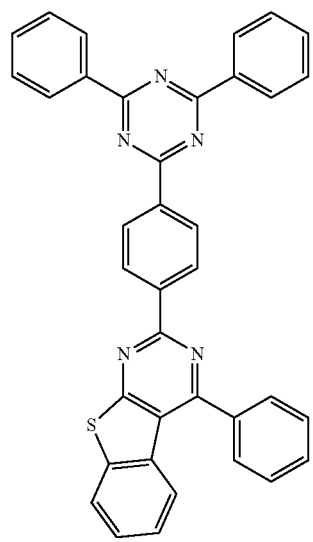
2-2
2-3
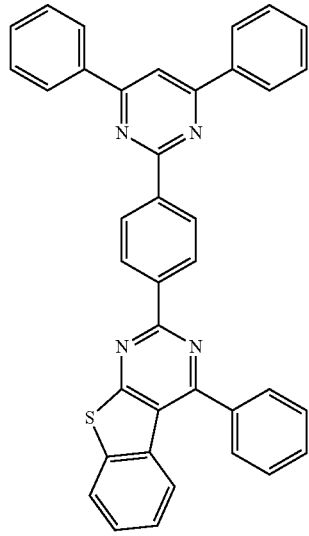
2-4
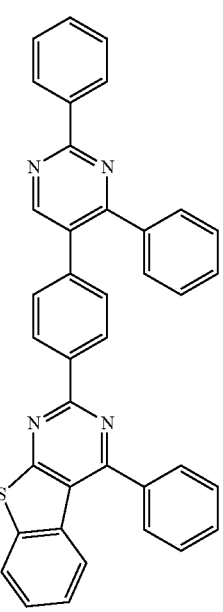
2-5
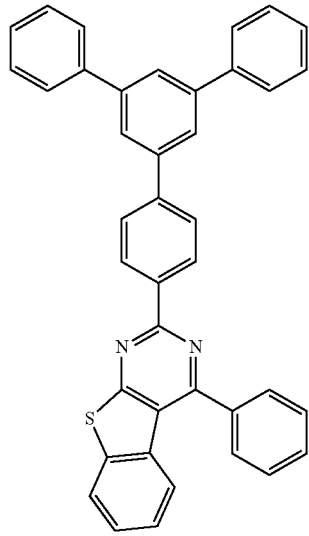

2-6
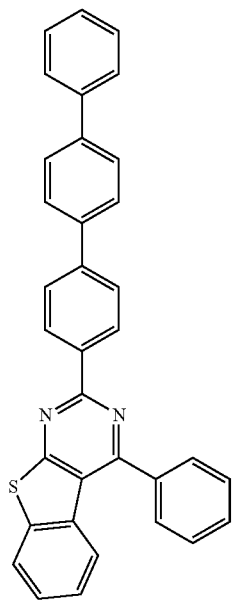
2-7
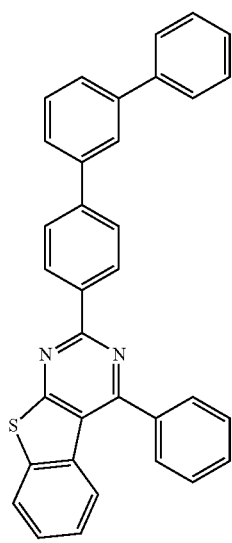
2-8
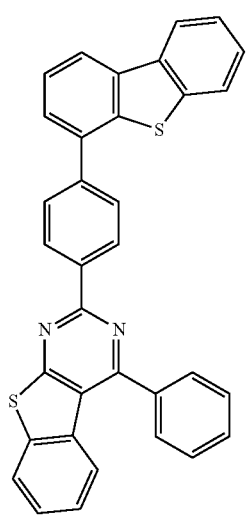
2-9
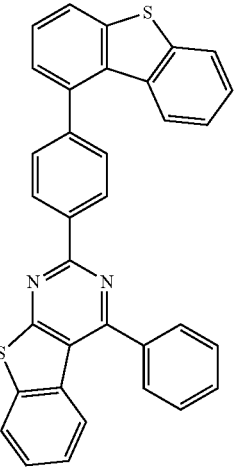
2-10
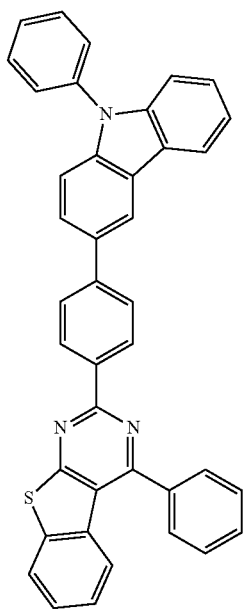
2-11
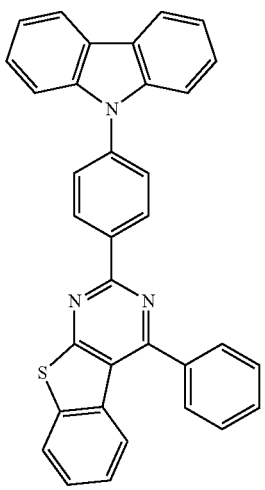

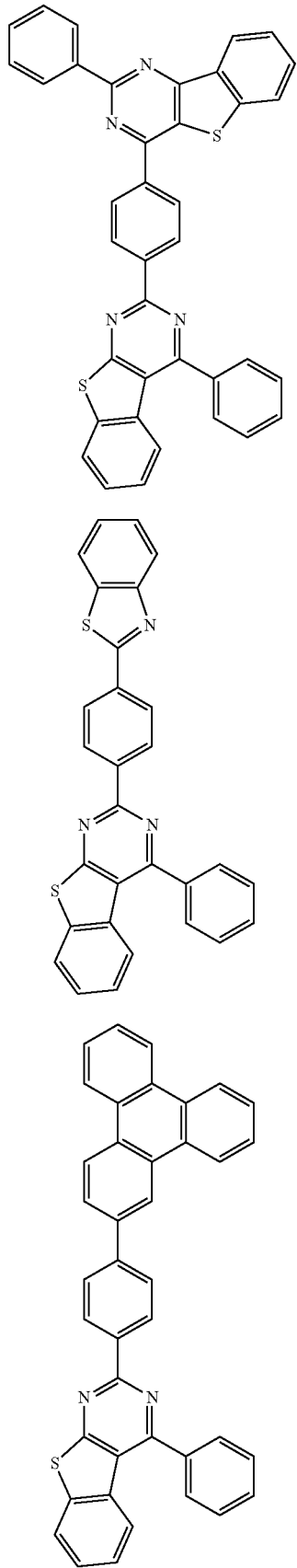
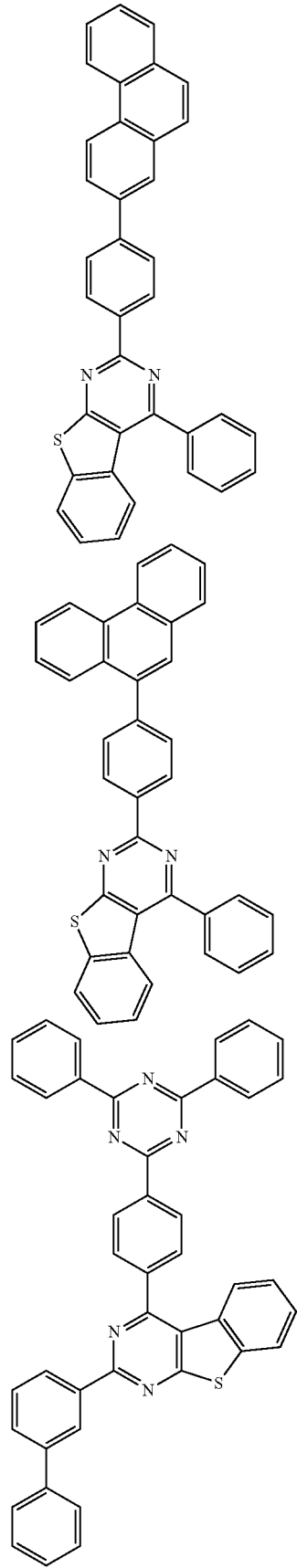

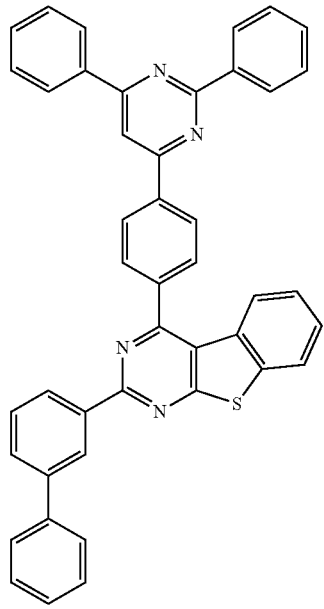# 2-18
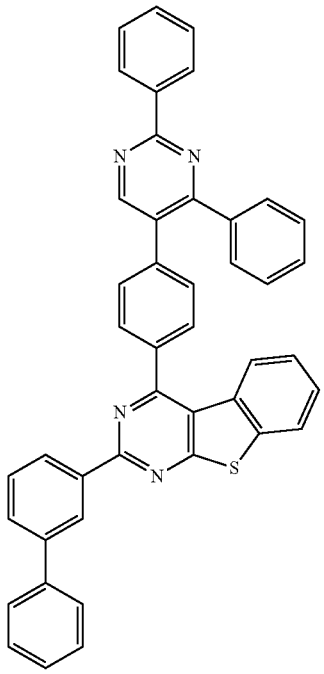# 2-20
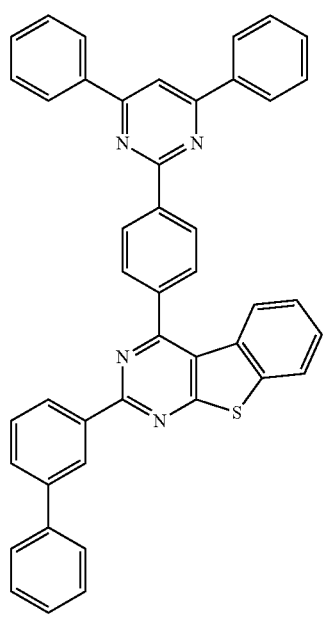# 2-19
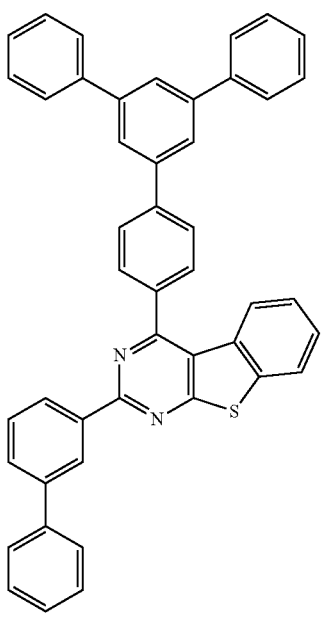# 2-21

2-22
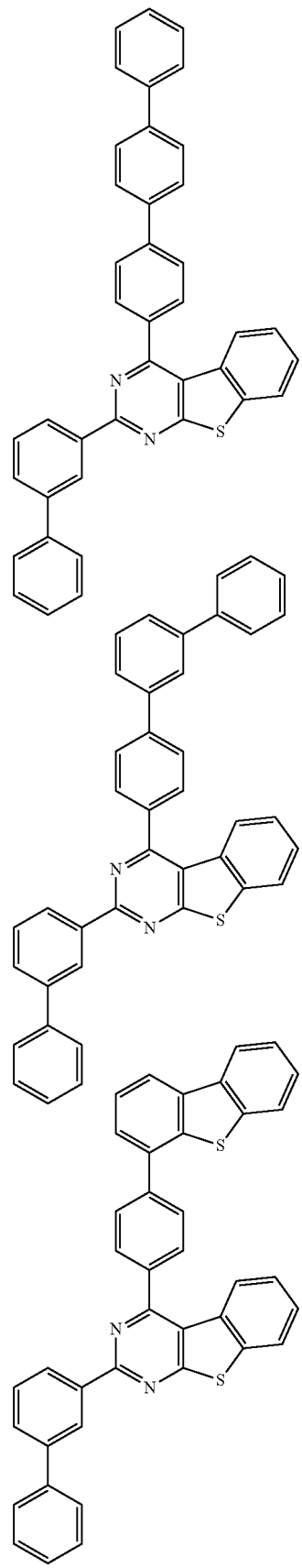
2-23
2-24
2-25
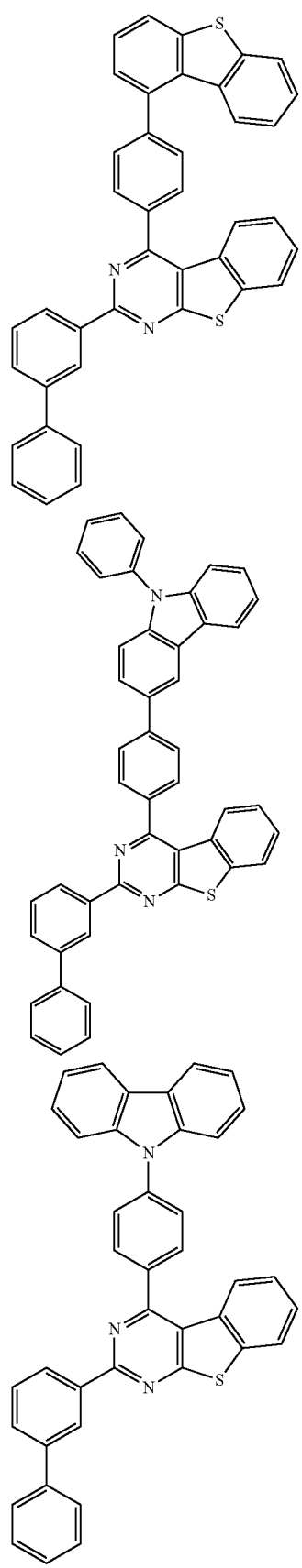
2-26
2-27

2-28
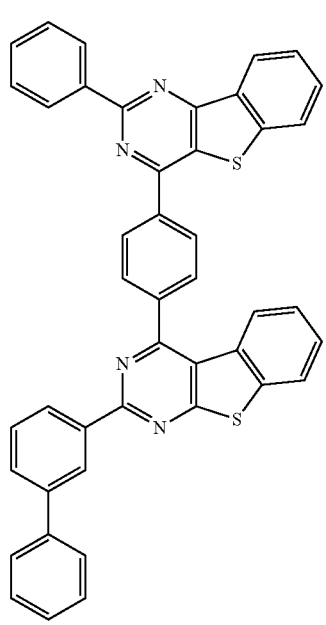
2-29
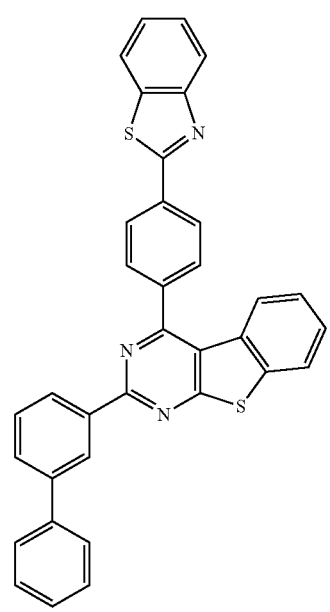
2-30
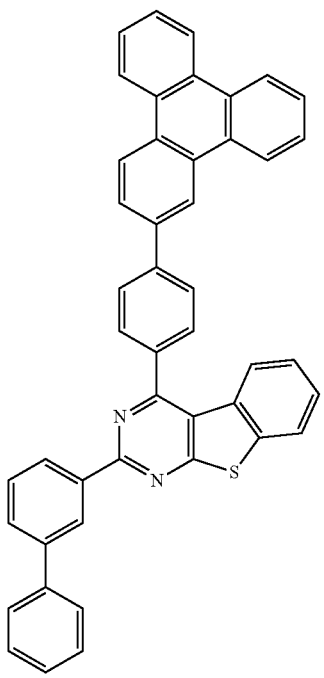
2-31
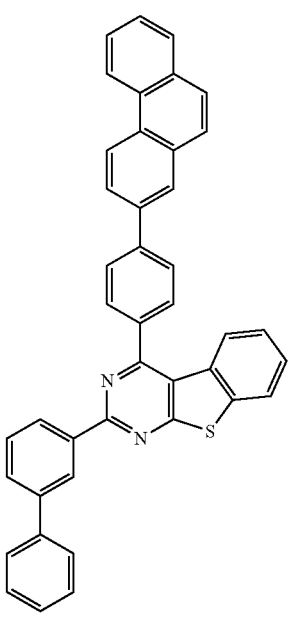

97
-continued
98
-continued
2-32
2-34
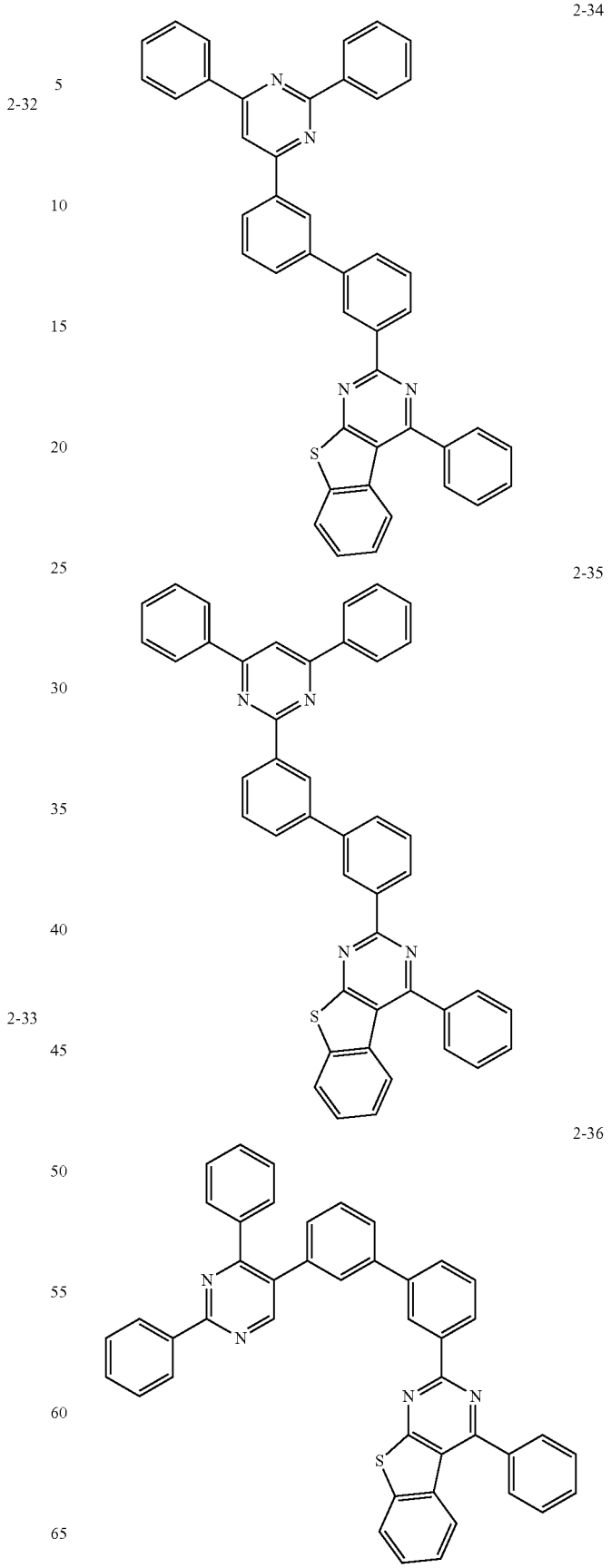
2-33
2-35
2-36

2-37
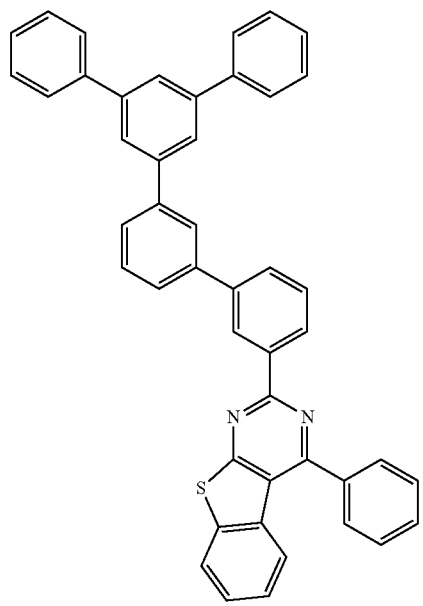
2-38
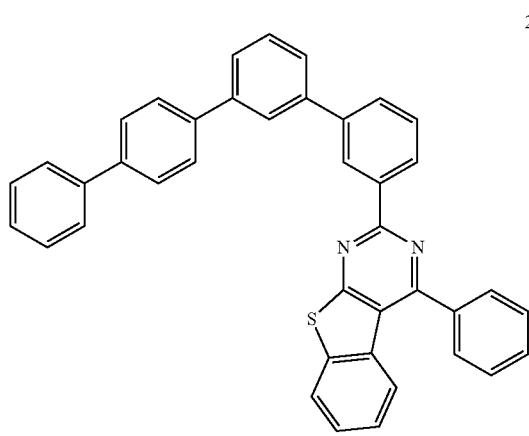
2-39
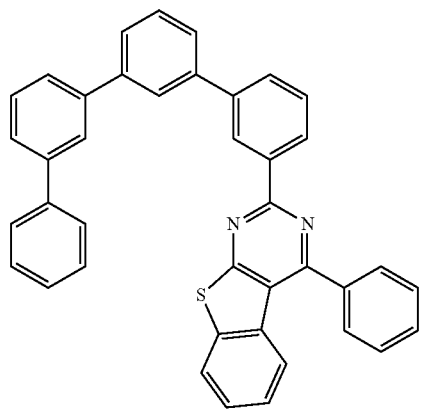
2-40
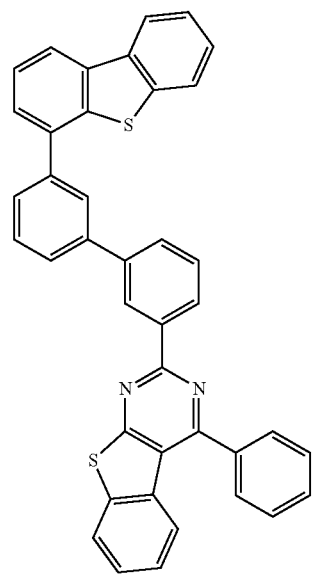
2-41
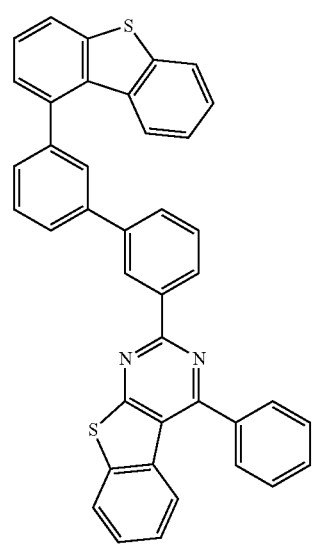

101
-continued
2-42
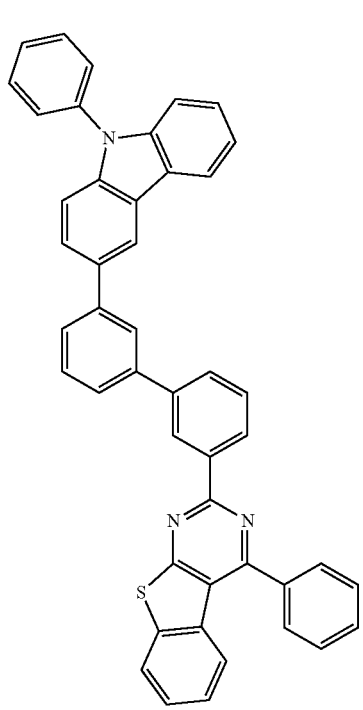
2-43
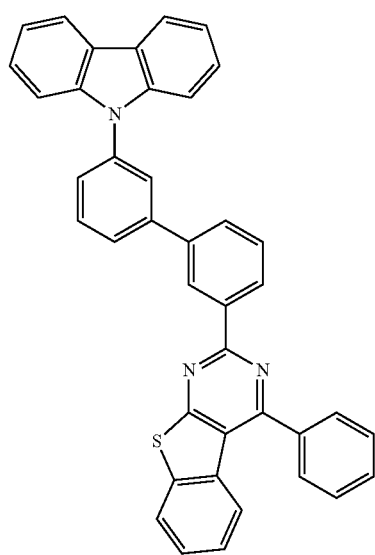
102
-continued
2-44
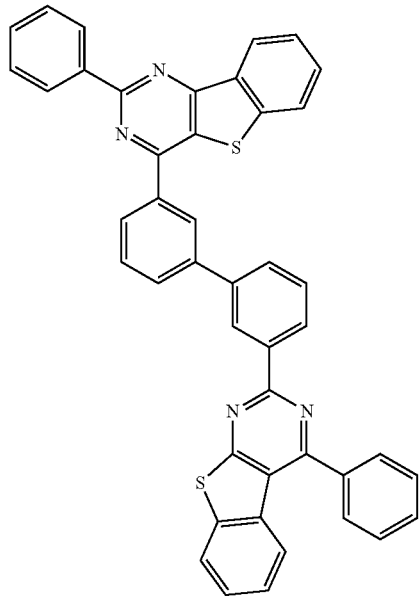
2-45
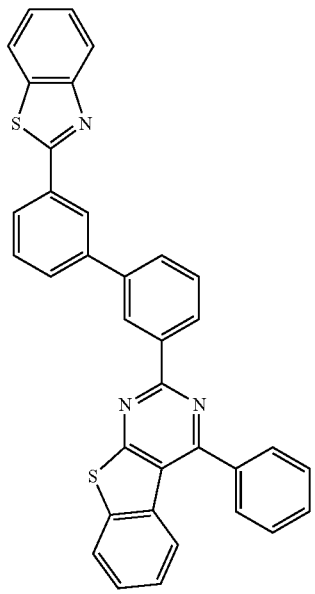

2-46
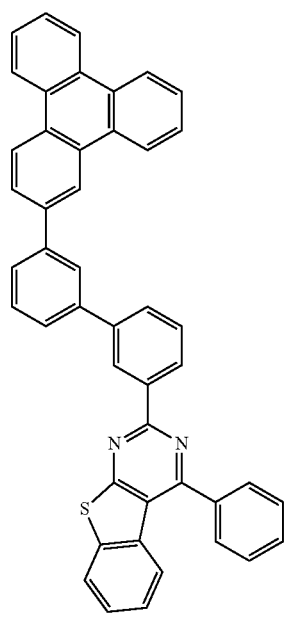
2-47
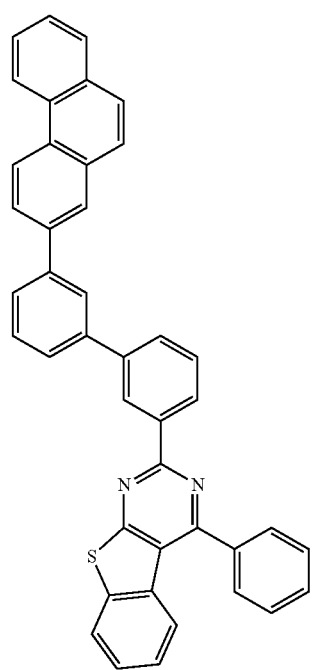
2-48
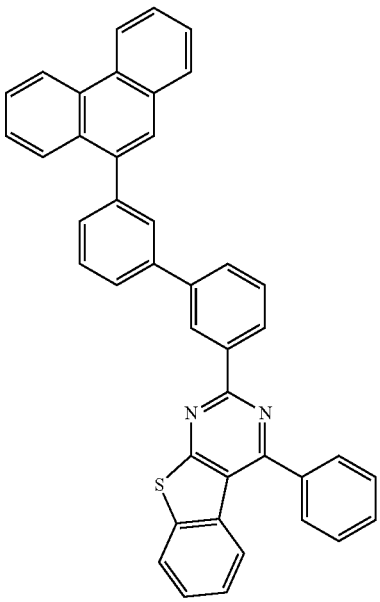
2-49
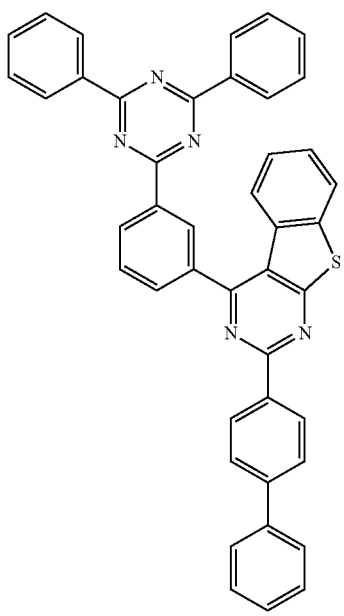

105
-continued
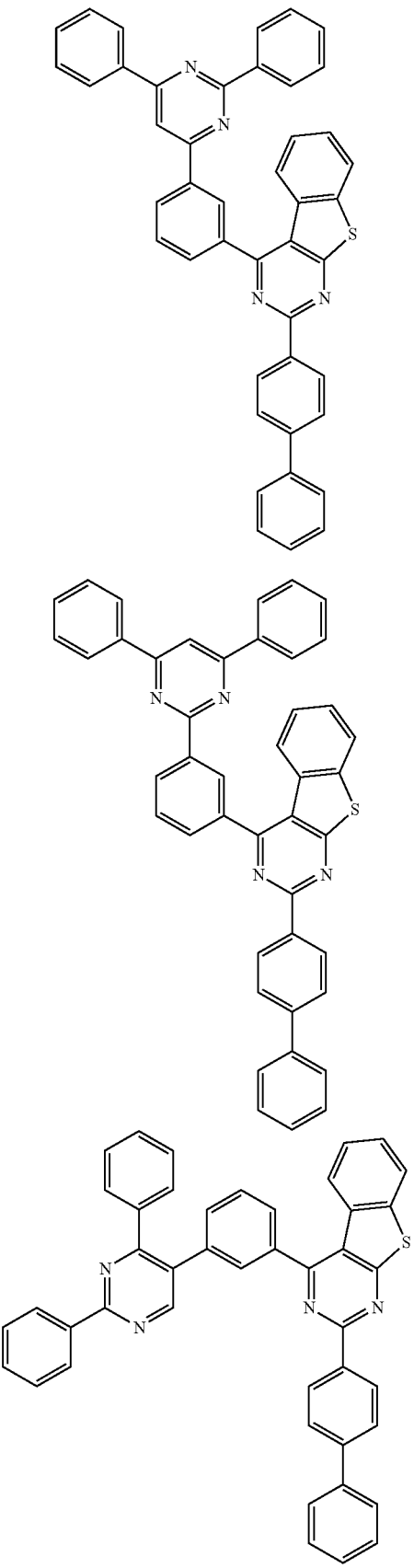
2-50
2-51
2-52
106
-continued
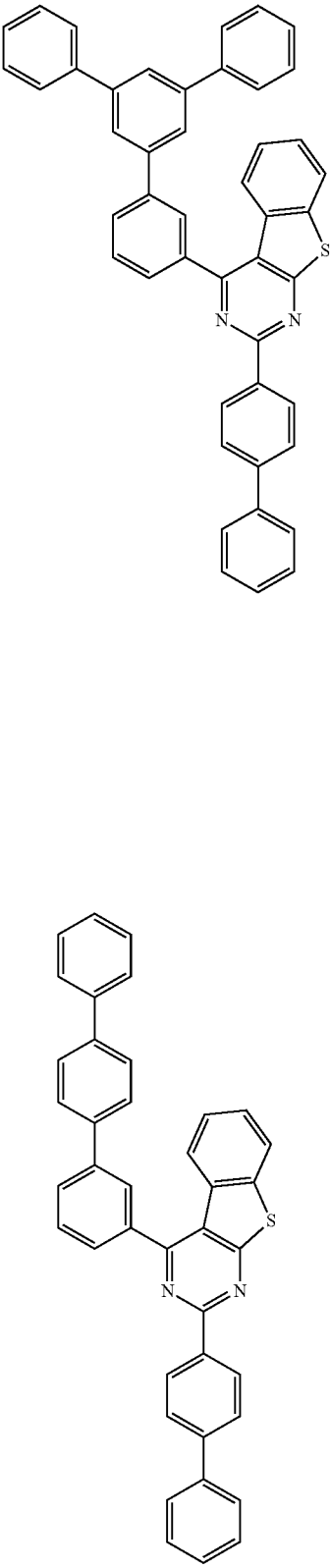
2-53
2-54

107
-continued
108
-continued
2-55
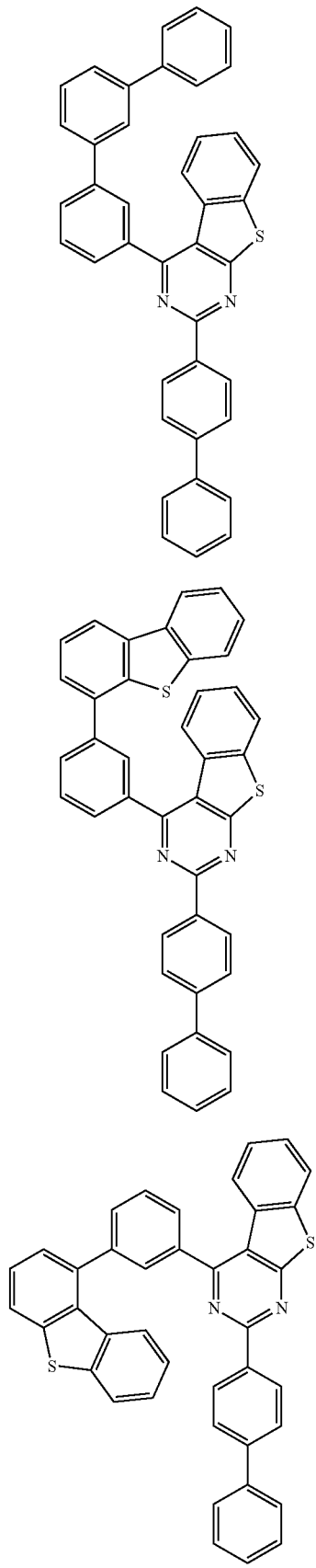
2-56
2-57
2-58
2-59

2-60
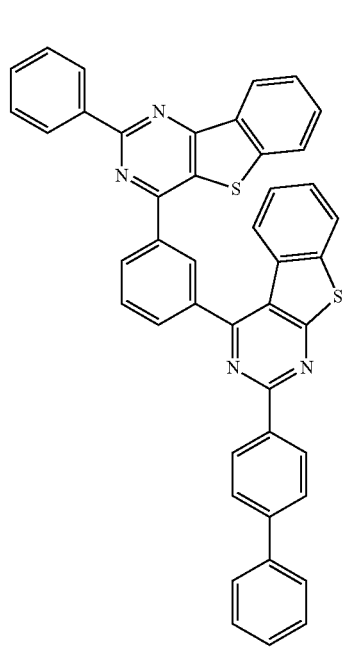
2-62
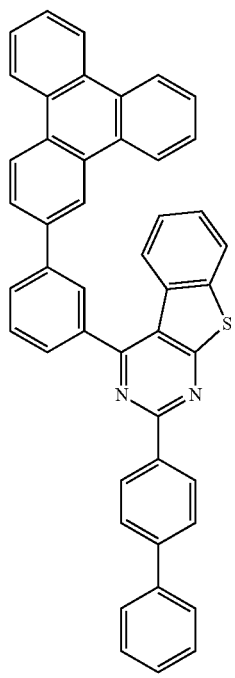
2-61
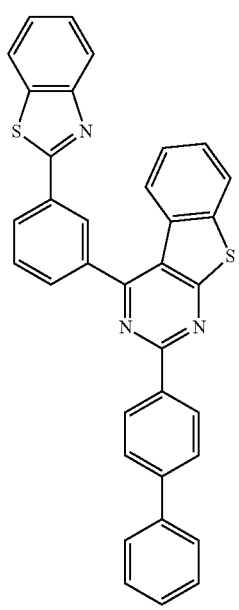
2-63
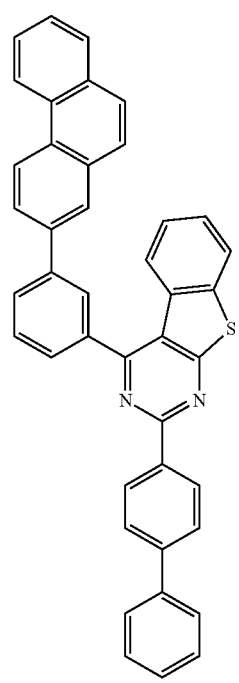

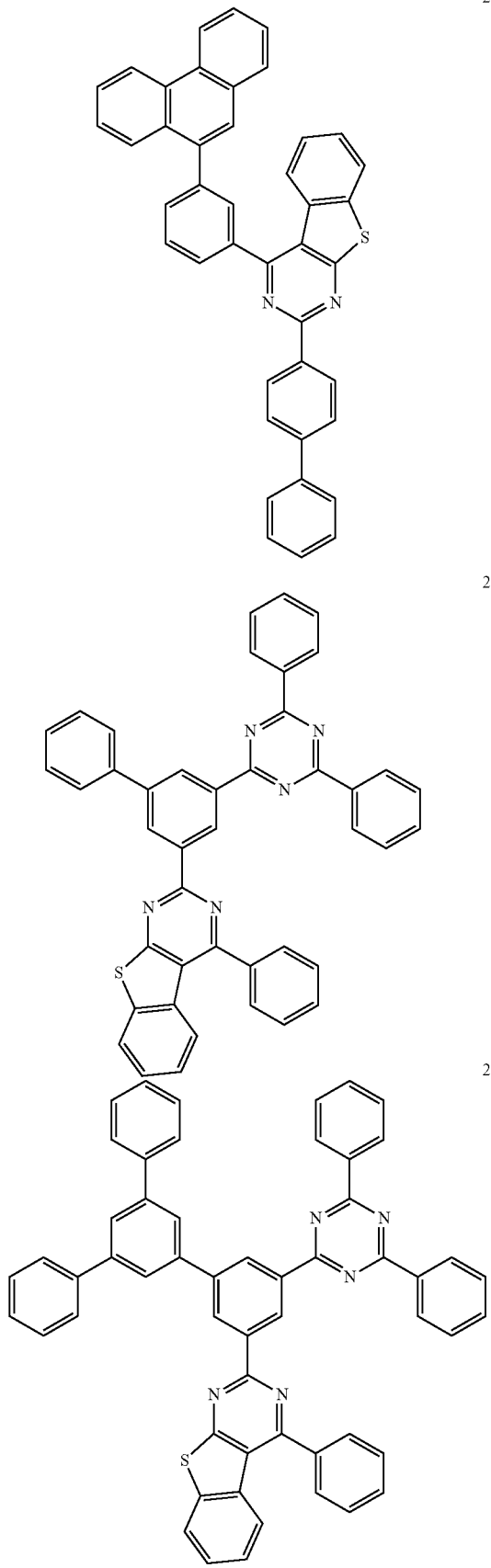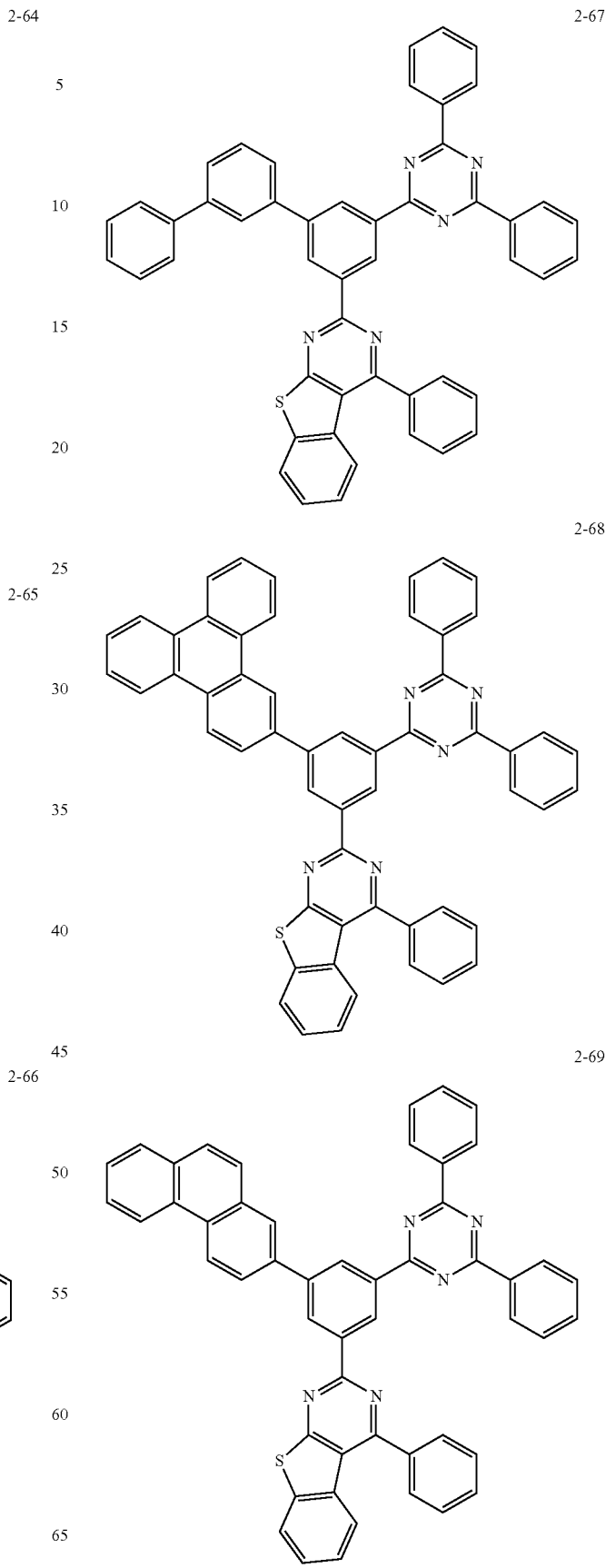

2-70
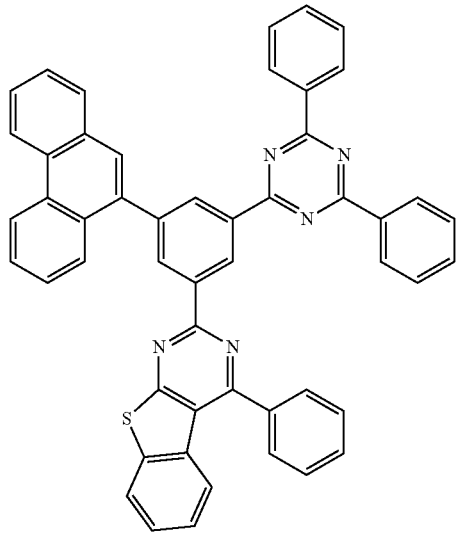
2-73
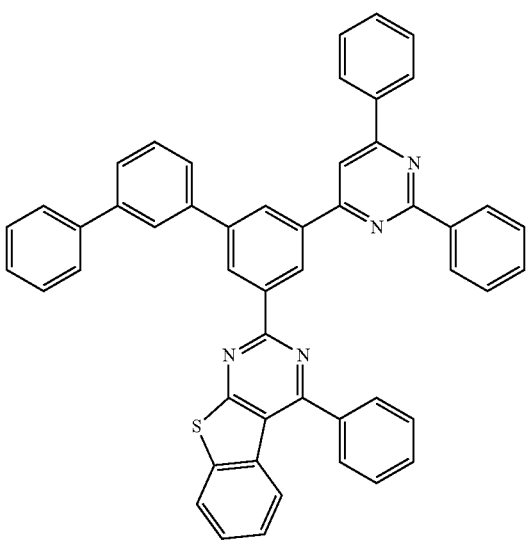
2-71
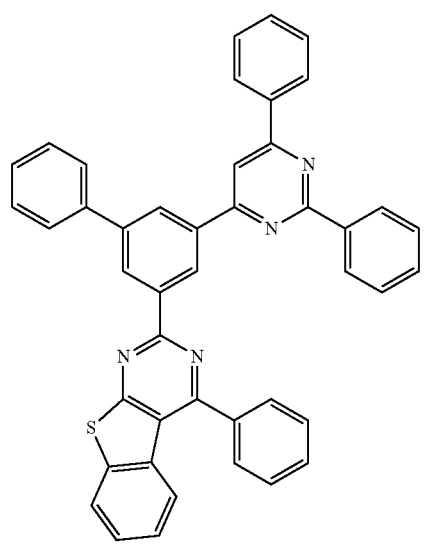
2-74
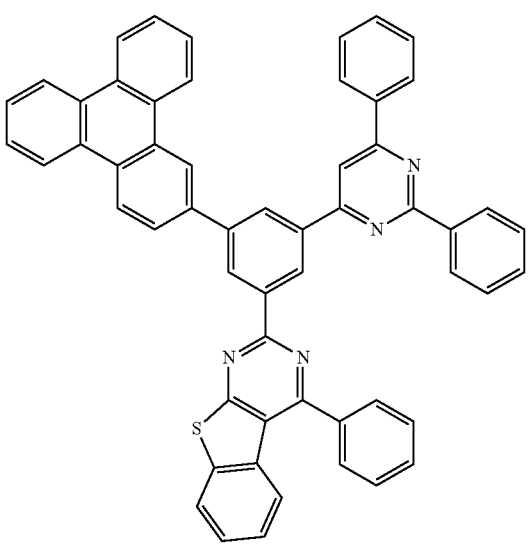
2-72
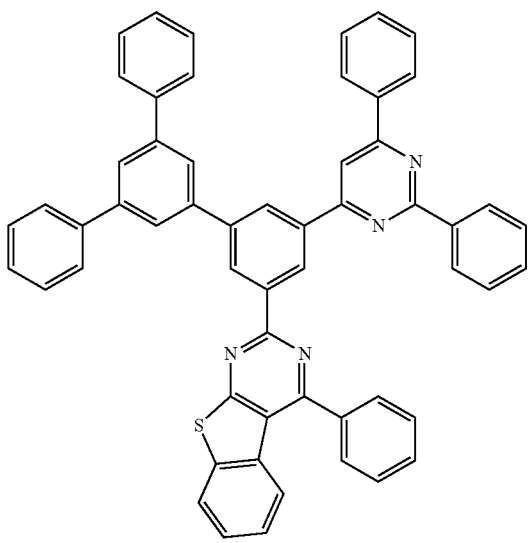
2-75
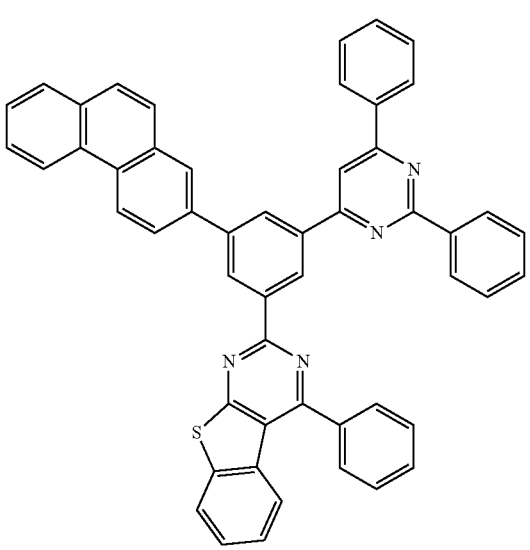

2-76
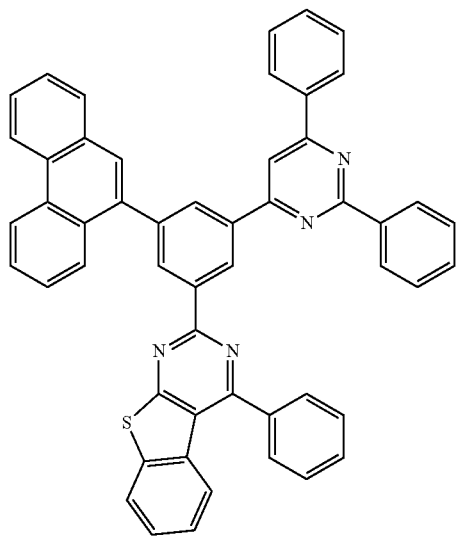
2-77
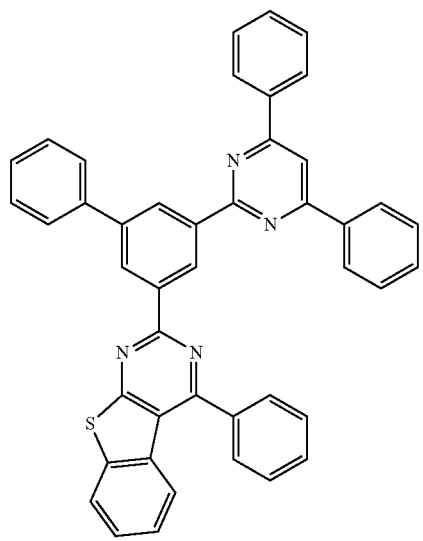
2-78
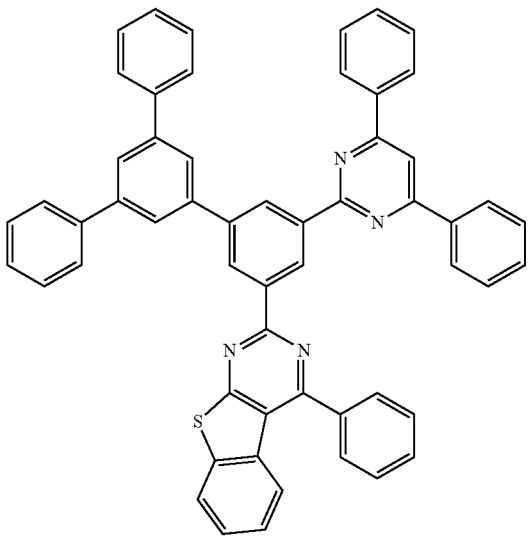
2-79
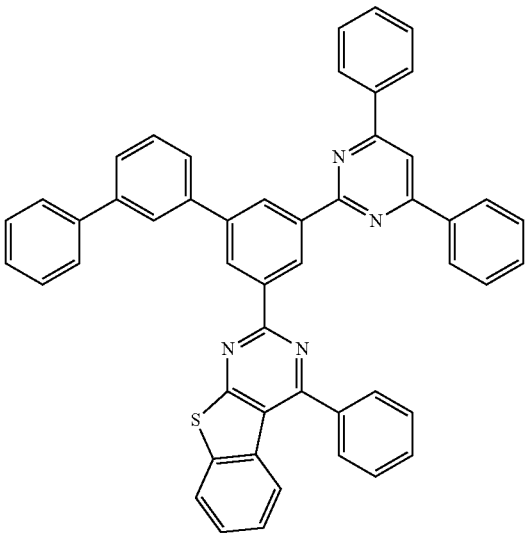
2-80
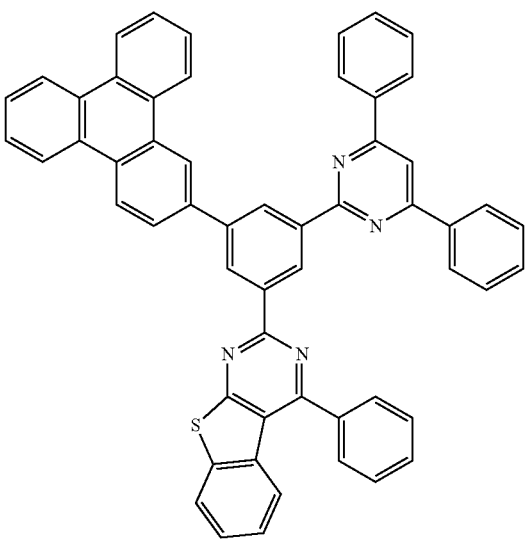
2-81
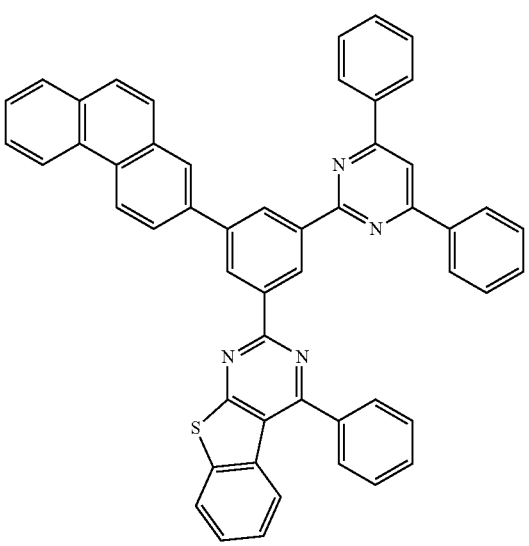

2-82
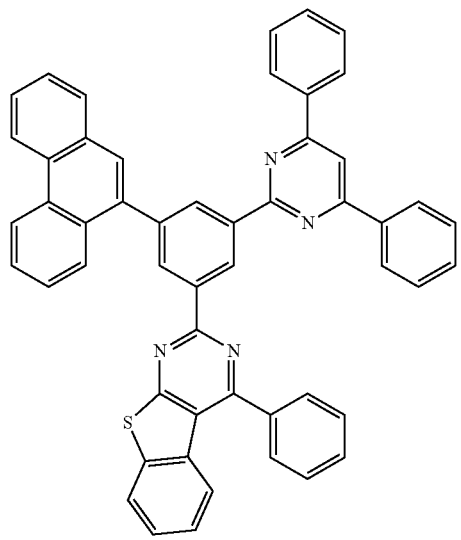
2-85
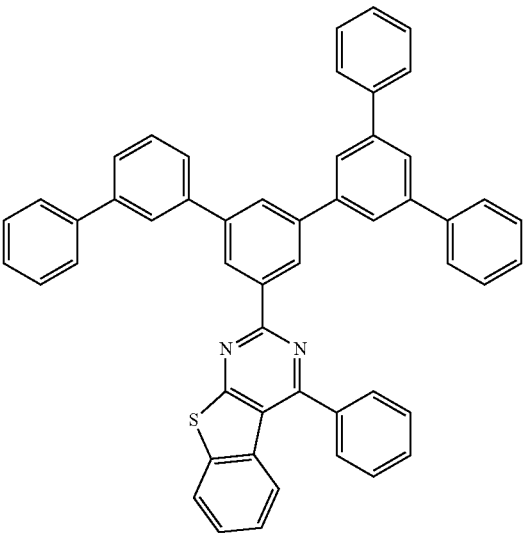
2-83
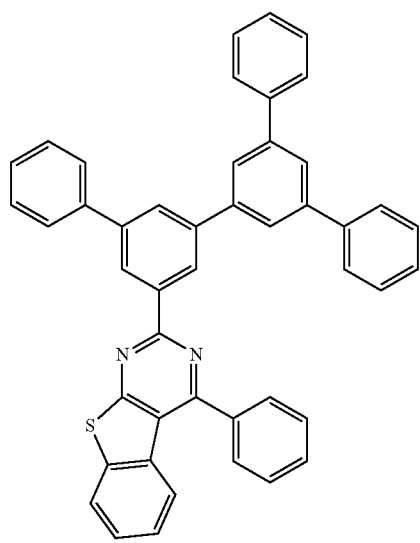
2-86
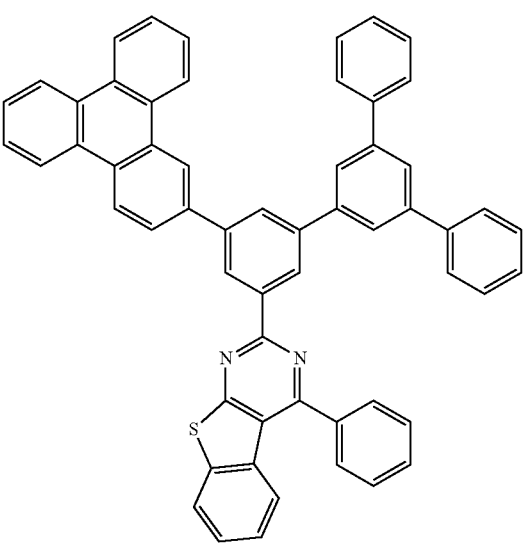
2-84
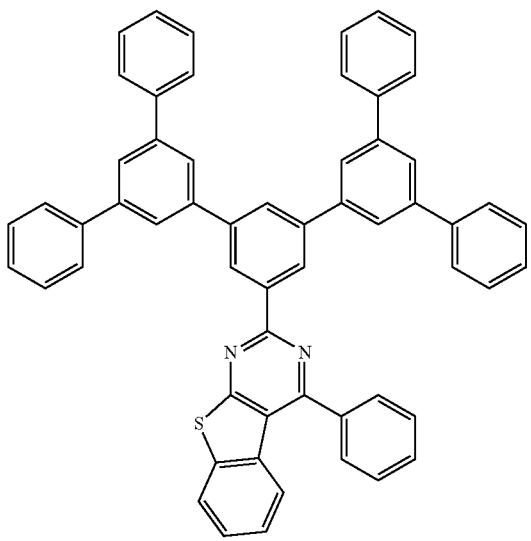
2-87
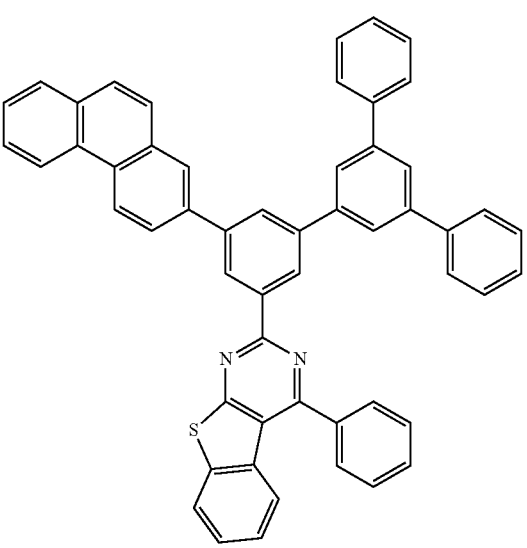

2-88
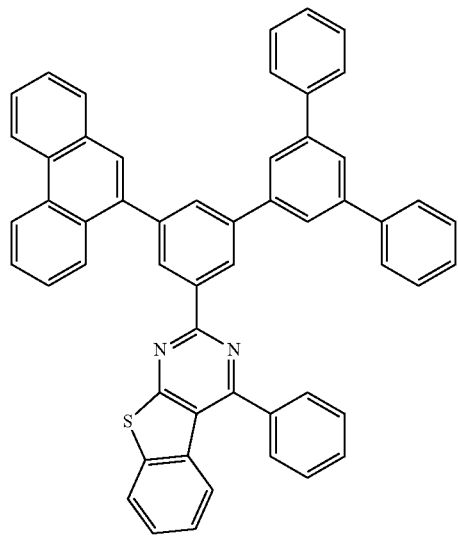
2-89
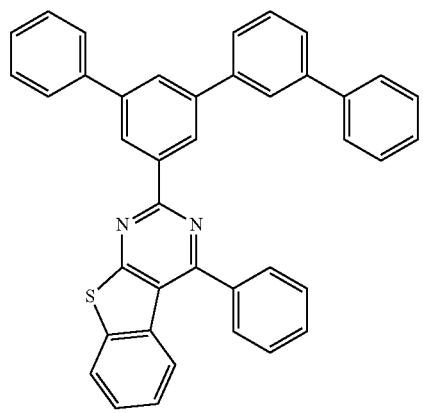
2-90
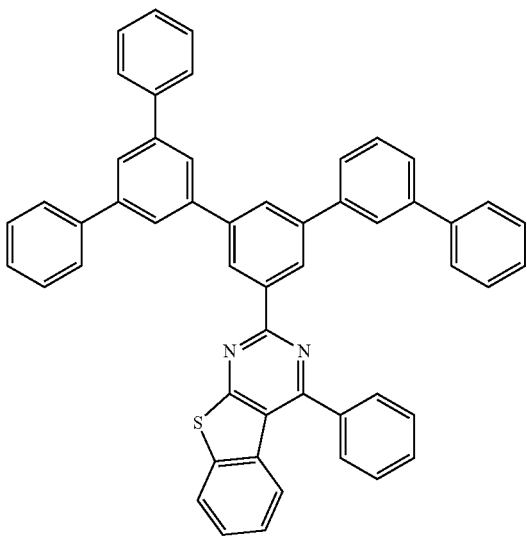
2-91
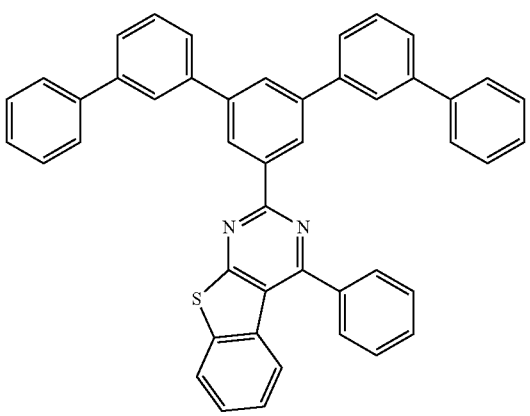
2-92
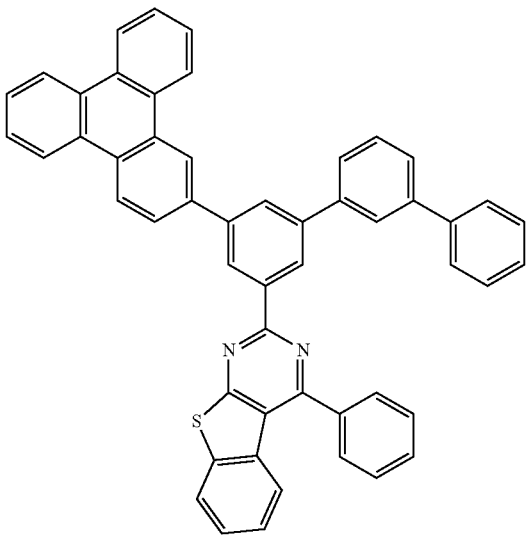
2-93
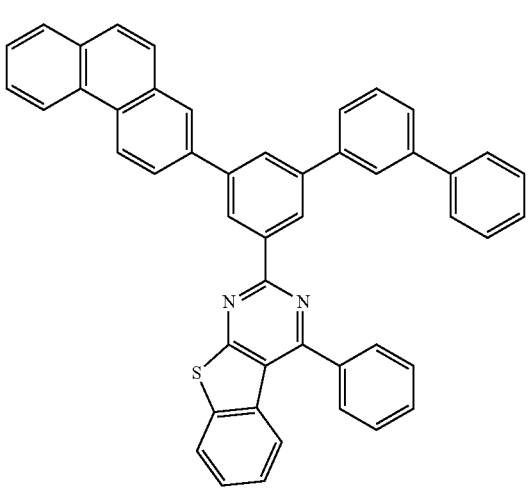

2-94
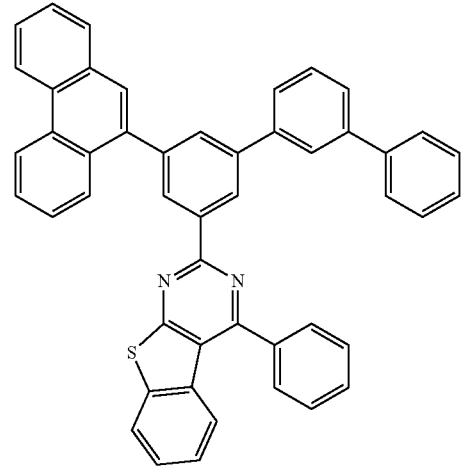
2-95
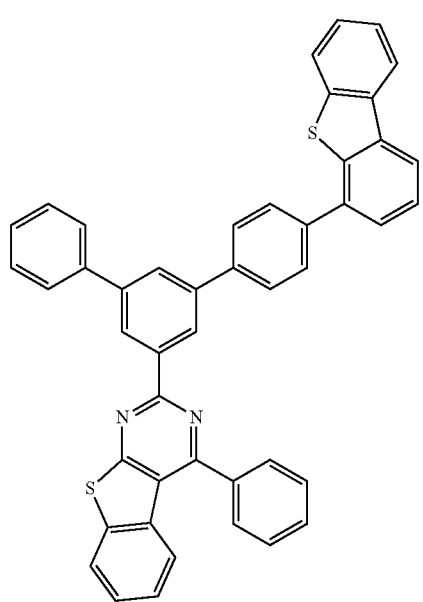
2-96
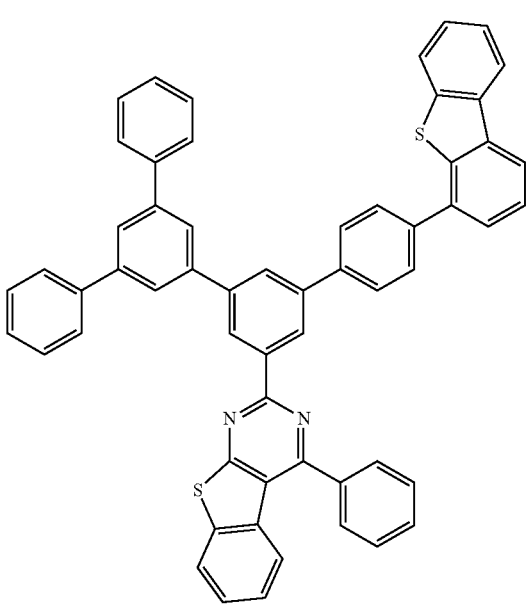
2-97
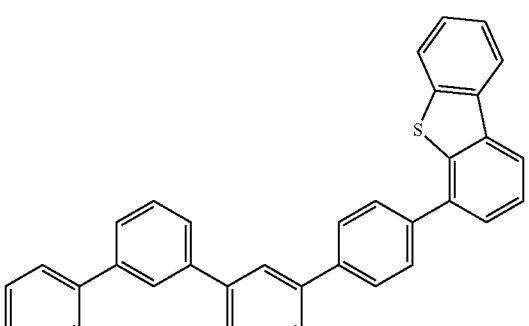
2-98
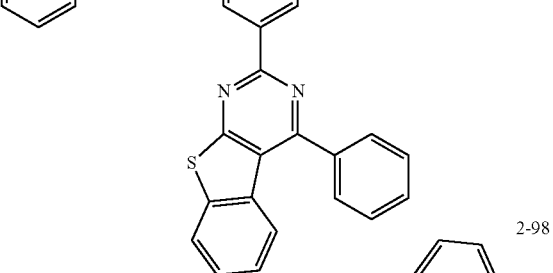
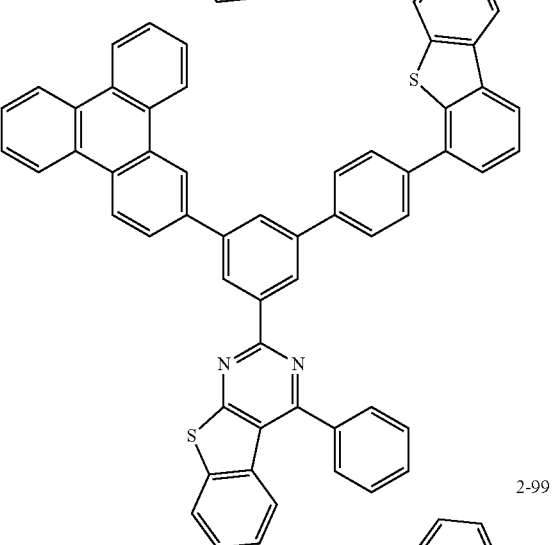
2-99
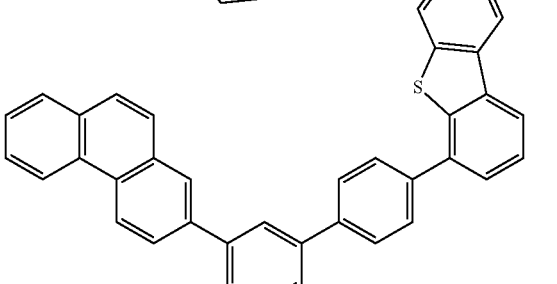
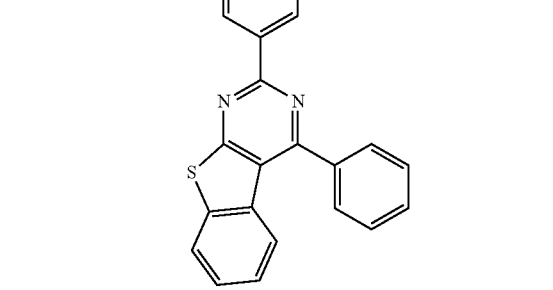

-continued
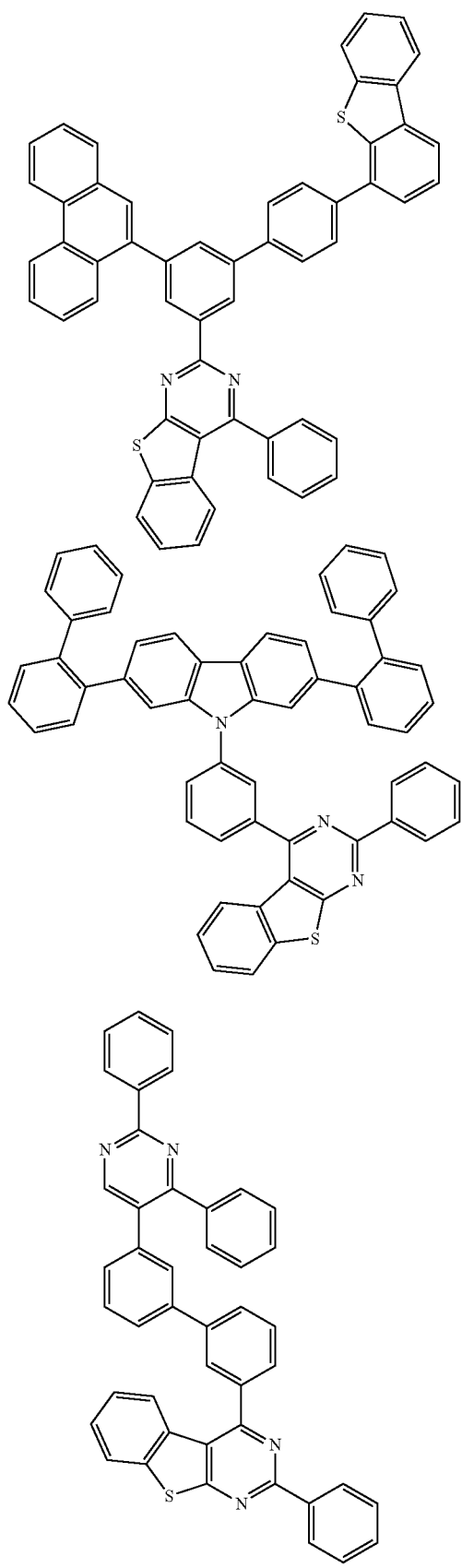
2-100
2-101
2-102
-continued
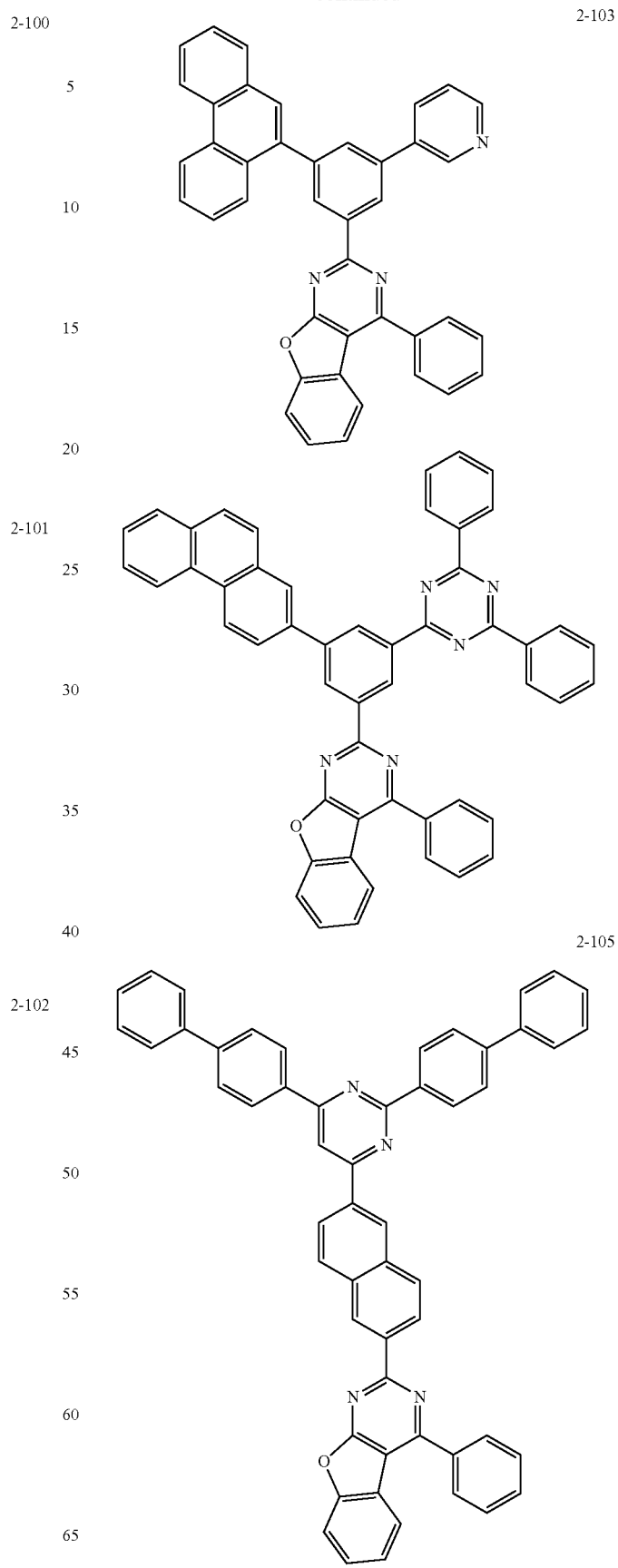
2-103
2-105

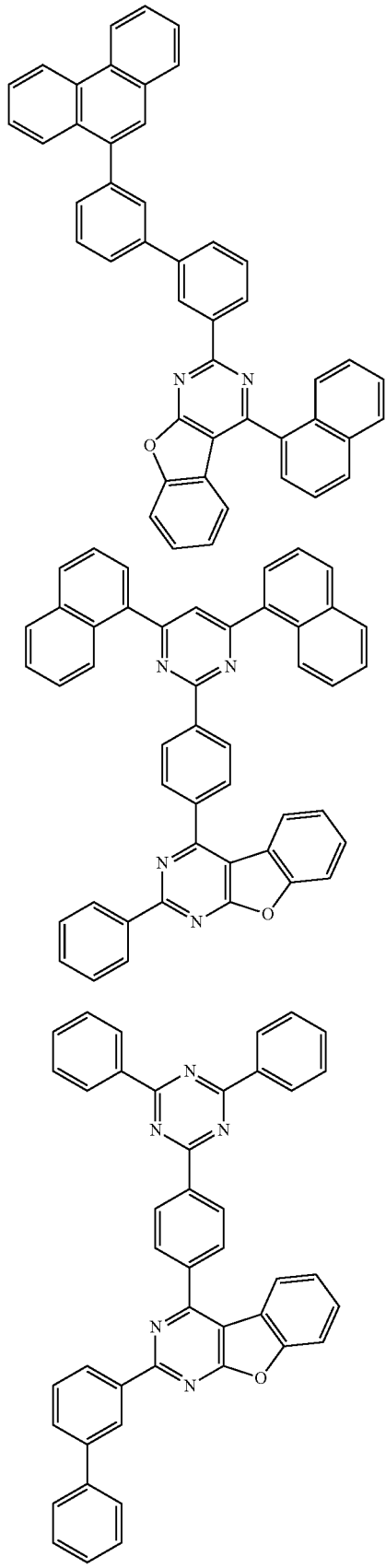
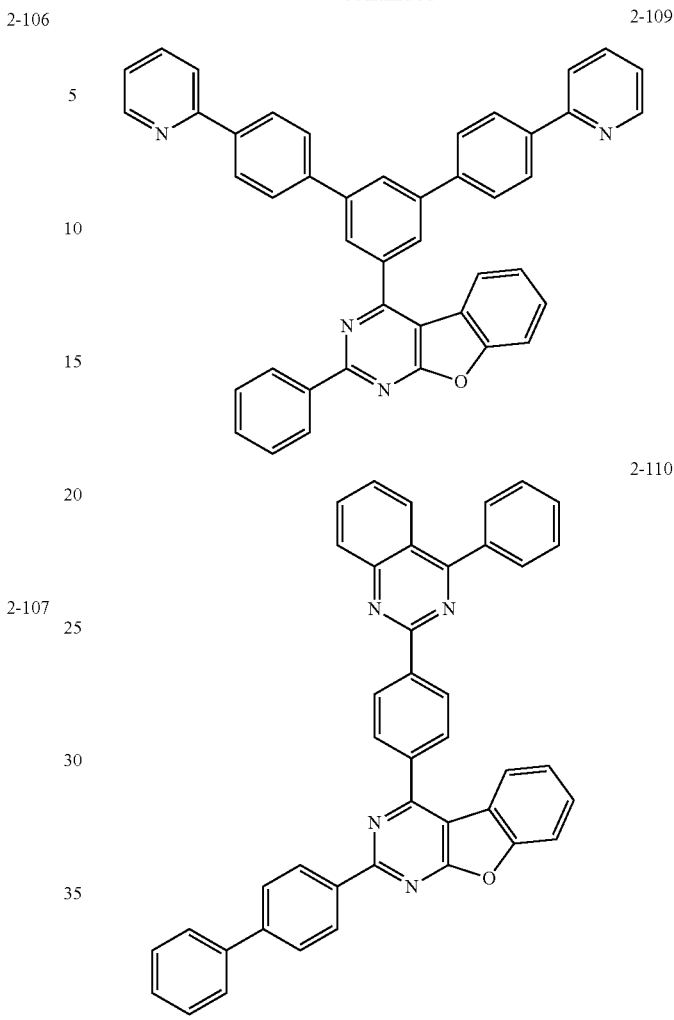

According to another embodiment, the present invention provides a compound for an organic electronic element, represented by Formula 1.

According to still another embodiment, the present invention provides an organic electronic element containing the compound represented by Formula 1.

Here, the organic electronic element may include: a first electrode; a second electrode; and an organic material layer disposed between the first electrode and the second electrode. The organic material layer may contain the compound represented by Formula 1, and the compound represented by Formula 1 may be contained in at least one of a hole injection layer, a hole transport layer, an auxiliary light emitting layer, or a light emitting layer, and an electron transport layer of the organic material layer. Especially, the compound represented by Formula 1 may be contained in a light emitting layer and an electron transport layer.

That is, the compound represented by Formula 1 may be used a material for the hole injection layer, the hole transport layer, the auxiliary light emitting layer, the light emitting layer, the electron transport layer, or electron injection layer. Specifically, the present invention provides an organic electronic element containing one of the compound represented by Formula 2 or 3 in the organic material layer, and more specifically, provides an organic electronic element containing the compound represented by the individual chemical formulas (1-1 to 1-201 and 2-1 to 2-110) in the organic material layer.

In still another embodiment, the present invention provides an organic electronic element, in which the compound is contained alone, the two or more different compounds are contained as a combination, or the compound is contained together with another compound in a combination of two or more in at least one of the hole injection layer, the hole transport layer, the auxiliary light emitting layer, the light emitting layer, the electron transport layer, and the electron injection layer of the organic material layer. In other words, the compounds corresponding to Formulas 1 to 3 may be contained alone in each layer; two or more kinds of compounds of Formulas 1 to 3 may be contained, or a mixture of the compound of claims 1 to 4 and a compound not corresponding to the present invention may be contained in each of the layers. Here, the compounds that do not correspond to the present invention may be a single compound or two or more kinds of compounds. Here, when the compound is combined together with another compound as a combination of two or more kinds of compounds, another compound may be a compound that is already known for each organic material layer, or a compound to be developed in the future. Here, the compounds contained in the organic material layer may be composed of only the same kind of compounds, or a mixture of two or more kinds of different compounds represented by formula 1.

In still another embodiment of the present invention, the present invention provides an organic electronic element further including a light efficiency improvement layer, which is formed on at least one of one side of one surface of the first electrode, which is opposite to the organic material layer and one side of one surface of the second electrode, which is opposite to the organic material layer.

Hereinafter, synthetic Embodiments of the compound represented by Formula 1 and manufacturing Embodiments of the organic electronic element according to the present invention will be described in detail by way of Embodiment. However, the following Embodiments are only for illustrative purposes and are not intended to limit the scope of the invention.

Synthesis Embodiments

The final products represented by Formula 1 according to the present invention are synthesized via reaction pathways of Reaction Scheme 1 and Reaction Scheme 2, but are not limited thereto.

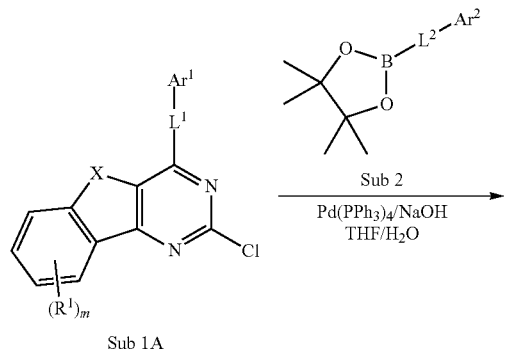

Sub 1A

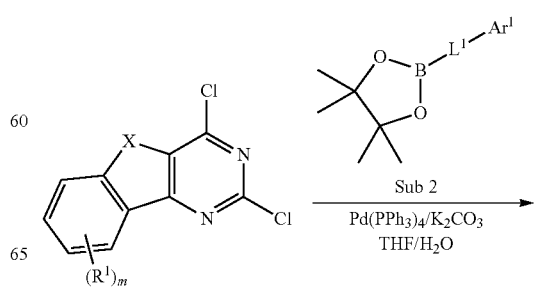

Final Product 1

<Reaction Scheme 2>

Sub 1B

Final Product 2

X, $R^1$, $Ar^1$, $Ar^2$, $L^1$, $L^2$, and m are defined as in claim 1.

I. Synthesis of Sub 1A and Sub 1B

Sub 1A and Sub 1B of Reaction Scheme 1 above may be synthesized by reaction pathways of Reaction Scheme 3 and Reaction Scheme 4, but are not limited thereto.

<Reaction Scheme 3>

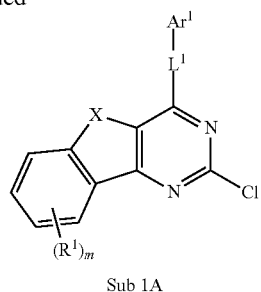

Sub 1A

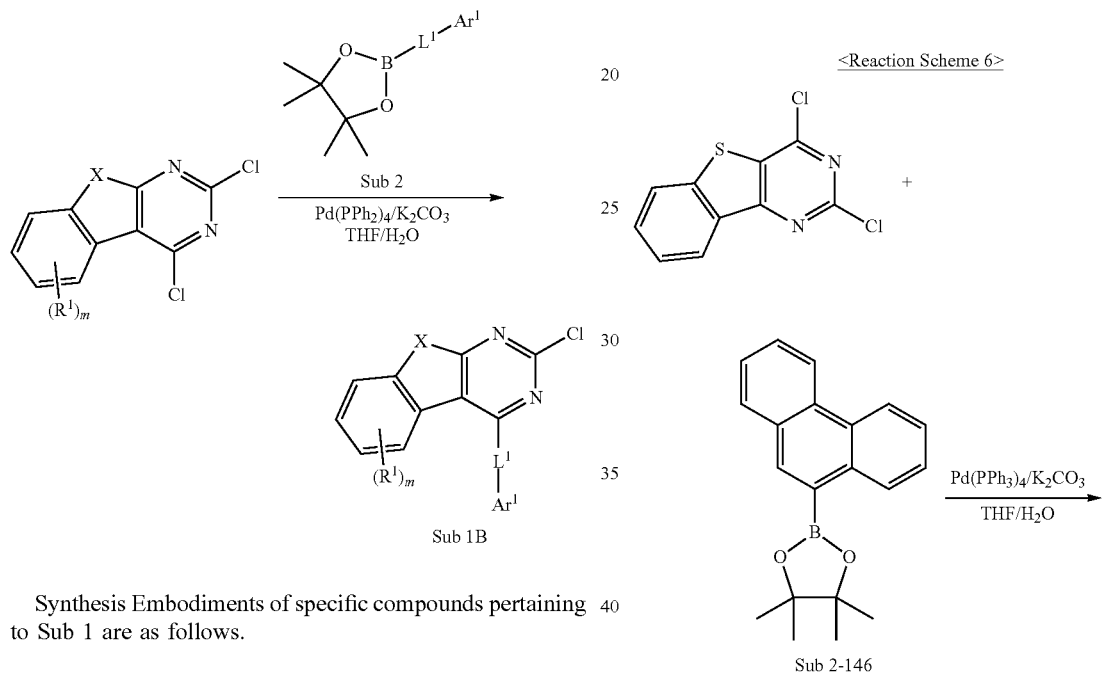

A starting material, 2,4-dichlorobenzo[4,5]thieno[3,2-d]pyrimidine (70.84 g, 277.7 mmol) was dissolved in THF in a round-bottom flask, and then Sub 2-136 (62.33 g, 305.4 mmol), $Pd(PPh_3)_4$ (12.83 g, 11.1 mmol), $K_2CO_3$ (115.13 g, 833 mmol), and water were added thereto, followed by stirring at 90□. Upon completion of the reaction, the reaction product was extracted with $CH_2Cl_2$ and water. The organic layer was dried over $MgSO_4$ and concentrated, and then the compound obtained was subjected to a silica gel column and recrystallization to give a product 36.26 g (yield: 44%).

2. Synthesis Embodiment of Sub 1A-9

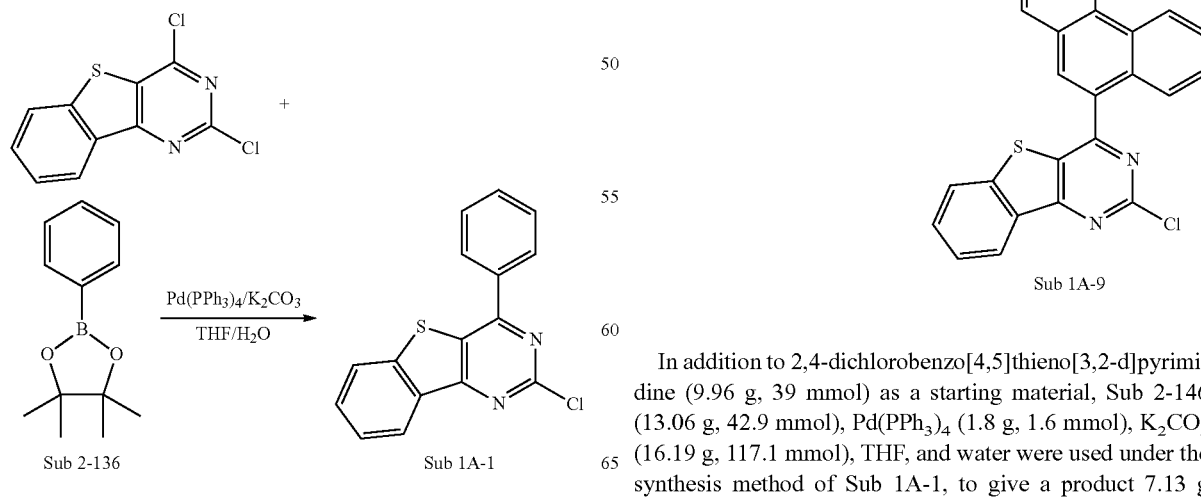

Synthesis Embodiments of specific compounds pertaining to Sub 1 are as follows.

1. Synthesis Embodiment of Sub 1A-1

In addition to 2,4-dichlorobenzo[4,5]thieno[3,2-d]pyrimidine (9.96 g, 39 mmol) as a starting material, Sub 2-146 (13.06 g, 42.9 mmol), $Pd(PPh_3)_4$ (1.8 g, 1.6 mmol), $K_2CO_3$ (16.19 g, 117.1 mmol), THF, and water were used under the synthesis method of Sub 1A-1, to give a product 7.13 g (yield: 46%).

3. Synthesis Embodiment of Sub 1A-16

4. Synthesis Embodiment of Sub 1A-60

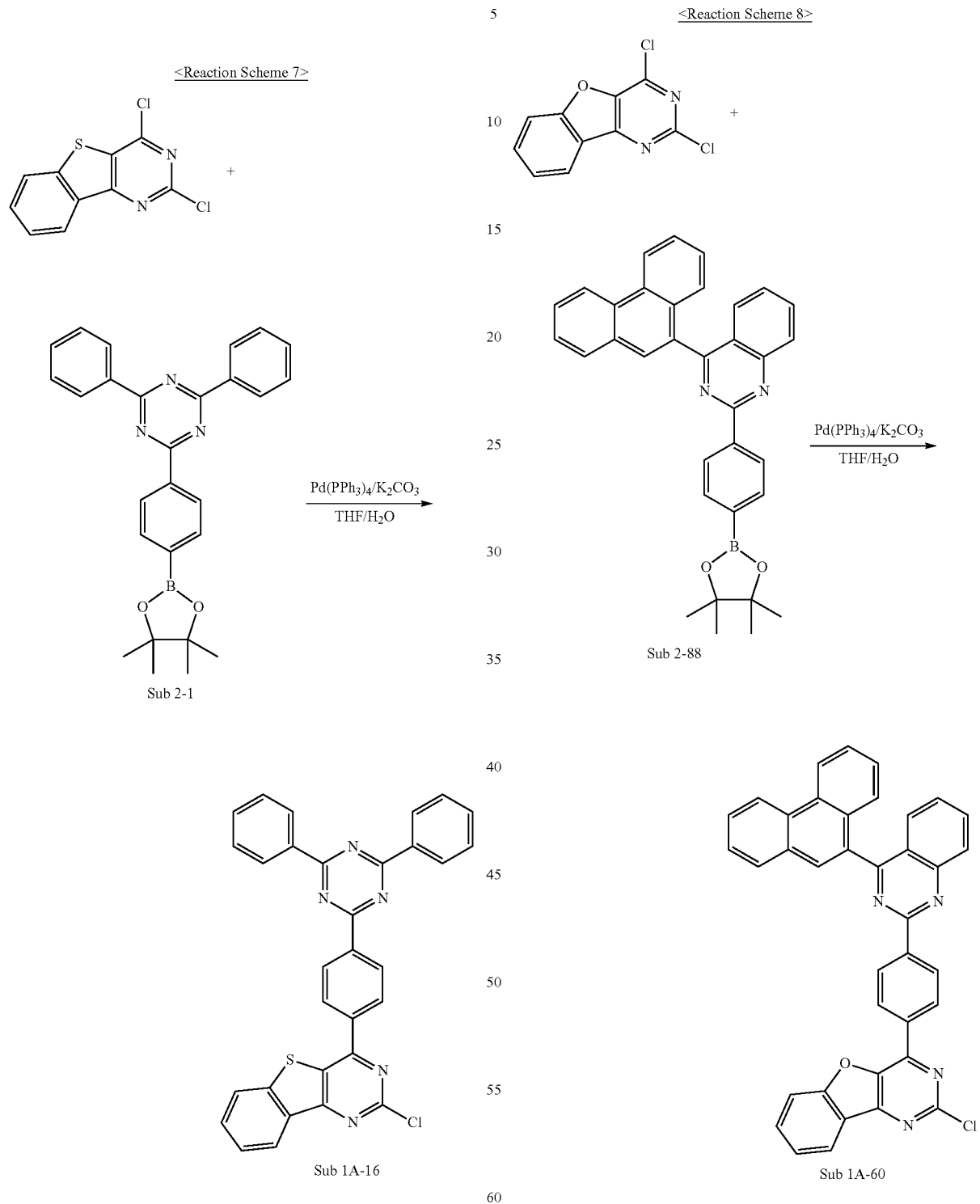

In addition to 2,4-dichlorobenzo[4,5]thieno[3,2-d]pyrimidine (9.87 g, 38.7 mmol) as a starting material, Sub 2-1 (18.53 g, 42.6 mmol), Pd(PPh$_3$)$_4$ (1.79 g, 1.5 mmol), K$_2$CO$_3$ (16.04 g, 116.1 mmol), THF, and water were used under the synthesis method of Sub 1A-1, to give a product 8.58 g (yield: 42%).

In addition to 2,4-dichlorobenzofuro[3,2-d]pyrimidine (8.51 g, 35.6 mmol) as a starting material, Sub 2-88 (19.91 g, 39.2 mmol), Pd(PPh$_3$)$_4$ (1.65 g, 1.4 mmol), K$_2$CO$_3$ (14.76 g, 106.8 mmol), THF, and water were used under the synthesis method of Sub 1A-1, to give a product 8.12 g (yield: 39%).

5. Synthesis Embodiment of Sub 1B-1

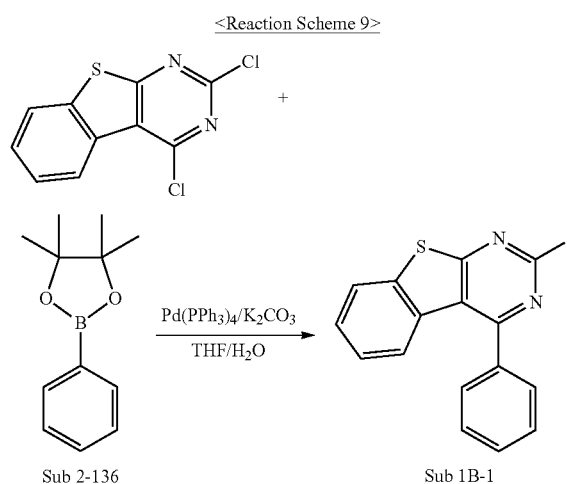

<Reaction Scheme 9>

Sub 2-136 → Sub 1B-1

In addition to 2,4-dichlorobenzo[4,5]thieno[2,3-d]pyrimidine (19.78 g, 77.5 mmol) as a starting material, Sub 2-136 (17.4 g, 85.3 mmol), Pd(PPh$_3$)$_4$ (3.58 g, 3.1 mmol), K$_2$CO$_3$ (32.15 g, 232.6 mmol), THF, and water were used under the synthesis method of Sub 1A-1, to give a product 10.81 g (yield: 47%).

6. Synthesis Embodiment of Sub 1B-38

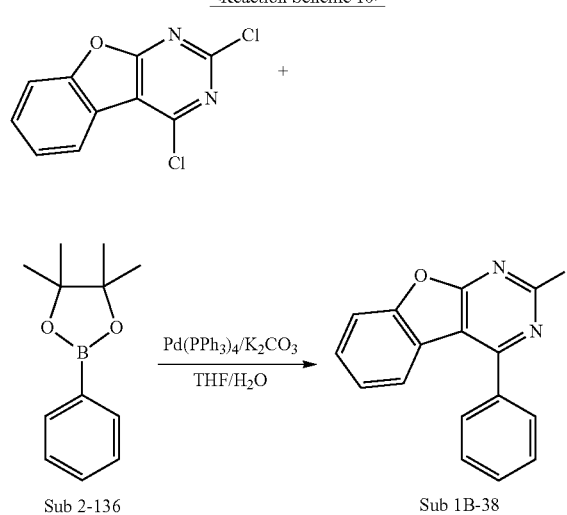

<Reaction Scheme 10>

Sub 2-136 → Sub 1B-38

In addition to 2,4-dichlorobenzofuro[2,3-d]pyrimidine (9.06 g, 37.9 mmol) as a starting material, Sub 2-136 (8.51 g, 41.7 mmol), Pd(PPh$_3$)$_4$ (1.75 g, 1.5 mmol), K$_2$CO$_3$ (15.71 g, 113.7 mmol), THF, and water were used under the synthesis method of Sub 1A-1, to give a product 5.11 g (yield: 48%).

7. Synthesis Embodiment of Sub 1B-43

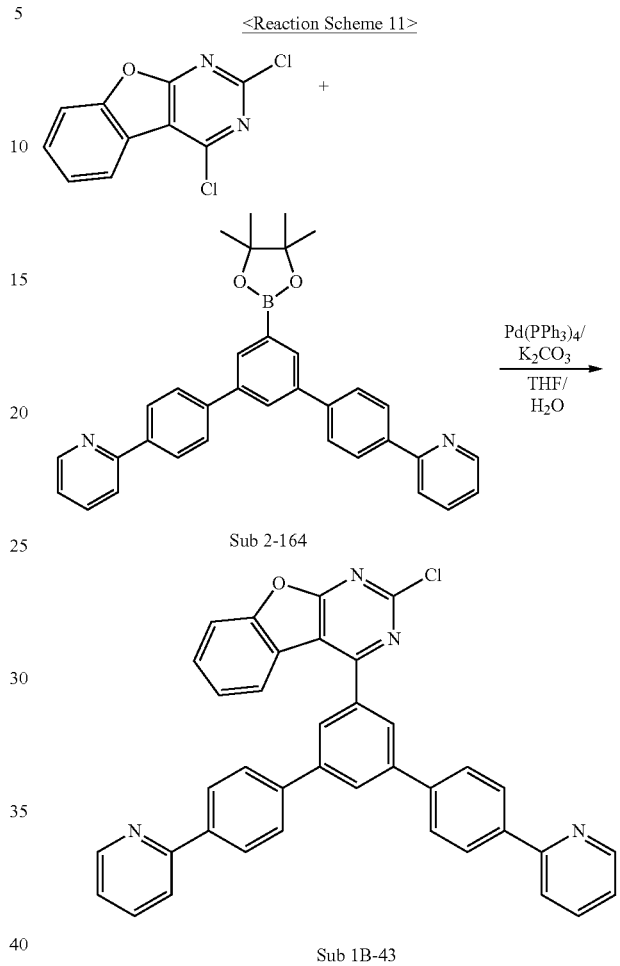

<Reaction Scheme 11>

Sub 2-164 → Sub 1B-43

In addition to 2,4-dichlorobenzofuro[2,3-d]pyrimidine (13.23 g, 55.3 mmol) as a starting material, Sub 2-164 (31.07 g, 60.9 mmol), Pd(PPh$_3$)$_4$ (2.56 g, 2.2 mmol), K$_2$CO$_3$ (22.95 g, 166 mmol), THF, and water were used under the synthesis method of Sub 1A-1, to give a product 13.97 g (yield: 43%).

The compounds pertaining to Sub 1A and Sub 1B may be compounds below, but are not limited thereto. Table 1 below shows FD-MS values of the compounds pertaining to Sub 1A and Sub 1B.

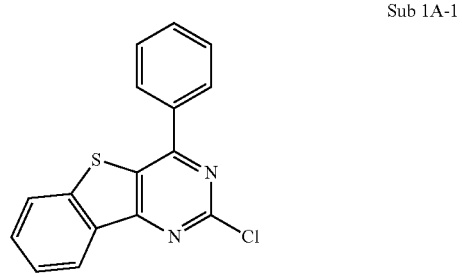

Sub 1A-1

Sub 1A-2
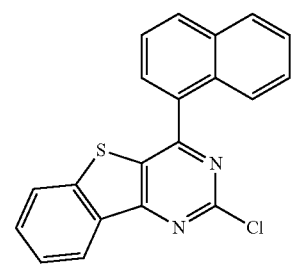
Sub 1A-3
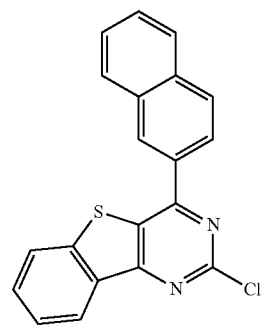
Sub 1A-4
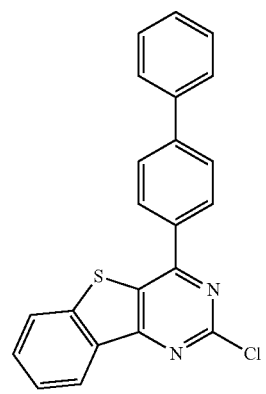
Sub 1A-5
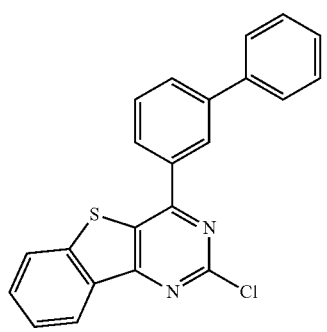
Sub 1A-6
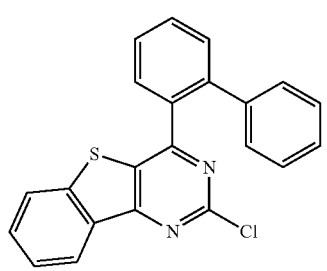
Sub 1A-7
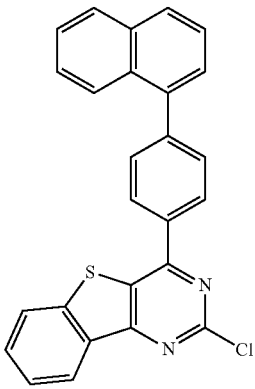
Sub 1A-8
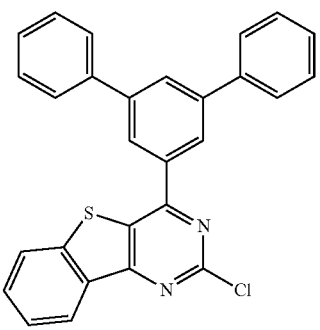
Sub 1A-9
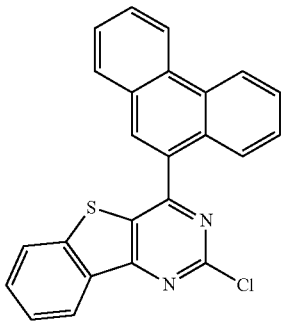
Sub 1A-10
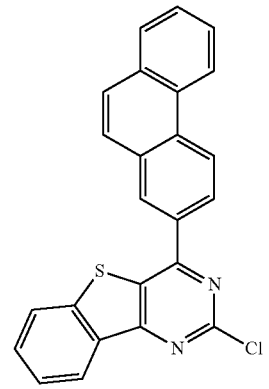

Sub 1A-11
Sub 1A-12
Sub 1A-13
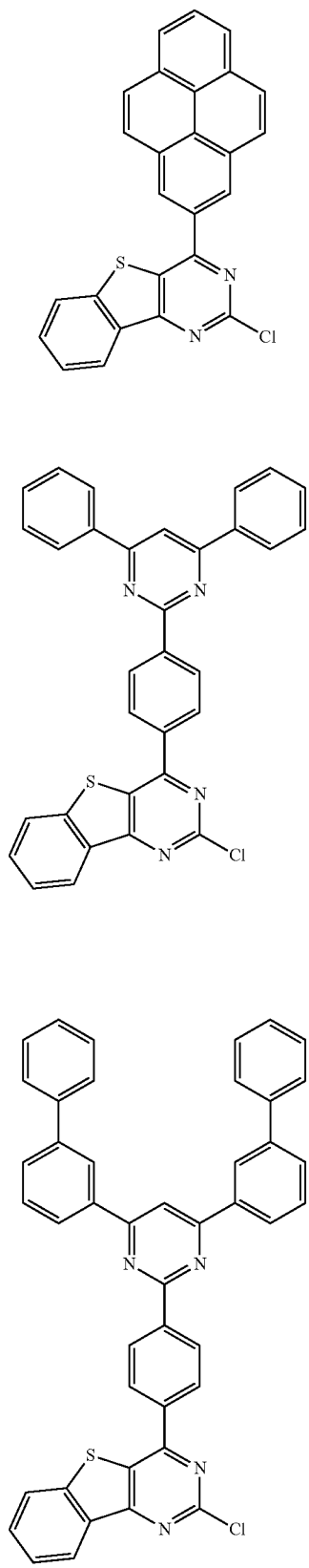
Sub 1A-14
Sub 1A-15
Sub 1A-16
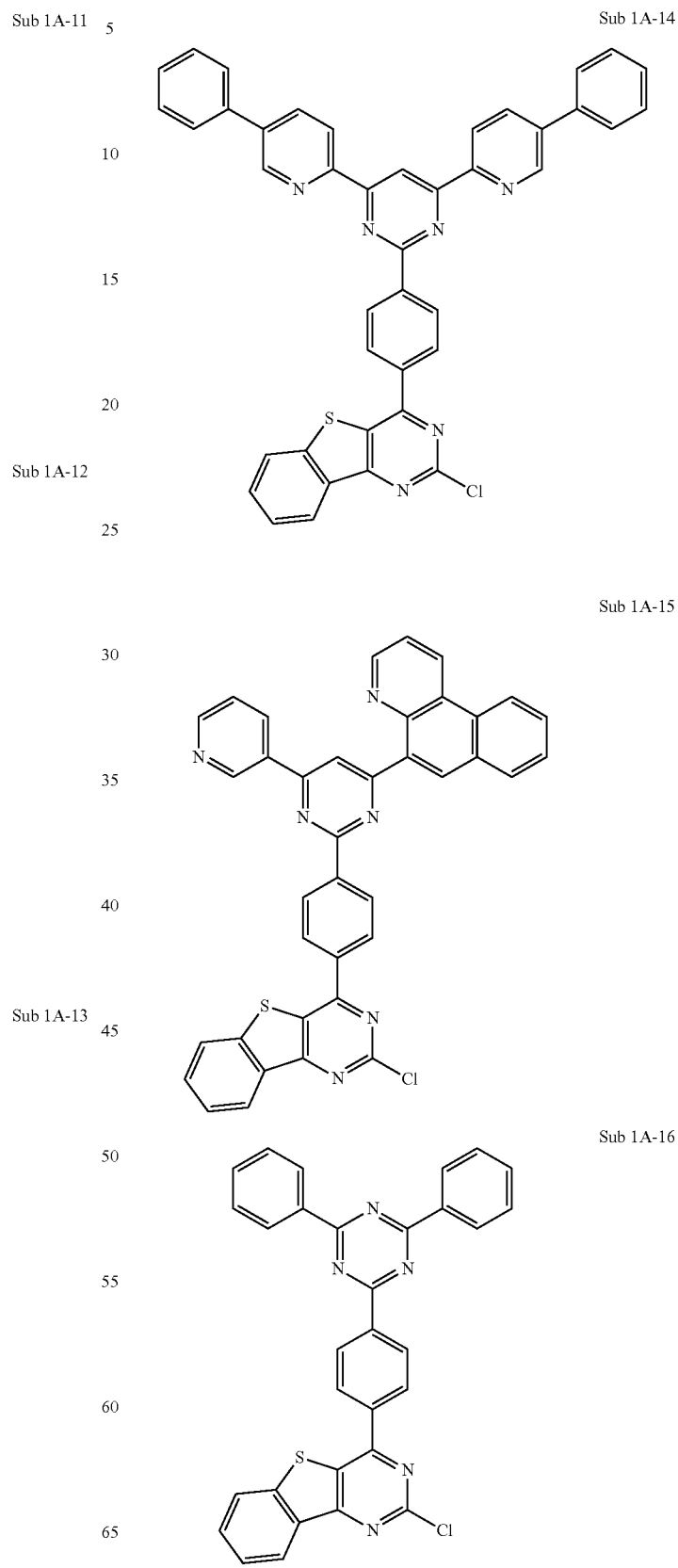

Sub 1A-17
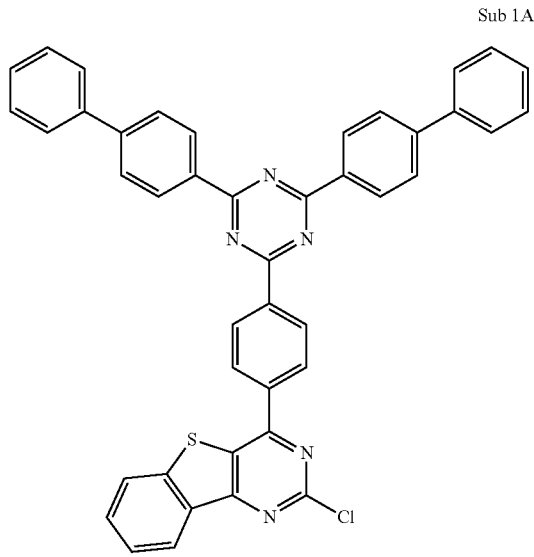
Sub 1A-18
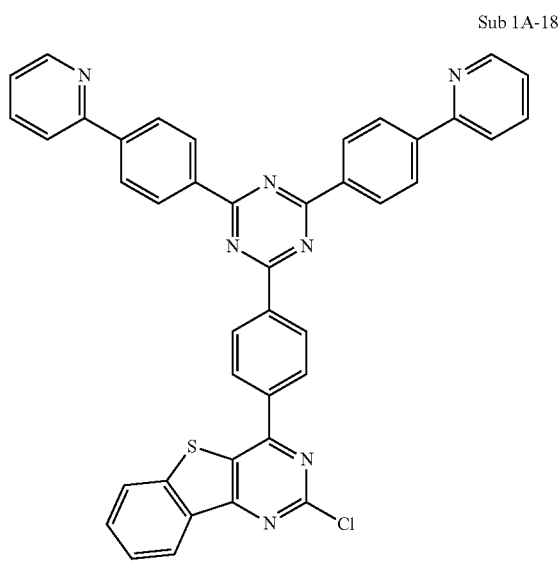
Sub 1A-19
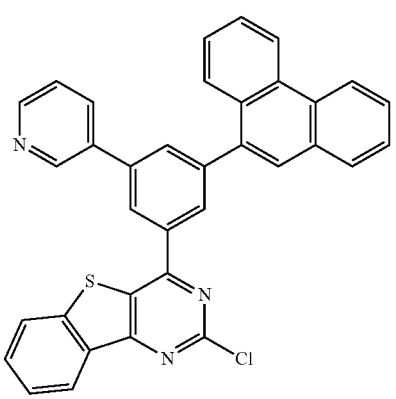
Sub 1A-20
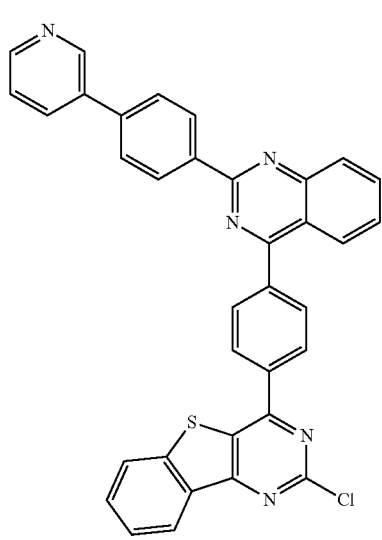
Sub 1A-21
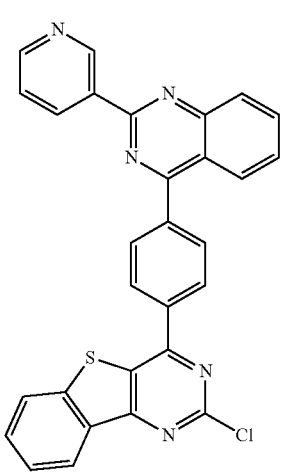
Sub 1A-22
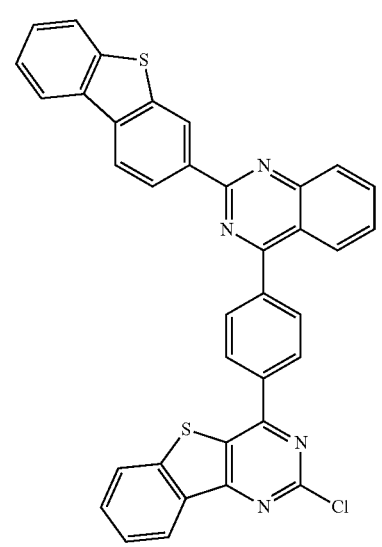

-continued
Sub 1A-23
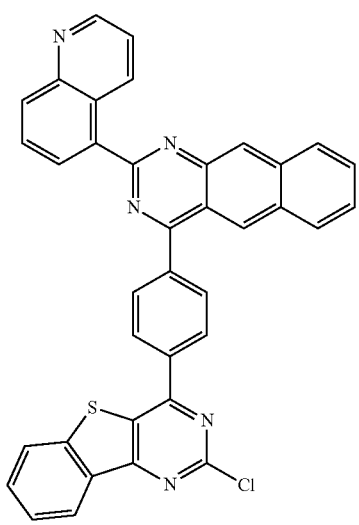
Sub 1A-24
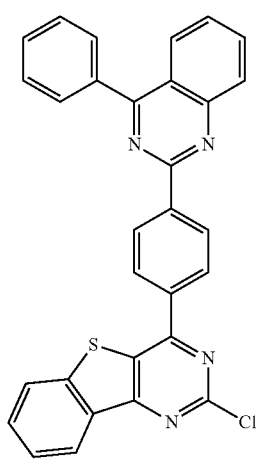
Sub 1A-25
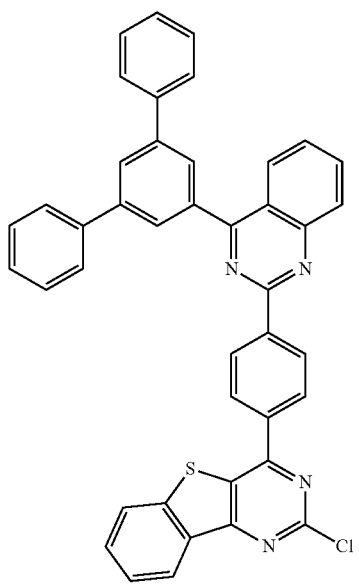
-continued
Sub 1A-26
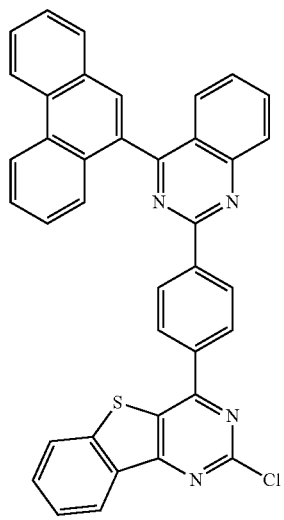
Sub 1A-27
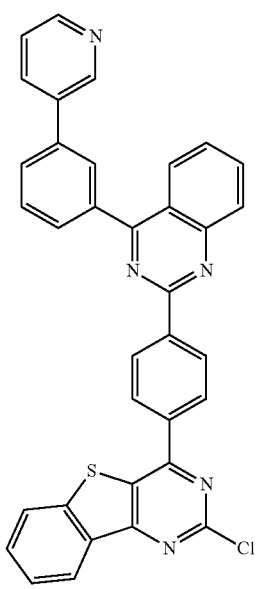
Sub 1A-28
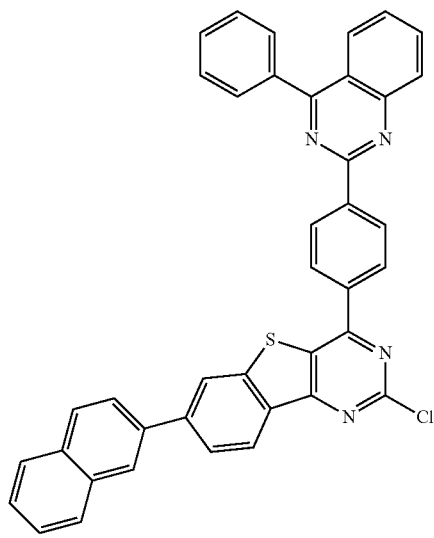

-continued
Sub 1A-29
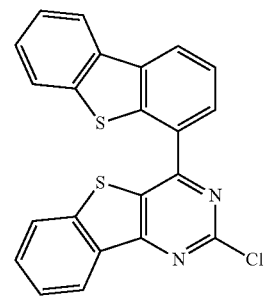
Sub 1A-30
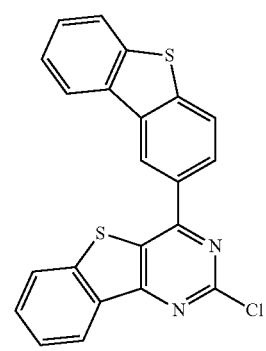
Sub 1A-31
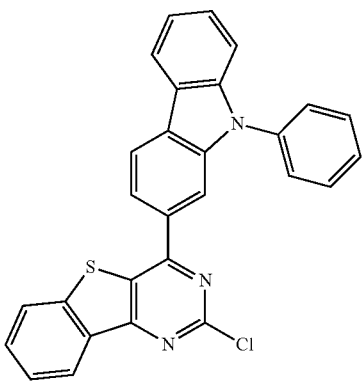
Sub 1A-32
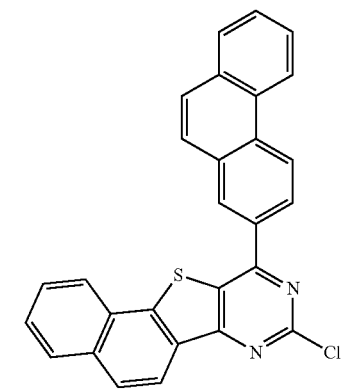
-continued
Sub 1A-33
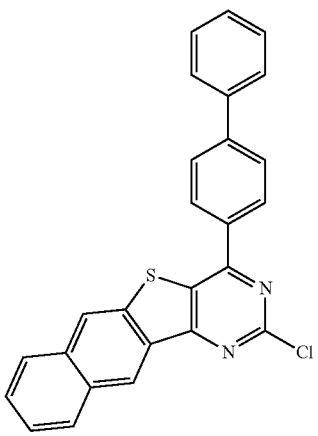
Sub 1A-34
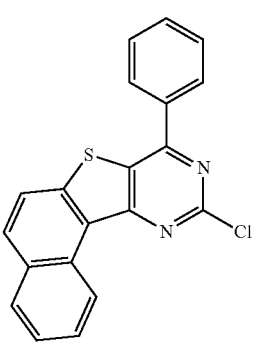
Sub 1A-35
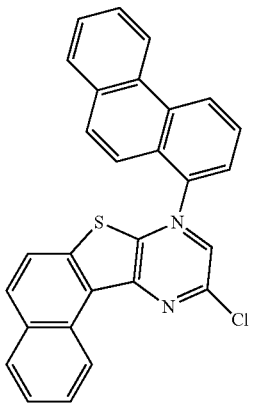
Sub 1A-36
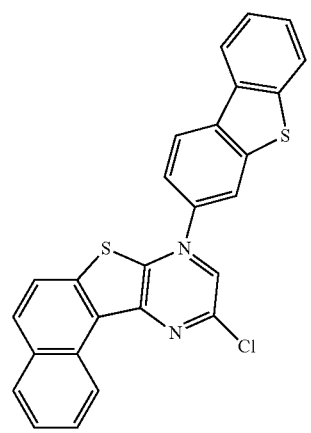

Sub 1A-37
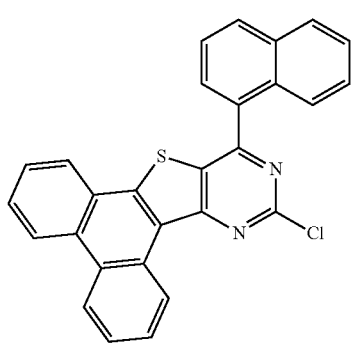
Sub 1A-38
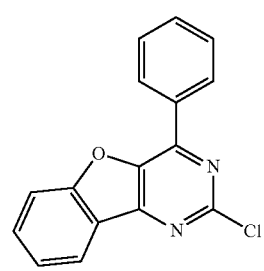
Sub 1A-39
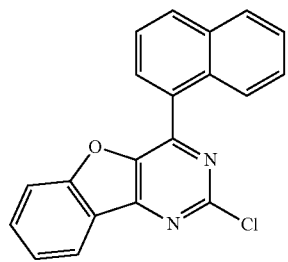
Sub 1A-40
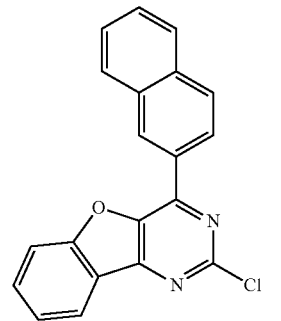
Sub 1A-41
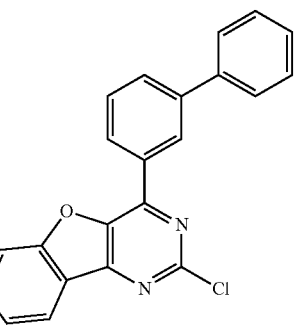
Sub 1A-42
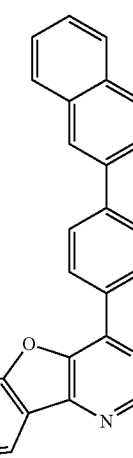
Sub 1A-43
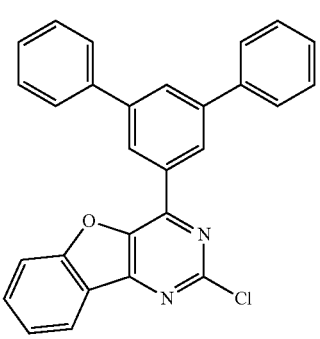
Sub 1A-44
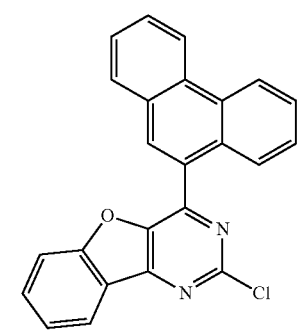
Sub 1A-45
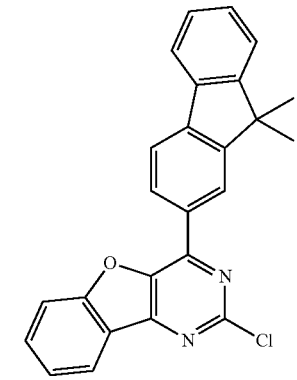

Sub 1A-46
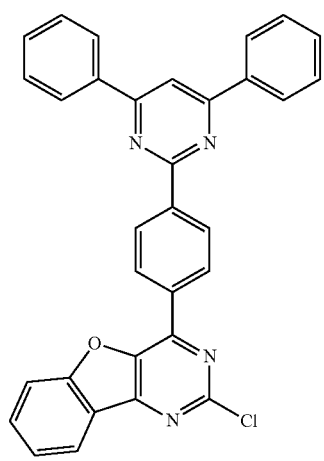
Sub 1A-47
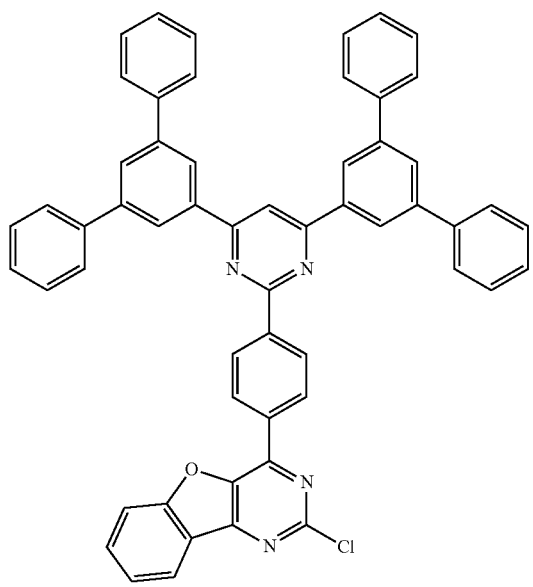
Sub 1A-48
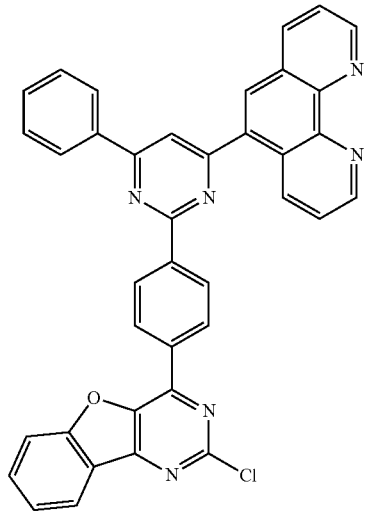
Sub 1A-49
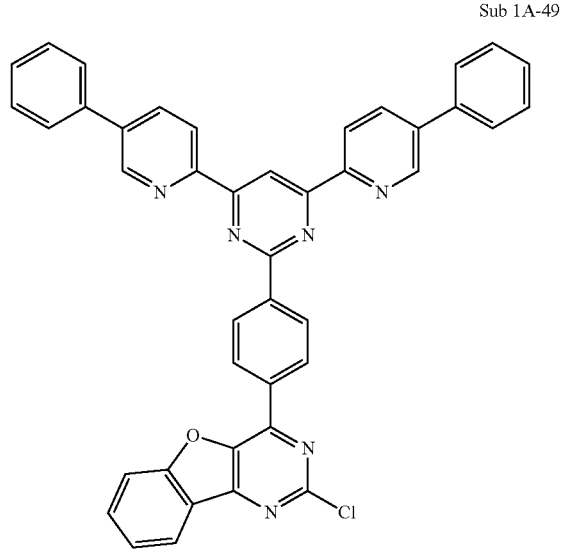
Sub 1A-50
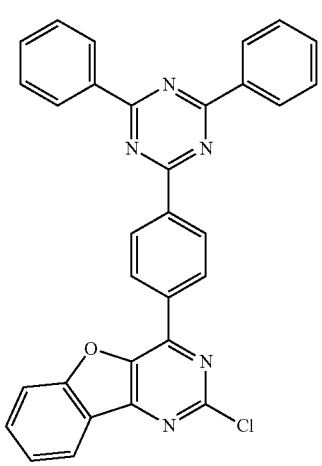
Sub 1A-51
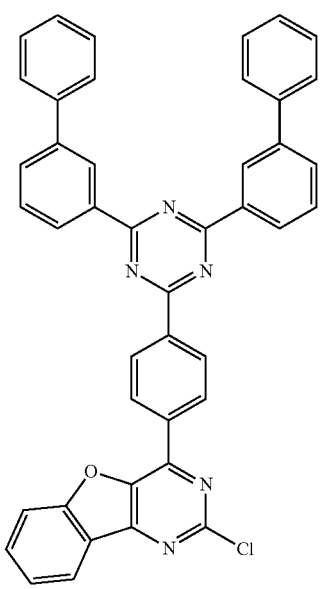

-continued
Sub 1A-52
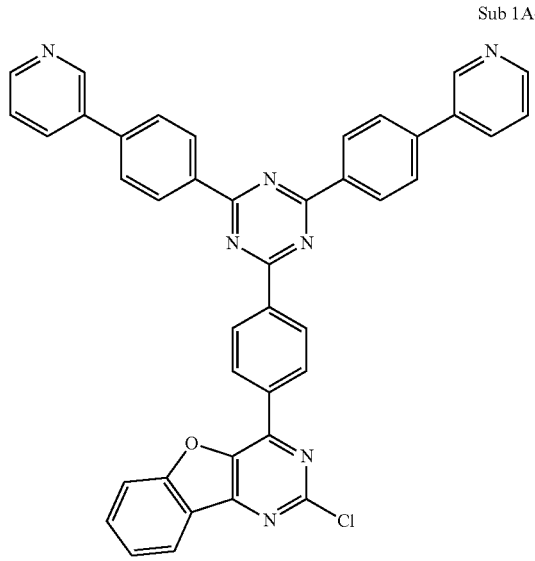
Sub 1A-53
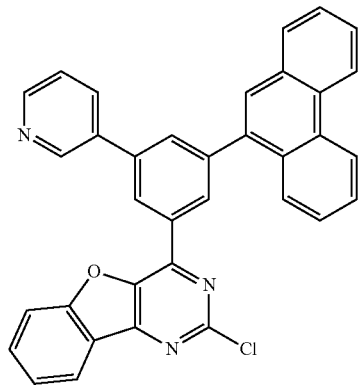
Sub 1A-54
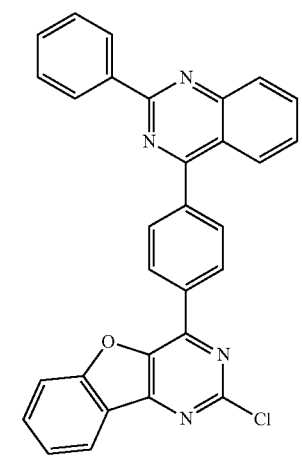
-continued
Sub 1A-55
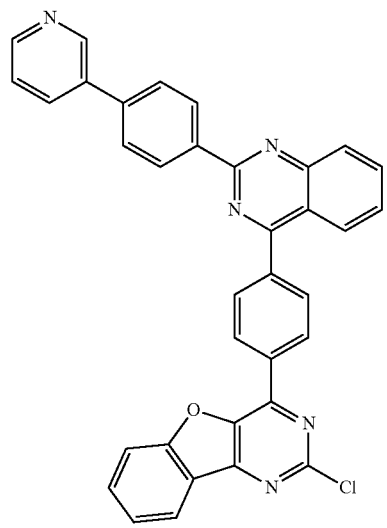
Sub 1A-56
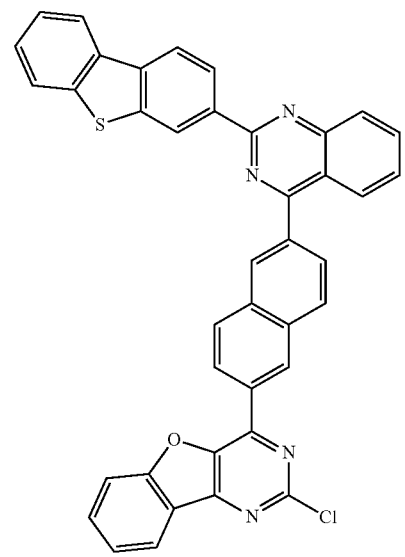
Sub 1A-57
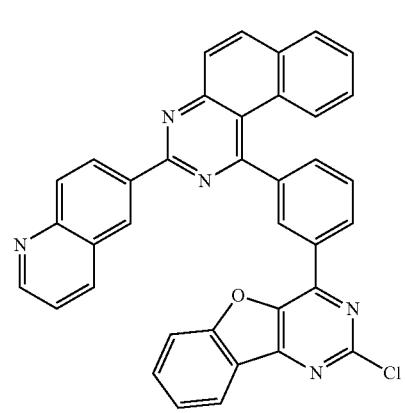

Sub 1A-58
Sub 1A-59
Sub 1A-60
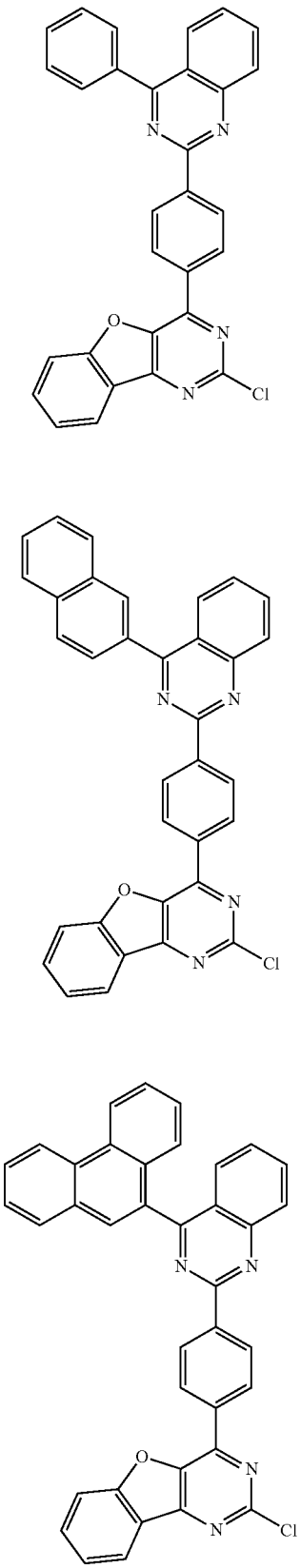
Sub 1A-61
Sub 1A-62
Sub 1A-63
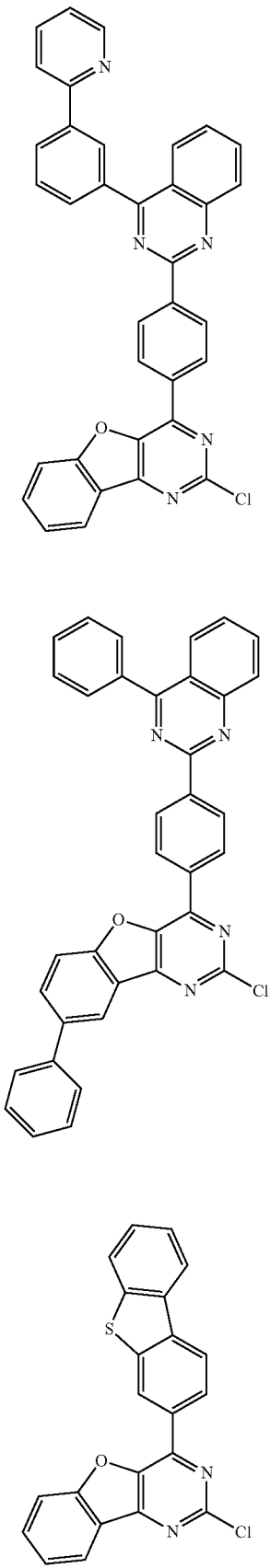

Sub 1A-64
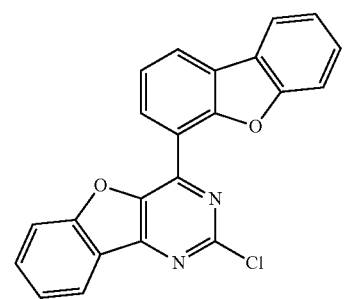
Sub 1A-65
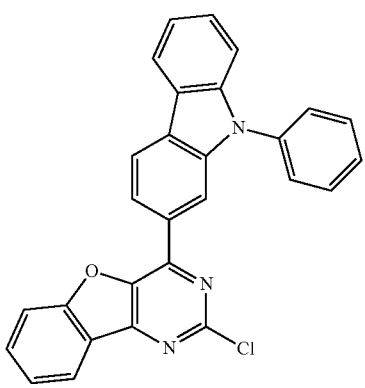
Sub 1A-66
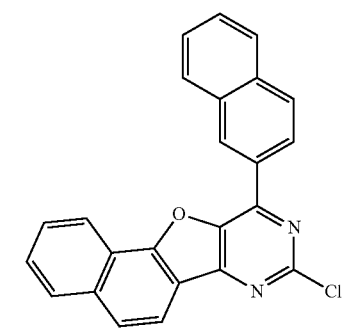
Sub 1A-67
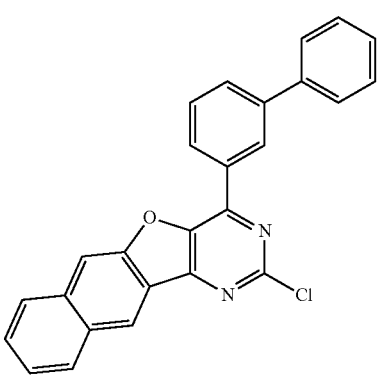
Sub 1A-68
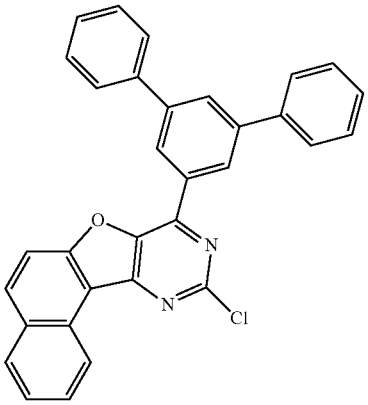
Sub 1A-69
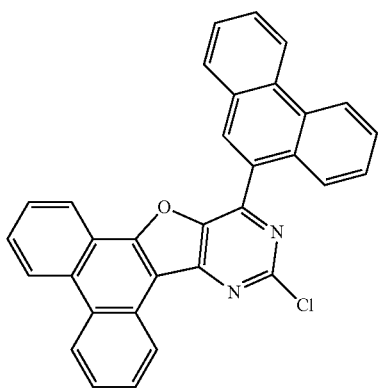
Sub 1B-1
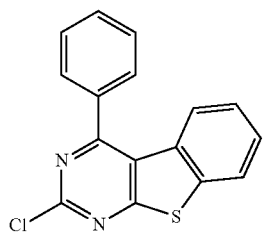
Sub 1B-2
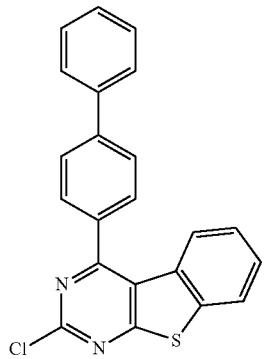

Sub 1B-3
Sub 1B-4
Sub 1B-5
Sub 1B-6
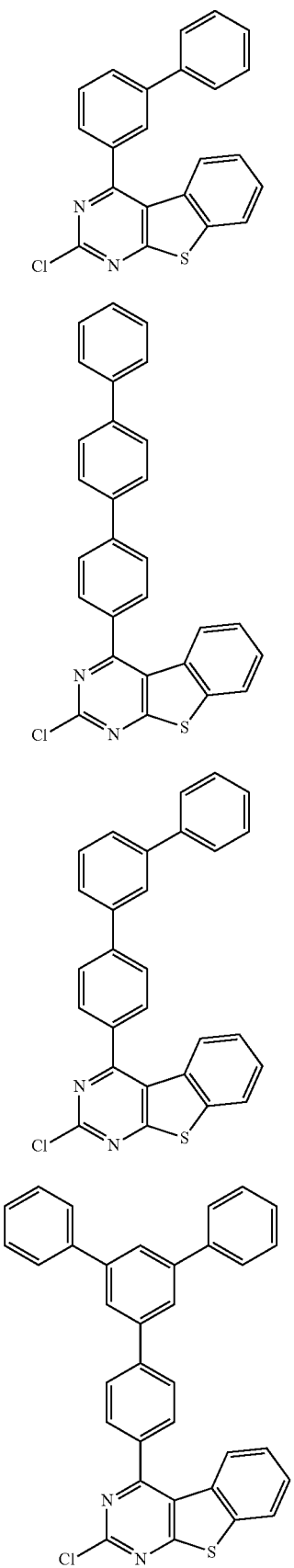
Sub 1B-7
Sub 1B-8
Sub 1B-9
Sub 1B-10
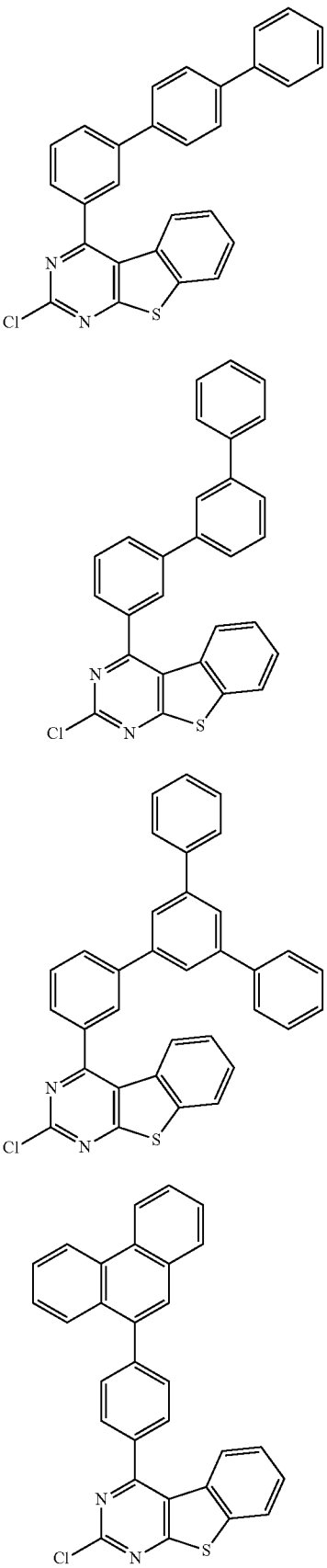

-continued
Sub 1B-11
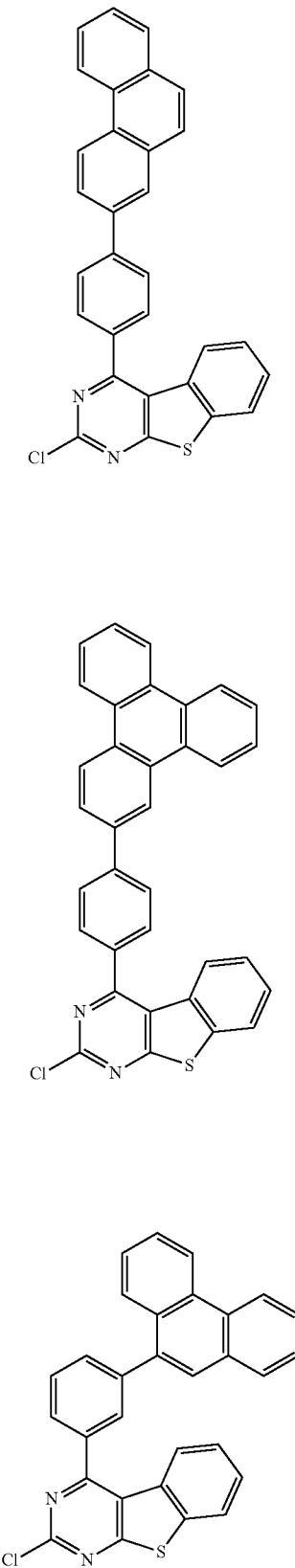
Sub IB-12
Sub IB-13
-continued
Sub IB-14
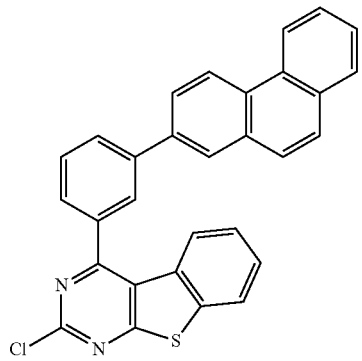
Sub IB-15
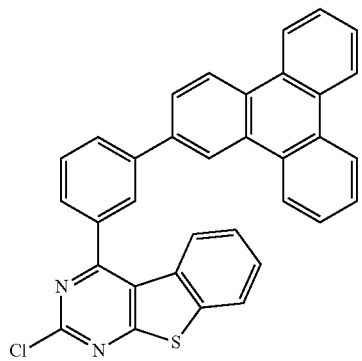
Sub 1B-16
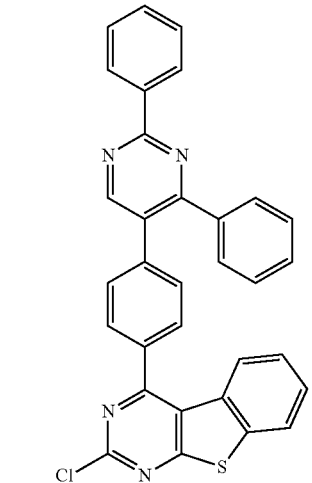
Sub 1B-17
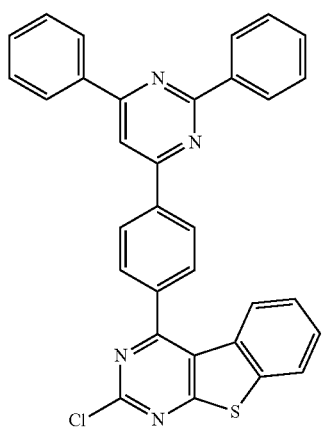

Sub 1B-18
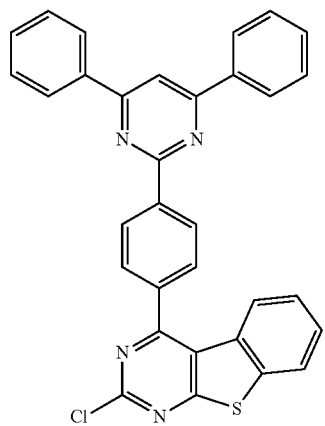
Sub 1B-19
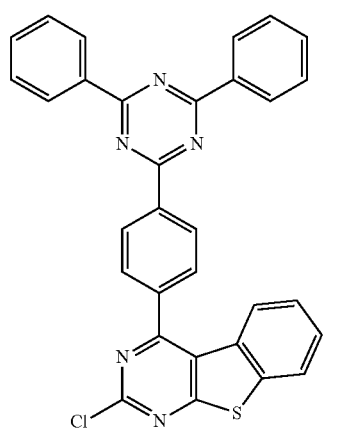
Sub 1B-20
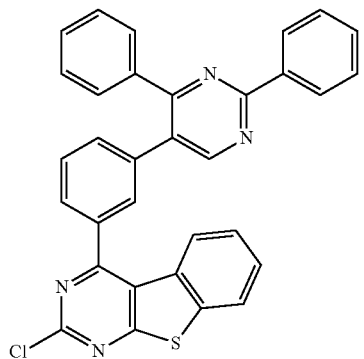
Sub 1B-21
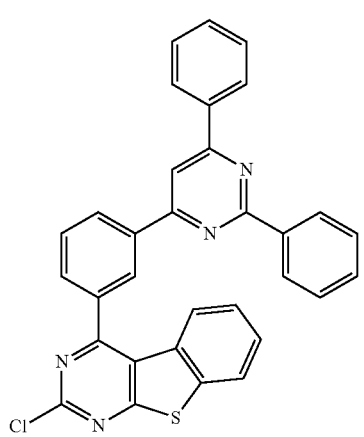
Sub 1B-22
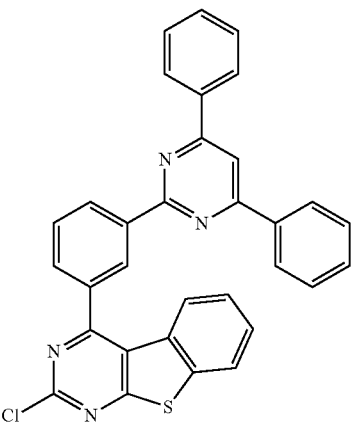
Sub 1B-23
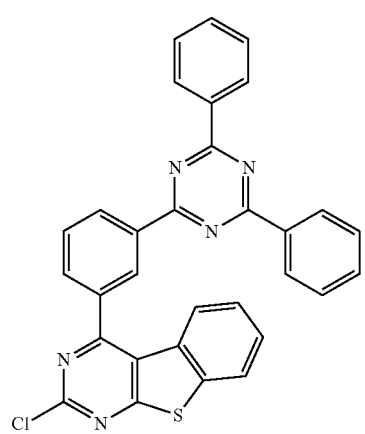
Sub 1B-24
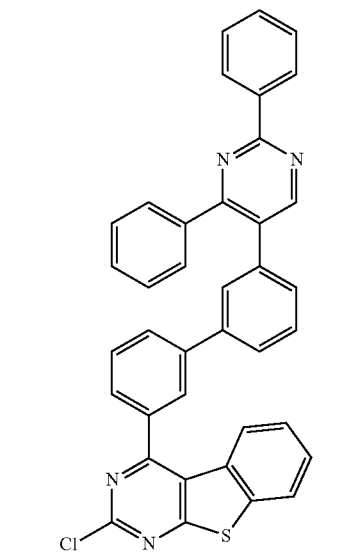

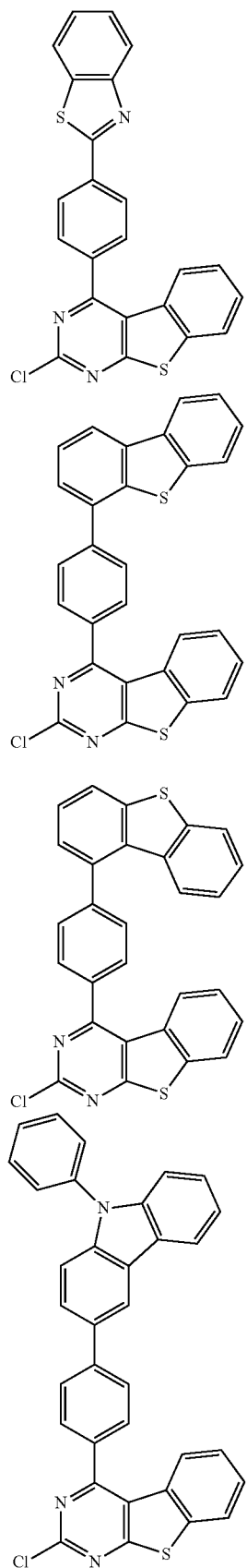
Sub 1B-25
Sub 1B-26
Sub 1B-27
Sub 1B-28
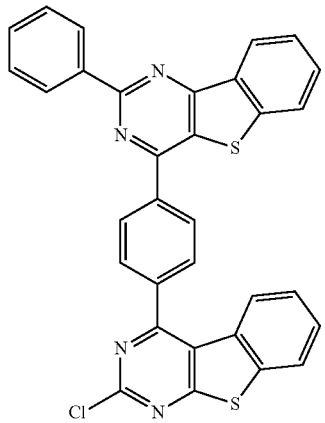
Sub 1B-29
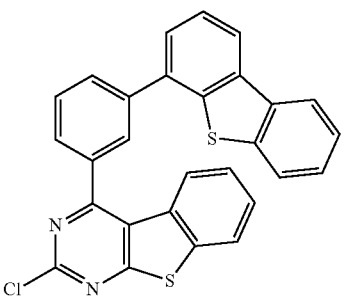
Sub 1B-30
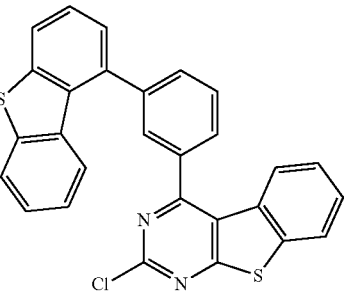
Sub 1B-31
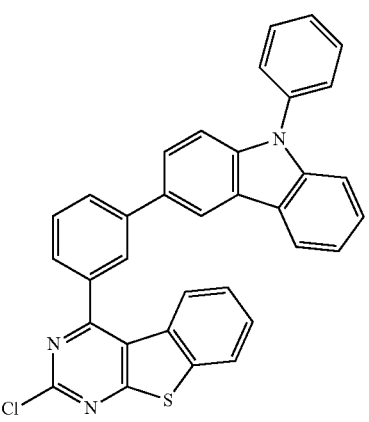
Sub 1B-32

-continued
Sub 1B-33
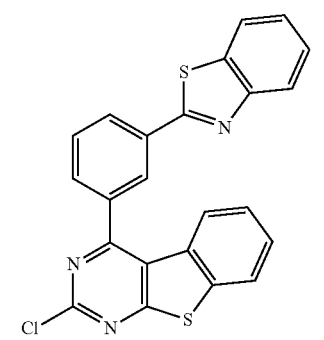
Sub 1B-34
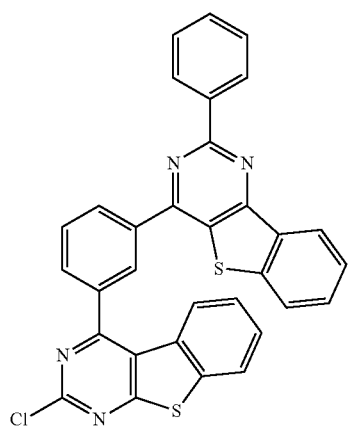
Sub 1B-35
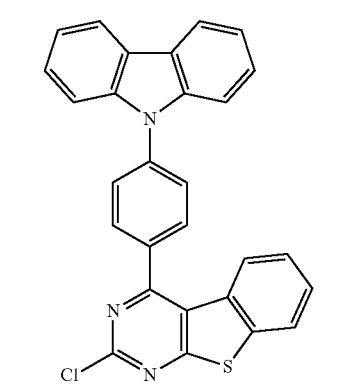
Sub 1B-36
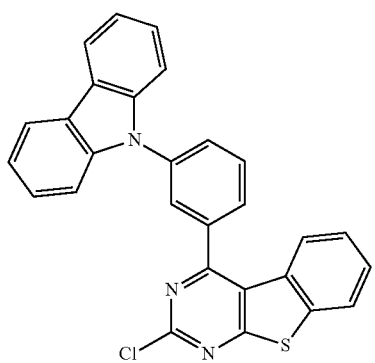
-continued
Sub 1B-37
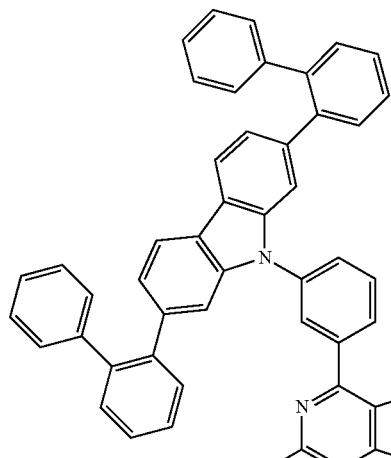
Sub 1B-38
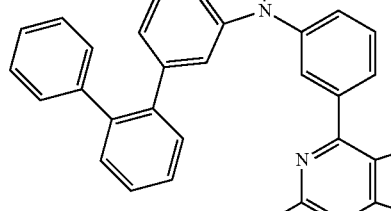
Sub 1B-39
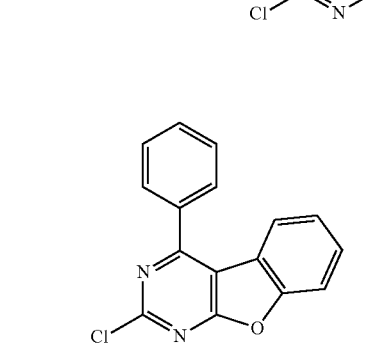
Sub 1B-40
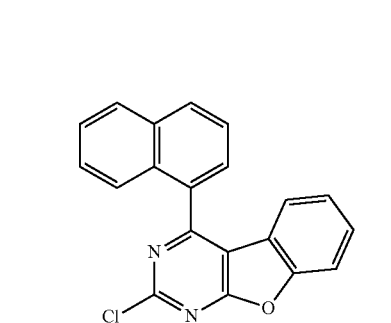

-continued

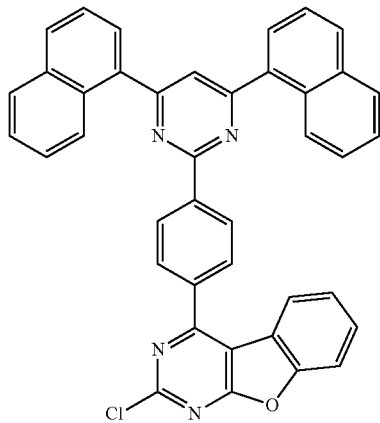
Sub 1B-41

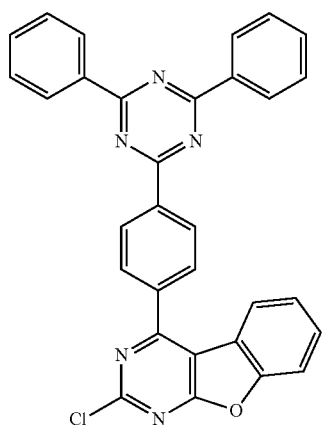
Sub 1B-43

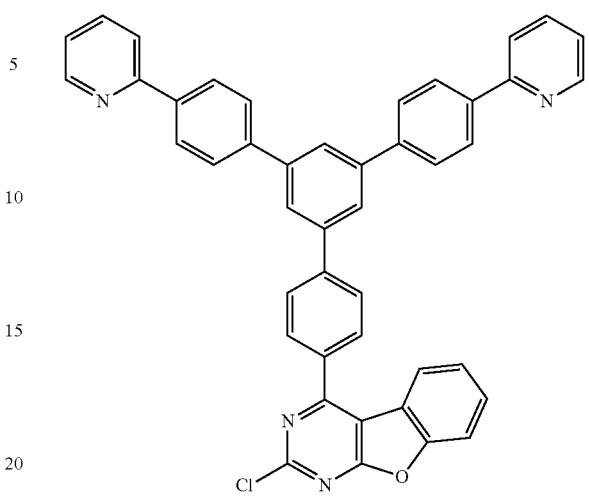
Sub 1B-43

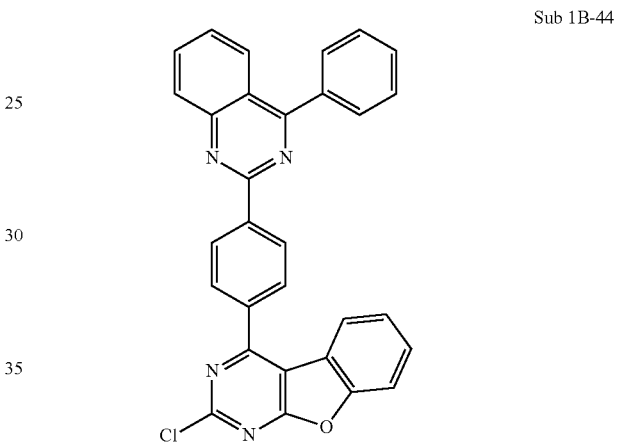
Sub 1B-44

TABLE 1

| Compound | FD-MS | Compound | FD-MS |
|---|---|---|---|
| Sub 1A-1 | m/z = 296.02($C_{16}H_9ClN_2S$ = 296.77) | Sub 1A-2 | m/z = 346.03($C_{20}H_{11}ClN_2S$ = 346.83) |
| Sub 1A-3 | m/z = 346.03($C_{20}H_{11}ClN_2S$ = 346.83) | Sub 1A-4 | m/z = 372.05($C_{22}H_{13}ClN_2S$ = 372.87) |
| Sub 1A-5 | m/z = 372.05($C_{22}H_{13}ClN_2S$ = 372.87) | Sub 1A-6 | m/z = 372.05($C_{22}H_{13}ClN_2S$ = 372.87) |
| Sub 1A-7 | m/z = 422.06($C_{26}H_{15}ClN_2S$ = 422.93) | Sub 1A-8 | m/z = 448.08($C_{28}H_{17}ClN_2S$ = 448.97) |
| Sub 1A-9 | m/z = 396.05($C_{24}H_{13}ClN_2S$ = 396.89) | Sub 1A-10 | m/z = 396.05($C_{24}H_{13}ClN_2S$ = 396.89) |
| Sub 1A-11 | m/z = 420.05($C_{26}H_{13}ClN_2S$ = 420.91) | Sub 1A-12 | m/z = 526.10($C_{32}H_{19}ClN_4S$ = 527.04) |
| Sub 1A-13 | m/z = 678.16($C_{44}H_{27}ClN_4S$ = 679.23) | Sub 1A-14 | m/z = 680.15($C_{42}H_{25}ClN_6S$ = 681.21) |
| Sub 1A-15 | m/z = 628.12($C_{38}H_{21}ClN_6S$ = 629.13) | Sub 1A-16 | m/z = 527.10($C_{31}H_{18}ClN_5S$ = 528.03) |
| Sub 1A-17 | m/z = 679.16($C_{43}H_{26}ClN_5S$ = 680.22) | Sub 1A-18 | m/z = 681.15($C_{41}H_{24}ClN_7S$ = 682.19) |
| Sub 1A-19 | m/z = 549.11($C_{35}H_{20}ClN_3S$ = 550.12) | Sub 1A-20 | m/z = 577.11($C_{35}H_{20}ClN_5S$ = 578.08) |
| Sub 1A-21 | m/z = 501.08($C_{29}H_{16}ClN_5S$ = 501.99) | Sub 1A-22 | m/z = 606.07($C_{36}H_{19}ClN_4S_2$ = 607.15) |
| Sub 1A-23 | m/z = 601.11($C_{37}H_{20}ClN_5S$ = 602.11) | Sub 1A-24 | m/z = 500.09($C_{30}H_{17}ClN_4S$ = 501.00) |
| Sub 1A-25 | m/z = 652.15($C_{42}H_{25}ClN_4S$ = 653.19) | Sub 1A-26 | m/z = 600.12($C_{38}H_{21}ClN_4S$ = 601.12) |
| Sub 1A-27 | m/z = 577.11($C_{35}H_{20}ClN_5S$ = 578.08) | Sub 1A-28 | m/z = 626.13($C_{40}H_{23}ClN_4S$ = 627.16) |
| Sub 1A-29 | m/z = 402.01($C_{22}H_{11}ClN_2S_2$ = 402.92) | Sub 1A-30 | m/z = 402.01($C_{22}H_{11}ClN_2S_2$ = 402.92) |
| Sub 1A-31 | m/z = 461.08($C_{28}H_{16}ClN_3S$ = 461.96) | Sub 1A-32 | m/z = 446.06($C_{28}H_{15}ClN_2S$ = 446.95) |
| Sub 1A-33 | m/z = 422.06($C_{26}H_{15}ClN_2S$ = 422.93) | Sub 1A-34 | m/z = 346.03($C_{20}H_{11}ClN_2S$ = 346.83) |
| Sub 1A-35 | m/z = 446.06($C_{28}H_{15}ClN_2S$ = 446.95) | Sub 1A-36 | m/z = 452.02($C_{16}H_{13}ClN_2S_2$ = 452.98) |
| Sub 1A-37 | m/z = 446.06($C_{28}H_{15}ClN_2S$ = 446.95) | Sub 1A-38 | m/z = 280.04($C_{16}H_9ClN_2O$ = 280.71) |
| Sub 1A-39 | m/z = 330.06($C_{20}H_{11}ClN_2O$ = 330.77) | Sub 1A-40 | m/z = 330.06($C_{20}H_{11}ClN_2O$ = 330.77) |
| Sub 1A-41 | m/z = 356.07($C_{22}H_{13}ClN_2O$ = 356.80) | Sub 1A-42 | m/z = 406.09($C_{26}H_{15}ClN_2O$ = 406.86) |
| Sub 1A-43 | m/z = 432.10($C_{28}H_{17}ClN_2O$ = 432.90) | Sub 1A-44 | m/z = 380.07($C_{24}H_{13}ClN_2O$ = 380.83) |
| Sub 1A-45 | m/z = 396.10($C_{25}H_{17}ClN_2O$ = 396.87) | Sub 1A-46 | m/z = 510.12($C_{32}H_{19}ClN_4O$ = 510.97) |
| Sub 1A-47 | m/z = 814.25($C_{56}H_{35}ClN_4O$ = 815.36) | Sub 1A-48 | m/z = 612.15($C_{38}H_{21}ClN_6O$ = 613.07) |
| Sub 1A-49 | m/z = 664.18($C_{42}H_{25}ClN_6O$ = 665.14) | Sub 1A-50 | m/z = 511.12($C_{31}H_{18}ClN_5O$ = 511.96) |
| Sub 1A-51 | m/z = 663.18($C_{43}H_{26}ClN_5O$ = 664.15) | Sub 1A-52 | m/z = 665.17($C_{41}H_{24}ClN_7O$ = 666.13) |
| Sub 1A-53 | m/z = 533.13($C_{35}H_{20}ClN_3O$ = 534.01) | Sub 1A-54 | m/z = 484.11($C_{30}H_{17}ClN_4O$ = 484.94) |
| Sub 1A-55 | m/z = 561.14($C_{35}H_{20}ClN_5O$ = 562.02) | Sub 1A-56 | m/z = 640.11($C_{40}H_{21}ClN_4OS$ = 641.14) |

TABLE 1-continued

| Compound | FD-MS | Compound | FD-MS |
|---|---|---|---|
| Sub 1A-57 | m/z = 585.14($C_{37}H_{20}ClN_5O$ = 586.04) | Sub 1A-58 | m/z = 484.11($C_{30}H_{17}ClN_4O$ = 484.94) |
| Sub 1A-59 | m/z = 534.12($C_{34}H_{19}ClN_4O$ = 534.99) | Sub 1A-60 | m/z = 584.14($C_{38}H_{21}ClN_4O$ = 585.05) |
| Sub 1A-61 | m/z = 561.14($C_{35}H_{20}ClN_5O$ = 562.02) | Sub 1A-62 | m/z = 560.14($C_{36}H_{21}ClN_4O$ = 561.03) |
| Sub 1A-63 | m/z = 386.03($C_{22}H_{11}ClN_2OS$ = 386.85) | Sub 1A-64 | m/z = 370.05($C_{22}H_{11}ClN_2O_2$ = 370.79) |
| Sub 1A-65 | m/z = 445.10($C_{28}H_{18}ClN_3O$ = 445.90) | Sub 1A-66 | m/z = 380.07($C_{24}H_{13}ClN_2O$ = 380.83) |
| Sub 1A-67 | m/z = 406.09($C_{26}H_{15}ClN_2O$ = 406.86) | Sub 1A-68 | m/z = 482.12($C_{32}H_{19}ClN_2O$ = 482.96) |
| Sub 1A-69 | m/z = 480.10($C_{32}H_{17}ClN_2O$ = 480.94) | | |
| Sub 1B-1 | m/z = 296.02($C_{16}H_9ClN_2S$ = 296.77) | Sub 1B-2 | m/z = 372.05($C_{22}H_{13}ClN_2S$ = 372.87) |
| Sub 1B-3 | m/z = 372.05($C_{22}H_{13}ClN_2S$ = 372.87) | Sub 1B-4 | m/z = 448.08($C_{28}H_{17}ClN_2S$ = 448.97) |
| Sub 1B-5 | m/z = 448.08($C_{78}H_{17}ClN_2S$ = 448.97) | Sub 1B-6 | m/z = 524.11($C_{34}H_{21}ClN_2S$ = 525.06) |
| Sub 1B-7 | m/z = 448.08($C_{28}H_{17}ClN_2S$ = 448.97) | Sub 1B-8 | m/z = 448.08($C_{28}H_{17}ClN_2S$ = 448.97) |
| Sub 1B-9 | m/z = 524.11($C_{34}H_{21}ClN_2S$ = 525.06) | Sub 1B-10 | m/z = 472.08($C_{30}H_{17}ClN_2S$ = 472.99) |
| Sub 1B-11 | m/z = 472.08($C_{30}H_{17}ClN_2S$ = 472.99) | Sub 1B-12 | m/z = 522.10($C_{34}H_{19}ClN_2S$ = 523.05) |
| Sub 1B-13 | m/z = 472.08($C_{30}H_{17}ClN_2S$ = 472.99) | Sub 1B-14 | m/z = 472.08($C_{30}H_{17}ClN_2S$ = 472.99) |
| Sub 1B-15 | m/z = 522.10($C_{34}H_{19}ClN_2S$ = 523.05) | Sub 1B-16 | m/z = 526.10($C_{32}H_{19}ClN_4S$ = 527.04) |
| Sub 1B-17 | m/z = 526.10($C_{32}H_{19}ClN_4S$ = 527.04) | Sub 1B-18 | m/z = 526.10($C_{32}H_{19}ClN_4S$ = 527.04) |
| Sub 1B-19 | m/z = 527.10($C_{31}H_{18}ClN_3S$ = 528.03) | Sub 1B-20 | m/z = 526.10($C_{37}H_{19}ClN_4S$ = 527.04) |
| Sub 1B-21 | m/z = 526.10($C_{37}H_{19}ClN_4S$ = 527.04) | Sub 1B-22 | m/z = 526.10($C_{37}H_{19}ClN_4S$ = 527.04) |
| Sub 1B-23 | m/z = 527.10($C_{31}H_{18}ClN_5S$ = 528.03) | Sub 1B-24 | m/z = 602.13($C_{38}H_{23}ClN_4S$ = 603.13) |
| Sub 1B-25 | m/z = 429.02($C_{23}H_{12}ClN_3S_2$ = 429.94) | Sub 1B-26 | m/z = 478.04($C_{28}H_{15}ClN_2S_2$ = 479.02) |
| Sub 1B-27 | m/z = 478.04($C_{28}H_{15}ClN_2S_2$ = 479.02) | Sub 1B-28 | m/z = 537.11($C_{34}H_{20}ClN_3S$ = 538.06) |
| Sub 1B-29 | m/z = 556.06($C_{32}H_{17}ClN_4S_2$ = 557.09) | Sub 1B-30 | m/z = 478.04($C_{28}H_{15}ClN_2S_2$ = 479.02) |
| Sub 1B-31 | m/z = 478.04($C_{28}H_{15}ClN_2S_2$ = 479.02) | Sub 1B-32 | m/z = 537.11($C_{34}H_{20}ClN_3S$ = 538.06) |
| Sub 1B-33 | m/z = 429.02($C_{23}H_{12}ClN_3S_2$ = 429.94) | Sub 1B-34 | m/z = 556.06($C_{32}H_{17}ClN_4S_2$ = 557.09) |
| Sub 1B-35 | m/z = 461.08($C_{28}H_{16}ClN_3S$ = 461.96) | Sub 1B-36 | m/z = 461.08($C_{28}H_{16}ClN_3S$ = 461.96) |
| Sub 1B-37 | m/z = 765.20($C_{52}H_{32}ClN_3S$ = 766.35) | Sub 1B-38 | m/z = 280.04($C_{16}H_9ClN_2O$ = 280.71) |
| Sub 1B-39 | m/z = 330.06($C_{20}H_{11}ClN_2O$ = 330.77) | Sub 1B-40 | m/z = 356.07($C_{22}H_{13}ClN_2O$ = 356.80) |
| Sub 1B-41 | m/z = 610.16($C_{40}H_{23}ClN_4O$ = 611.09) | Sub 1B-42 | m/z = 511.12($C_{31}H_{18}ClN_2O$ = 511.96) |
| Sub 1B-43 | m/z = 586.16($C_{38}H_{23}ClN_4O$ = 587.07) | Sub 1B-44 | m/z = 484.11($C_{30}H_{17}ClN_4O$ = 484.94) |

II. Synthesis of Sub 2

Sub 2 of Reaction Scheme 1 above may be synthesized by reaction pathways of Reaction Scheme 12 and Reaction Scheme 13, but are not limited thereto.

<Reaction Scheme 12>

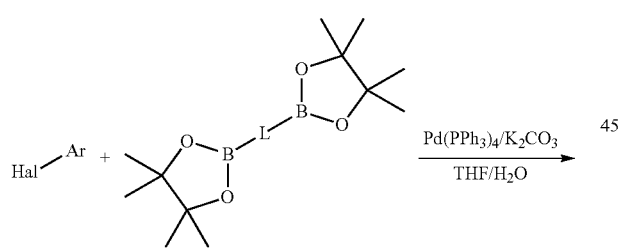

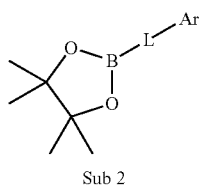

Sub 2

<Reaction Scheme 13>

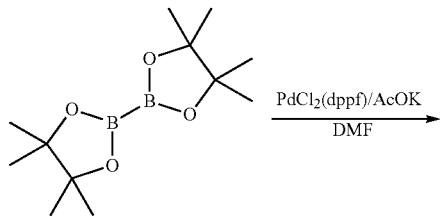

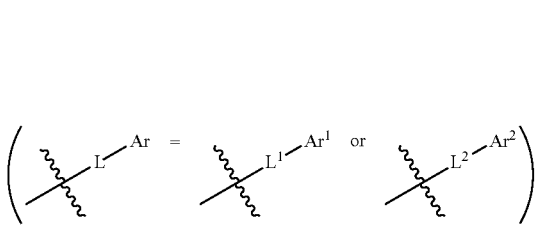

Sub 2

Ar and L are defined as below, and Hal is Br or Cl.

Synthesis Embodiments of specific compounds pertaining to Sub 2 are as follows.

1. Synthesis Embodiment of Sub 2-1

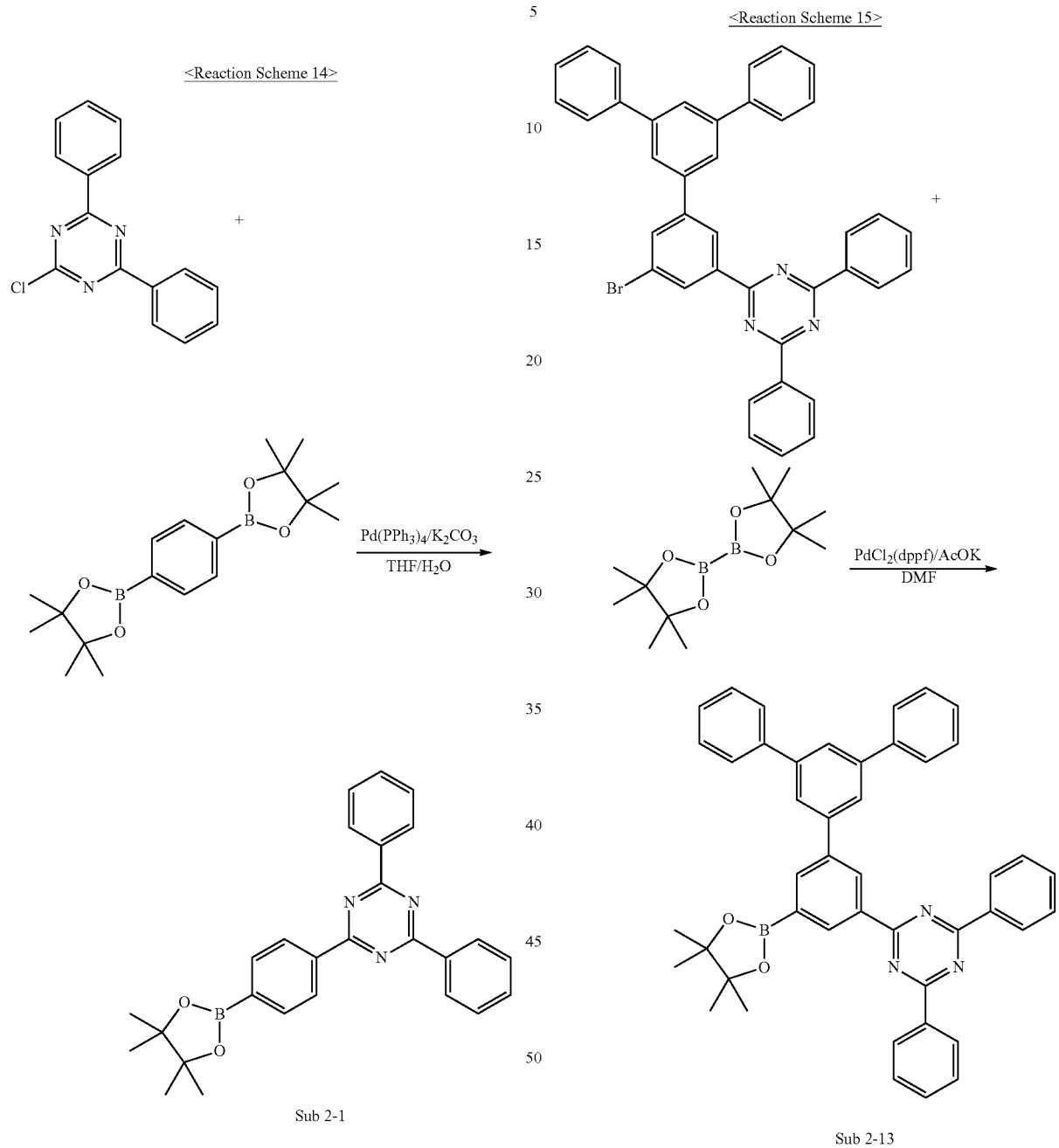

Sub 2-1

A starting material, 2-chloro-4,6-diphenyl-1,3,5-triazine (42.86 g, 160.1 mmol) was dissolved in THF in a round-bottom flask, and then 1,4-bis(4,4,5,5-tetramethyl-1,3,2-dioxaborolan-2-yl)benzene (58.12 g, 176.1 mmol), Pd(PPh$_3$)$_4$ (7.4 g, 6.4 mmol), K$_2$CO$_3$ (66.38 g, 480.3 mmol), and water were added thereto, followed by stirring at 80☐. Upon completion of the reaction, the reaction product was extracted with CH$_2$Cl$_2$ and water. The organic layer was dried over MgSO$_4$ and concentrated, and then, the compound obtained was subjected to a silica gel column and recrystallization to give a product 28.58 g (yield: 41%).

2. Synthesis Embodiment of Sub 2-13

Sub 2-13

A starting material, 2-(5-bromo-5'-phenyl-[1,1':3',1''-terphenyl]-3-yl)-4,6-diphenyl-1,3,5-triazine (17.92 g, 29.1 mmol) was dissolved in DMF in a round-bottom flask, and then Bis(pinacolato)diboron (8.12 g, 32 mmol), Pd(dppf)Cl$_2$ (0.71 g, 0.9 mmol), KOAc (8.56 g, 87.2 mmol) were added thereto, followed by stirring at 90☐. Upon completion of the reaction, DMF was removed through distillation, followed by extraction with CH$_2$Cl$_2$ and water. The organic layer was dried over MgSO$_4$ and concentrated, and then, the compound obtained was subjected to a silica gel column and recrystallization to give a product 11.38 g (yield: 59%).

3. Synthesis Embodiment of Sub 2-15

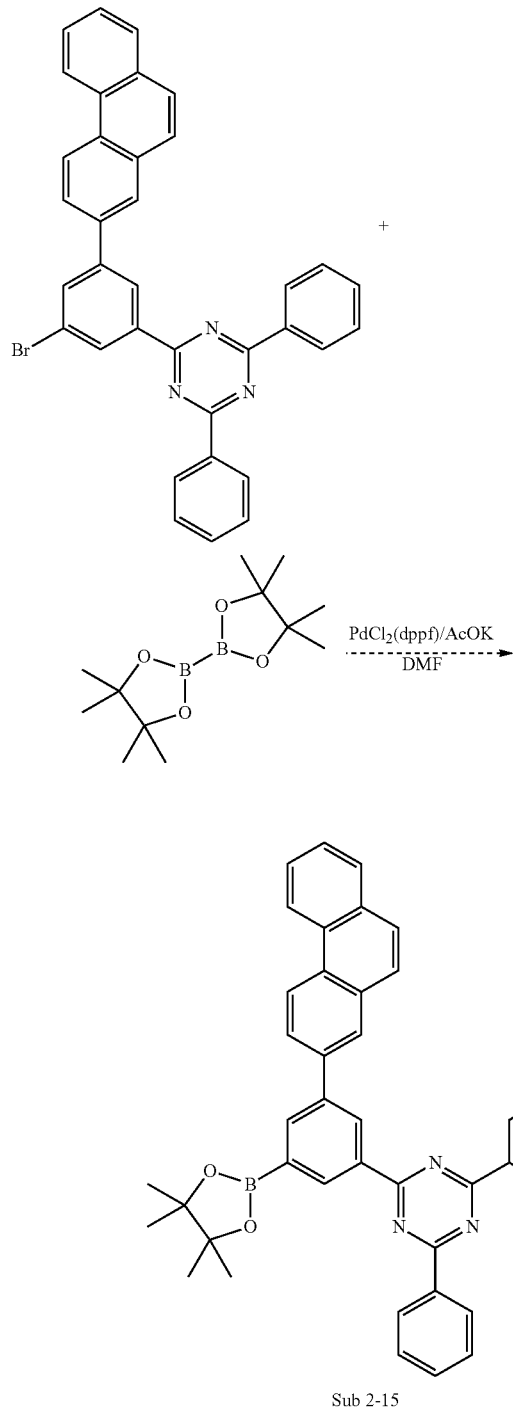

<Reaction Scheme 16>

Sub 2-15

In addition to 2-(3-bromo-5-(phenanthren-2-yl)phenyl)-4,6-diphenyl-1,3,5-triazine (16.53 g, 29.3 mmol) as a starting material, Bis(pinacolato)diboron (8.18 g, 32.2 mmol), Pd(dppf)Cl$_2$ (0.72 g, 0.9 mmol), KOAc (8.62 g, 87.9 mmol), and DMF were used under the synthesis method of Sub 2-13, to give a product 10.92 g (yield: 61%).

4. Synthesis Embodiment of Sub 2-42

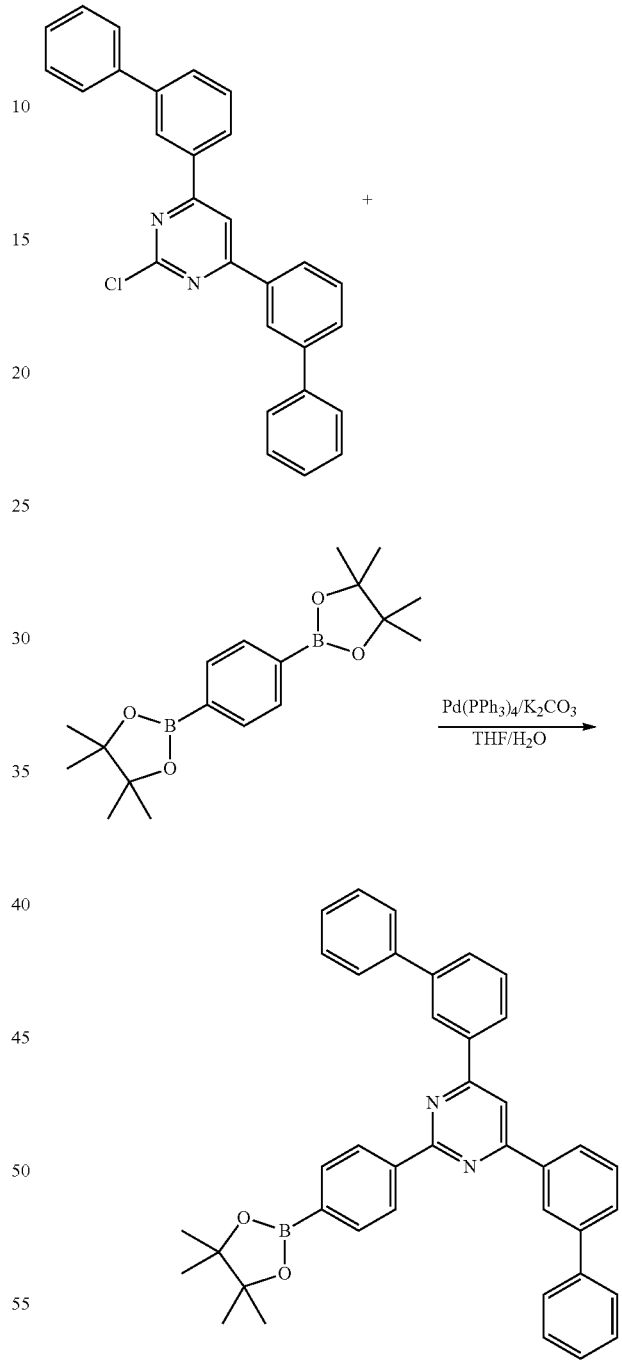

<Reaction Scheme 17>

Sub 2-42

In addition to 4,6-di([1,1'-biphenyl]-3-yl)-2-chloropyrimidine (17.21 g, 41.1 mmol) as a starting material, 1,4-bis(4,4,5,5-tetramethyl-1,3,2-dioxaborolan-2-yl)benzene (14.91 g, 45.2 mmol), Pd(PPh$_3$)$_4$ (1.9 g, 1.6 mmol), K$_2$CO$_3$ (17.03 g, 123.2 mmol), THF, and water were used under the synthesis method of Sub 2-1, to give a product 9.16 g (yield: 38%).

5. Synthesis Embodiment of Sub 2-88

<Reaction Scheme 18>

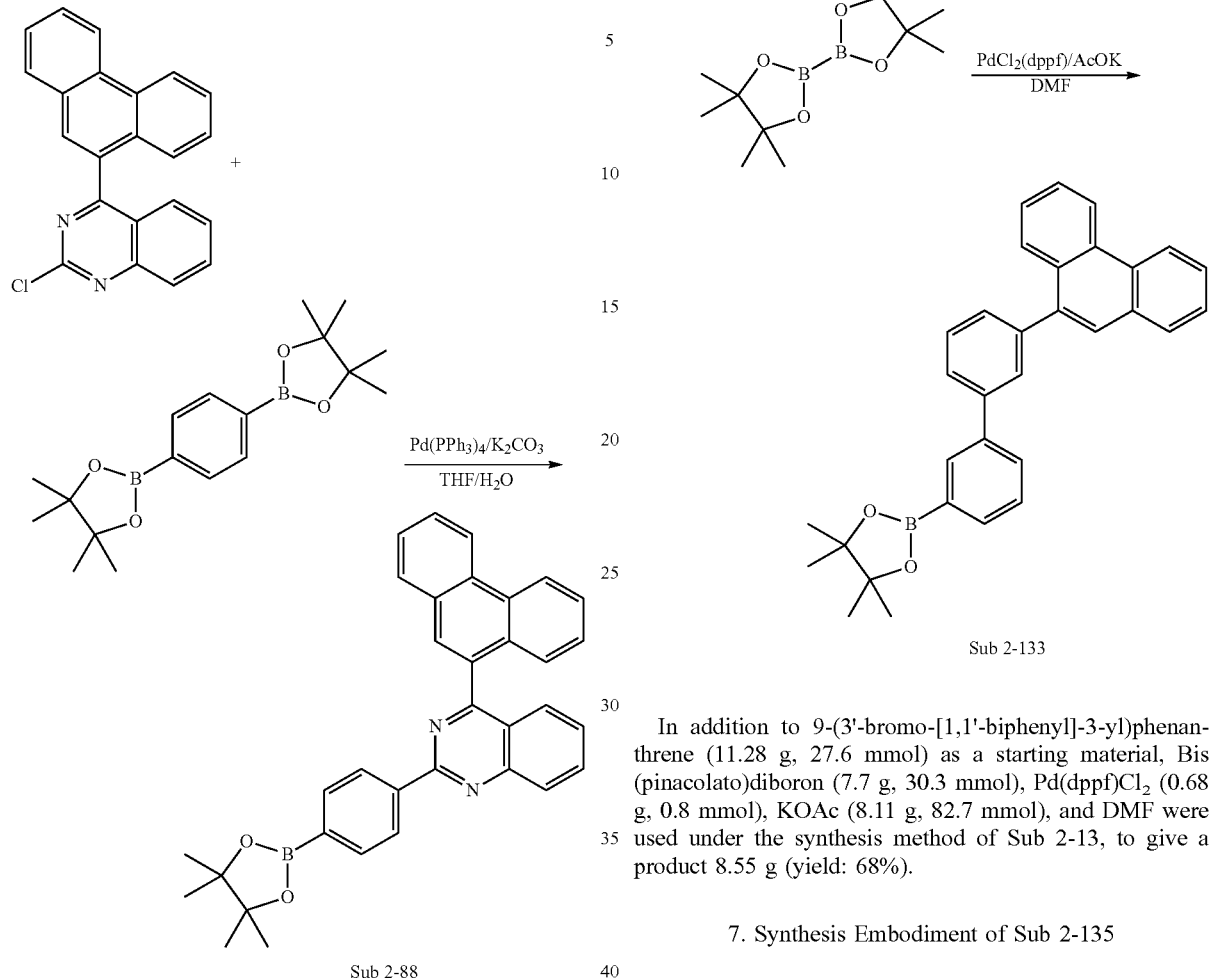

Sub 2-88

In addition to 2-chloro-4-(phenanthren-9-yl)quinazoline (54.73 g, 160.6 mmol) as a starting material, 1,4-bis(4,4,5,5-tetramethyl-1,3,2-dioxaborolan-2-yl)benzene (58.3 g, 176.6 mmol), Pd(PPh₃)₄ (7.42 g, 6.4 mmol), K₂CO₃ (66.58 g, 481.8 mmol), THF, and water were used under the synthesis method of Sub 2-1, to give a product 29.39 g (yield: 36%).

6. Synthesis Embodiment of Sub 2-133

<Reaction Scheme 19>

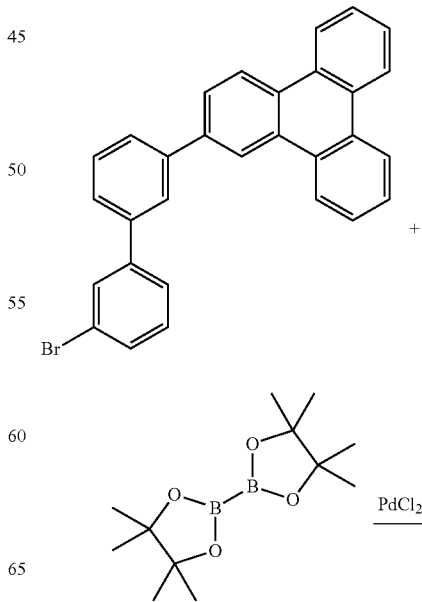

Sub 2-133

In addition to 9-(3'-bromo-[1,1'-biphenyl]-3-yl)phenanthrene (11.28 g, 27.6 mmol) as a starting material, Bis(pinacolato)diboron (7.7 g, 30.3 mmol), Pd(dppf)Cl₂ (0.68 g, 0.8 mmol), KOAc (8.11 g, 82.7 mmol), and DMF were used under the synthesis method of Sub 2-13, to give a product 8.55 g (yield: 68%).

7. Synthesis Embodiment of Sub 2-135

<Reaction Scheme 20>

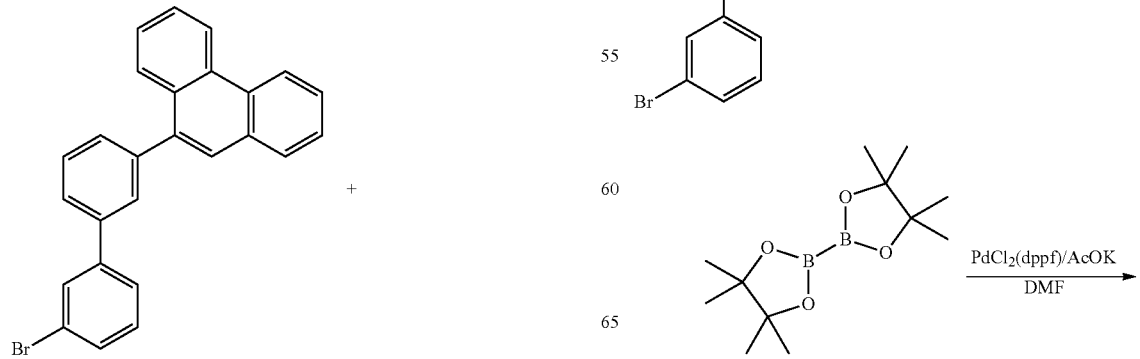

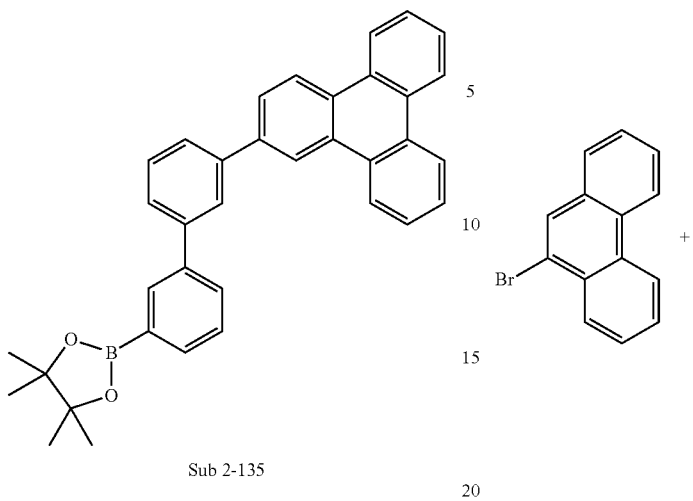

Sub 2-135

In addition to 2-(3'-bromo-[1,1'-biphenyl]-3-yl)triphenylene (13.49 g, 29.4 mmol) as a starting material, Bis(pinacolato)diboron (8.2 g, 32.3 mmol), Pd(dppf)Cl₂ (0.72 g, 0.9 mmol), KOAc (8.65 g, 88.1 mmol), and DMF were used under the synthesis method of Sub 2-13, to give a product 9.52 g (yield: 64%).

8. Synthesis Embodiment of Sub 2-136

<Reaction Scheme 21>

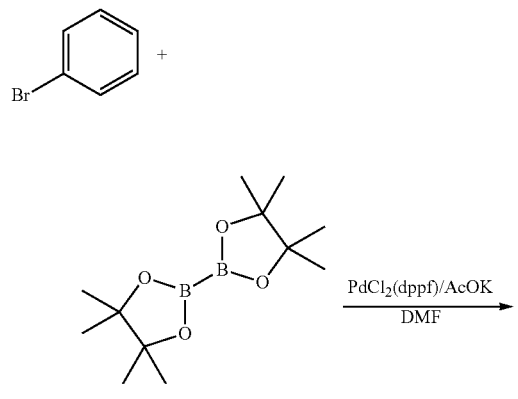

Sub 2-136

In addition to bromobenzene (88.71 g, 565 mmol) as a starting material, Bis(pinacolato)diboron (157.82 g, 621.5 mmol), Pd(dppf)Cl₂ (13.84 g, 16.9 mmol), KOAc (166.35 g, 1695 mmol), and DMF were used under the synthesis method of Sub 2-13, to give a product 99.16 g (yield: 86%).

9. Synthesis Embodiment of Sub 2-146

<Reaction Scheme 22>

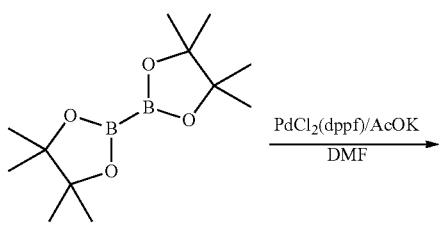

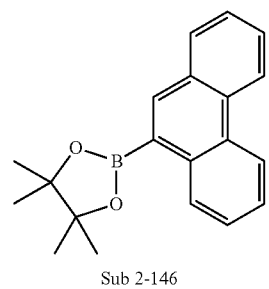

Sub 2-146

In addition to 9-bromophenanthrene (21.04 g, 81.8 mmol) as a starting material, Bis(pinacolato)diboron (22.86 g, 90 mmol), Pd(dppf)Cl₂ (2 g, 2.5 mmol), KOAc (24.09 g, 245.5 mmol), and DMF were used under the synthesis method of Sub 2-13, to give a product 18.17 g (yield: 73%).

10. Synthesis Embodiment of Sub 2-162

<Reaction Scheme 23>

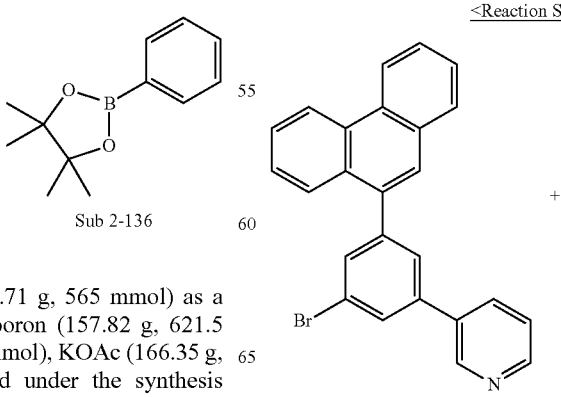

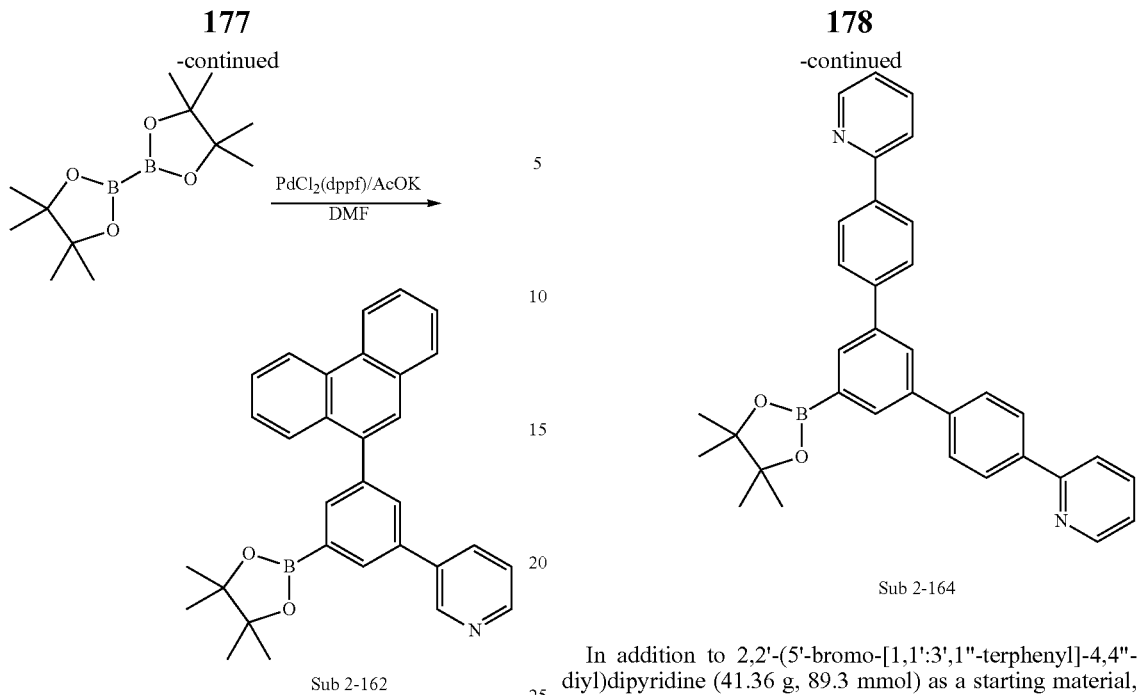

Sub 2-162

In addition to 3-(3-bromo-5-(phenanthren-9-yl)phenyl)pyridine (26.32 g, 64.1 mmol) as a starting material, Bis(pinacolato)diboron (17.92 g, 70.6 mmol), Pd(dppf)Cl₂ (1.57 g, 1.9 mmol), KOAc (18.89 g, 192.4 mmol), and DMF were used under the synthesis method of Sub 2-13, to give a product 16.72 g (yield: 57%).

11. Synthesis Embodiment of Sub 2-164

<Reaction Scheme 24>

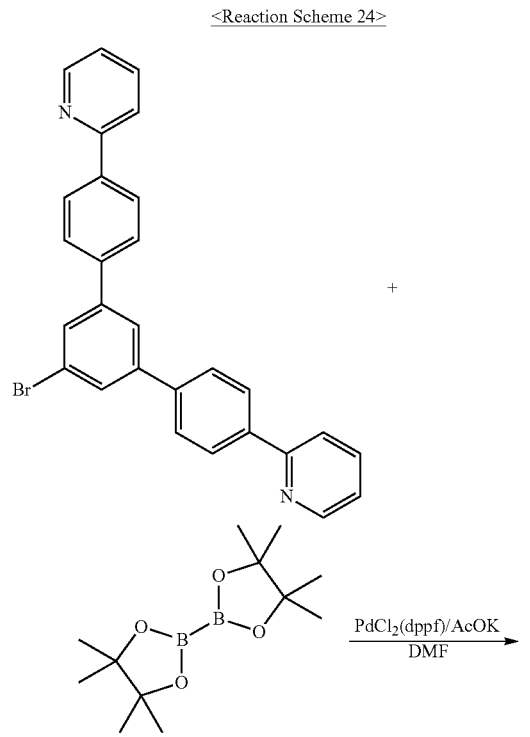

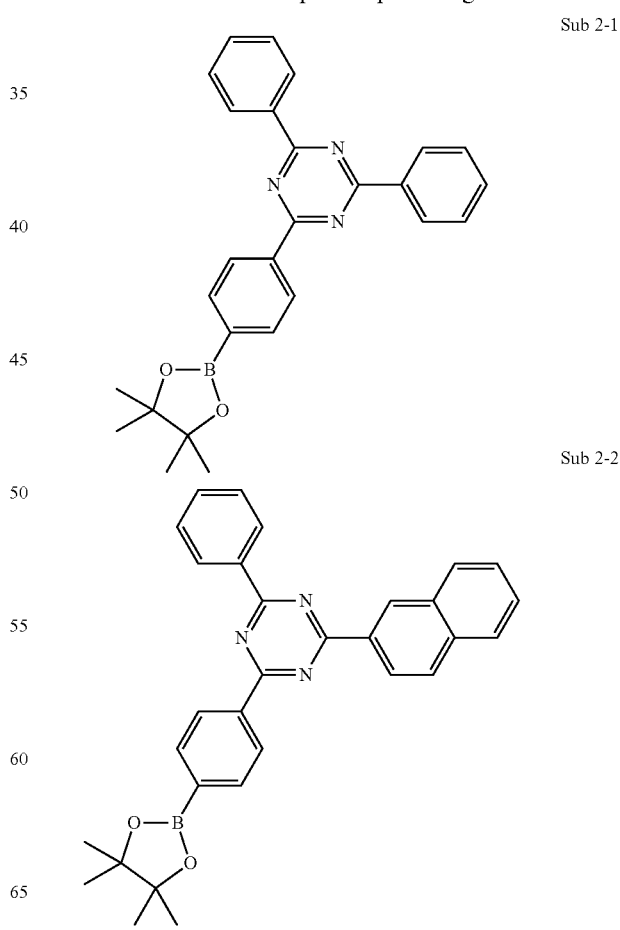

Sub 2-164

In addition to 2,2'-(5'-bromo-[1,1':3',1''-terphenyl]-4,4''-diyl)dipyridine (41.36 g, 89.3 mmol) as a starting material, Bis(pinacolato)diboron (24.93 g, 98.2 mmol), Pd(dppf)Cl₂ (2.19 g, 2.7 mmol), KOAc (26.28 g, 267.8 mmol), and DMF were used under the synthesis method of Sub 2-13, to give a product 34.17 g (yield: 75%).

The compounds pertaining to Sub 2 may be compounds below, but are not limited thereto. Table 2 below shows FD-MS values of the compounds pertaining to Sub 2.

Sub 2-3
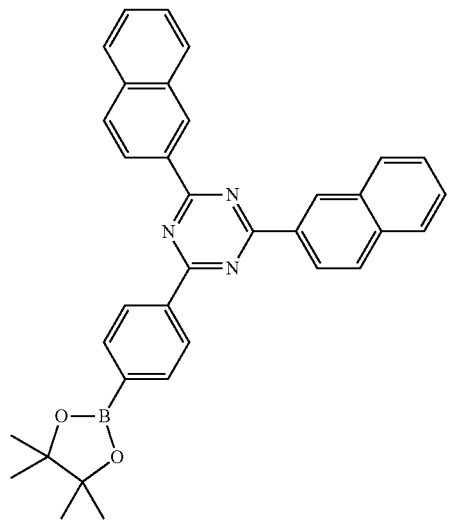
Sub 2-4
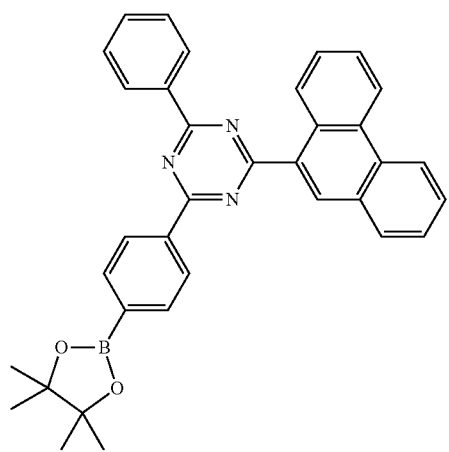
Sub 2-5
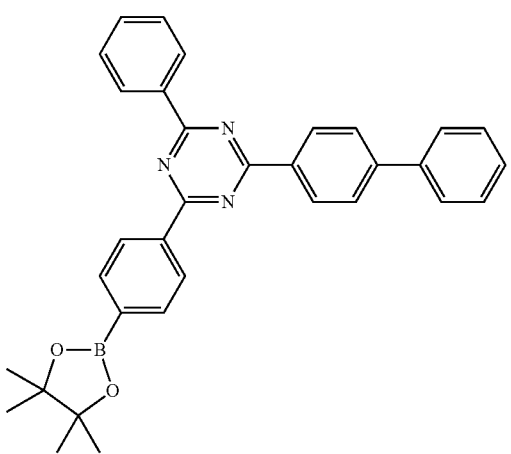
Sub 2-6
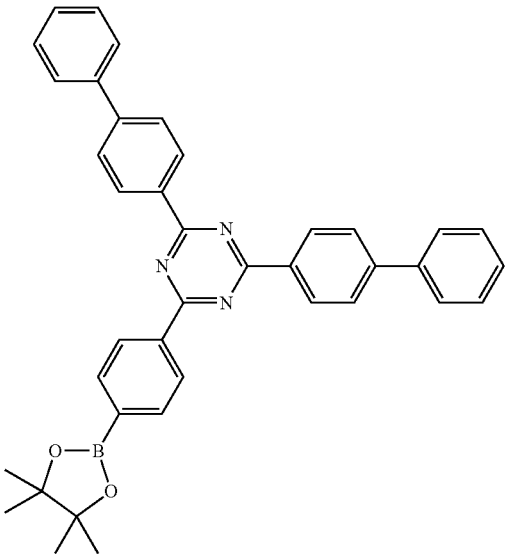
Sub 2-7
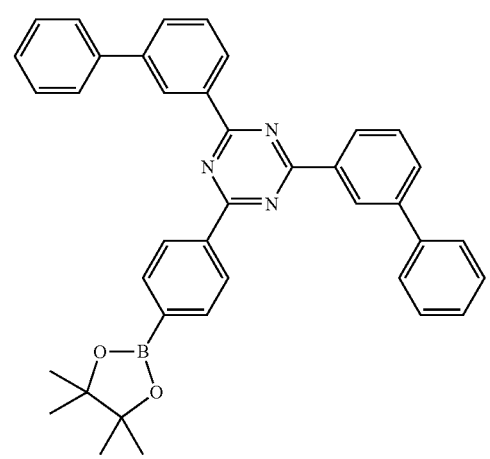
Sub 2-8
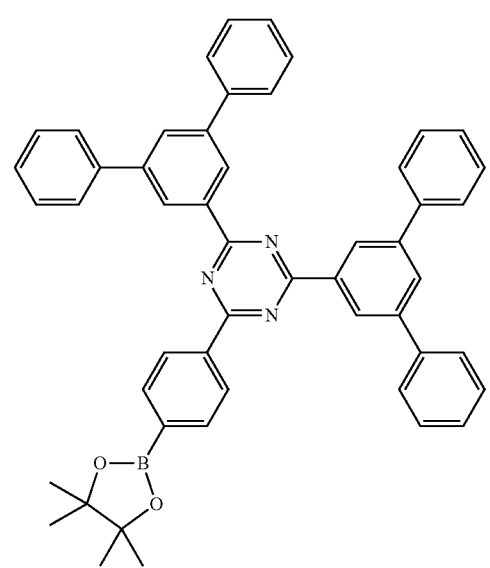

Sub 2-9
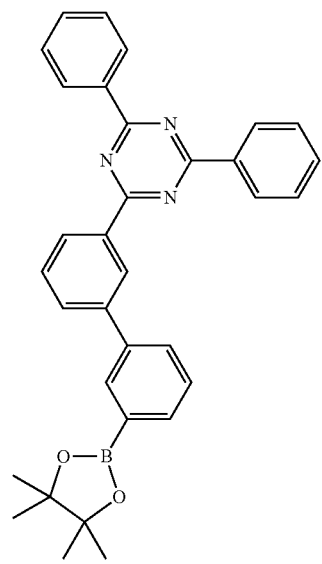
Sub 2-13
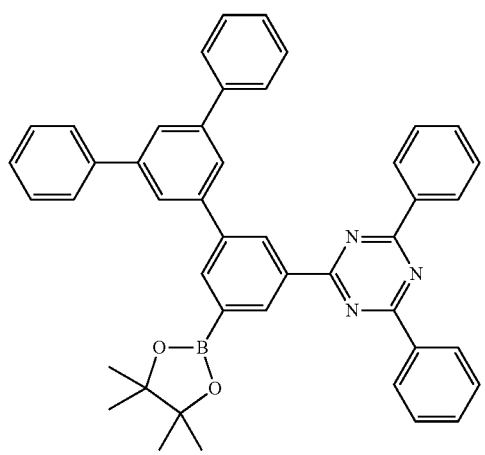
Sub 2-10
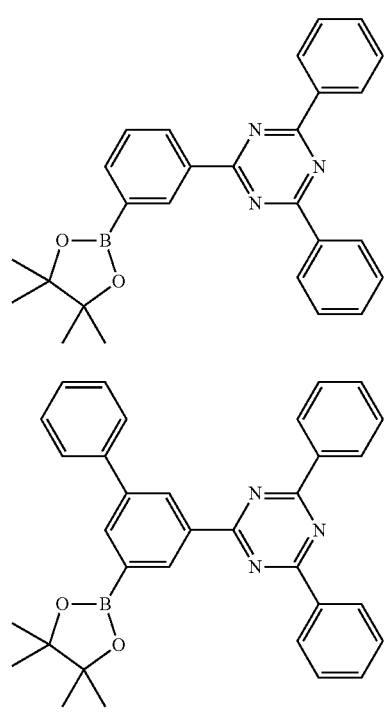
Sub 2-14
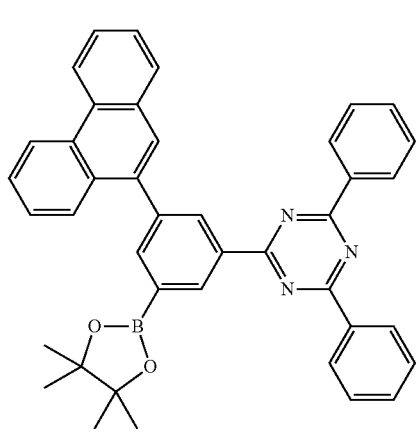
Sub 2-11
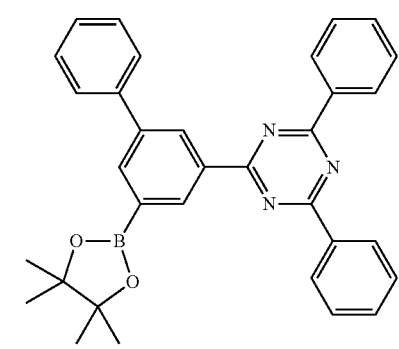
Sub 2-15
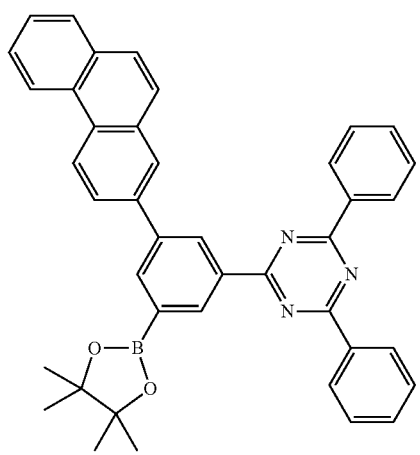
Sub 2-12
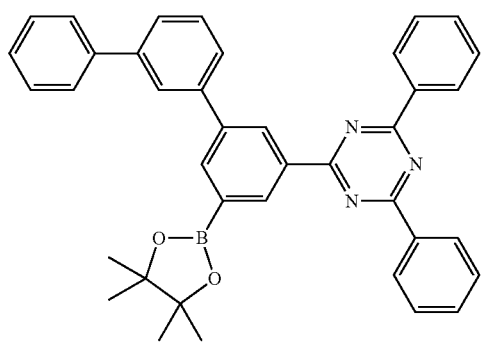

Sub 2-16
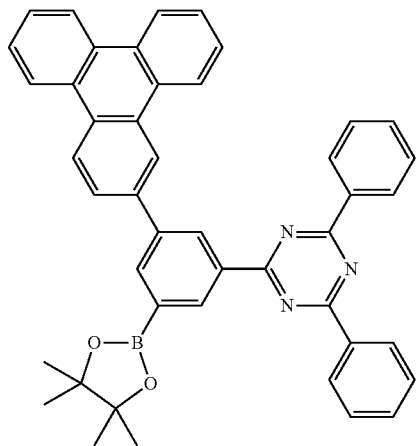
Sub 2-17
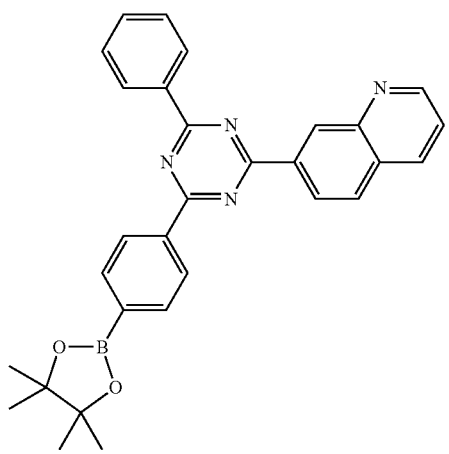
Sub 2-18
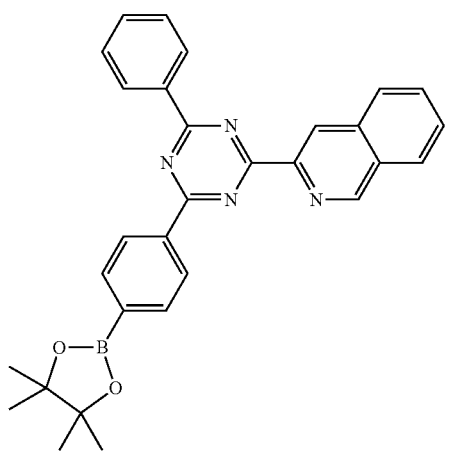
Sub 2-19
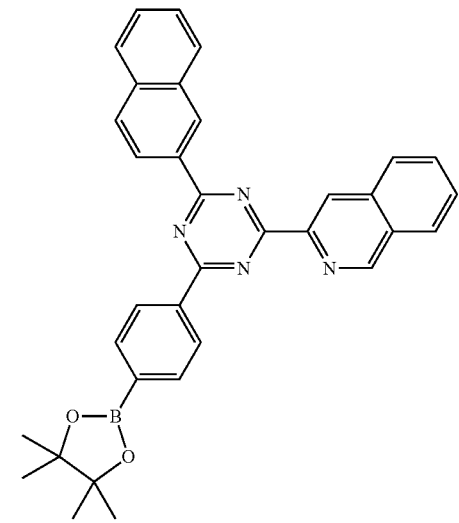
Sub 2-20
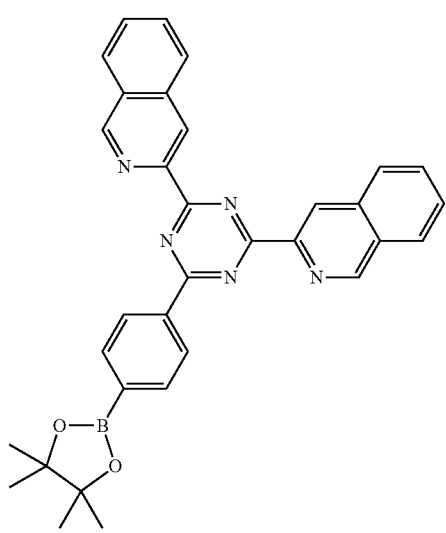
Sub 2-21
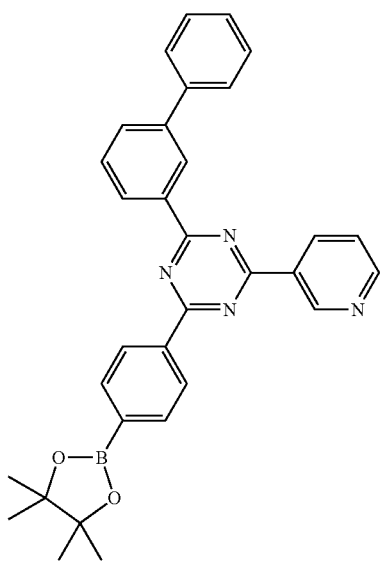

Sub 2-22
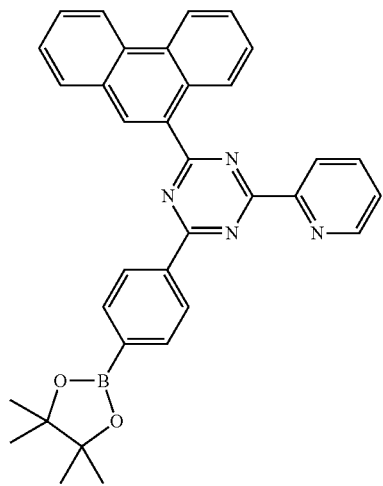
Sub 2-23
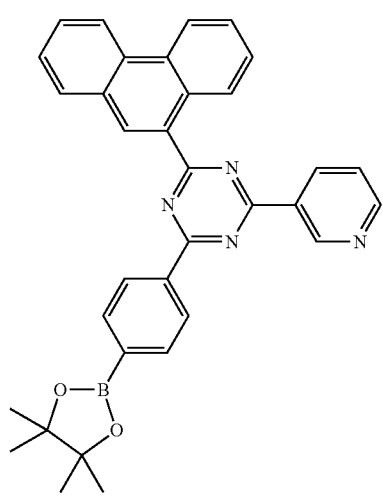
Sub 2-24
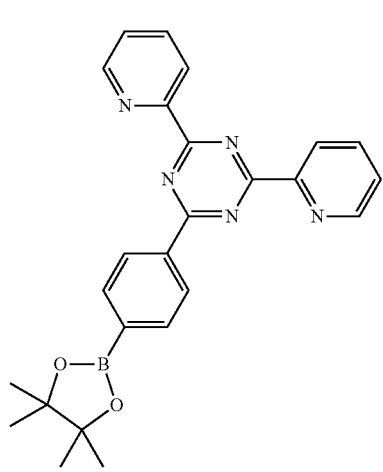
Sub 2-25
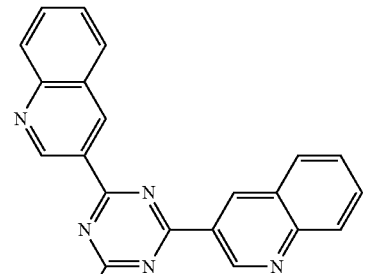
Sub 2-26
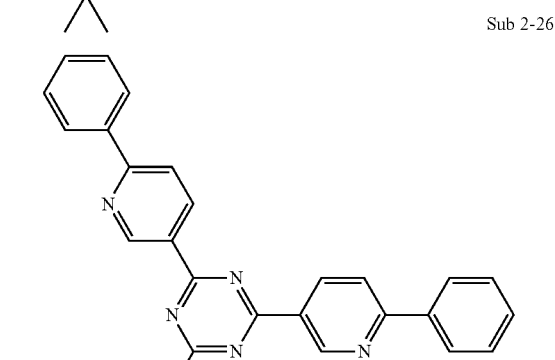
Sub 2-27
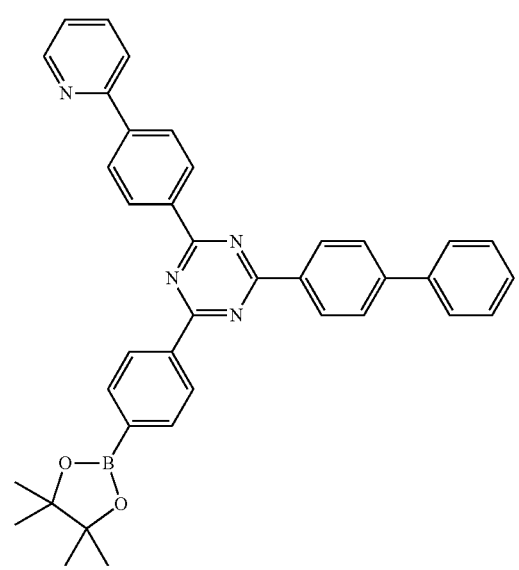

Sub 2-28
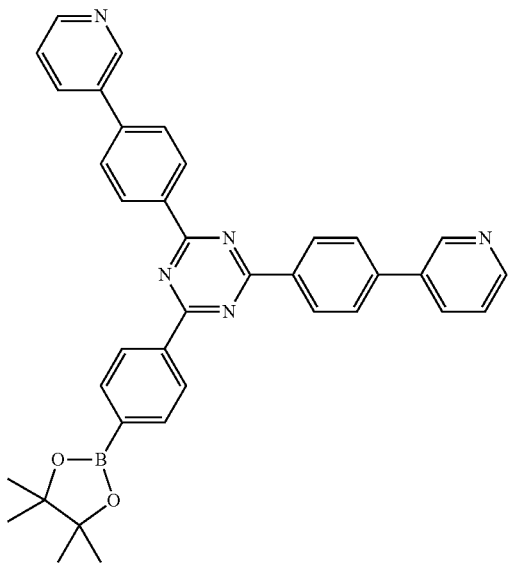
Sub 2-31
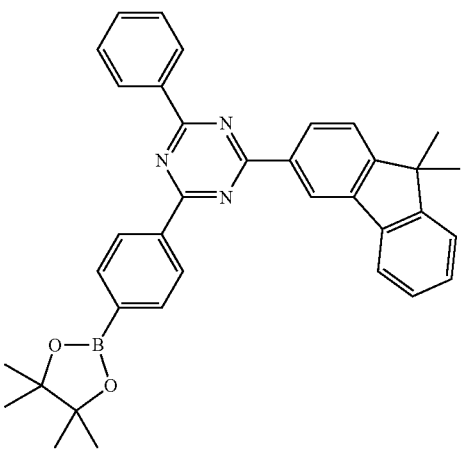
Sub 2-29
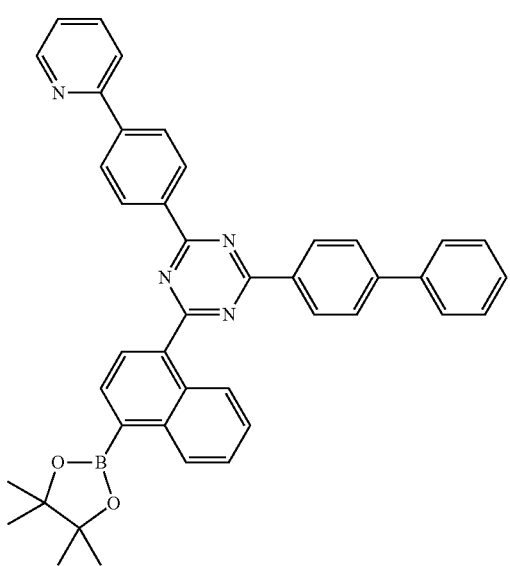
Sub 2-32
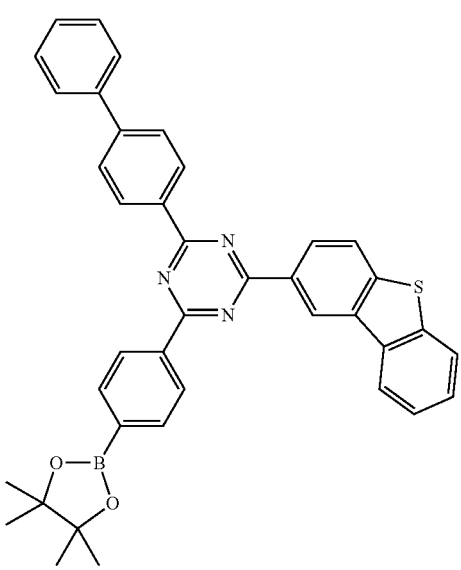
Sub 2-30
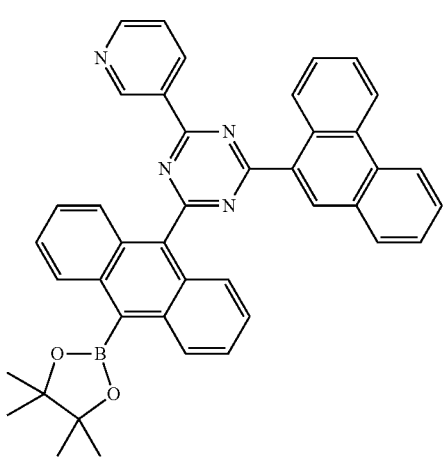
Sub 2-33
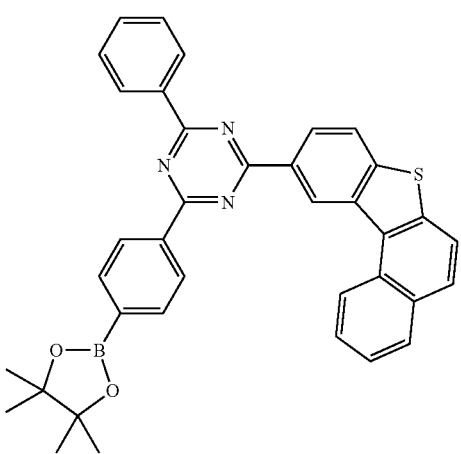

-continued
Sub 2-34
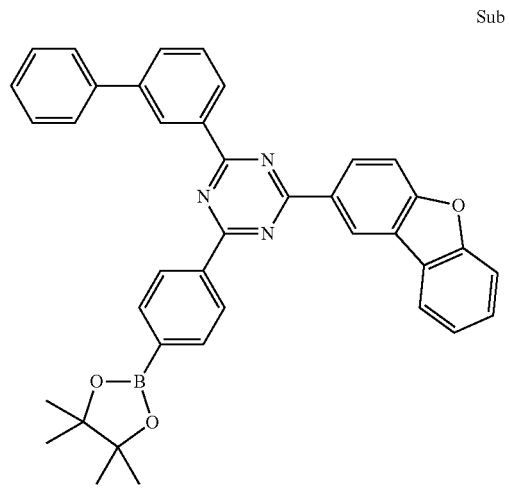
Sub 2-35
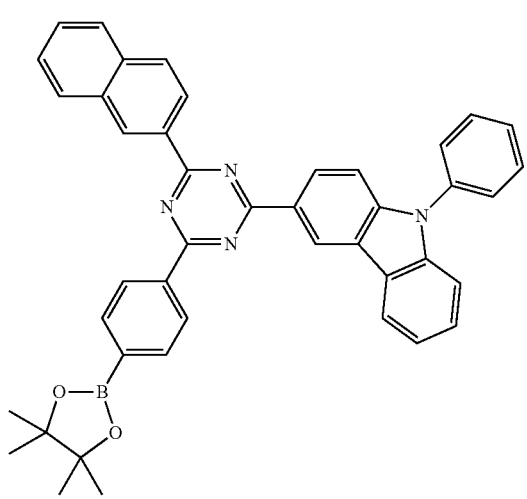
Sub 2-36
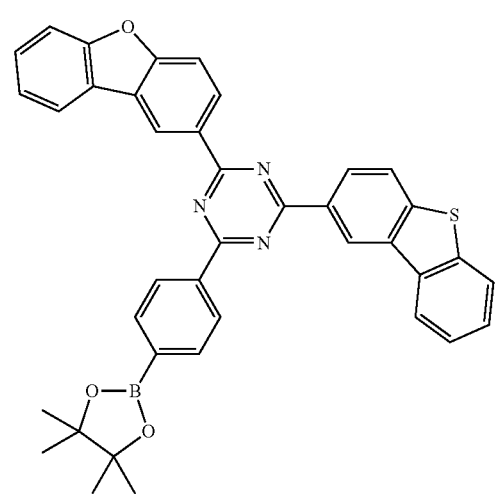
-continued
Sub 2-37
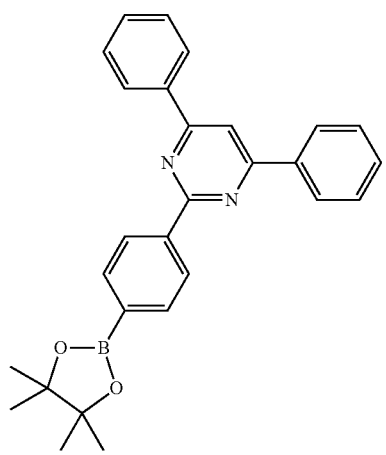
Sub 2-38
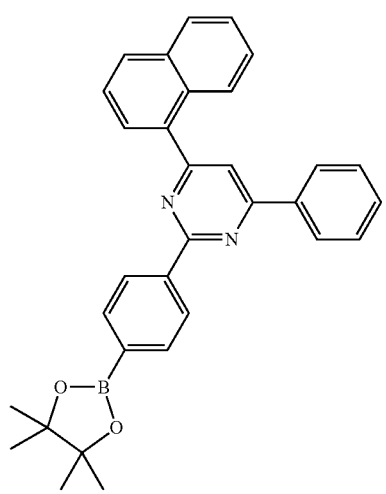
Sub 2-39
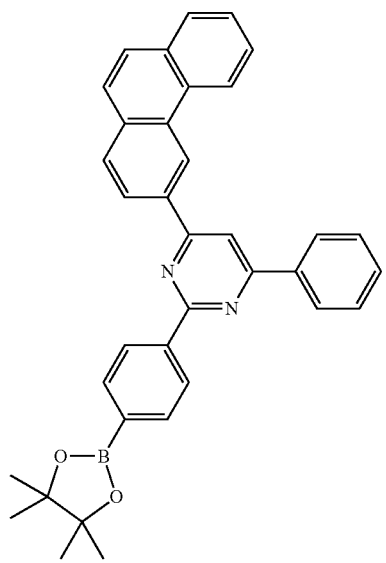

Sub 2-40
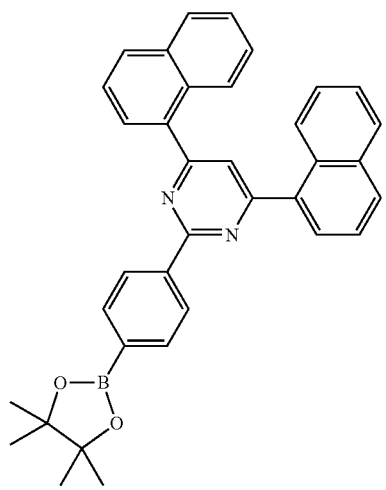
Sub 2-41
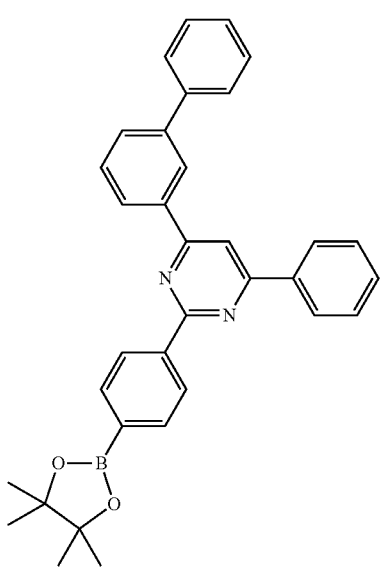
Sub 2-42
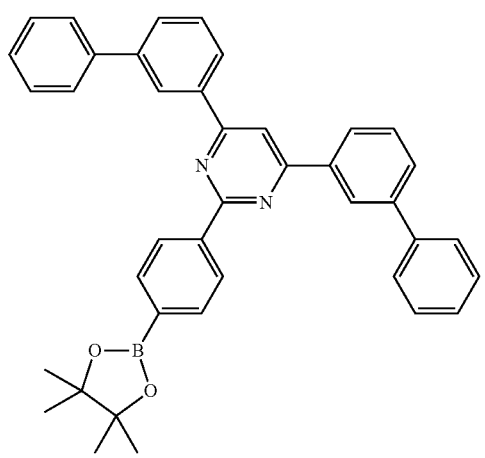
Sub 2-43
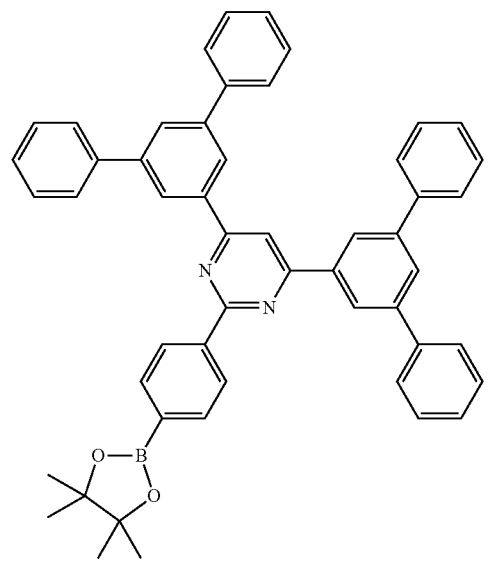
Sub 2-44
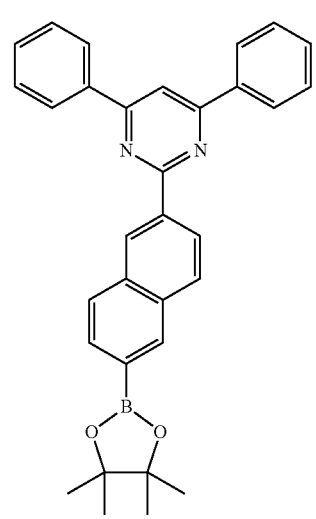
Sub 2-45
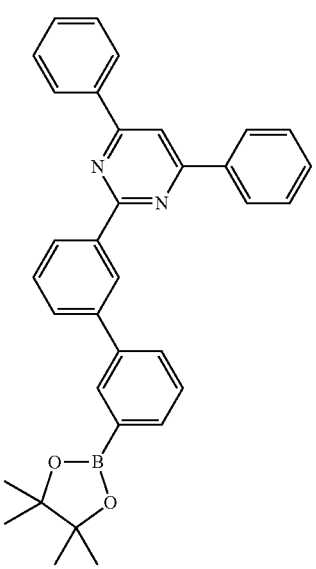

Sub 2-46
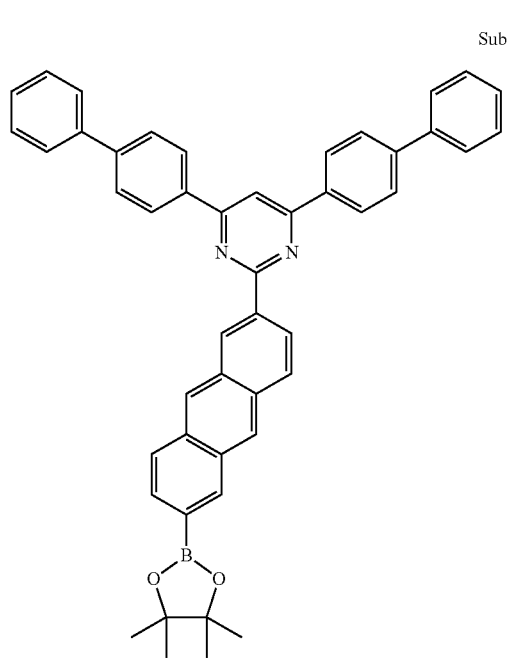
Sub 2-49
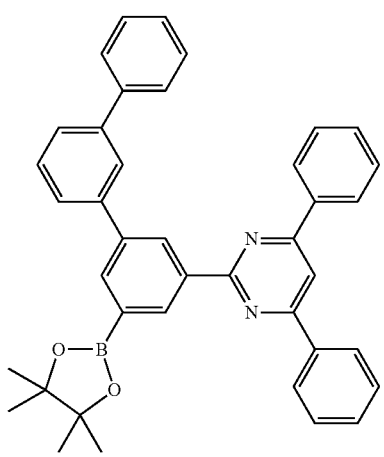
Sub 2-47
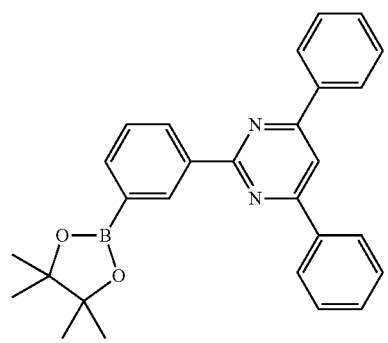
Sub 2-50
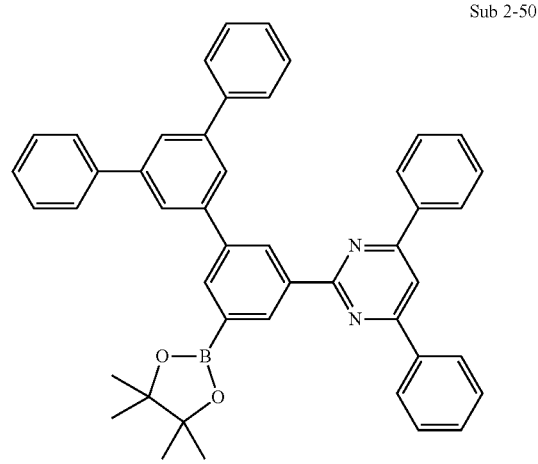
Sub 2-48
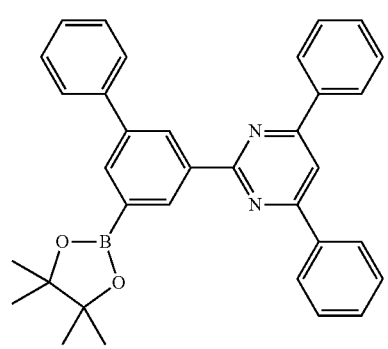
Sub 2-51
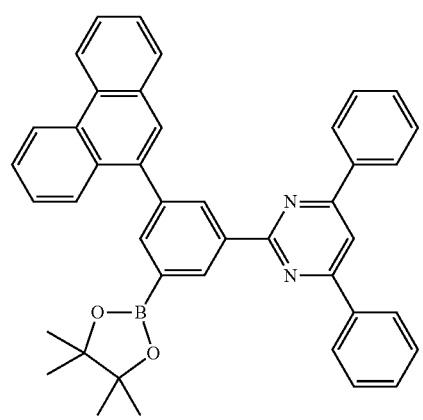

Sub 2-52
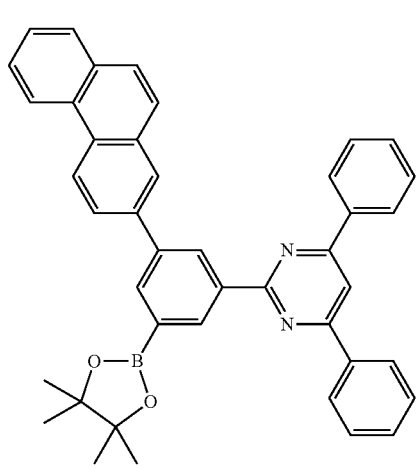
Sub 2-53
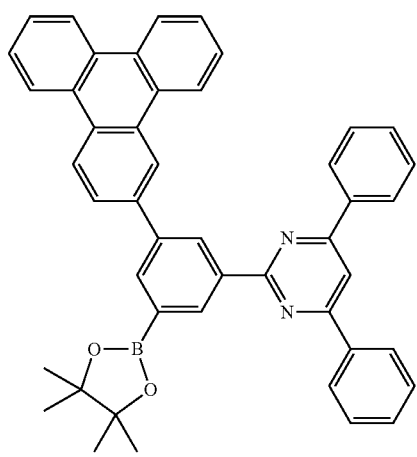
Sub 2-54
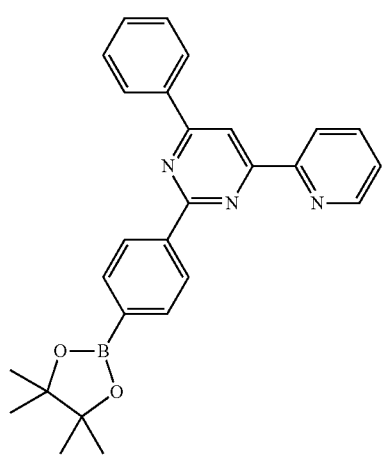
Sub 2-55
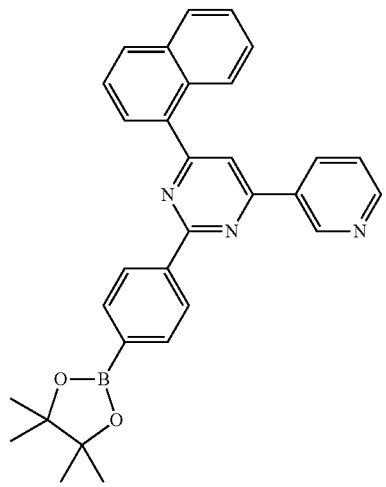
Sub 2-56
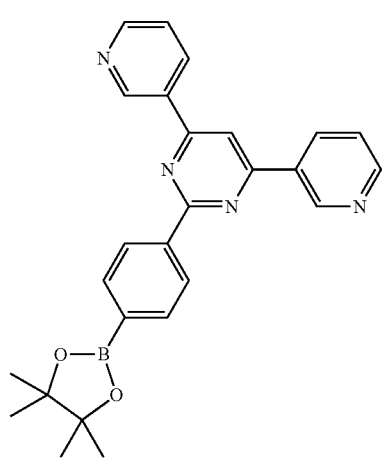
Sub 2-57
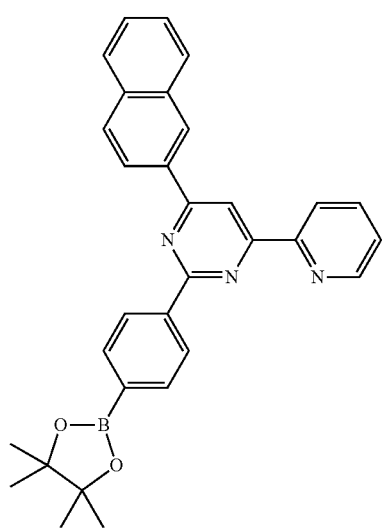

Sub 2-58
Sub 2-59
Sub 2-60
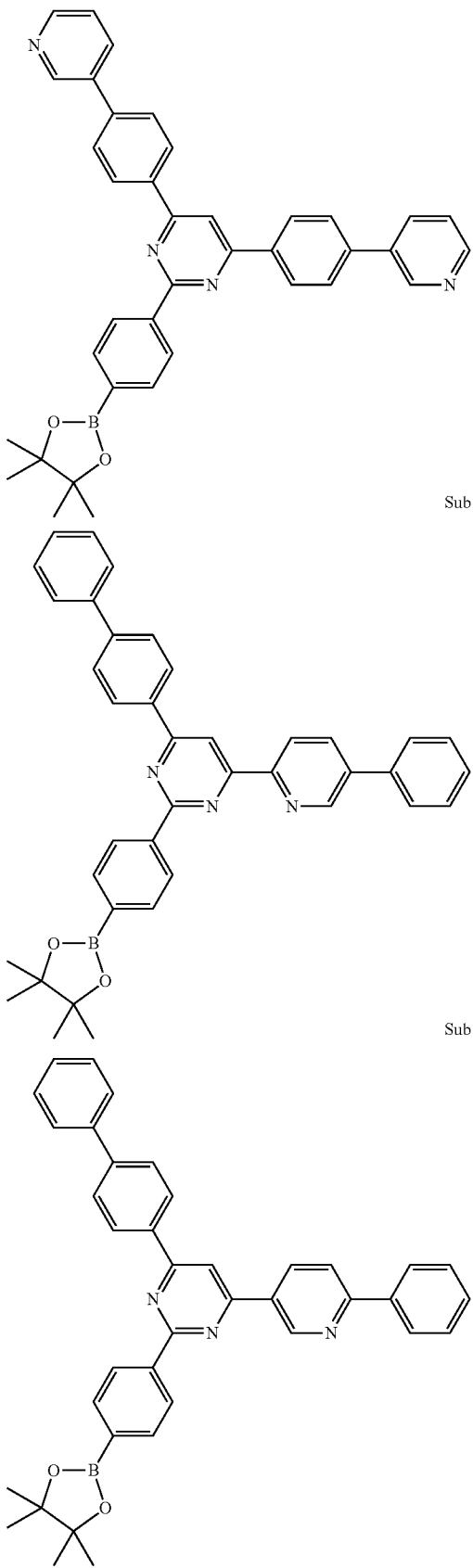
Sub 2-61
Sub 2-62
Sub 2-63
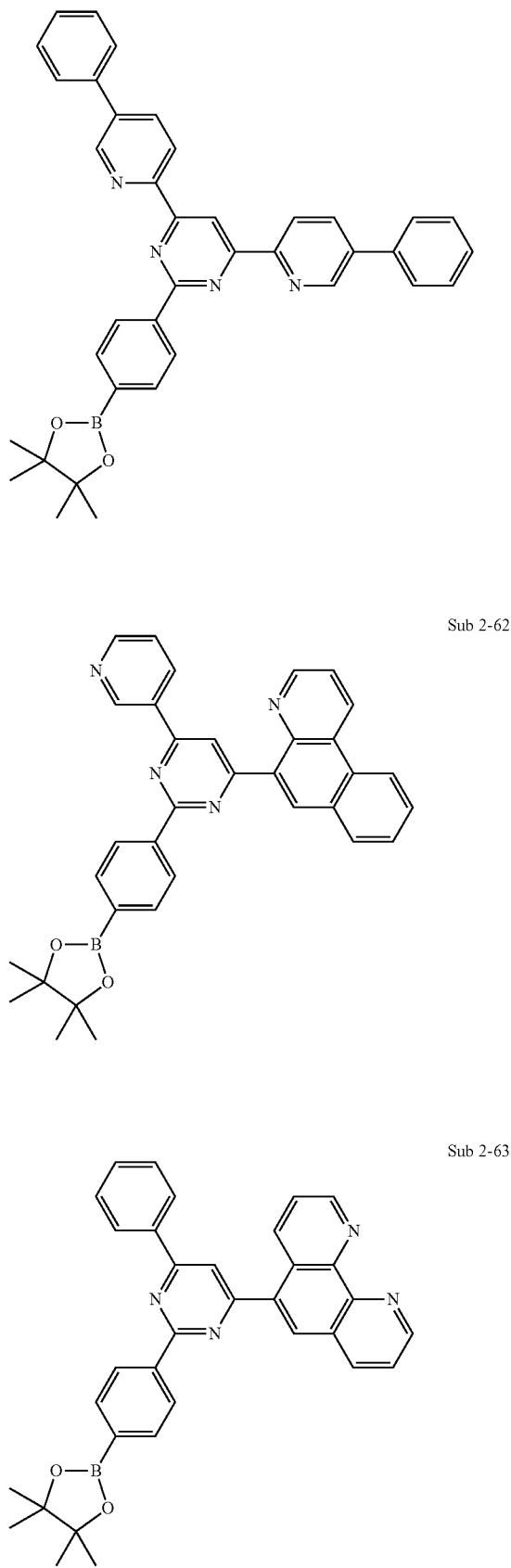

Sub 2-64
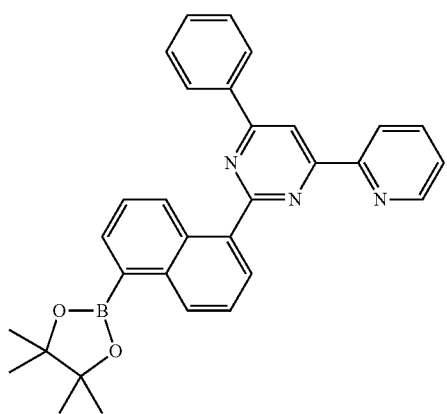
Sub 2-65
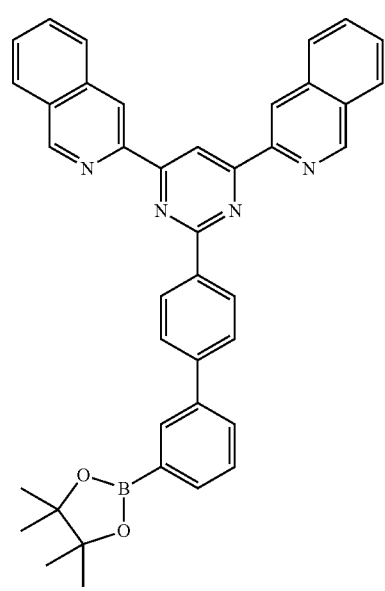
Sub 2-66
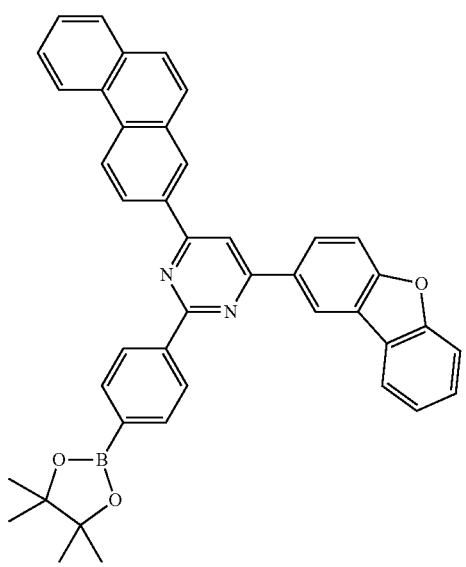
Sub 2-67
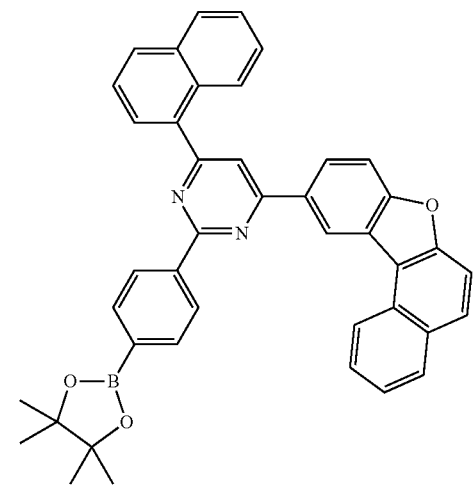
Sub 2-68
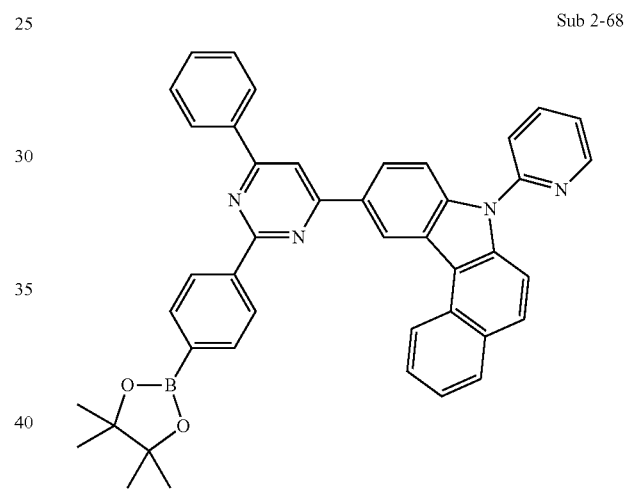
Sub 2-69
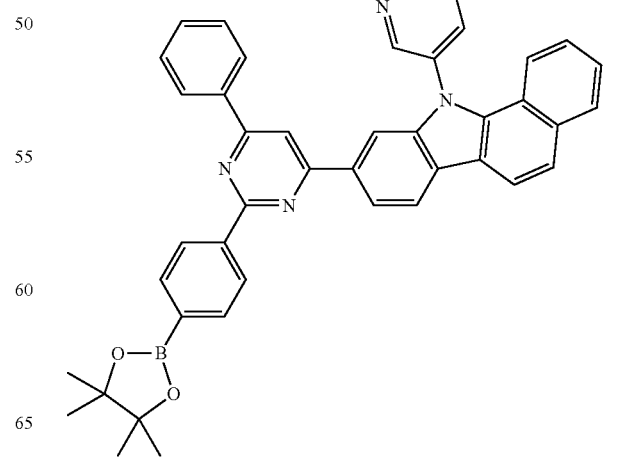

Sub 2-70
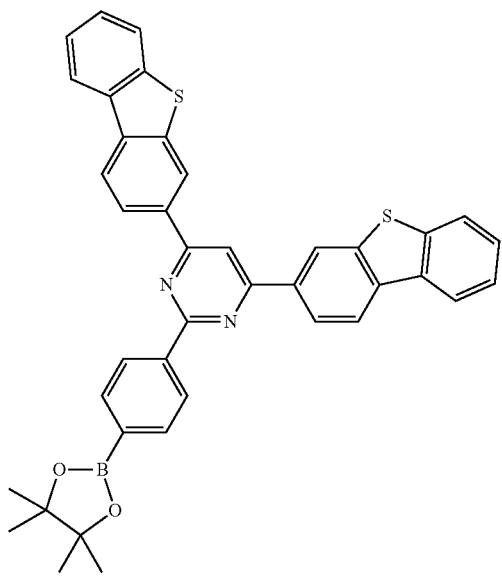
Sub 2-71
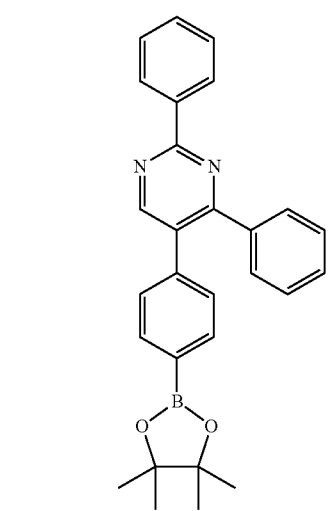
Sub 2-72
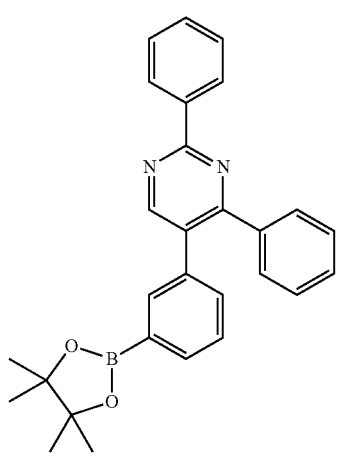
Sub 2-73
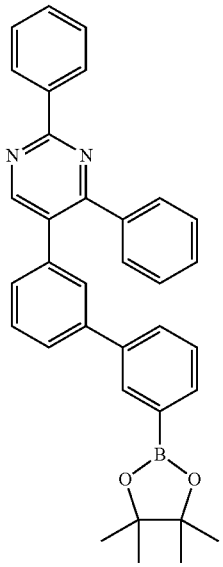
Sub 2-74
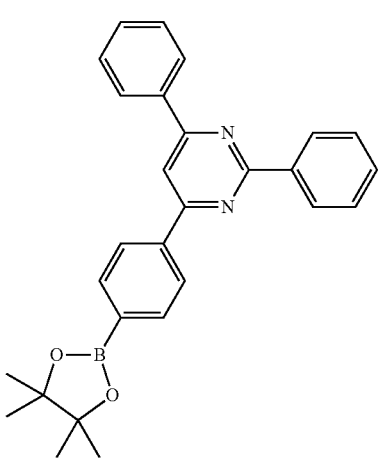
Sub 2-75
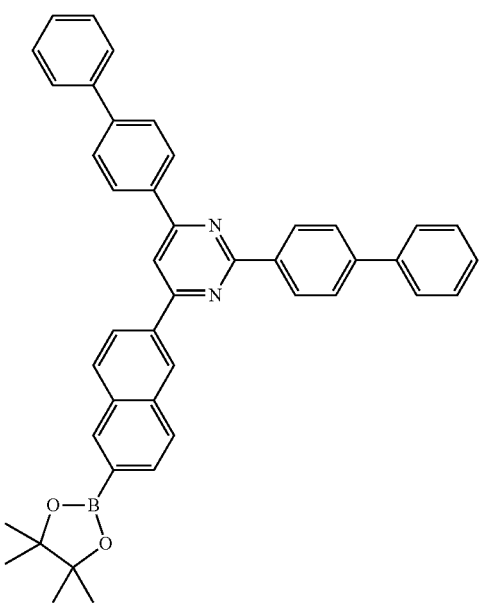

Sub 2-76
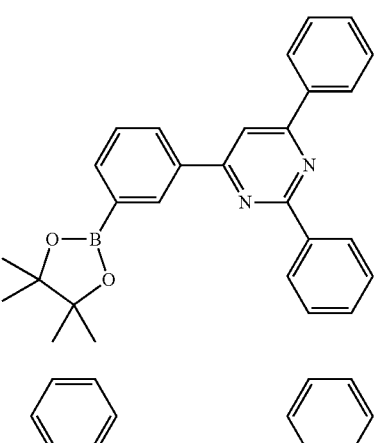
Sub 2-80
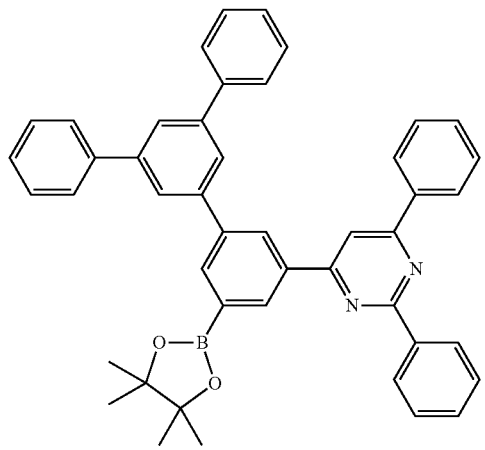
Sub 2-77
Sub 2-81
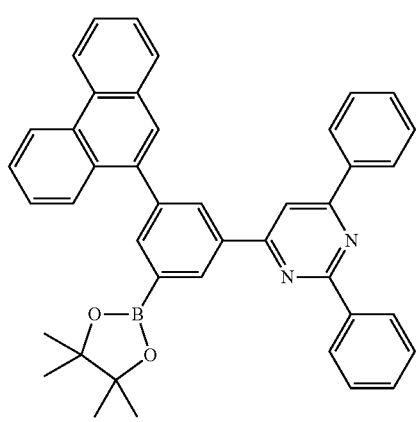
Sub 2-78
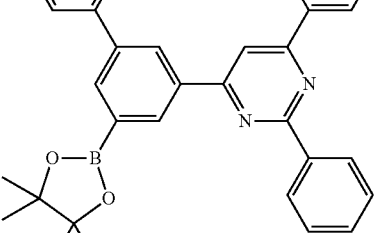
Sub 2-79
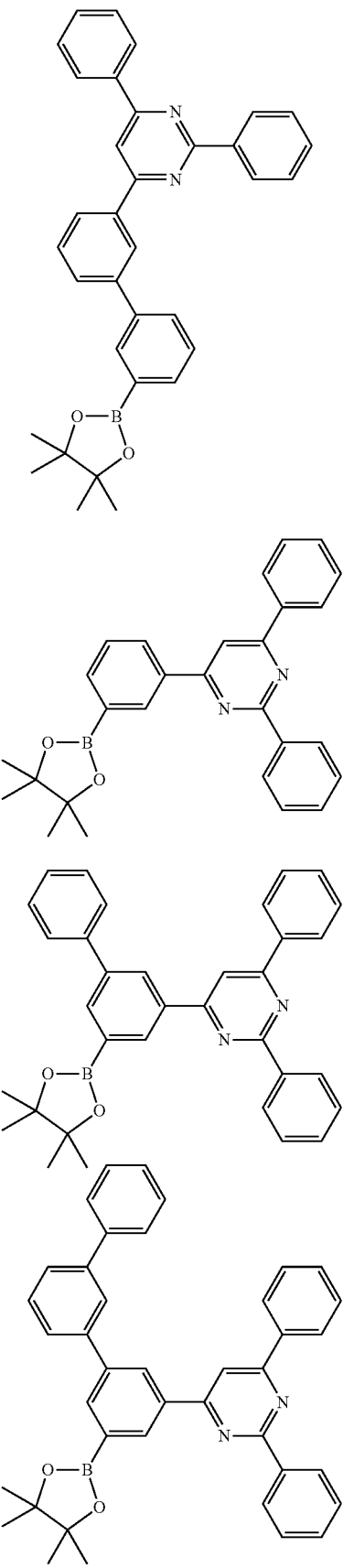
Sub 2-82
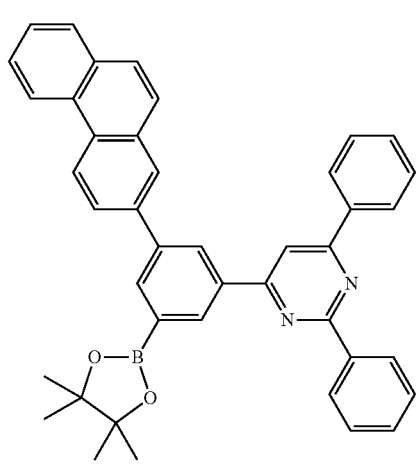

Sub 2-83
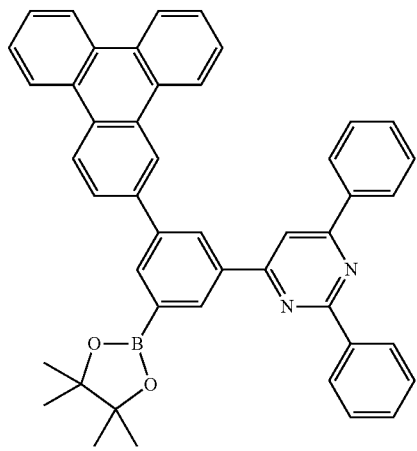
Sub 2-84
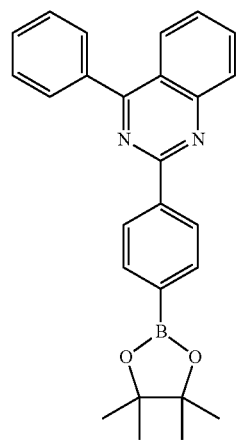
Sub 2-85
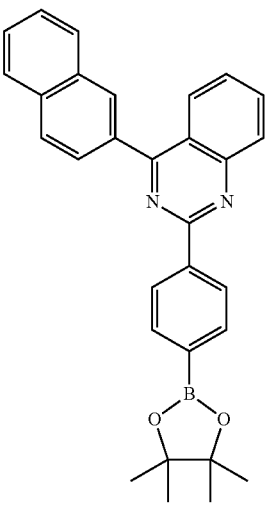
Sub 2-86
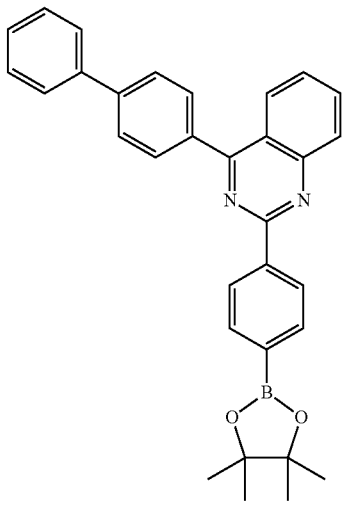
Sub 2-87
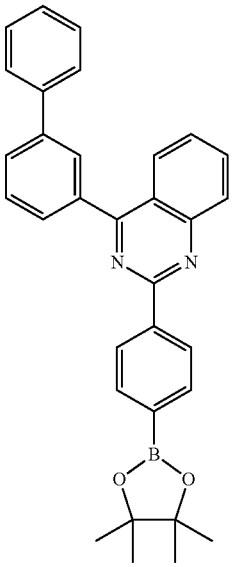
Sub 2-88
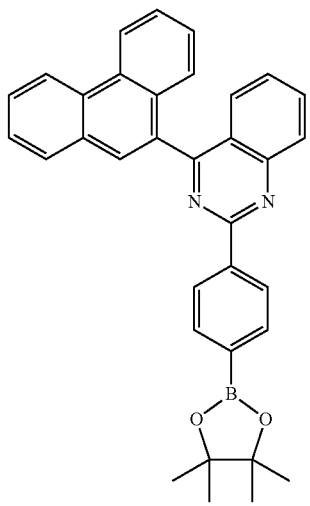

Sub 2-89
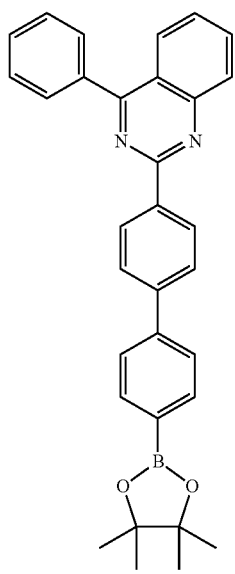
Sub 2-90
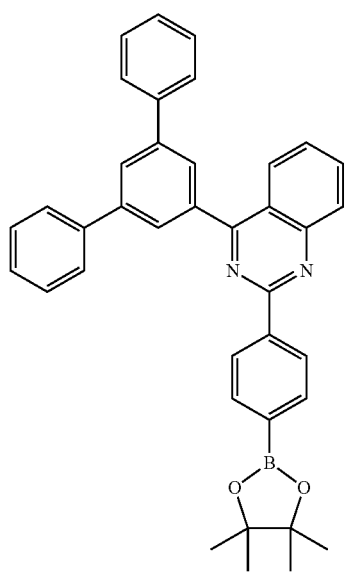
Sub 2-91
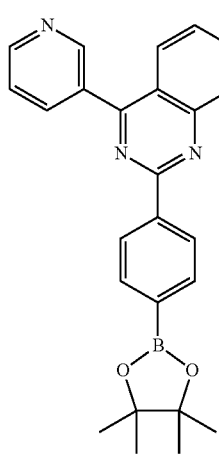
Sub 2-92
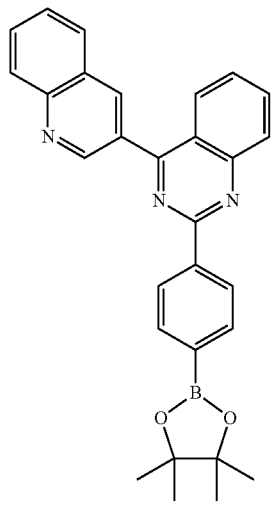
Sub 2-93
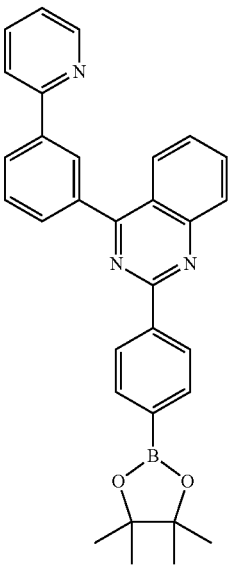
Sub 2-94
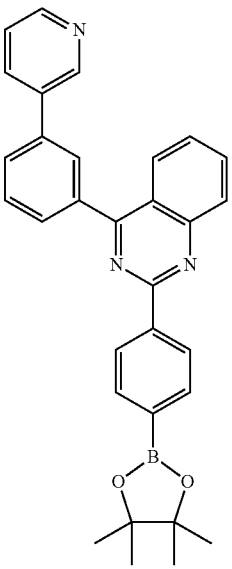

Sub 2-95
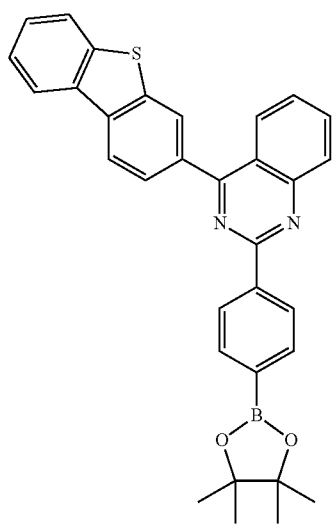
Sub 2-98
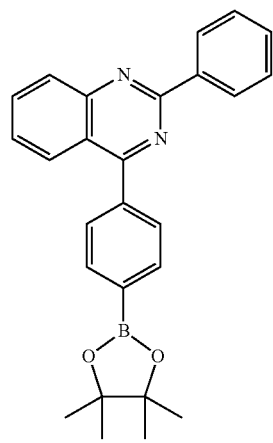
Sub 2-96
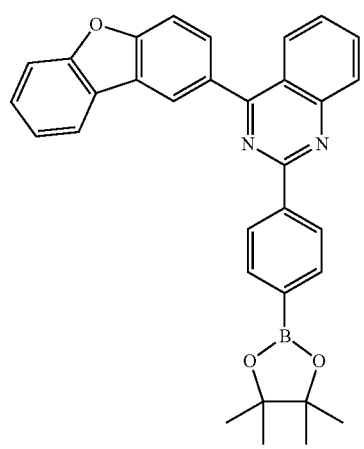
Sub 2-99
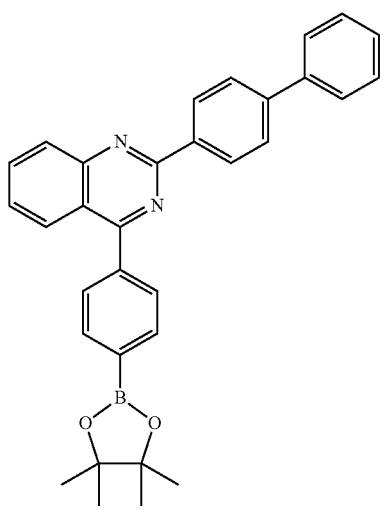
Sub 2-97
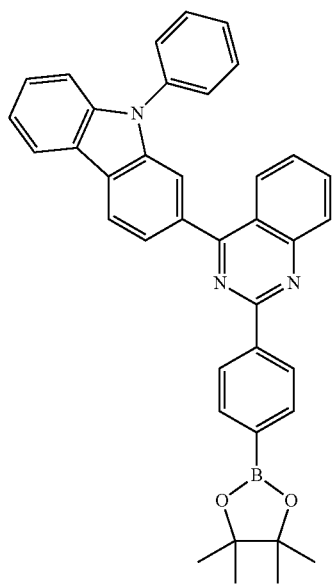
Sub 2-100
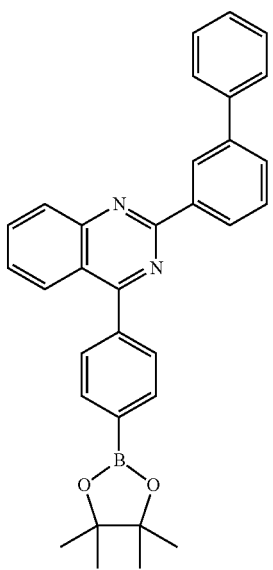

Sub 2-101
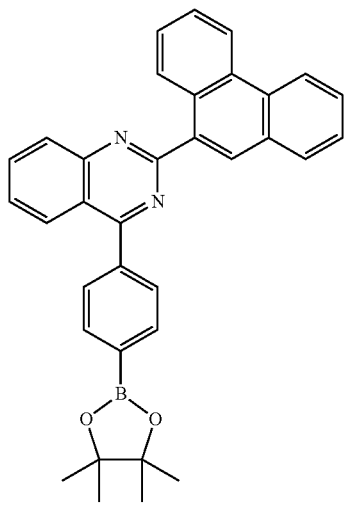
Sub 2-104
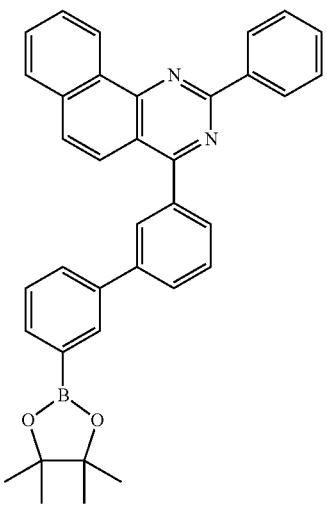
Sub 2-102
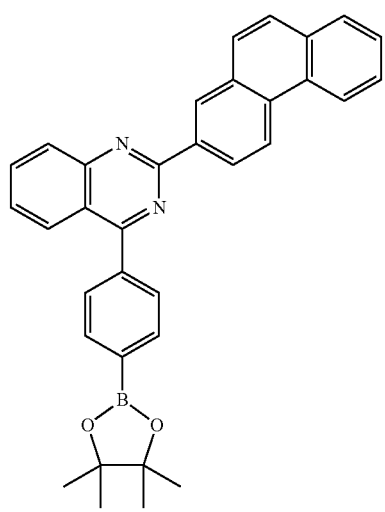
Sub 2-105
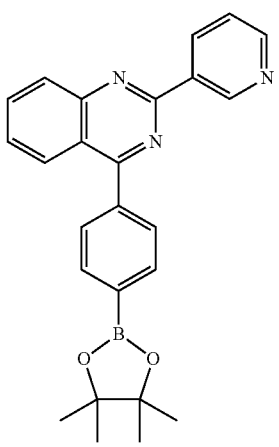
Sub 2-103
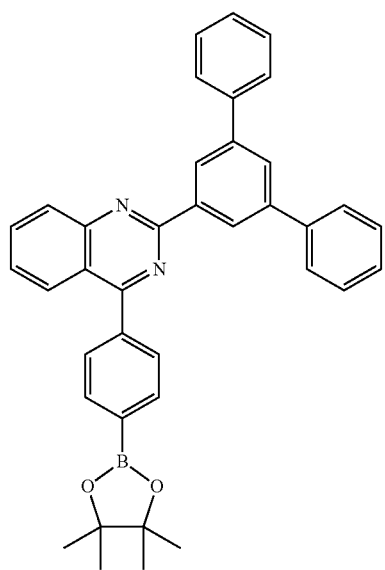
Sub 2-106
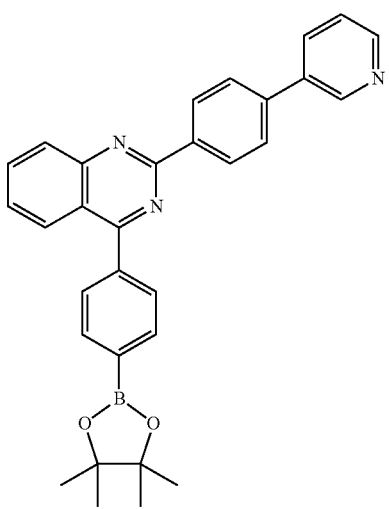

Sub 2-107
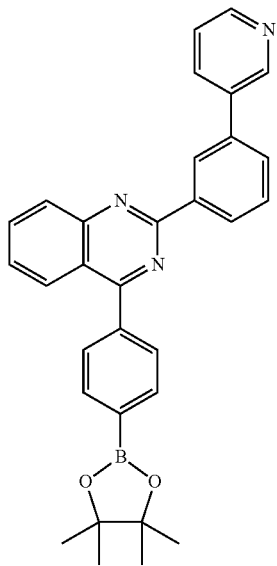
Sub 2-108
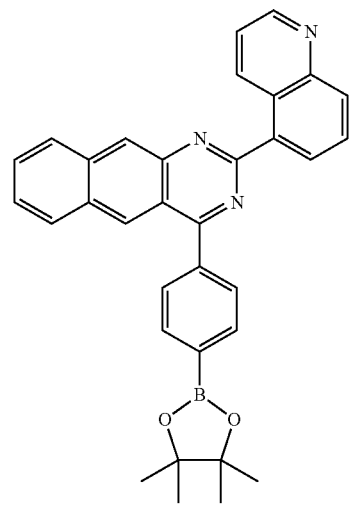
Sub 2-109
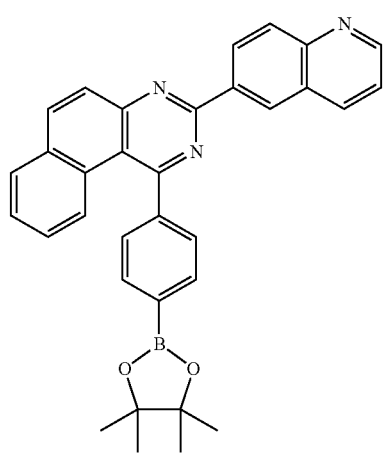
Sub 2-110
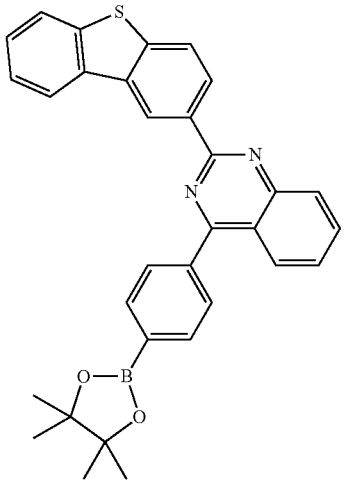
Sub 2-111
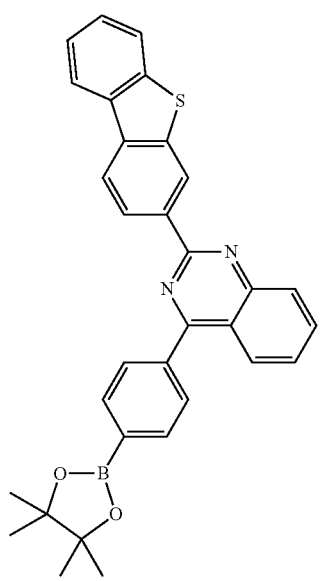
Sub 2-112
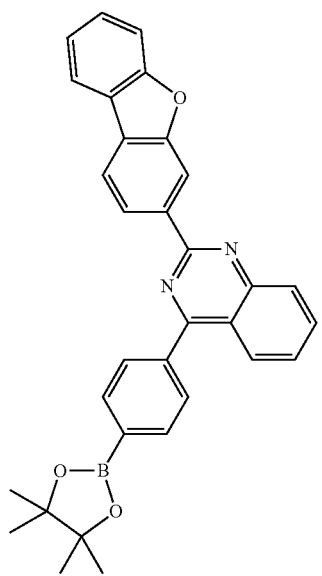

Sub 2-113
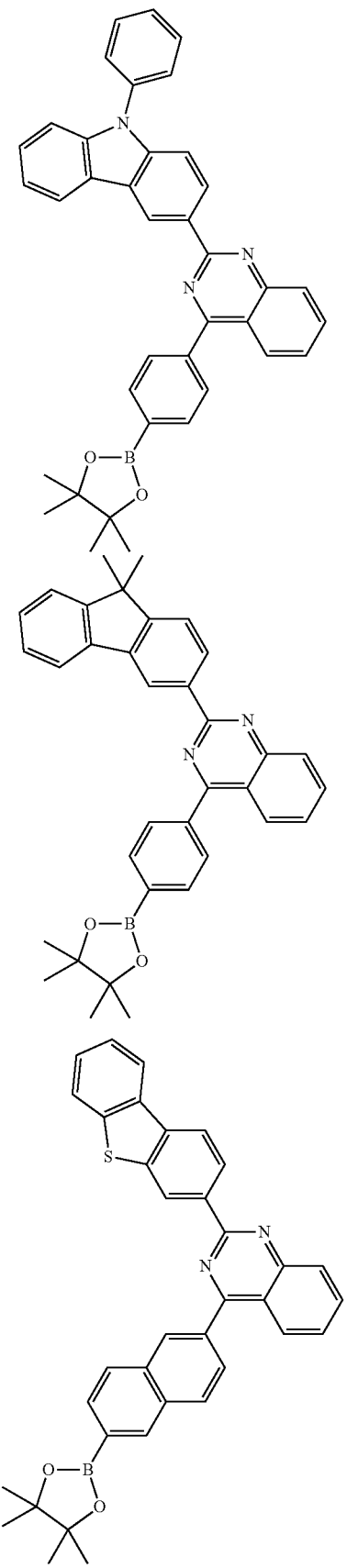
Sub 2-114
Sub 2-115
Sub 2-116
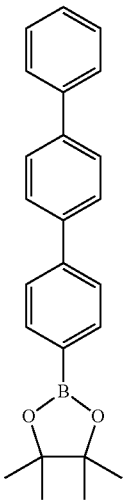
Sub 2-117
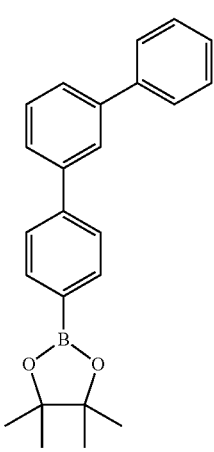
Sub 2-118
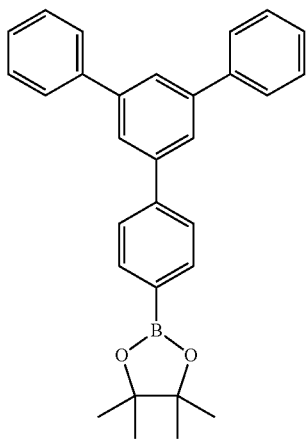

-continued
Sub 2-119
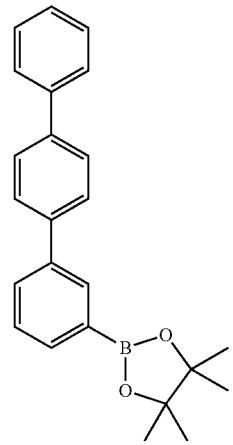
Sub 2-120
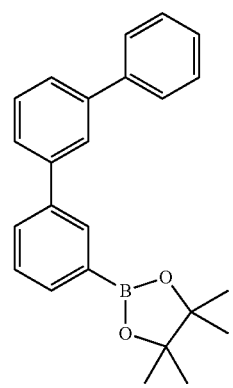
Sub 2-121
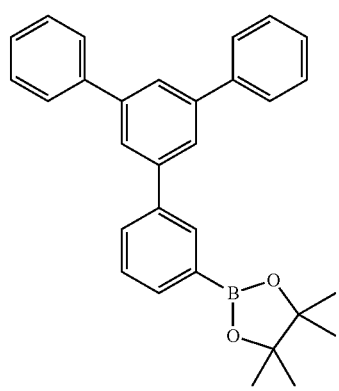
-continued
Sub 2-122
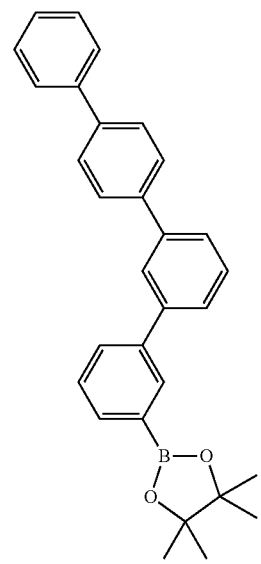
Sub 2-123
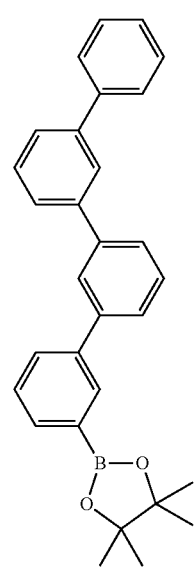
Sub 2-124
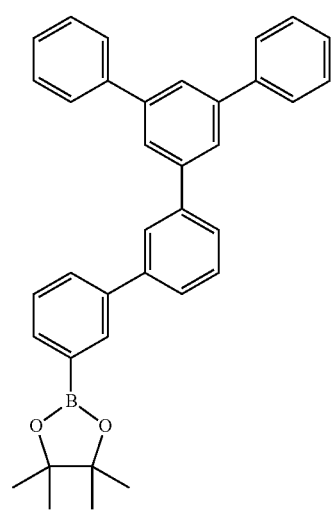

Sub 2-125
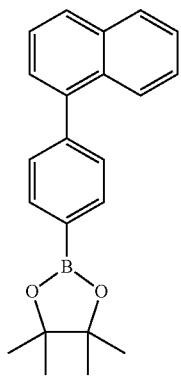
Sub 2-126
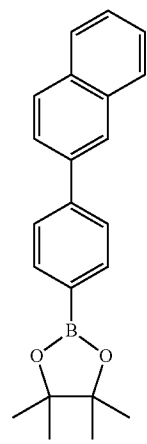
Sub 2-127
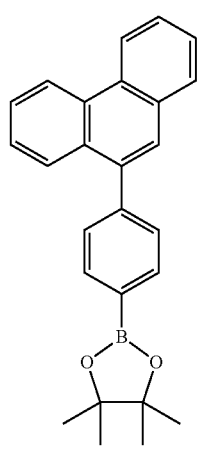
Sub 2-128
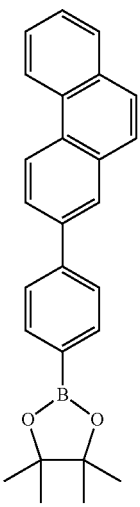
Sub 2-129
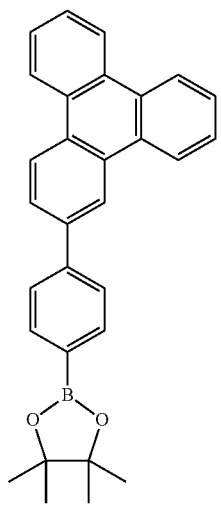
Sub 2-130
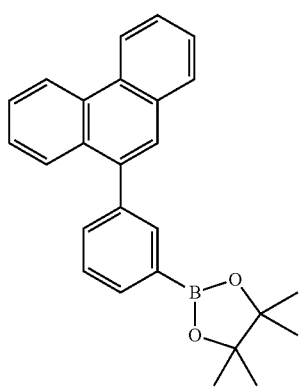

Sub 2-131
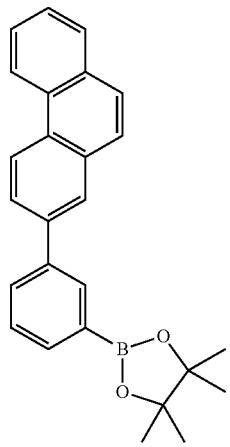
Sub 2-132
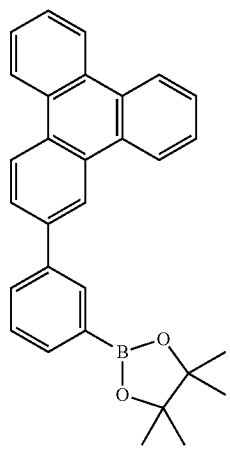
Sub 2-133
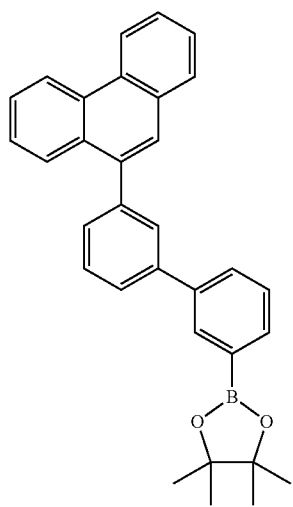
Sub 2-134
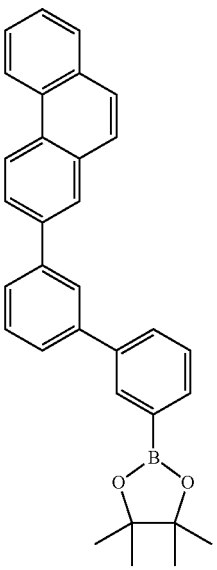
Sub 2-135
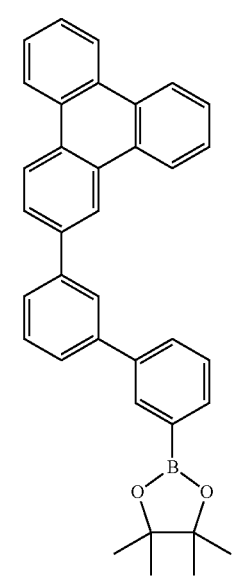
Sub 2-136
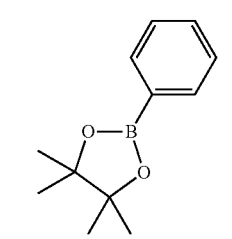
Sub 2-137
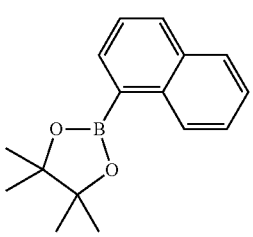

Sub 2-138
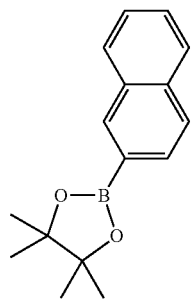
Sub 2-139
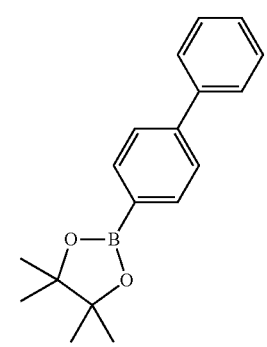
Sub 2-140
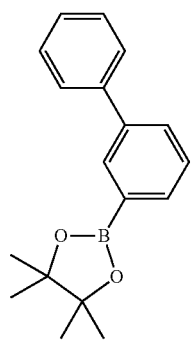
Sub 2-141
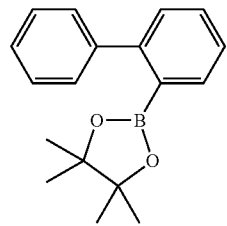
Sub 2-142
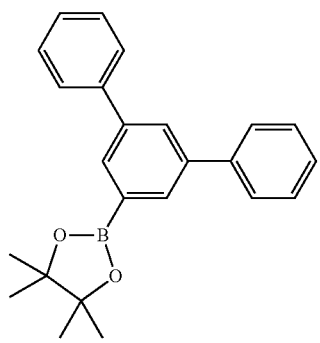
Sub 2-143
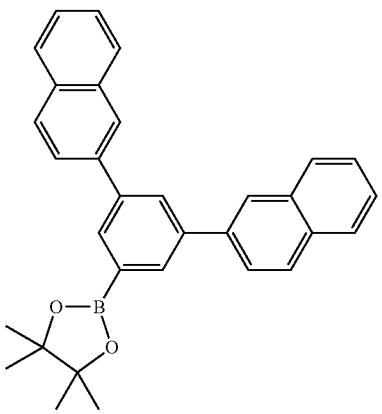
Sub 2-144
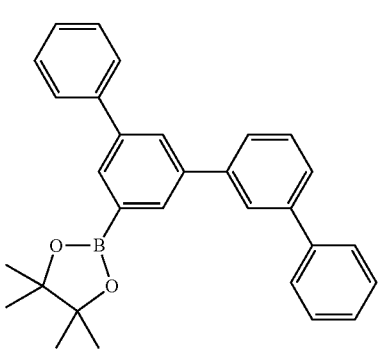
Sub 2-145
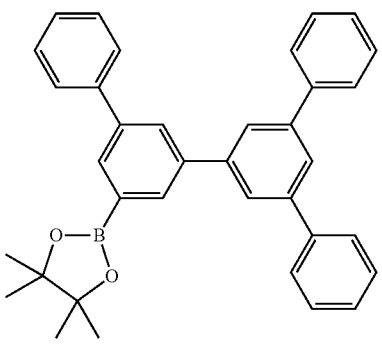
Sub 2-146
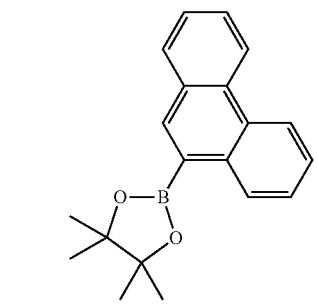

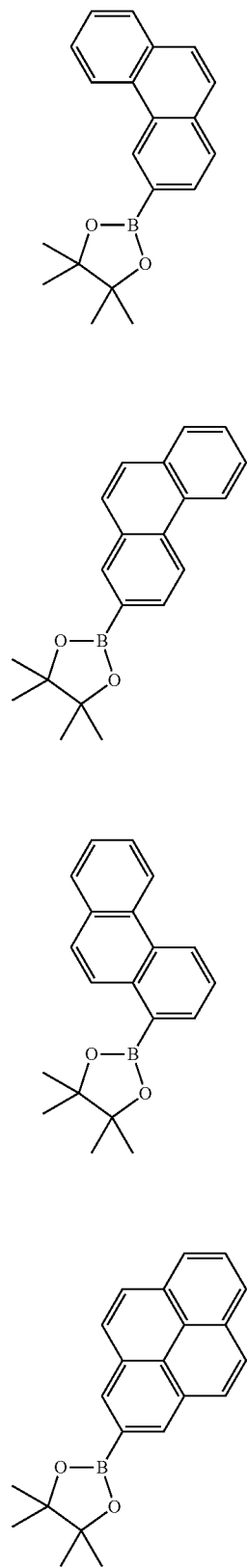
Sub 2-147
Sub 2-148
Sub 2-149
Sub 2-150
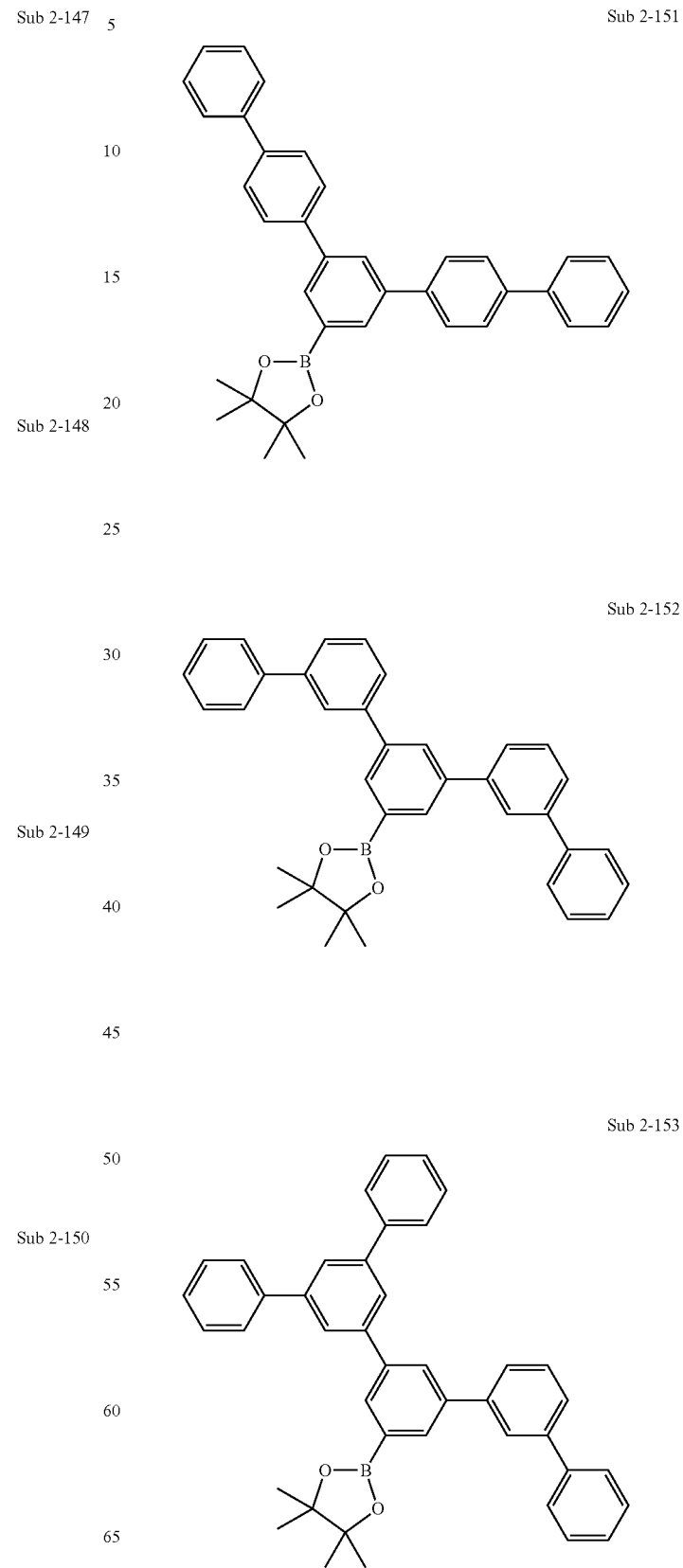
Sub 2-151
Sub 2-152
Sub 2-153

Sub 2-154
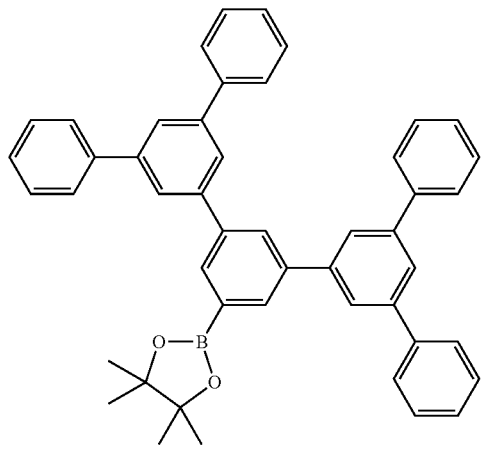
Sub 2-157
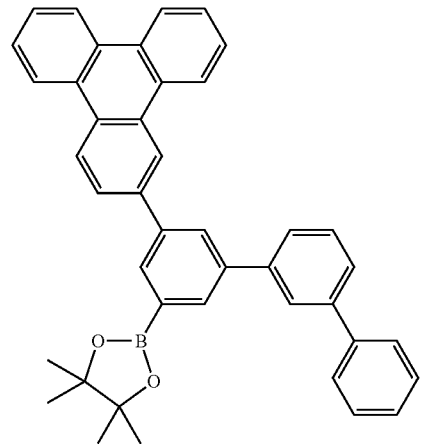
Sub 2-155
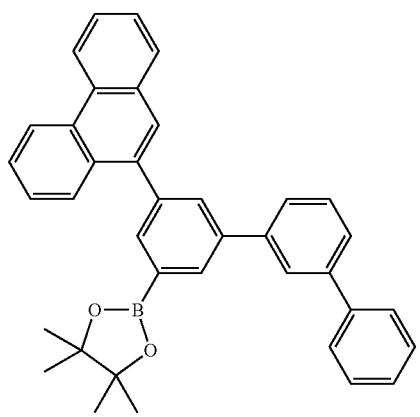
Sub 2-158
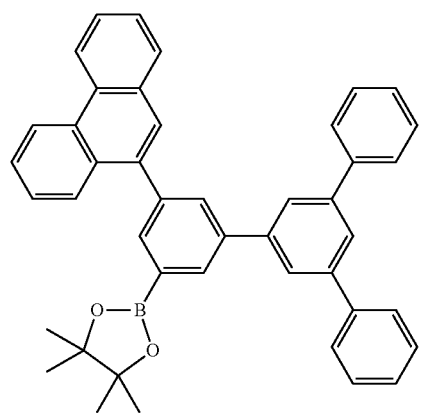
Sub 2-156
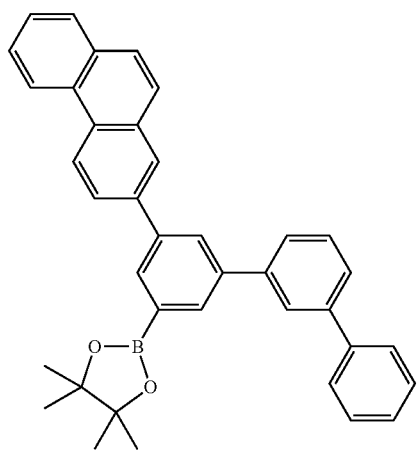
Sub 2-159
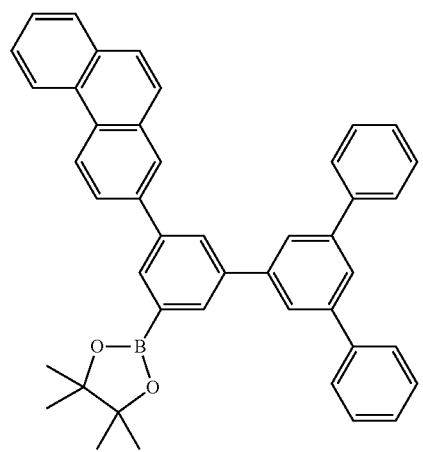

Sub 2-160
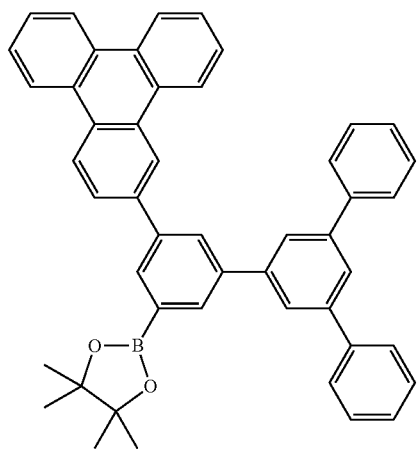
Sub 2-161
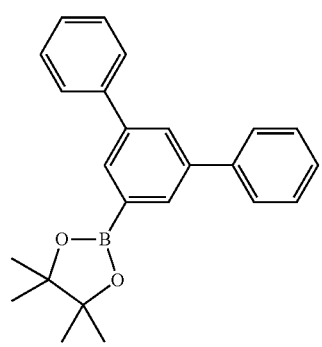
Sub 2-162
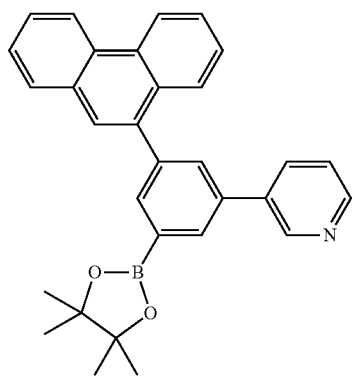
Sub 2-163
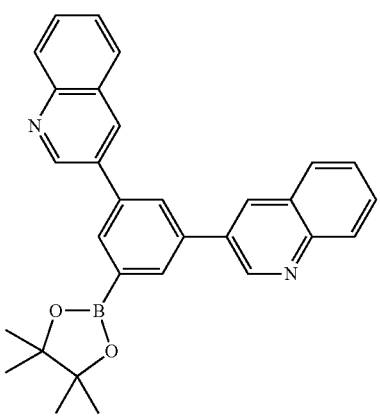
Sub 2-164
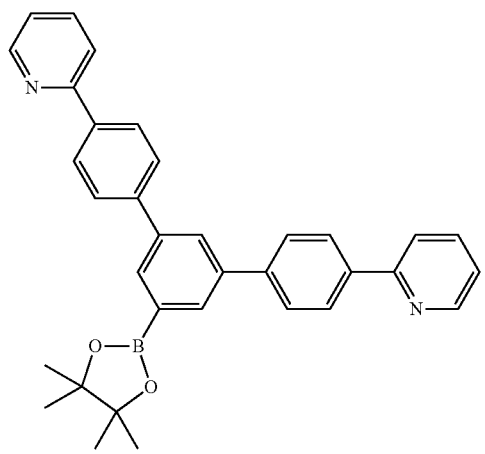
Sub 2-165
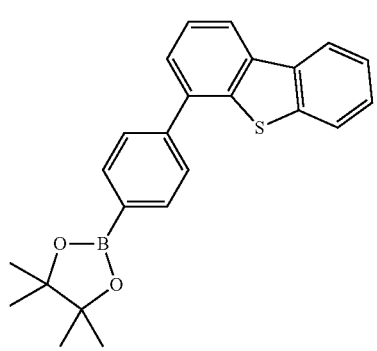
Sub 2-166
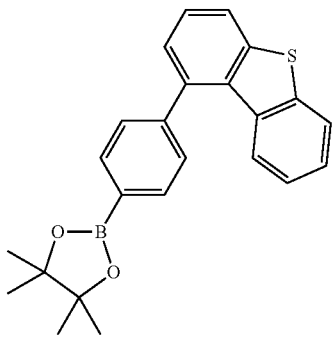
Sub 2-167
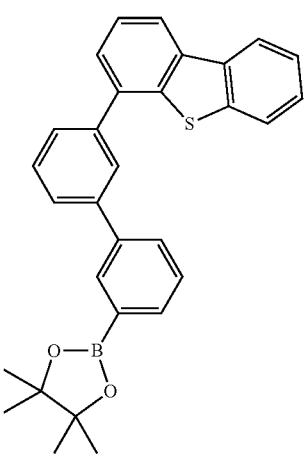

Sub 2-168
Sub 2-169
Sub 2-170
Sub 2-171
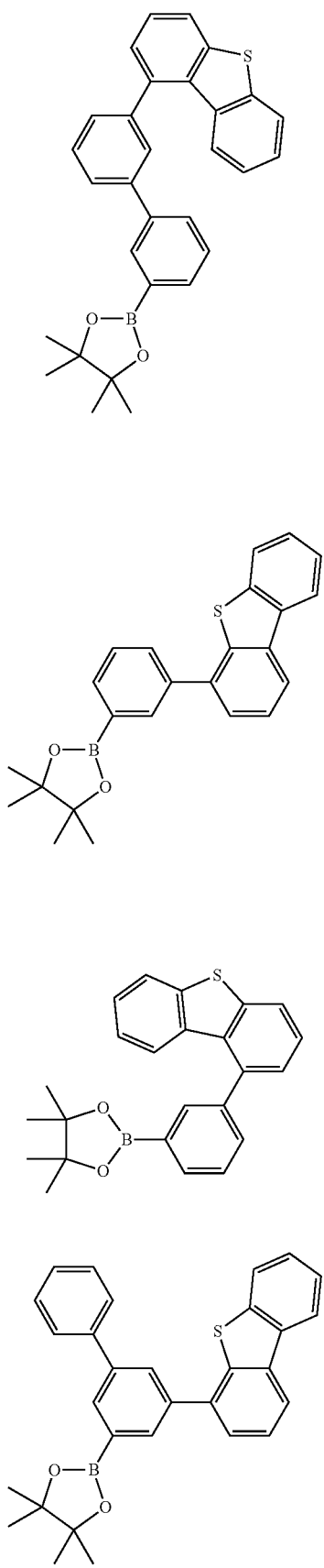
Sub 2-172
Sub 2-173
Sub 2-174
Sub 2-175
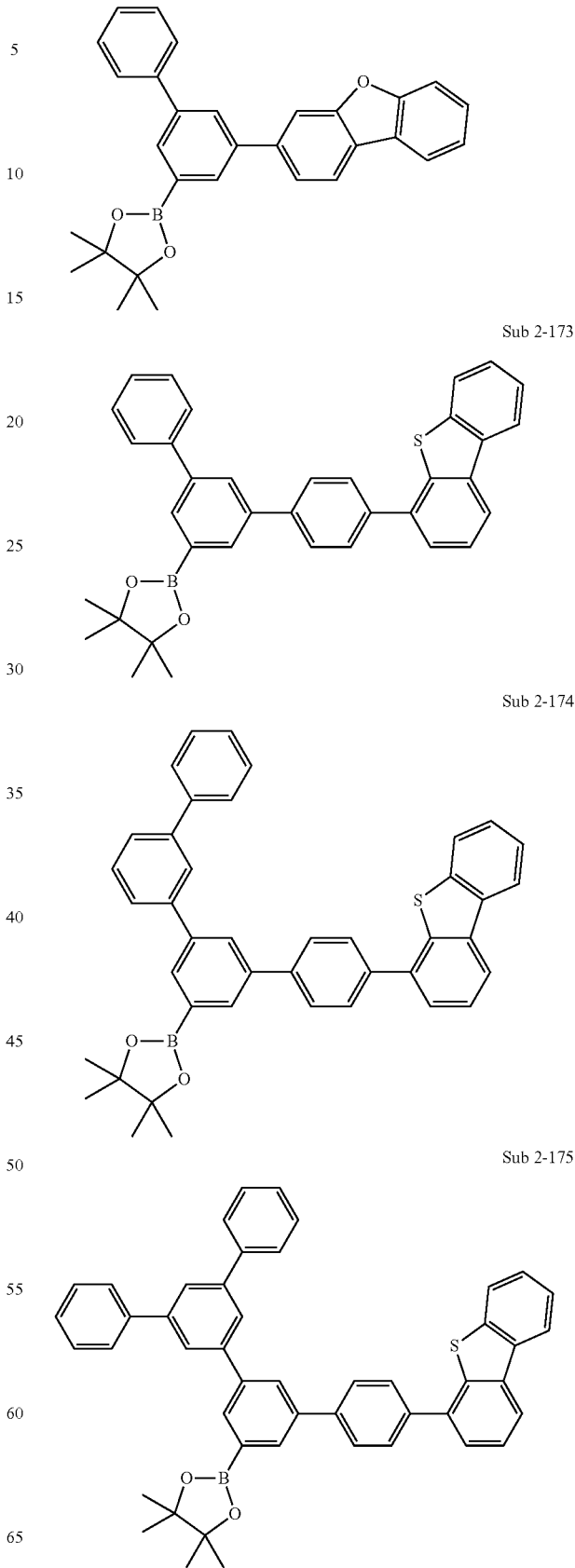

Sub 2-176
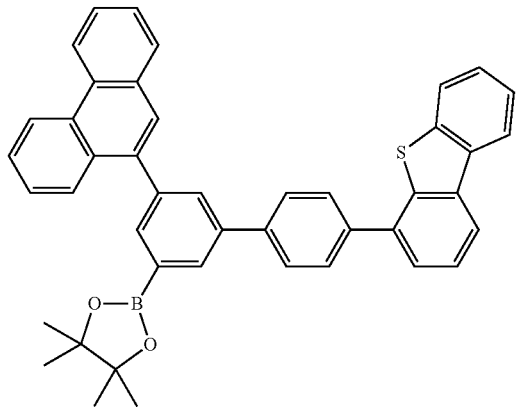
Sub 2-177
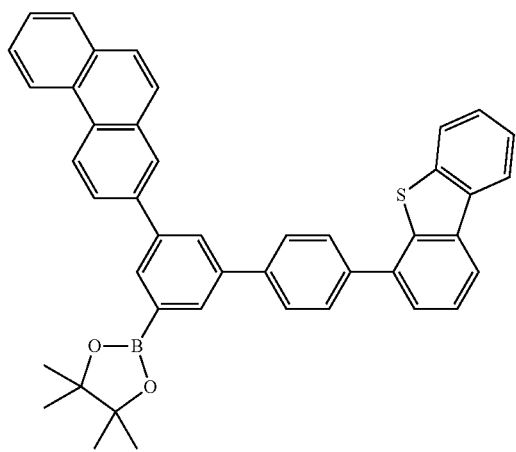
Sub 2-178
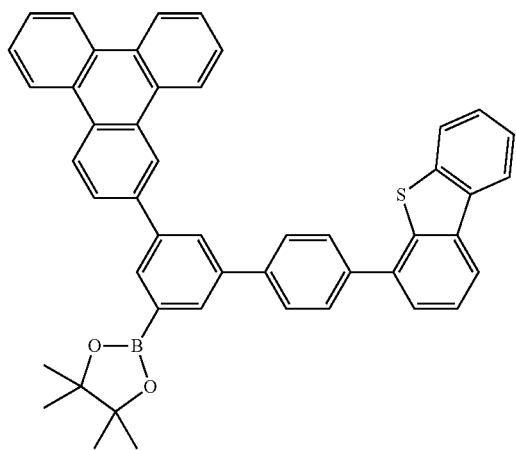
Sub 2-179
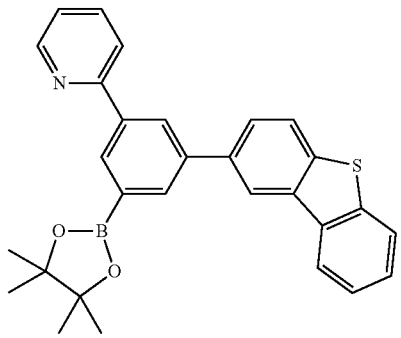
Sub 2-180
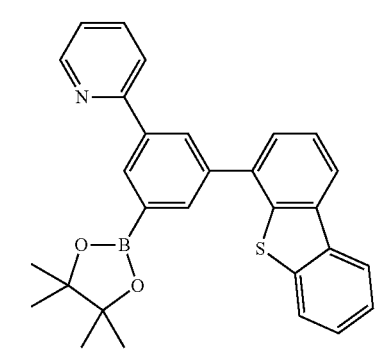
Sub 2-181
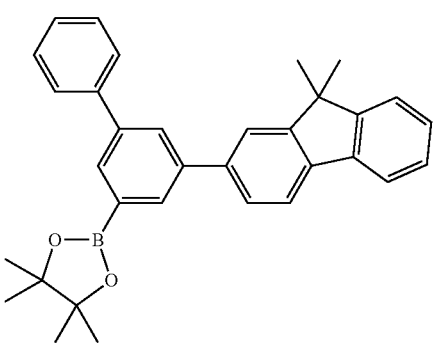
Sub 2-182
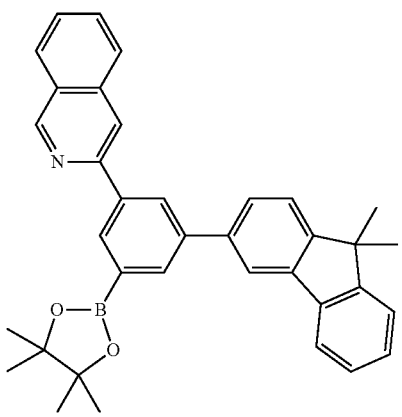

-continued
Sub 2-183
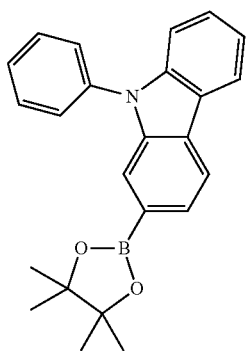
Sub 2-184
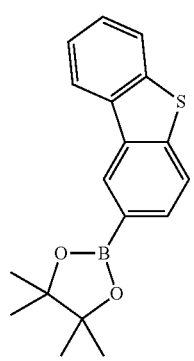
Sub 2-185
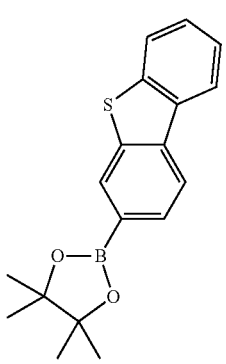
Sub 2-186
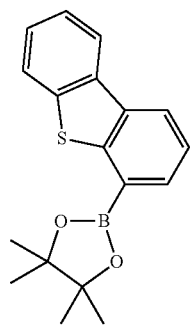
-continued
Sub 2-187
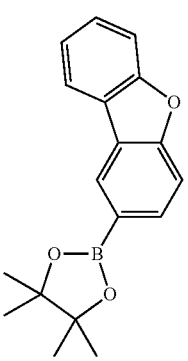
Sub 2-188
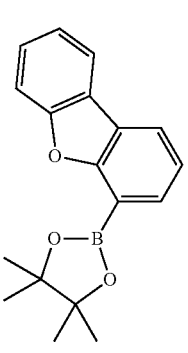
Sub 2-189
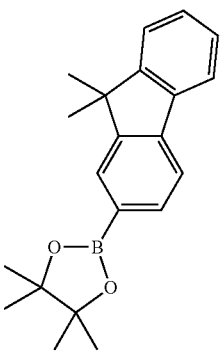
Sub 2-190
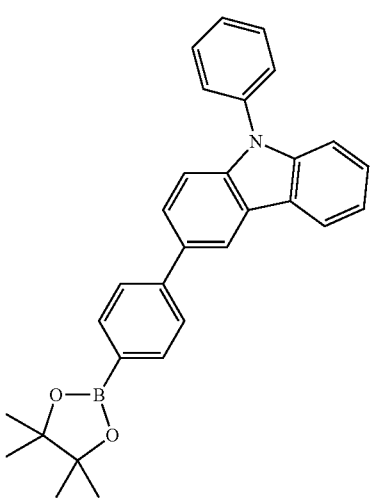

Sub 2-191
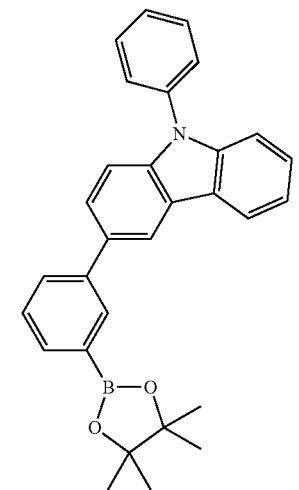
Sub 2-192
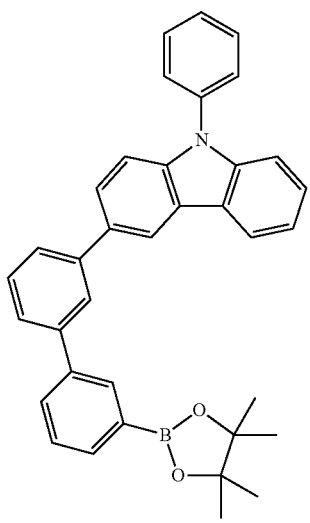
Sub 2-193
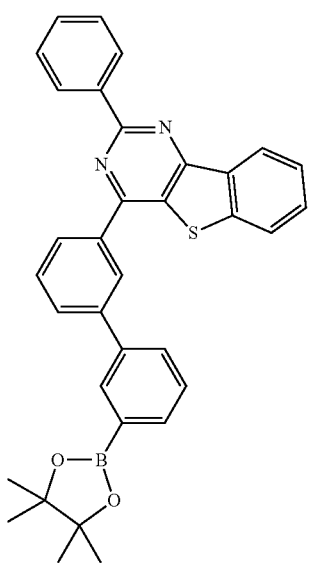
Sub 2-194
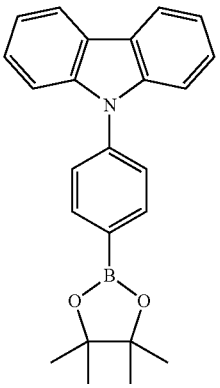
Sub 2-195
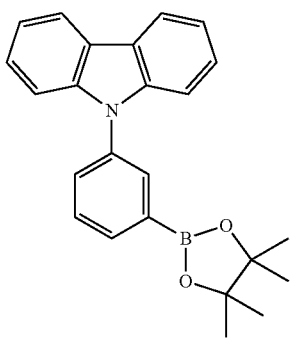
Sub 2-196
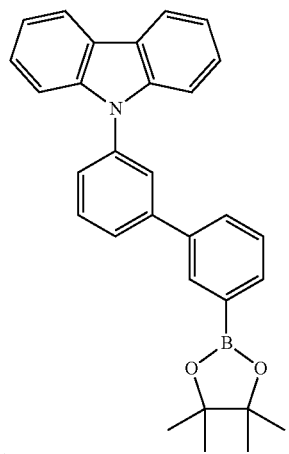
Sub 2-197
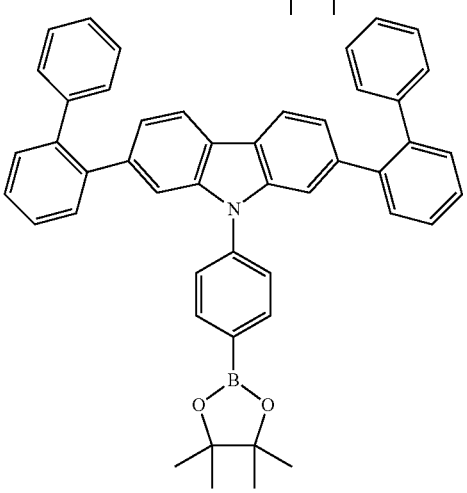

Sub 2-198
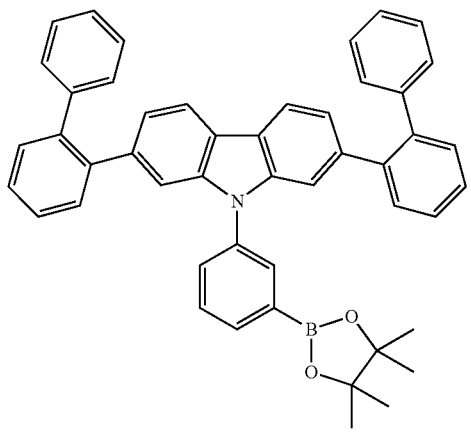
Sub 2-199
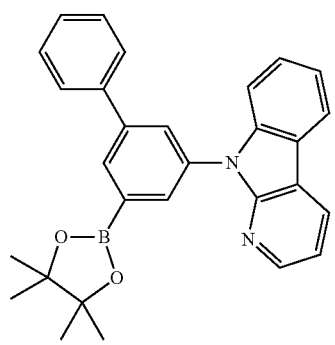
Sub 2-200
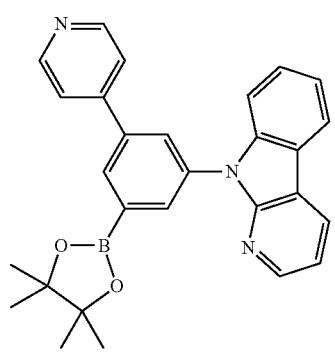
Sub 2-201
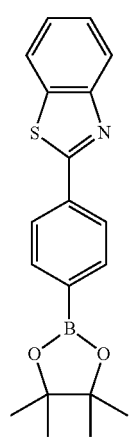
Sub 2-202
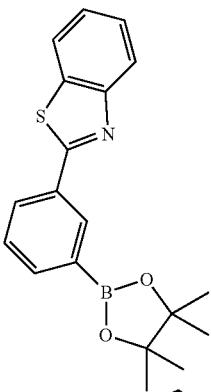
Sub 2-203
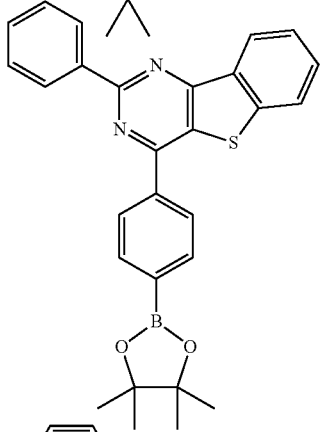
Sub 2-204
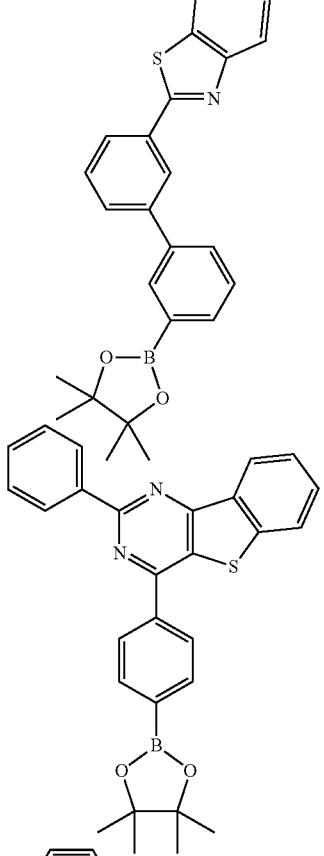
Sub 2-205
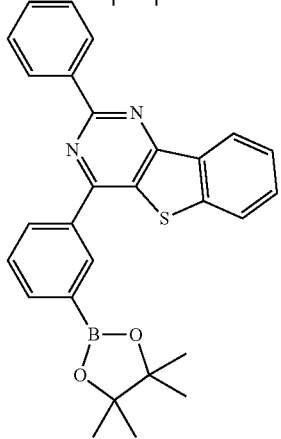

TABLE 2

| Compound | FD-MS | Compound | FD-MS |
| --- | --- | --- | --- |
| Sub 2-1 | m/z = 435.21($C_{27}H_{26}BN_3O_2$ = 435.33) | Sub 2-2 | m/z = 485.23($C_{31}H_{28}BN_3O_2$ = 485.38) |
| Sub 2-3 | m/z = 535.24($C_{35}H_{30}BN_3O_2$ = 535.44) | Sub 2-4 | m/z = 535.24($C_{35}H_{30}BN_3O_2$ = 535.44) |
| Sub 2-5 | m/z = 511.24($C_{33}H_{30}BN_3O_2$ = 511.42) | Sub 2-6 | m/z = 587-27($C_{39}H_{34}BN_3O_2$ = 587.52) |
| Sub 2-7 | m/z = 587.27($C_{39}H_{34}BN_3O_2$ = 587.52) | Sub 2-8 | m/z = 739.34($C_{51}H_{42}BN_3O_2$ = 739.71) |
| Sub 2-9 | m/z = 511.24($C_{33}H_{30}BN_3O_2$ = 511.42) | Sub 2-10 | m/z = 435.21($C_{27}H_{26}BN_3O_2$ = 435.33) |
| Sub 2-11 | m/z = 511.24($C_{33}H_{30}BN_3O_2$ = 511.42) | Sub 2-12 | m/z = 587.27($C_{39}H_{34}BN_3O_2$ = 587.52) |
| Sub 2-13 | m/z = 663.31($C_{45}H_{38}BN_3O_2$ = 663.61) | Sub 2-14 | m/z = 611.27($C_{41}H_{34}BN_3O_2$ = 611.54) |
| Sub 2-15 | m/z = 611.27($C_{41}H_{34}BN_3O_2$ = 611.54) | Sub 2-16 | m/z = 661.29($C_{45}H_{36}BN_3O_2$ = 661.60) |
| Sub 2-17 | m/z = 486.22($C_{30}H_{27}BN_4O_2$ = 486.37) | Sub 2-18 | m/z = 486.22($C_{30}H_{27}BN_4O_2$ = 486.37) |
| Sub 2-19 | m/z = 536.24($C_{34}H_{29}BN_4O_2$ = 536.43) | Sub 2-20 | m/z = 537.23($C_{33}H_{28}BN_5O_2$ = 537.42) |
| Sub 2-21 | m/z = 512.24($C_{32}H_{29}BN_4O_2$ = 512.41) | Sub 2-22 | m/z = 536.24($C_{34}H_{29}BN_4O_2$ = 536.43) |
| Sub 2-23 | m/z = 536.24($C_{34}H_{29}BN_4O_2$ = 536.43) | Sub 2-24 | m/z = 437.20($C_{25}H_{24}BN_5O_2$ = 437.30) |
| Sub 2-25 | m/z = 537.23($C_{33}H_{28}BN_5O_2$ = 537.42) | Sub 2-26 | m/z = 589.26($C_{37}H_{42}BN_5O_2$ = 589.49) |
| Sub 2-27 | m/z = 589.26($C_{37}H_{32}BN_5O_2$ = 589.49) | Sub 2-28 | m/z = 589.26($C_{37}H_{32}BN_5O$ = 589.49) |
| Sub 2-29 | m/z = 639.28($C_{41}H_{34}BN_5O_2$ = 639.55) | Sub 2-30 | m/z = 636.27($C_{42}H_{53}BN_4O_2$ = 636.55) |
| Sub 2-31 | m/z = 551.27($C_{36}H_{34}BN_3O_2$ = 551.49) | Sub 2-32 | m/z = 617.23($C_{39}H_{32}BN_3O_2S$ = 617.57) |
| Sub 2-33 | m/z = 591.22($C_{37}H_{30}BN_3O_2S$ = 591.53) | Sub 2-34 | m/z = 601.25($C_{39}H_{32}BN_3O_3$ = 601.50) |
| Sub 2-35 | m/z = 650.29($C_{43}H_{36}BN_4O_2$ = 650.57) | Sub 2-36 | m/z = 631.21($C_{39}H_{30}BN_3O_3S$ = 631.55) |
| Sub 2-37 | m/z = 434.22($C_{28}H_{27}BN_2O_2$ = 434.34) | Sub 2-38 | m/z = 484.23($C_{32}H_{23}BN_2O_2$ = 484.40) |
| Sub 2-39 | m/z = 534.25($C_{36}H_{31}BN_2O_2$ = 534.45) | Sub 2-40 | m/z = 534.25($C_{36}H_{31}BN_2O_2$ = 534.45) |
| Sub 2-41 | m/z = 510.25($C_{34}H_{31}BN_2O_2$ = 510.43) | Sub 2-42 | m/z = 586.28($C_{40}H_{36}BN_2O_2$ = 586.53) |
| Sub 2-43 | m/z = 738.34($C_{52}H_{43}BN_2O_2$ = 738.72) | Sub 2-44 | m/z = 484.23($C_{32}H_{29}BN_2O_2$ = 484.40) |
| Sub 2-45 | m/z = 510.25($C_{34}H_{31}BN_2O_2$ = 510.43) | Sub 2-46 | m/z = 686.31($C_{48}H_{49}BN_2O_2$ = 686.65) |
| Sub 2-47 | m/z = 434.22($C_{28}H_{27}BN_2O_2$ = 434.34) | Sub 2-48 | m/z = 510.25($C_{34}H_{31}BN_2O_2$ = 510.43) |
| Sub 2-49 | m/z = 586.28($C_{40}H_{35}BN_2O_2$ = 586.53) | Sub 2-50 | m/z = 662.31($C_{48}H_{39}BN_2O_2$ = 662.63) |
| Sub 2-51 | m/z = 610.28($C_{42}H_{38}BN_2O_2$ = 610.55) | Sub 2-52 | m/z = 610.28($C_{42}H_{35}BN_2O_2$ = 610.55) |
| Sub 2-53 | m/z = 660.29($C_{46}H_{37}BN_2O_2$ = 660.61) | Sub 2-54 | m/z = 435.21($C_{27}H_{26}BN_3O_2$ = 435.33) |
| Sub 2-55 | m/z = 485.23($C_{31}H_{28}BN_3O_2$ = 485.38) | Sub 2-56 | m/z = 436.21($C_{28}H_{28}BN_4O_2$ = 436.31) |
| Sub 2-57 | m/z = 485.23($C_{31}H_{28}BN_3O_2$ = 485.38) | Sub 2-58 | m/z = 588.27($C_{34}H_{33}BN_4O_2$ = 588.51) |
| Sub 2-59 | m/z = 587.27($C_{39}H_{34}BN_3O_2$ = 587.52) | Sub 2-60 | m/z = 587.27($C_{39}H_{48}BN_3O_2$ = 587.52) |
| Sub 2-61 | m/z = 588.27($C_{38}H_{33}BN_4O_2$ = 588.51) | Sub 2-62 | m/z = 536.24($C_{34}H_{23}BN_4O_2$ = 536.43) |
| Sub 2-63 | m/z = 536.24($C_{34}H_{23}BN_4O_2$ = 536.43) | Sub 2-64 | m/z = 485.23($C_{31}H_{28}BN_3O_2$ = 485.38) |
| Sub 2-65 | m/z = 612.27($C_{40}H_{33}BN_4O_2$ = 612.53) | Sub 2-66 | m/z = 624.26($C_{42}H_{33}BN_2O_3$ = 624.53) |
| Sub 2-67 | m/z = 624.26($C_{42}H_{33}BN_2O_3$ = 624.53) | Sub 2-68 | m/z = 650.29($C_{43}H_{35}BN_4O_2$ = 650.57) |
| Sub 2-69 | m/z = 650.29($C_{43}H_{35}BN_4O_2$ = 650.57) | Sub 2-70 | m/z = 646.19($C_{40}H_{31}BN_2O_2S_2$ = 646.63) |
| Sub 2-71 | m/z = 434.22($C_{28}H_{27}BN_2O_2$ = 434.34) | Sub 2-72 | m/z = 434.22($C_{28}H_{27}BN_2O_2$ = 434.34) |
| Sub 2-73 | m/z = 510.25($C_{34}H_{31}BN_2O_2$ = 510.43) | Sub 2-74 | m/z = 434.22($C_{28}H_{27}BN_2O_2$ = 434.34) |
| Sub 2-75 | m/z = 636.29($C_{44}H_{37}BN_2O_2$ = 636.59) | Sub 2-76 | m/z = 510.25($C_{34}H_{31}BN_2O_2$ = 510.43) |
| Sub 2-77 | m/z = 434.22($C_{28}H_{27}BN_2O_2$ = 434.34) | Sub 2-78 | m/z = 510.25($C_{34}H_{31}BN_2O_2$ = 510.43) |
| Sub 2-79 | m/z = 586.28($C_{40}H_{35}BN_2O_2$ = 586.53) | Sub 2-80 | m/z = 662.31($C_{40}H_{39}BN_2O_2$ = 662.63) |
| Sub 2-81 | m/z = 610.28($C_{42}H_{35}BN_2O_2$ = 610.55) | Sub 2-82 | m/z = 610.28($C_{42}H_{35}BN_2O_2$ = 610.55) |
| Sub 2-83 | m/z = 660.29($C_{46}H_{37}BN_2O_2$ = 660.61) | Sub 2-84 | m/z = 408.20($C_{28}H_{25}BN_2O_2$ = 408.30) |
| Sub 2-85 | m/z = 458.22($C_{30}H_{27}BN_2O_2$ = 458.36) | Sub 2-86 | m/z = 484.23($C_{32}H_{28}BN_2O_2$ = 484.40) |
| Sub 2-87 | m/z = 484.23($C_{32}H_{29}BN_2O_2$ = 484.40) | Sub 2-88 | m/z = 508.23($C_{34}H_{29}BN_2O_2$ = 508.42) |
| Sub 2-89 | m/z = 484.23($C_{32}H_{29}BN_2O_2$ = 484.40) | Sub 2-90 | m/z = 560.26($C_{38}H_{33}BN_2O_2$ = 560.49) |
| Sub 2-91 | m/z = 409.20($C_{25}H_{24}BN_3O_2$ = 409.29) | Sub 2-92 | m/z = 459.21($C_{29}H_{26}BN_3O_2$ = 459.35) |
| Sub 2-93 | m/z = 485.23($C_{31}H_{28}BN_3O_2$ = 485.38) | Sub 2-94 | m/z = 485.23($C_{31}H_{28}BN_3O_2$ = 485.38) |
| Sub 2-95 | m/z = 514.19($C_{32}H_{27}BN_2O_2S$ = 514.44) | Sub 2-96 | m/z = 498.21($C_{32}H_{27}BN_2O_3$ = 498.38) |
| Sub 2-97 | m/z = 573.26($C_{38}H_{32}BN_3O_2$ = 573.49) | Sub 2-98 | m/z = 408.20($C_{26}H_{25}BN_2O_2$ = 408.30) |
| Sub 2-99 | m/z = 484.23($C_{32}H_{29}BN_2O_2$ = 484.40) | Sub 2-100 | m/z = 484.23($C_{32}H_{29}BN_2O_2$ = 484.40) |

TABLE 2-continued

| Compound | FD-MS | Compound | FD-MS |
|---|---|---|---|
| Sub 2-101 | m/z = 508.23($C_{34}H_{29}BN_2O_2$ = 508.42) | Sub 2-102 | m/z = 508.23($C_{34}H_{29}BN_2O_2$ = 508.42) |
| Sub 2-103 | m/z = 560.26($C_{38}H_{33}BN_2O_2$ = 560.49) | Sub 2-104 | m/z = 534.25($C_{36}H_{31}BN_2O_2$ = 534.45) |
| Sub 2-105 | m/z = 409.20($C_{25}H_{24}BN_3O_2$ = 409.29) | Sub 2-106 | m/z = 485.23($C_{31}H_{28}BN_3O_2$ = 485.38) |
| Sub 2-107 | m/z = 485.23($C_{31}H_{28}BN_3O_2$ = 485.38) | Sub 2-108 | m/z = 509.23($C_{33}H_{28}BN_3O_2$ = 509.41) |
| Sub 2-109 | m/z = 509.23($C_{33}H_{28}BN_3O_2$ = 509.41) | Sub 2-110 | m/z = 514.19($C_{32}H_{27}BN_2O_2S$ = 514.44) |
| Sub 2-111 | m/z = 514.19($C_{32}H_{27}BN_2O_2S$ = 514.44) | Sub 2-112 | m/z = 498.21($C_{32}H_{27}BN_2O_3$ = 498.38) |
| Sub 2-113 | m/z = 573.26($C_{38}H_{32}BN_3O_2$ = 573.49) | Sub 2-114 | m/z = 524.26($C_{35}H_{33}BN_2O_2$ = 524.46) |
| Sub 2-115 | m/z = 564.20($C_{36}H_{29}BN_2O_2S$ = 564.50) | Sub 2-116 | m/z = 356.19($C_{24}H_{26}BO_2$ = 356.27) |
| Sub 2-117 | m/z = 356.19($C_{24}H_{25}BO_2$ = 356.27) | Sub 2-118 | m/z = 432.23($C_{33}H_{29}BO_2$ = 432.36) |
| Sub 2-119 | m/z = 356.19($C_{24}H_{25}BO_2$ = 356.27) | Sub 2-120 | m/z = 356.19($C_{24}H_{25}BO_2$ = 356.27) |
| Sub 2-121 | m/z = 432.23($C_{30}H_{29}BO_2$ = 432.36) | Sub 2-122 | m/z = 432.23($C_{33}H_{29}BO_2$ = 432.36) |
| Sub 2-123 | m/z = 432.23($C_{30}H_{29}BO_2$ = 432.36) | Sub 2-124 | m/z = 508.26($C_{38}H_{33}BO_2$ = 508.46) |
| Sub 2-125 | m/z = 330.18($C_{22}H_{23}BO_2$ = 330.23) | Sub 2-126 | m/z = 330.18($C_{22}H_{23}BO_2$ = 330.23) |
| Sub 2-127 | m/z = 380.19($C_{26}H_{25}BO_2$ = 380.29) | Sub 2-128 | m/z = 380.19($C_{26}H_{25}BO_2$ = 380.29) |
| Sub 2-129 | m/z = 430.21($C_{30}H_{27}BO_2$ = 430.35) | Sub 2-130 | m/z = 380.19($C_{26}H_{25}BO_2$ = 380.29) |
| Sub 2-131 | m/z = 380.19($C_{26}H_{25}BO_2$ = 380.29) | Sub 2-132 | m/z = 430.21($C_{33}H_{27}BO_2$ = 430.35) |
| Sub 2-133 | m/z = 456.23($C_{32}H_{29}BO_2$ = 456.38) | Sub 2-134 | m/z = 456.23($C_{32}H_{29}BO_2$ = 456.38) |
| Sub 2-135 | m/z = 506.24($C_{36}H_{31}BO_2$ = 506.44) | Sub 2-136 | m/z = 204.13($C_{12}H_{17}BO_2$ = 204.07) |
| Sub 2-137 | m/z = 254.15($C_{16}H_{19}BO_2$ = 254.13) | Sub 2-138 | m/z = 254.15($C_{16}H_{19}BO_2$ = 254.13) |
| Sub 2-139 | m/z = 280.16($C_{18}H_{21}BO_2$ = 280.17) | Sub 2-140 | m/z = 280.16($C_{18}H_{21}BO_2$ = 280.17) |
| Sub 2-141 | m/z = 280.16($C_{18}H_{21}BO_2$ = 280.17) | Sub 2-142 | m/z = 356.19($C_{24}H_{25}BO_2$ = 356.27) |
| Sub 2-143 | m/z = 456.23($C_{32}H_{29}BO_2$ = 456.38) | Sub 2-144 | m/z = 432.23($C_{33}H_{29}BO_2$ = 432.36) |
| Sub 2-145 | m/z = 508.26($C_{36}H_{33}BO_2$ = 508.46) | Sub 2-146 | m/z = 304.16($C_{20}H_{21}BO_2$ = 304.19) |
| Sub 2-147 | m/z = 304.16($C_{20}H_{21}BO_2$ = 304.19) | Sub 2-148 | m/z = 304.16($C_{20}H_{21}BO_2$ = 304.19) |
| Sub 2-149 | m/z = 304.16($C_{20}H_{21}BO_2$ = 304.19) | Sub 2-150 | m/z = 328.16($C_{22}H_{21}BO_2$ = 328.21) |
| Sub 2-151 | m/z = 508.26($C_{36}H_{33}BO_2$ = 508.46) | Sub 2-152 | m/z = 508.26($C_{36}H_{33}BO_2$ = 508.46) |
| Sub 2-153 | m/z = 584.29($C_{42}H_{37}BO_2$ = 584.55) | Sub 2-154 | m/z = 660.32($C_{48}H_{41}BO_2$ = 660.65) |
| Sub 2-155 | m/z = 532.26($C_{36}H_{33}BO_2$ = 532.48) | Sub 2-156 | m/z = 532.26($C_{38}H_{33}BO_2$ = 532.48) |
| Sub 2-157 | m/z = 582.27($C_{47}H_{35}BO_2$ = 582.54) | Sub 2-158 | m/z = 608.29($C_{44}H_{47}BO_2$ = 608.57) |
| Sub 2-159 | m/z = 608.29($C_{44}H_{37}BO_2$ = 608.57) | Sub 2-160 | m/z = 658.30($C_{48}H_{33}BO_2$ = 658.63) |
| Sub 2-161 | m/z = 357.19($C_{23}H_{24}BNO_2$ = 357.25) | Sub 2-162 | m/z = 457.22($C_{31}H_{28}BNO_2$ = 457.37) |
| Sub 2-163 | m/z = 458.22($C_{30}H_{37}BN_2O_2$ = 458.36) | Sub 2-164 | m/z = 510.25($C_{34}H_{31}BN_2O_2$ = 510.43) |
| Sub 2-165 | m/z = 386.15($C_{24}H_{23}BO_2S$ = 386.31) | Sub 2-166 | m/z = 386.15($C_{24}H_{23}BO_2S$ = 386.31) |
| Sub 2-167 | m/z = 462.18($C_{30}H_{27}BO_2S$ = 462.41) | Sub 2-168 | m/z = 462.18($C_{30}H_{27}BO_2S$ = 462.41) |
| Sub 2-169 | m/z = 386.15($C_{24}H_{23}BO_2S$ = 386.31) | Sub 2-170 | m/z = 386.15($C_{24}H_{23}BO_2S$ = 386.31) |
| Sub 2-171 | m/z = 462.18($C_{30}H_{27}BO_2S$ = 462.41) | Sub 2-172 | m/z = 446.21($C_{30}H_{27}BO_3$ = 446.34) |
| Sub 2-173 | m/z = 538.21($C_{36}H_{31}BO_2S$ = 538.51) | Sub 2-174 | m/z = 614.25($C_{42}H_{33}BO_2S$ = 614.60) |
| Sub 2-175 | m/z = 690.28($C_{48}H_{39}BO_2S$ = 690.70) | Sub 2-176 | m/z = 638.25($C_{44}H_{35}BO_2S$ = 638.62) |
| Sub 2-177 | m/z = 638.25($C_{44}H_{35}BO_2S$ = 638.62) | Sub 2-178 | m/z = 688.26($C_{48}H_{37}BO_2S$ = 688.68) |
| Sub 2-179 | m/z = 463.18($C_{29}H_{24}BNO_2S$ = 463.40) | Sub 2-180 | m/z = 463.18($C_{29}H_{26}BNO_2S$ = 463.40) |
| Sub 2-181 | m/z = 472.26($C_{33}H_{33}BO_2$ = 472.42) | Sub 2-182 | m/z = 523.27($C_{38}H_{34}BNO_2$ = 523.47) |
| Sub 2-183 | m/z = 369.19($C_{24}H_{24}BNO_2$ = 369.26) | Sub 2-184 | m/z = 310.12($C_{38}H_{19}BO_2S$ = 310.22) |
| Sub 2-185 | m/z = 310.12($C_{18}H_{19}BO_2S$ = 310.22) | Sub 2-186 | m/z = 310.12($C_{18}H_{19}BO_2S$ = 310.22) |
| Sub 2-187 | m/z = 294.14($C_{18}H_{19}BO_3$ = 294.15) | Sub 2-188 | m/z = 294.14($C_{18}H_{19}BO_3$ = 294.15) |
| Sub 2-189 | m/z = 320.19($C_{21}H_{25}BO_2$ = 320.23) | Sub 2-190 | m/z = 445.22($C_{30}H_{23}BNO_2$ = 445.36) |
| Sub 2-191 | m/z = 445.22($C_{30}H_{28}BNO_2$ = 445.36) | Sub 2-192 | m/z = 521.25($C_{36}H_{33}BNO_2$ = 521.46) |
| Sub 2-193 | m/z = 540.20($C_{34}H_{29}BN_2O_2S$ = 540.48) | Sub 2-194 | m/z = 369.19($C_{24}H_{24}BNO_2$ = 369.26) |
| Sub 2-195 | m/z = 369.19($C_{24}H_{24}BNO_2$ = 369.26) | Sub 2-196 | m/z = 445.22($C_{30}H_{28}BNO_2$ = 445.36) |
| Sub 2-197 | m/z = 673.32($C_{48}H_{40}BNO_2$ = 673.65) | Sub 2-198 | m/z = 673.32($C_{48}H_{40}BNO_2$ = 673.65) |
| Sub 2-199 | m/z = 446.22($C_{20}H_{27}BN_2O_2$ = 446.35) | Sub 2-200 | m/z = 447.21($C_{28}H_{26}BN_3O_2$ = 447.34) |
| Sub 2-201 | m/z = 337.13($C_{19}H_{20}BNO_2S$ = 337.24) | Sub 2-202 | m/z = 337.13($C_{19}H_{20}BNO_2S$ = 337.24) |
| Sub 2-203 | m/z = 413.16($C_{25}H_{24}BNO_2S$ = 413.34) | Sub 2-204 | m/z = 464.17($C_{28}H_{25}BN_2O_2S$ = 464.39) |
| Sub 2-205 | m/z = 464.17($C_{28}H_{25}BN_2O_2S$ = 464.39) | | |

☐ . . . Product Synthesis

Sub 1A or Sub 1B (1 eq.) were dissolved in THF in a round-bottom flask, and then Sub 2 (1 eq.), Pd(PPh$_3$)$_4$ (0.04 eq.), NaOH (3 eq.), and water were added, followed by stirring at 75☐. Upon completion of the reaction, the reaction product was extracted with CH$_2$Cl$_2$ and water. The organic layer was dried over MgSO$_4$ and concentrated, and then the compound obtained was subjected to a silica gel column and recrystallization to give a final product.

1. Synthesis Embodiment 1-1

<Reaction Scheme 25>

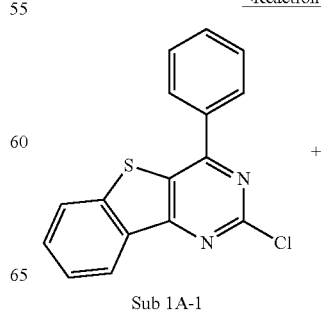

Sub 1A-1

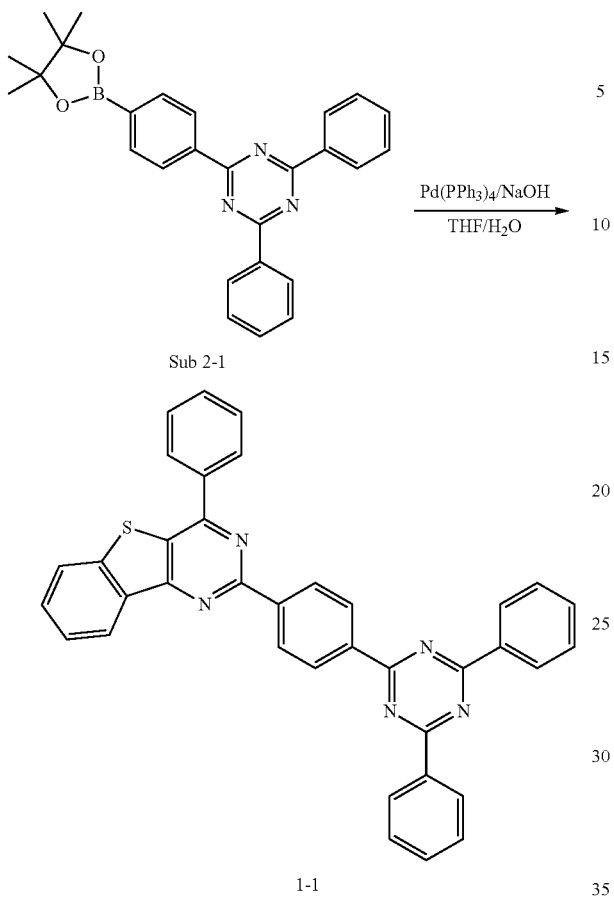

Sub 1A-1 (5.45 g, 18.4 mmol) obtained in the above synthesis was dissolved in THF in a round-bottom flask, and then Sub 2-1 (7.99 g, 18.4 mmol), Pd(PPh₃)₄ (0.85 g, 0.7 mmol), NaOH (2.2 g, 55.1 mmol), and water were added, followed by stirring at 75□. Upon completion of the reaction, the reaction product was extracted with CH₂Cl₂ and water. The organic layer was dried over MgSO₄ and concentrated, and then the compound obtained was subjected to a silica gel column and recrystallization to give a product 7.43 g (yield: 71%).

2. Synthesis Embodiment 1-25

In addition to Sub 1A-1 (4.04 g, 13.6 mmol) obtained from the synthesis above, Sub 2-42 (7.98 g, 13.6 mmol), Pd(PPh₃)₄ (0.63 g, 0.5 mmol), NaOH (1.63 g, 40.8 mmol), THF, and water were used under the method of synthesis 1-1 to give a product 6.77 g (yield: 69%).

3. Synthesis Embodiment 1-43

<Reaction Scheme 26>

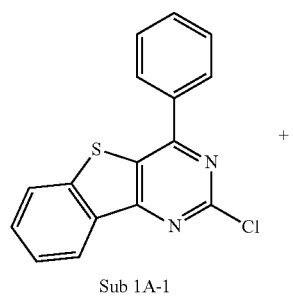

Sub 1A-1

<Reaction Scheme 27>

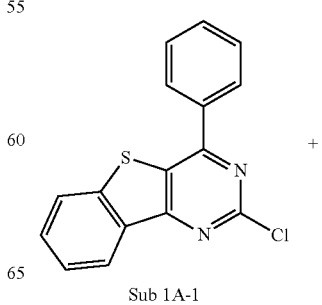

Sub 1A-1

247

-continued

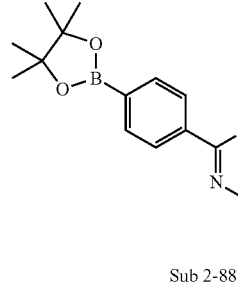

Sub 2-88

Pd(PPh₃)₄/NaOH
THF/H₂O
→

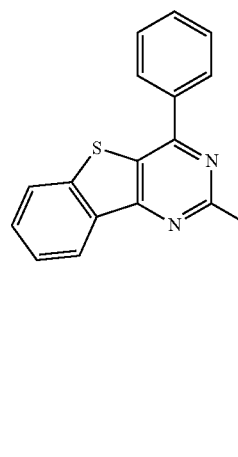

1-43

In addition to Sub 1A-1 (4.7 g, 15.8 mmol) obtained from the synthesis above, Sub 2-88 (8.05 g, 15.8 mmol), Pd(PPh₃)₄ (0.73 g, 0.6 mmol), NaOH (1.9 g, 47.5 mmol), THF, and water were used under the method of synthesis 1-1 to give a product 6.82 g (yield: 67%).

4. Synthesis Embodiment 1-86

<Reaction Scheme 28>

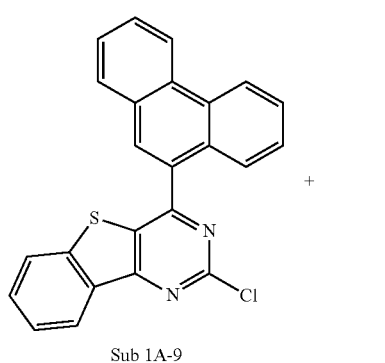

Sub 1A-9

248

-continued

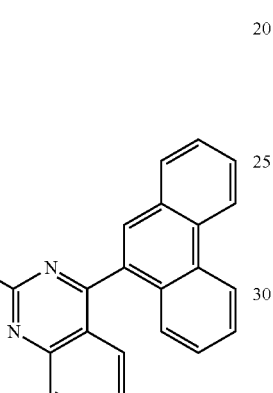

Sub 2-162

Pd(PPh₃)₄/NaOH
THF/H₂O
→

1-86

In addition to Sub 1A-9 (6.9 g, 17.4 mmol) obtained from the synthesis above, Sub 2-162 (7.65 g, 17.4 mmol), Pd(PPh₃)₄ (0.8 g, 0.7 mmol), NaOH (2.09 g, 52.2 mmol), THF, and water were used under the method of synthesis 1-1 to give a product 7.82 g (yield: 65%).

5. Synthesis Embodiment 1-117

<Reaction Scheme 29>

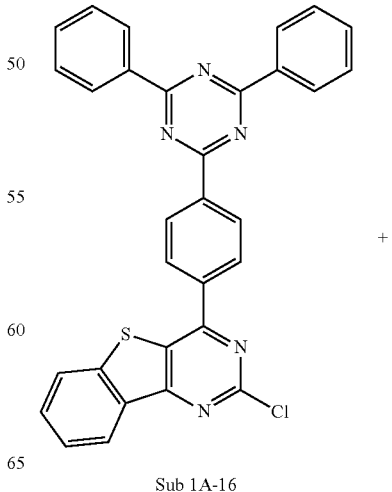

+

Sub 1A-16

-continued

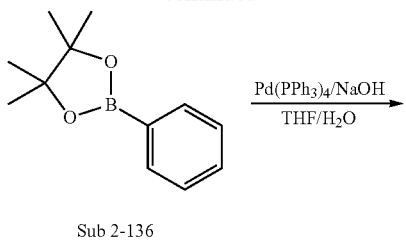

Sub 2-136

-continued

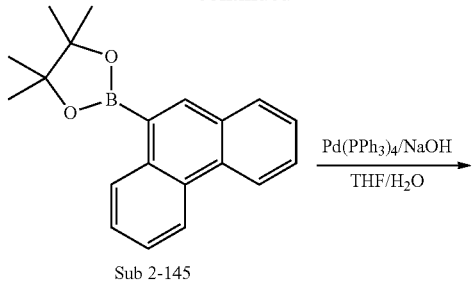

Sub 2-145

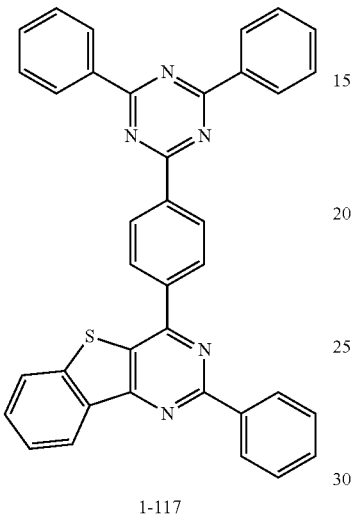

1-117

In addition to Sub 1A-16 (8.37 g, 15.9 mmol) obtained from the synthesis above, Sub 2-136 (3.23 g, 15.9 mmol), Pd(PPh$_3$)$_4$ (0.73 g, 0.6 mmol), NaOH (1.9 g, 47.6 mmol), THF, and water were used under the method of synthesis 1-1 to give a product 6.59 g (yield: 73%).

6. Synthesis Embodiment 1-142

<Reaction Scheme 30>

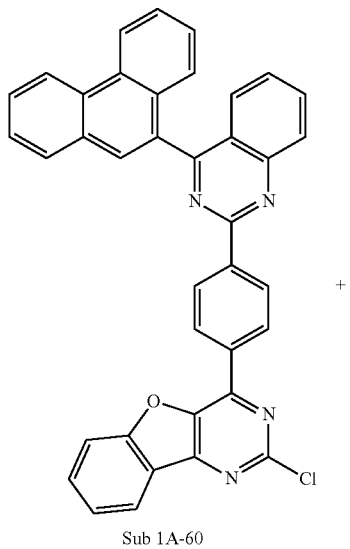

Sub 1A-60

+

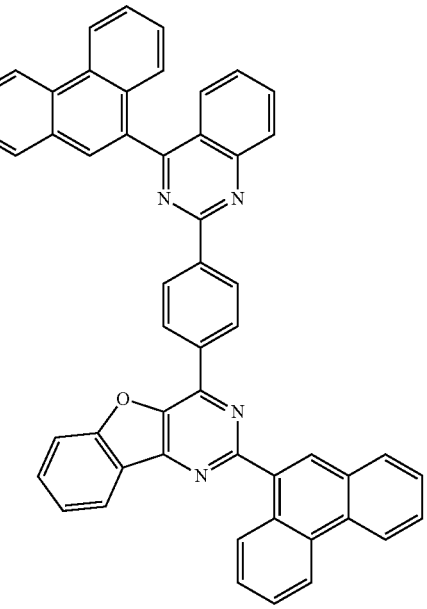

1-142

In addition to Sub 1A-60 (7.72 g, 13.2 mmol) obtained from the synthesis above, Sub 2-146 (4.01 g, 13.2 mmol), Pd(PPh$_3$)$_4$ (0.61 g, 0.5 mmol), NaOH (1.58 g, 39.6 mmol), THF, and water were used under the method of synthesis 1-1 to give a product 6.14 g (yield: 64%).

7. Synthesis Embodiment 1-161

<Reaction Scheme 31>

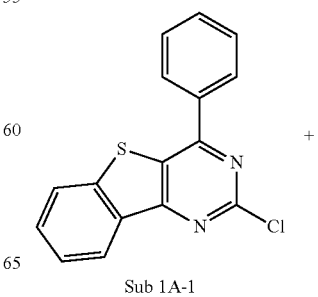

Sub 1A-1

+

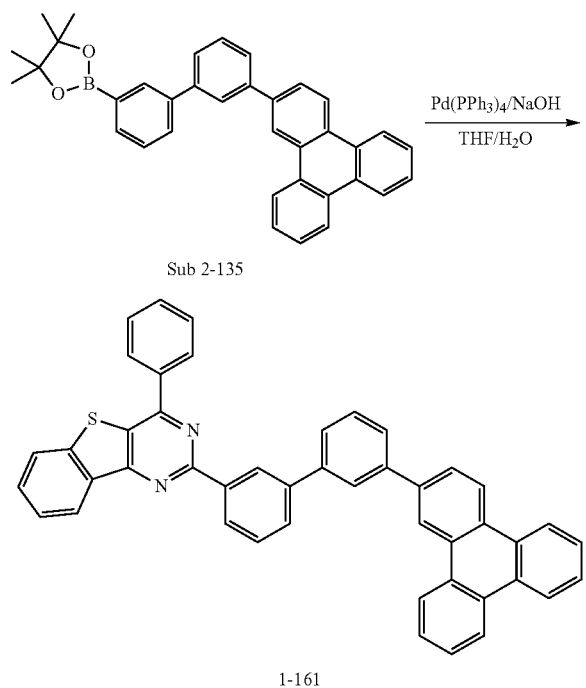

Sub 2-135

1-161

In addition to Sub 1A-1 (4.83 g, 16.3 mmol) obtained from the synthesis above, Sub 2-135 (8.24 g, 16.3 mmol), Pd(PPh$_3$)$_4$ (0.75 g, 0.7 mmol), NaOH (1.95 g, 48.8 mmol), THF, and water were used under the method of synthesis 1-1 to give a product 6.88 g (yield: 66%).

8. Synthesis Embodiment 1-166

<Reaction Scheme 32>

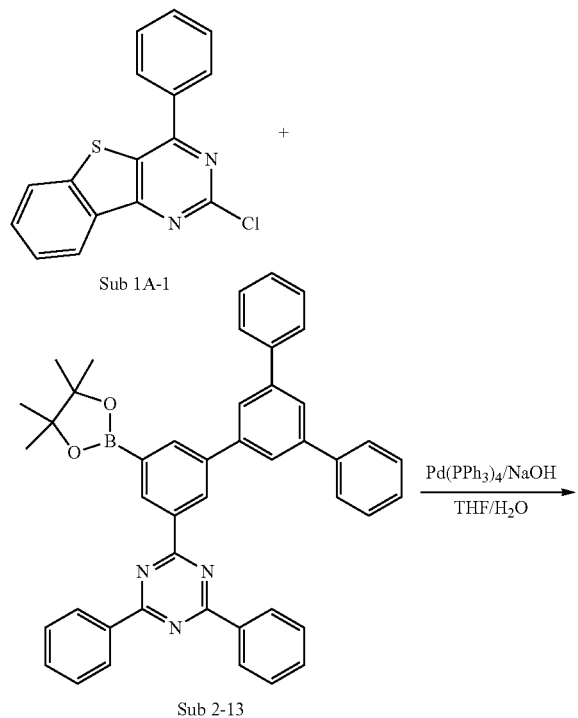

Sub 1A-1

Sub 2-13

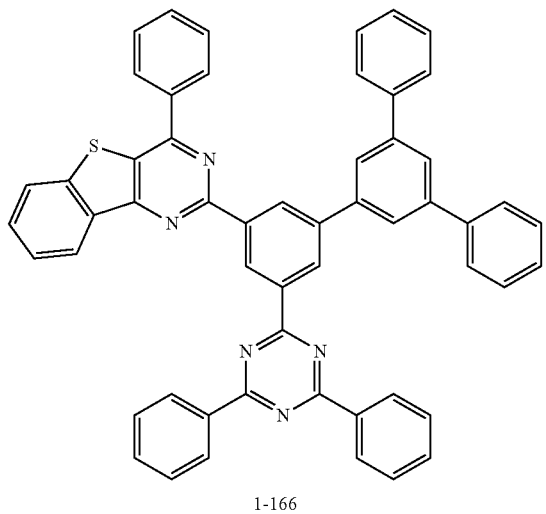

1-166

In addition to Sub 1A-1 (4.64 g, 15.6 mmol) obtained from the synthesis above, Sub 2-13 (10.38 g, 15.6 mmol), Pd(PPh$_3$)$_4$ (0.72 g, 0.6 mmol), NaOH (1.88 g, 46.9 mmol), THF, and water were used under the method of synthesis 1-1 to give a product 8.48 g (yield: 68%).

9. Synthesis Embodiment 2-48

<Reaction Scheme 33>

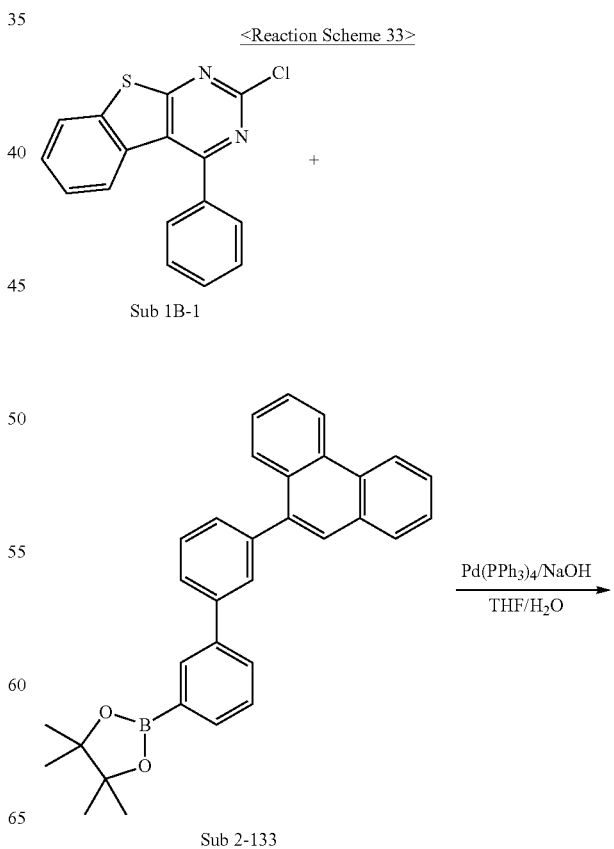

Sub 1B-1

Sub 2-133

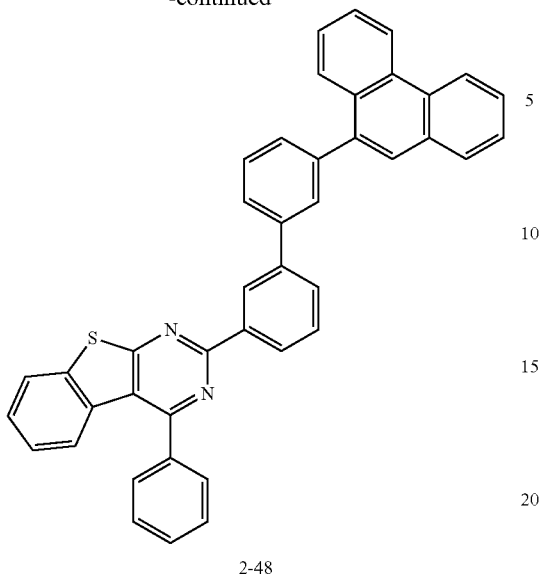

2-48

In addition to Sub 1B-1 (4.99 g, 16.8 mmol) obtained from the synthesis above, Sub 2-133 (7.67 g, 16.8 mmol), Pd(PPh$_3$)$_4$ (0.78 g, 0.7 mmol), NaOH (2.02 g, 50.4 mmol), THF, and water were used under the method of synthesis 1-1 to give a product 6.65 g (yield: 67%).

10. Synthesis Embodiment 2-69

<Reation Scheme 34>

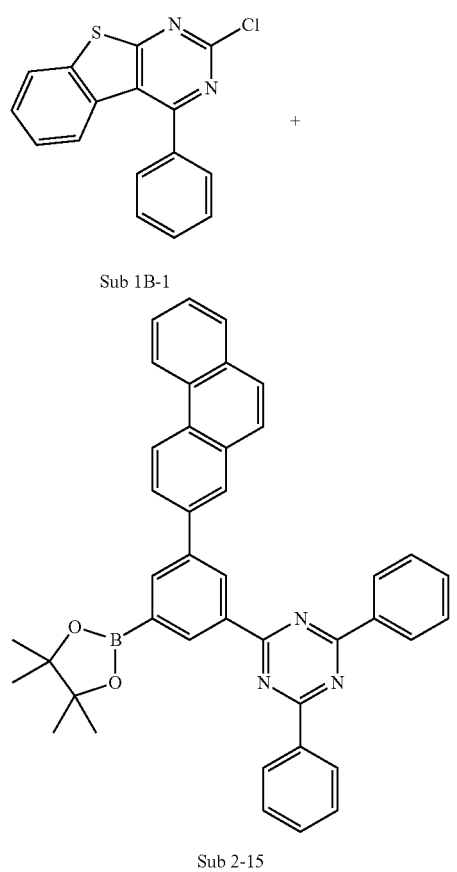

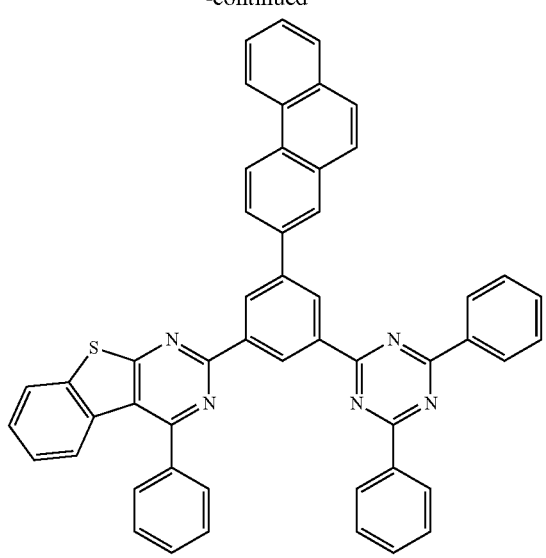

Sub 2-69

In addition to Sub 1B-1 (4.64 g, 15.6 mmol) obtained from the synthesis above, Sub 2-15 (9.56 g, 15.6 mmol), Pd(PPh$_3$)$_4$ (0.72 g, 0.6 mmol), NaOH (1.88 g, 46.9 mmol), THF, and water were used under the method of synthesis 1-1 to give a product 7.58 g (yield: 65%).

11. Synthesis Embodiment 2-103

<Reaction Scheme 35>

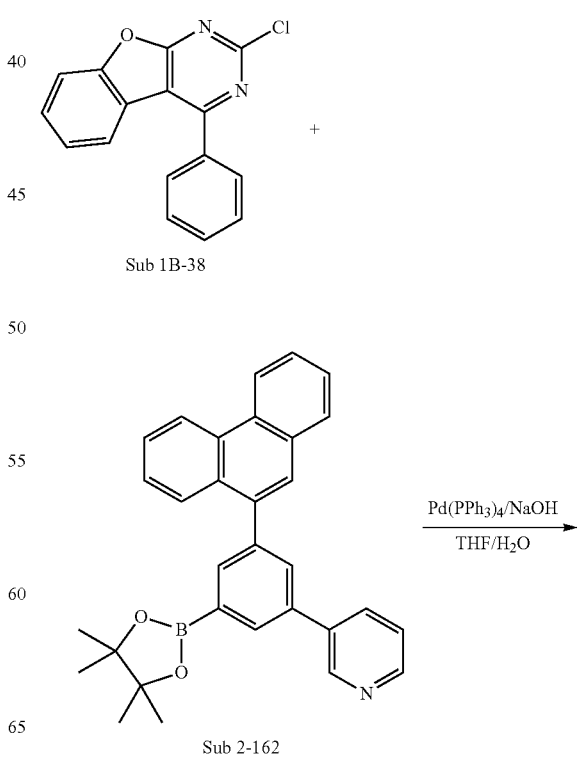

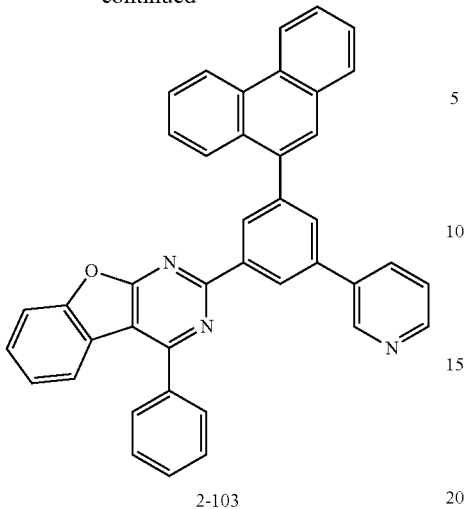

2-103

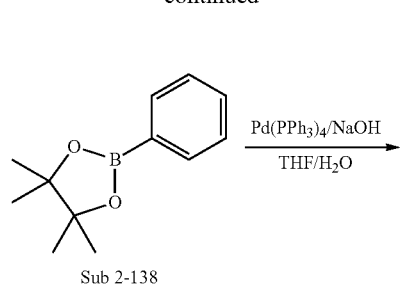

Sub 2-138

In addition to Sub 1B-38 (4.83 g, 17.2 mmol) obtained from the synthesis above, Sub 2-162 (7.87 g, 17.2 mmol), Pd(PPh$_3$)$_4$ (0.8 g, 0.7 mmol), NaOH (2.06 g, 51.6 mmol), THF, and water were used under the method of synthesis 1-1 to give a product 6.64 g (yield: 67%).

12. Synthesis Embodiment 2-109

<Reaction Scheme 36>

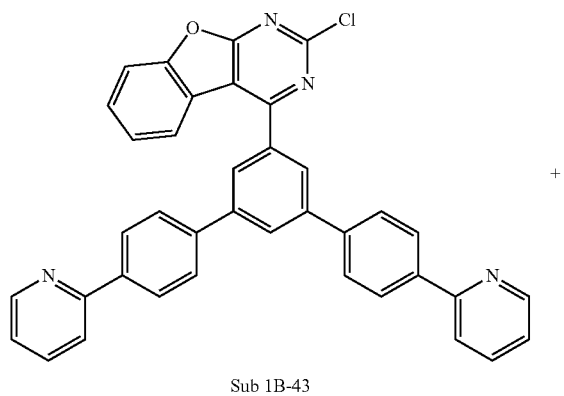

Sub 1B-43

+

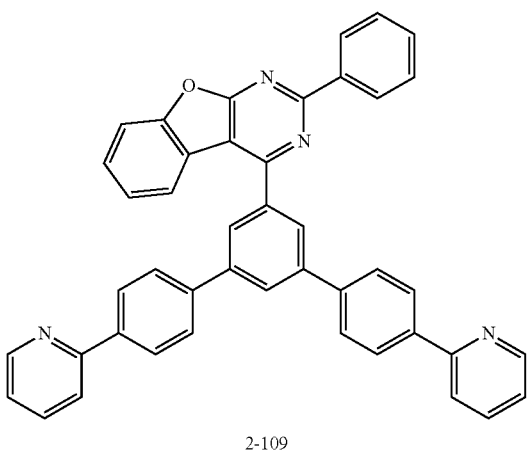

2-109

In addition to Sub 1B-43 (11.86 g, 20.2 mmol) obtained from the synthesis above, Sub 2-136 (4.12 g, 20.2 mmol), Pd(PPh$_3$)$_4$ (0.93 g, 0.8 mmol), NaOH (2.42 g, 60.6 mmol), THF, and water were used under the method of synthesis 1-1 to give a product 7.37 g (yield: 58%).

Meanwhile, FD-MS values of compounds 1-1 to 2-110 according to an embodiment of the present invention, which were prepared according to the synthesis Embodiments above, are shown in table 3 below.

TABLE 3

| Compound | FD-MS | Compound | FD-MS |
| --- | --- | --- | --- |
| 1-1 | m/z = 569.17($C_{37}H_{23}N_5S$ = 569.68) | 1-2 | m/z = 619.18($C_{41}H_{25}N_5S$ = 619.74) |
| 1-3 | m/z = 645.20($C_{43}H_{27}N_5S$ = 645.77) | 1-4 | m/z = 669.20($C_{45}H_{27}N_5S$ = 669.79) |
| 1-5 | m/z = 721.23($C_{49}H_{31}N_5S$ = 721.87) | 1-6 | m/z = 873.29($C_{61}H_{39}N_5S$ = 874.06) |
| 1-7 | m/z = 669.20($C_{45}H_{27}N_5S$ = 669.79) | 1-8 | m/z = 620.18($C_{40}H_{24}N_6S$ = 620.72) |
| 1-9 | m/z = 670.19($C_{44}H_{26}N_6S$ = 670.78) | 1-10 | m/z = 571.16($C_{35}H_{21}N_7S$ = 571.65) |
| 1-11 | m/z = 671.19($C_{43}H_{25}N_7S$ = 671.77) | 1-12 | m/z = 723.22($C_{47}H_{29}N_7S$ = 723.85) |
| 1-13 | m/z = 670.19($C_{44}H_{26}N_6S$ = 670.78) | 1-14 | m/z = 765.17($C_{49}H_{27}N_5OS_2$ = 765.90) |
| 1-15 | m/z = 685.23($C_{46}H_{31}N_5S$ = 685.84) | 1-16 | m/z = 723.22($C_{47}H_{23}N_7S$ = 723.85) |
| 1-17 | m/z = 751.19($C_{49}H_{29}N_5S_2$ = 751.92) | 1-18 | m/z = 735.21($C_{43}H_{29}N_5OS$ = 735.85) |
| 1-19 | m/z = 784.24($C_{53}H_{32}N_6S$ = 784.93) | 1-20 | m/z = 725.17($C_{47}H_{27}N_5S_2$ = 725.88) |
| 1-21 | m/z = 568.17($C_{38}H_{24}N_4S$ = 568.69) | 1-22 | m/z = 618.19($C_{42}H_{26}N_4S$ = 618.75) |
| 1-23 | m/z = 644.20($C_{44}H_{28}N_4S$ = 644.78) | 1-24 | m/z = 568.17($C_{38}H_{24}N_4S$ = 568.69) |
| 1-25 | m/z = 720.23($C_{30}H_{32}N_4S$ = 720.88) | 1-26 | m/z = 668.20($C_{46}H_{28}N_4S$ = 668.81) |
| 1-27 | m/z = 668.20($C_{45}H_{28}N_4S$ = 668.81) | 1-28 | m/z = 569.17($C_{37}H_{23}N_5S$ = 568.68) |
| 1-29 | m/z = 619.18($C_{41}H_{25}N_5S$ = 619.74) | 1-30 | m/z = 758.21($C_{52}H_{33}N_4OS$ = 758.89) |
| 1-31 | m/z = 570.16($C_{36}H_{22}N_6S$ = 570.67) | 1-32 | m/z = 780.15($C_{53}H_{28}N_4S_3$ = 780.98) |
| 1-33 | m/z = 758.21($C_{52}H_{30}N_4OS$ = 758.89) | 1-34 | m/z = 784.24($C_{53}H_{32}N_6S$ = 784.93) |

TABLE 3-continued

| Compound | FD-MS | Compound | FD-MS |
|---|---|---|---|
| 1-35 | m/z = 784.24($C_{53}H_{32}N_6S$ = 784.93) | 1-36 | m/z = 722.23($C_{48}H_{32}N_6S$ = 722.86) |
| 1-37 | m/z = 721.23($C_{43}H_{31}N_5S$ = 721.87) | 1-38 | m/z = 721.23($C_{43}H_{31}N_5S$ = 721.87) |
| 1-39 | m/z = 722.23($C_{48}H_{30}N_6S$ = 722.86) | 1-40 | m/z = 619.18($C_{41}H_{25}N_5S$ = 619.74) |
| 1-41 | m/z = 542.16($C_{36}H_{22}N_4S$ = 542.65) | 1-42 | m/z = 618.19($C_{42}H_{26}N_4S$ = 618.75) |
| 1-43 | m/z = 642.19($C_{44}H_{26}N_4S$ = 642.77) | 1-44 | m/z = 543.15($C_{35}H_{21}N_5S$ = 543.64) |
| 1-45 | m/z = 593.17($C_{30}H_{23}N_5S$ = 593.70) | 1-46 | m/z = 648.14($C_{42}H_{24}N_4S_2$ = 648.80) |
| 1-47 | m/z = 632.17($C_{42}H_{24}N_4OS$ = 632.73) | 1-48 | m/z = 707.21($C_{48}H_{29}N_5S$ = 707.84) |
| 1-49 | m/z = 542.16($C_{38}H_{22}N_4S$ = 542.65) | 1-50 | m/z = 618.19($C_{42}H_{26}N_4S$ = 618.75) |
| 1-51 | m/z = 694.22($C_{48}H_{30}N_4S$ = 694.84) | 1-52 | m/z = 642.19($C$=$H_{26}N_4S$ = 642.77) |
| 1-53 | m/z = 619.18($C_{41}H_{25}N_5S$ = 619.74) | 1-54 | m/z = 632.17($C_{42}H_{24}N_4OS$ = 632.73) |
| 1-55 | m/z = 648.14($C_{42}H_{24}N_4S_2$ = 648.80) | 1-56 | m/z = 707.21($C_{48}H_{23}N_5S$ = 707.84) |
| 1-57 | m/z = 658.22($C_{45}H_{30}N_4S$ = 658.81) | 1-58 | m/z = 490.15($C_{34}H_{22}N_2S$ = 490.62) |
| 1-59 | m/z = 624.21($C_{46}H_{30}N_2S$ = 642.81) | 1-60 | m/z = 590.18($C_{42}H_{26}N_2S$ = 590.73) |
| 1-61 | m/z = 491.15($C_{33}H_{21}N_3S$ = 491.60) | 1-62 | m/z = 591.18($C_{41}H_{25}N_3S$ = 591.72) |
| 1-63 | m/z = 592.17($C_{40}H_{24}N_4S$ = 592.71) | 1-64 | m/z = 644.20($C_{44}H_{28}N_4S$ = 644.78) |
| 1-65 | m/z = 580.16($C_{40}H_{24}N_2OS$ = 580.70) | 1-66 | m/z = 596.14($C_{40}H_{24}N_2S_2$ = 596.76) |
| 1-67 | m/z = 580.17($C_{34}H_{24}N_4S$ = 580.70) | 1-68 | m/z = 581.17($C_{83}H_{23}N_5S$ = 581.69) |
| 1-69 | m/z = 656.19($C_{46}H_{26}N_2OS$ = 656.79) | 1-70 | m/z = 597.13($C_{30}H_{23}N_3S_2$ = 597.75) |
| 1-71 | m/z = 606.21($C_{43}H_{30}N_2S$ = 606.78) | 1-72 | m/z = 657.22($C$=$H_{31}N_3S$ = 657.82) |
| 1-73 | m/z = 645.20($C_{43}H_{27}N_5S$ = 645.77) | 1-74 | m/z = 797.26($C_{55}H_{35}N_5S$ = 797.95) |
| 1-75 | m/z = 726.17($C_{46}H_{26}N_6S_2$ = 726.87) | 1-76 | m/z = 836.25($C_{55}H_{32}N_8S$ = 836.96) |
| 1-77 | m/z = 694.22($C_{48}H_{30}N_4S$ = 694.84) | 1-78 | m/z = 725.17($C_{47}H_{27}N_5S_2$ = 725.88) |
| 1-79 | m/z = 822.26($C_{56}H_{34}N_6S$ = 822.97) | 1-80 | m/z = 722.23($C_{48}H_{30}N_6S$ = 722.86) |
| 1-81 | m/z = 694.22($C_{48}H_{30}N_4S$ = 694.84) | 1-82 | m/z = 695.21($C_{47}H_{29}N_5S$ = 695.83) |
| 1-83 | m/z = 642.19($C_{54}H_{26}N_4S$ = 642.77) | 1-84 | m/z = 717.20($C_{48}H_{27}N_5S$ = 717.84) |
| 1-85 | m/z = 540.17($C_{38}H_{24}N_2S$ = 540.68) | 1-86 | m/z = 691.21($C_{49}H_{29}N_3S$ = 691.84) |
| 1-87 | m/z = 668.20($C_{46}H_{28}N_4S$ = 688.81) | 1-88 | m/z = 694.22($C_{48}H_{30}N_4S$ = 694.84) |
| 1-89 | m/z = 743.21($C_{51}H_{29}N_5S$ = 743.87) | 1-90 | m/z = 738.15($C_{48}H_{26}N_4OS_2$ = 738.88) |
| 1-91 | m/z = 743.21($C_{51}H_{29}N_5S$ = 743.87) | 1-92 | m/z = 619.18($C_{41}H_{25}N_5S$ = 619.74) |
| 1-93 | m/z = 569.17($C_{37}H_{28}N_5S$ = 569.68) | 1-94 | m/z = 773.24($C_{51}H_{31}N_7S$ = 773.90) |
| 1-95 | m/z = 770.23($C_{52}H_{30}N_6S$ = 770.90) | 1-96 | m/z = 619.18($C_{41}H_{25}N_5S$ = 619.74) |
| 1-97 | m/z = 618.19($C_{42}H_{26}N_4S$ = 618.75) | 1-98 | m/z = 746.23($C_{50}H_{30}N_6S$ = 746.88) |
| 1-99 | m/z = 668.20($C_{46}H_{28}N_4S$ = 668.81) | 1-100 | m/z = 618.19($C_{42}H_{26}N_4S$ = 618.75) |
| 1-101 | m/z = 820.27($C_{58}H_{36}N_4S$ = 821.00) | 1-102 | m/z = 553.19($C_{37}H_{23}N_5O$ = 553.61) |
| 1-103 | m/z = 706.25($C_{48}H_{30}N_6O$ = 706.79) | 1-104 | m/z = 757.26($C_{51}H_{31}N_7O$ = 757.84) |
| 1-105 | m/z = 705.23($C_{47}H_{27}N_7O$ = 705.76) | 1-106 | m/z = 552.20($C_{38}H_{24}N_4O$ = 552.62) |
| 1-107 | m/z = 858.31($C_{50}H_{38}N_6O$ = 858.98) | 1-108 | m/z = 869.32($C_{52}H_{39}N_5O$ = 870.01) |
| 1-109 | m/z = 526.18($C_{36}H_{22}N_4O$ = 526.59) | 1-110 | m/z = 702.24($C_{50}H_{30}N_4O$ = 702.80) |
| 1-111 | m/z = 729.25($C_{53}H_{31}N_5O$ = 729.82) | 1-112 | m/z = 716.22($C_{60}H_{28}N_4O_2$ = 716.78) |
| 1-113 | m/z = 474.17($C_{34}H_{22}N_2O$ = 474.55) | 1-114 | m/z = 681.25($C_{47}H_{31}N_5O$ = 681.78) |
| 1-115 | m/z = 575.20($C_{41}H_{25}N_3O$ = 575.66) | 1-116 | m/z = 687.14($C_{45}H_{25}N_3OS_2$ = 687.83) |
| 1-117 | m/z = 569.17($C_{37}H_{23}N_5S$ = 569.68) | 1-118 | m/z = 797.26($C_{55}H_{35}N_5S$ = 797.96) |
| 1-119 | m/z = 591.18($C_{41}H_{25}N_3S$ = 591.72) | 1-120 | m/z = 823.25($C_{55}H_{33}N_7S$ = 823.96) |
| 1-121 | m/z = 568.17($C_{38}H_{24}N_4S$ = 568.69) | 1-122 | m/z = 796.27($C_{56}H_{36}N_4S$ = 796.98) |
| 1-123 | m/z = 822.26($C_{56}H_{34}N_6S$ = 822.97) | 1-124 | m/z = 772.24($C_{52}H_{32}N_6S$ = 772.92) |
| 1-125 | m/z = 542.16($C_{36}H_{22}N_4S$ = 542.65) | 1-126 | m/z = 742.22($C_{52}H_{30}N_4S$ = 742.89) |
| 1-127 | m/z = 725.17($C_{47}H_{27}N_5S_2$ = 725.88) | 1-128 | m/z = 810.28($C_{57}H_{38}N_4S$ = 811.00) |
| 1-129 | m/z = 553.19($C_{37}H_{23}N_5O$ = 553.61) | 1-130 | m/z = 781.28($C_{55}H_{35}N_5O$ = 781.90) |
| 1-131 | m/z = 575.20($C_{42}H_{25}N_3O$ = 575.66) | 1-132 | m/z = 807.27($C_{55}H_{33}N_2O$ = 807.90) |
| 1-133 | m/z = 626.21($C_{44}H_{26}N_4O$ = 626.70) | 1-134 | m/z = 772.19($C_{52}H_{28}N_4O_2S$ = 772.87) |
| 1-135 | m/z = 727.24($C_{51}H_{29}N_5O$ = 727.81) | 1-136 | m/z = 703.24($C_{49}H_{29}N_5O$ = 703.79) |
| 1-137 | m/z = 552.20($C_{38}H_{24}N_4O$ = 552.62) | 1-138 | m/z = 932.35($C_{68}H_{44}N_4O$ = 933.10) |
| 1-139 | m/z = 806.28($C_{56}H_{34}N_6O$ = 806.91) | 1-140 | m/z = 756.26($C_{52}H_{32}N_6O$ = 756.85) |
| 1-141 | m/z = 526.18($C_{36}H_{22}N_4O$ = 526.59) | 1-142 | m/z = 726.24($C_{52}H_{30}N_4O$ = 726.82) |
| 1-143 | m/z = 709.19($C_{47}H_{27}N_5OS$ = 709.82) | 1-144 | m/z = 692.26($C_{43}H_{32}N_4O$ = 692.80) |
| 1-145 | m/z = 619.18($C_{41}H_{25}N_5S$ = 619.74) | 1-146 | m/z = 847.28($C_{59}H_{37}N_5S$ = 848.02) |
| 1-147 | m/z = 872.27($C_{50}H_{36}N_6S$ = 873.03) | 1-148 | m/z = 820.24($C_{56}H_{32}N_6S$ = 820.96) |
| 1-149 | m/z = 754.27($C_{54}H_{34}N_4O$ = 754.87) | 1-150 | m/z = 680.23($C_{46}H_{28}N_6O$ = 680.75) |
| 1-151 | m/z = 753.25($C_{53}H_{31}N_5O$ = 753.85) | 1-152 | m/z = 854.28($C_{60}H_{34}N_6O$ = 854.95) |
| 1-153 | m/z = 592.17($C_{40}H_{24}N_4S$ = 592.71) | 1-154 | m/z = 744.23($C_{52}H_{32}N_4S$ = 744.90) |
| 1-155 | m/z = 676.23($C_{48}H_{28}N_4O$ = 676.76) | 1-156 | m/z = 826.27($C_{60}H_{34}N_4O$ = 826.94) |
| 1-157 | m/z = 692.20($C_{48}H_{28}N_4S$ = 692.83) | 1-158 | m/z = 774.19($C_{52}H_{30}N_4S_2$ = 774.95) |
| 1-159 | m/z = 602.21($C_{42}H_{26}N_4O$ = 602.68) | 1-160 | m/z = 668.20($C_{46}H_{28}N_4S$ = 668.81) |
| 1-161 | m/z = 640.20($C_{46}H_{28}N_2S$ = 640.79) | 1-162 | m/z = 590.18($C_{42}H_{26}N_2S$ = 590.73) |
| 1-163 | m/z = 590.18($C_{42}H_{26}N_2S$ = 590.73) | 1-164 | m/z = 807.27($C_{58}H_{37}N_2S$ = 808.00) |
| 1-165 | m/z = 644.20($C_{44}H_{28}N_4S$ = 644.78) | 1-166 | m/z = 797.26($C_{35}H_{35}N_5S$ = 797.96) |
| 1-167 | m/z = 721.23($C_{49}H_{31}N_5S$ = 721.87) | 1-168 | m/z = 795.25($C_{35}H_{33}N_5S$ = 795.95) |
| 1-169 | m/z = 745.23($C_{51}H_{31}N_5S$ = 745.89) | 1-170 | m/z = 745.23($C_{31}H_{31}N_5S$ = 745.89) |
| 1-171 | m/z = 644.20($C_{44}H_{28}N_4S$ = 644.78) | 1-172 | m/z = 796.27($C_{36}H_{36}N_4S$ = 796.98) |
| 1-173 | m/z = 720.23($C_{50}H_{32}N_4S$ = 720.88) | 1-174 | m/z = 794.25($C_{36}H_{34}N_4S$ = 794.96) |
| 1-175 | m/z = 744.23($C_{52}H_{32}N_4S$ = 744.90) | 1-176 | m/z = 744.23($C_{52}H_{32}N_4S$ = 744.90) |
| 1-177 | m/z = 644.20($C_{44}H_{28}N_4S$ = 644.78) | 1-178 | m/z = 796.27($C_{36}H_{36}N_4S$ = 796.98) |
| 1-179 | m/z = 720.23($C_{50}H_{32}N_4S$ = 720.88) | 1-180 | m/z = 794.25($C_{36}H_{34}N_4S$ = 794.96) |
| 1-181 | m/z = 744.23($C_{52}H_{32}N_4S$ = 744.90) | 1-182 | m/z = 744.23($C_{52}H_{32}N_4S$ = 744.90) |
| 1-183 | m/z = 642.21($C_{46}H_{30}N_2S$ = 642.81) | 1-184 | m/z = 794.28($C_{58}H_{38}N_2S$ = 795.00) |
| 1-185 | m/z = 718.24($C_{52}H_{34}N_2S$ = 718.90) | 1-186 | m/z = 792.26($C_{58}H_{36}N_2S$ = 792.98) |
| 1-187 | m/z = 742.24($C_{54}H_{34}N_2S$ = 742.93) | 1-188 | m/z = 742.24($C_{54}H_{34}N_2S$ = 742.93) |
| 1-189 | m/z = 566.18($C_{40}H_{26}N_2S$ = 566.71) | 1-190 | m/z = 718.24($C_{52}H_{34}N_2S$ = 718.90) |

TABLE 3-continued

| Compound | FD-MS | Compound | FD-MS |
|---|---|---|---|
| 1-191 | m/z = 642.21($C_{40}H_{30}N_2S$ = 642.81) | 1-192 | m/z = 716.23($C_{52}H_{32}N_2S$ = 716.89) |
| 1-193 | m/z = 666.21($C_{48}H_{30}N_2S$ = 666.83) | 1-194 | m/z = 566.21($C_{48}H_{30}N_2S$ = 666.83) |
| 1-195 | m/z = 671.17($C_{36}H_{28}N_2S_2$ = 672.86) | 1-196 | m/z = 824.23($C_{58}H_{36}N_2S_2$ = 825.05) |
| 1-197 | m/z = 748.20($C_{52}H_{32}N_2S_2$ = 748.95) | 1-198 | m/z = 822.22($C_{58}H_{34}N_2S_2$ = 823.03) |
| 1-199 | m/z = 772.20($C_{54}H_{32}N_2S_2$ = 772.98) | 1-200 | m/z = 772.20($C_{54}H_{32}N_2S_2$ = 772.98) |
| 1-201 | m/z = 645.20($C_{43}H_{27}N_5S$ = 645.77) | | |
| 2-1 | m/z = 569.17($C_{37}H_{23}N_3S$ = 569.68) | 2-2 | m/z = 568.17($C_{38}H_{24}N_4S$ = 568.69) |
| 2-3 | m/z = 568.17($C_{38}H_{24}N_4S$ = 568.69) | 2-4 | m/z = 568.17($C_{38}H_{24}N_4S$ = 568.69) |
| 2-5 | m/z = 566.18($C_{42}H_{26}N_2S$ = 566.71) | 2-6 | m/z = 490.15($C_{34}H_{22}N_2S$ = 490.62) |
| 2-7 | m/z = 490.15($C_{34}H_{22}N_2S$ = 490.62) | 2-8 | m/z = 520.11($C_{34}H_{20}N_2S_2$ = 520.67) |
| 2-9 | m/z = 520.11($C_{34}H_{20}N_2S_2$ = 520.67) | 2-10 | m/z = 579.18($C_{40}H_{25}N_3S$ = 579.71) |
| 2-11 | m/z = 503.15($C_{34}H_{21}N_3S$ = 503.62) | 2-12 | m/z = 598.13($C_{38}H_{22}N_4S_2$ = 598.74) |
| 2-13 | m/z = 471.09($C_{29}H_{17}N_3S_2$ = 471.60) | 2-14 | m/z = 564.17($C_{40}H_{24}N_2S$ = 564.70) |
| 2-15 | m/z = 514.15($C_{38}H_{27}N_2S$ = 514.64) | 2-16 | m/z = 514.15($C_{36}H_{22}N_2S$ = 514.64) |
| 2-17 | m/z = 645.20($C_{43}H_{27}N_3S$ = 645.77) | 2-18 | m/z = 644.20($C_{44}H_{28}N_4S$ = 644.78) |
| 2-19 | m/z = 644.20($C_{44}H_{28}N_4S$ = 644.78) | 2-20 | m/z = 644.20($C_{44}H_{28}N_4S$ = 644.78) |
| 2-21 | m/z = 642.21($C_{46}H_{30}N_2S$ = 642.81) | 2-22 | m/z = 566.18($C_{40}H_{26}N_2S$ = 566.71) |
| 2-23 | m/z = 566.18($C_{40}H_{26}N_2S$ = 566.71) | 2-24 | m/z = 596.14($C_{40}H_{24}N_2S_2$ = 596.76) |
| 2-25 | m/z = 596.14($C_{40}H_{24}N_2S_2$ = 596.76) | 2-26 | m/z = 655.21($C_{46}H_{29}N_3S$ = 655.81) |
| 2-27 | m/z = 579.18($C_{40}H_{25}N_3S$ = 579.71) | 2-28 | m/z = 674.16($C_{44}H_{26}N_4S_2$ = 674.83) |
| 2-29 | m/z = 547.12($C_{35}H_{21}N_3S_2$ = 547.69) | 2-30 | m/z = 640.20($C_{46}H_{28}N_2S$ = 640.79) |
| 2-31 | m/z = 590.18($C_{42}H_{26}N_2S$ = 590.73) | 2-32 | m/z = 590.18($C_{42}H_{26}N_2S$ = 590.73) |
| 2-33 | m/z = 645.20($C_{43}H_{27}N_5S$ = 645.77) | 2-34 | m/z = 644.20($C_{44}H_{28}N_4S$ = 644.78) |
| 2-35 | m/z = 644.20($C_{44}H_{28}N_4S$ = 644.78) | 2-36 | m/z = 644.20($C_{44}H_{28}N_4S$ = 644.78) |
| 2-37 | m/z = 642.21($C_{46}H_{30}N_2S$ = 642.81) | 2-38 | m/z = 566.18($C_{40}H_{26}N_2S$ = 566.71) |
| 2-39 | m/z = 566.18($C_{40}H_{26}N_2S$ = 566.71) | 2-40 | m/z = 596.14($C_{40}H_{24}N_2S_2$ = 596.76) |
| 2-41 | m/z = 596.14($C_{40}H_{24}N_2S_2$ = 596.76) | 2-42 | m/z = 655.21($C_{46}H_{29}N_3S$ = 655.81) |
| 2-43 | m/z = 579.18($C_{40}H_{25}N_3S$ = 579.71) | 2-44 | m/z = 674.16($C_{44}H_{26}N_4S_2$ = 674.83) |
| 2-45 | m/z = 547.12($C_{35}H_{21}N_3S_2$ = 547.69) | 2-46 | m/z = 640.20($C_{46}H_{28}N_2S$ = 640.79) |
| 2-47 | m/z = 590.18($C_{42}H_{26}N_2S$ = 590.73) | 2-48 | m/z = 590.18($C_{42}H_{26}N_2S$ = 590.73) |
| 2-49 | m/z = 645.20($C_{43}H_{27}N_3S$ = 645.77) | 2-50 | m/z = 644.20($C_{44}H_{25}N_4S$ = 644.78) |
| 2-51 | m/z = 644.20($C_{44}H_{28}N_4S$ = 644.78) | 2-52 | m/z = 644.20($C_{44}H_{28}N_4S$ = 644.78) |
| 2-53 | m/z = 642.21($C_{48}H_{30}N_2S$ = 642.81) | 2-54 | m/z = 566.18($C_{40}H_{26}N_2S$ = 566.71) |
| 2-55 | m/z = 566.18($C_{40}H_{26}N_2S$ = 566.71) | 2-56 | m/z = 596.14($C_{40}H_{24}N_2S_2$ = 596.76) |
| 2-57 | m/z = 596.14($C_{40}H_{24}N_2S_2$ = 596.76) | 2-58 | m/z = 655.21($C_{46}H_{29}N_3S$ = 655.81) |
| 2-59 | m/z = 579.18($C_{35}H_{25}N_3S$ = 579.71) | 2-60 | m/z = 674.16($C_{44}H_{26}N_4S_2$ = 674.83) |
| 2-61 | m/z = 547.12($C_{48}H_{21}N_3S_2$ = 547.69) | 2-62 | m/z = 640.20($C_{40}H_{28}N_2S$ = 640.79) |
| 2-63 | m/z = 590.18($C_{42}H_{25}N_2S$ = 590.73) | 2-64 | m/z = 590.18($C_{42}H_{26}N_2S$ = 590.73) |
| 2-65 | m/z = 645.20($C_{43}H_{27}N_3S$ = 645.77) | 2-66 | m/z = 797.26($C_{55}H_{35}N_3S$ = 797.96) |
| 2-67 | m/z = 721.23($C_{45}H_{31}N_3S$ = 721.87) | 2-68 | m/z = 795.25($C_{55}H_{33}N_5S$ = 795.95) |
| 2-69 | m/z = 745.23($C_{51}H_{31}N_5S$ = 745.89) | 2-70 | m/z = 745.23($C_{51}H_{31}N_5S$ = 745.89) |
| 2-71 | m/z = 644.20($C_{44}H_{29}N_4S$ = 644.78) | 2-72 | m/z = 796.27($C_{50}H_{36}N_4S$ = 796.98) |
| 2-73 | m/z = 720.23($C_{50}H_{32}N_4S$ = 720.88) | 2-74 | m/z = 794.25($C_{50}H_{34}N_4S$ = 794.96) |
| 2-75 | m/z = 744.23($C_{52}H_{32}N_4S$ = 744.90) | 2-76 | m/z = 744.23($C_{52}H_{32}N_4S$ = 744.90) |
| 2-77 | m/z = 644.20($C_{44}H_{28}N_4S$ = 644.78) | 2-78 | m/z = 796.67($C_{56}H_{36}N_4S$ = 796.98) |
| 2-79 | m/z = 720.23($C_{50}H_{32}N_4S$ = 720.88) | 2-80 | m/z = 794.25($C_{56}H_{34}N_4S$ = 794.96) |
| 2-81 | m/z = 744.23($C_{52}H_{32}N_4S$ = 744.90) | 2-82 | m/z = 744.23($C_{52}H_{32}N_4S$ = 744.90) |
| 2-83 | m/z = 642.21($C_{48}H_{30}N_2S$ = 642.81) | 2-84 | m/z = 794.28($C_{58}H_{38}N_2S$ = 795.00) |
| 2-85 | m/z = 718.24($C_{52}H_{34}N_2S$ = 718.90) | 2-86 | m/z = 792.26($C_{58}H_{36}N_2S$ = 792.98) |
| 2-87 | m/z = 742.24($C_{54}H_{34}N_2S$ = 742.93) | 2-88 | m/z = 742.24($C_{54}H_{34}N_2S$ = 742.93) |
| 2-89 | m/z = 566.18($C_{40}H_{26}N_2S$ = 566.71) | 2-90 | m/z = 718.24($C_{52}H_{34}N_2S$ = 718.90) |
| 2-91 | m/z = 642.21($C_{36}H_{30}N_2S$ = 642.81) | 2-92 | m/z = 716.23($C_{52}H_{32}N_2S$ = 716.89) |
| 2-93 | m/z = 666.21($C_{48}H_{30}N_2S$ = 666.83) | 2-94 | m/z = 566.21($C_{48}H_{30}N_2S$ = 666.83) |
| 2-95 | m/z = 672.17($C_{45}H_{28}N_2S_2$ = 672.86) | 2-96 | m/z = 716.23($C_{52}H_{32}N_2S$ = 716.89) |
| 2-97 | m/z = 748.20($C_{52}H_{32}N_2S_2$ = 748.95) | 2-98 | m/z = 822.22($C_{58}H_{34}N_2S_2$ = 823.03) |
| 2-99 | m/z = 772.20($C_{54}H_{32}N_2S_2$ = 772.98) | 2-100 | m/z = 772.20($C_{54}H_{32}N_2S_2$ = 772.98) |
| 2-101 | m/z = 807.27($C_{58}H_{37}N_3S$ = 808.00) | 2-102 | m/z = 644.20($C_{44}H_{28}N_4S$ = 644.78) |
| 2-103 | m/z = 575.20($C_{41}H_{29}N_3O$ = 575.66) | 2-104 | m/z = 729.25($C_{51}H_{11}N_5O$ = 729.82) |
| 2-105 | m/z = 754.27($C_{54}H_{34}N_4O$ = 754.87) | 2-106 | m/z = 624.22($C_{46}H_{28}N_2O$ = 624.73) |
| 2-107 | m/z = 652.23($C_{45}H_{28}N_4O$ = 652.74) | 2-108 | m/z = 629.22($C_{43}H_{27}N_5O$ = 629.71) |
| 2-109 | m/z = 628.23($C_{44}H_{28}N_4O$ = 628.72) | 2-110 | m/z = 602.21($C_{42}H_{26}N_4O$ = 602.68) |

Meanwhile, the synthesis Embodiments of the present invention, represented by Formula 1, have been described, but these are based on a Suzuki cross-coupling reaction and a Miyaura boration reaction. A person skilled in the art could easily understand that the above reactions proceed even though, besides the substituents specified in the specific synthesis Embodiments, the other substituents (X, $R^1$, $Ar^1$, $Ar^2$, $L^1$, $L^2$, and m) defined in Formula 1 are bonded.

For Embodiment, all of the reaction of a starting material→Sub 1A in Reaction Scheme 3, the reaction of a starting material→Sub 1B in Reaction Scheme 4, and the reaction of a starting material→Sub 2 in Reaction Scheme 12, and the reactions in Reaction Schemes 25 to 36, are based on the Suzuki cross-coupling reaction; the reaction of a starting material→Sub 2 in Reaction Scheme 13 is based on the Miyaura boration reaction. The above reactions will proceed even though substituents that are not specified therein are bonded.

Manufacture and Evaluation of Organic Electronic Element

[Embodiment I-1] Green Organic Electronic Light Emitting Element (Electron Transport Layer)

An organic electronic light emitting element was manufactured by an ordinary method using the compound according to an embodiment of the present invention as a material for an electron transport layer. First, 4,4',4"-Tris[2-naphthyl(phenyl)amino]triphenylamine (hereinafter, abbreviated as "2-TNATA") was vacuum-deposited on an ITO layer (anode) formed on a galas substrate to form a hole injection layer with a thickness 60 nm, and then, 4,4',4"-bis(N-(1-naphthyl)-N-phenylamino]biphenyl (hereinafter, abbreviated as "NPD") was vacuum-deposited on the hole injection layer to form a hole injection layer with a thickness of 60 nm. Subsequently, 4,4'-N,N'-dicarbazole-biphenyl (hereinafter, abbreviated as "CBP") as a host material and tris(2-phenylpyridine)-iridium (hereinafter, abbreviated as "Ir(ppy)$_3$") as a dopant material were doped at a weight ratio of 95:5 to form a light emitting layer with a thickness of 30 nm on the hole transport layer. Then, (1,1'-bisphenyl)-4-olato)bis(2-methyl-8-quinolinolato)aluminum (hereinafter abbreviated as "BAlq") was vacuum-deposited with a thickness of 10 nm to form a hole blocking layer on the light emitting layer, and inventive compound 1-1 according to an embodiment of the present invention was vacuum-deposited with a thickness of nm to form an electron transport layer on the hole blocking layer. Thereafter, LiF as a halogenated alkali metal was deposited with a thickness of 0.2 nm to form an electron injection layer on the hole transport layer, and then Al was deposited with a thickness of 150 nm to form a cathode. Through the procedure described above, an organic electronic light emitting element was manufactured.

[Embodiment I-2] to [Embodiment I-166] Green Organic Electronic Light Emitting Element (Electron Transport Layer)

Organic electronic light emitting elements were manufactured by the same method as in Embodiment I-1 except that compounds 1-2 to 2-110 according to an embodiment of the present invention, listed on table 4 below, instead of compound 1-1 according to an embodiment of the present invention, were used as a material for an electron transport layer.

Comparative Example I-1

An organic electronic light emitting element was manufactured by the same method as in Embodiment I-1 except that comparative compound 1 below, instead of compound 1-1 according to an embodiment of the present invention, was used as a material for an electron transport layer.

Comparative Example I-2

An organic electronic light emitting element was manufactured by the same method as in Embodiment I-1 except that comparative compound I-2 below, instead of compound 1-1 according to an embodiment of the present invention, was used as a material for an electron transport layer.

Comparative Example I-3

An organic electronic light emitting element was manufactured by the same method as in Embodiment I-1 except that comparative compound I-3 below, instead of compound 1-1 according to an embodiment of the present invention, was used as a material for an electron transport layer.

Comparative Example I-4

An organic electronic light emitting element was manufactured by the same method as in Embodiment I-1 except that comparative compound I-4 below, instead of compound 1-1 according to an embodiment of the present invention, was used as a material for an electron transport layer.

Comparative Example I-5

An organic electronic light emitting element was manufactured by the same method as in Embodiment I-1 except that comparative compound I-5 below, instead of compound 1-1 according to an embodiment of the present invention, was used as a material for an electron transport layer.

Comparative Example I-6

An organic electronic light emitting element was manufactured by the same method as in Embodiment I-1 except that comparative compound I-6 below, instead of compound 1-1 according to an embodiment of the present invention, was used as a material for an electron transport layer.

Comparative Example I-7

An organic electronic light emitting element was manufactured by the same method as in Embodiment I-1 except that comparative compound I-7 below, instead of compound 1-1 according to an embodiment of the present invention, was used as a material for an electron transport layer.

Comparative Example I-8

An organic electronic light emitting element was manufactured by the same method as in Embodiment I-1 except that comparative compound I-8 below, instead of compound 1-1 according to an embodiment of the present invention, was used as a material for an electron transport layer.

Comparative Example I-9

An organic electronic light emitting element was manufactured by the same method as in Embodiment I-1 except that comparative compound I-9 below, instead of compound 1-1 according to an embodiment of the present invention, was used as a material for an electron transport layer.

<Comparative Compound I-1>

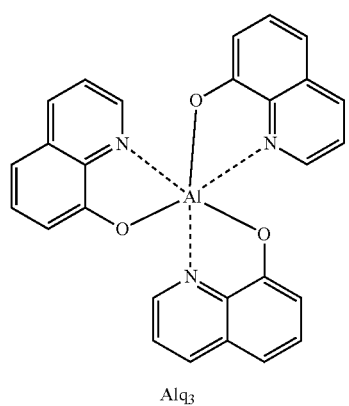

Alq$_3$

<Comparative Compound I-2>
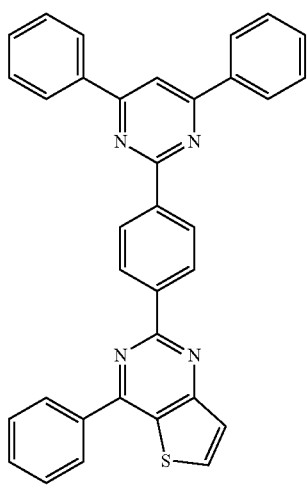
<Comparative Compound I-3>
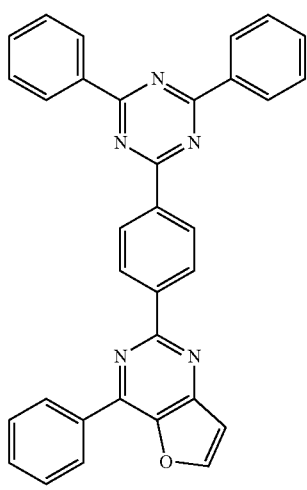
<Comparative Compound I-4>
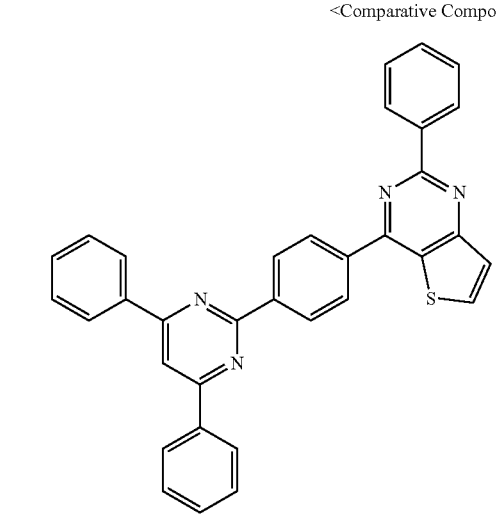
<Comparative Compound I-5>
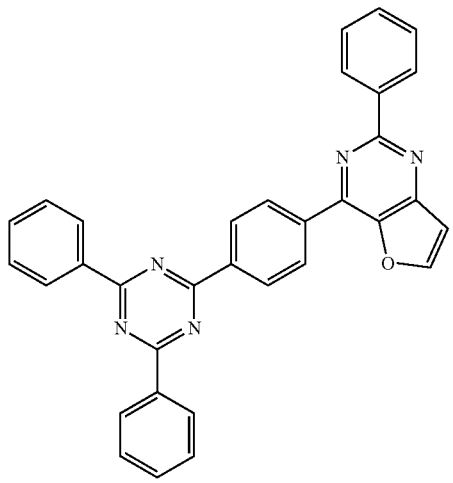
<Comparative Compound I-6>
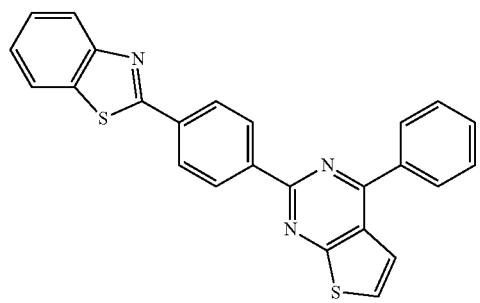
<Comparative Compound I-7>
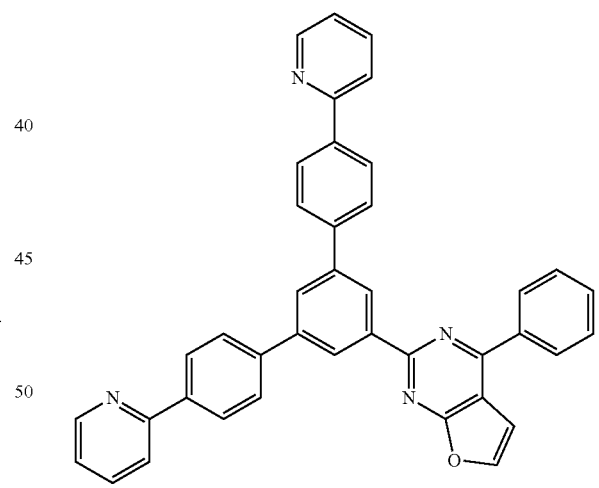
<Comparative Compound I-8>
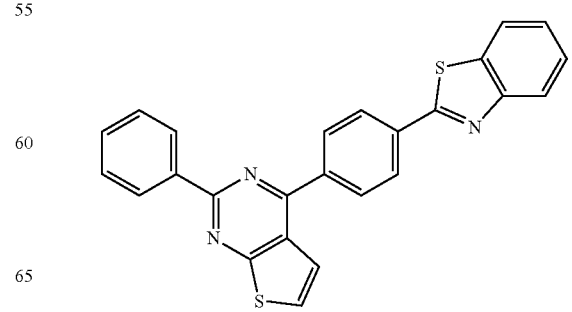

-continued

<Comparative Compound I-9>

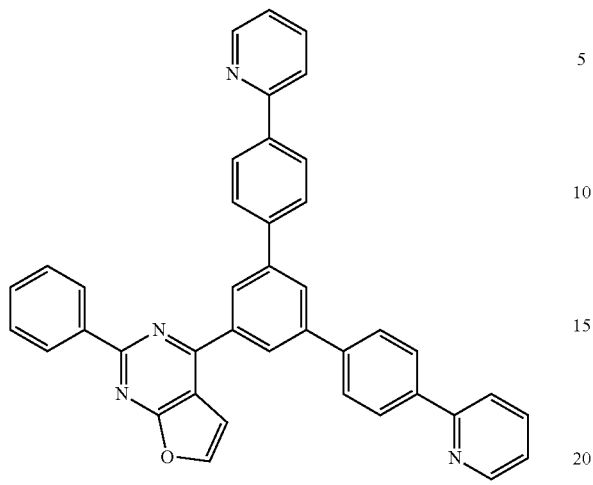

A forward bias DC voltage was applied to each of the organic electronic light emitting elements manufactured in Embodiments I-1 to I-166 and Comparative Examples I-1 to I-9 to measure electro-luminescence (EL) characteristics thereof by PR-650 (Photoresearch). Also, the T95 lifespan was measured by lifespan measuring equipment (Mcscience) at reference brightness of 5000 cd/m². The measurement results are shown in Table 4 below.

TABLE 4

| | | | | | | | | |
|---|---|---|---|---|---|---|---|---|
| Embodiment(I-134) | Compound(2-3) | 5.2 | 11.3 | 5000 | 44.1 | 153.0 | 0.33 | 0.62 |
| Embodiment(I-135) | Compound(2-4) | 5.3 | 11.8 | 5000 | 42.3 | 144.9 | 0.33 | 0.62 |
| Embodiment(I-136) | Compound(2-13) | 5.3 | 12.3 | 5000 | 40.6 | 140.3 | 0.33 | 0.61 |
| Embodiment(I-137) | Compound(2-16) | 5.5 | 11.8 | 5000 | 42.5 | 136.7 | 0.33 | 0.62 |
| Embodiment(I-138) | Compound(2-17) | 5.1 | 12.2 | 5000 | 41.1 | 137.1 | 0.33 | 0.61 |
| Embodiment(I-139) | Compound(2-18) | 5.1 | 11.7 | 5000 | 42.7 | 140.1 | 0.33 | 0.62 |
| Embodiment(I-140) | Compound(2-19) | 5.3 | 11.8 | 5000 | 42.3 | 139.5 | 0.33 | 0.61 |
| Embodiment(I-141) | Compound(2-20) | 5.3 | 12.4 | 5000 | 40.4 | 130.0 | 0.33 | 0.61 |
| Embodiment(I-142) | Compound(2-25) | 5.3 | 13.1 | 5000 | 38.1 | 131.2 | 0.33 | 0.61 |
| Embodiment(I-143) | Compound(2-29) | 5.4 | 12.4 | 5000 | 40.4 | 128.1 | 0.33 | 0.61 |
| Embodiment(I-144) | Compound(2-33) | 5.1 | 11.9 | 5000 | 42.1 | 141.8 | 0.33 | 0.61 |
| Embodiment(I-145) | Compound(2-34) | 5.1 | 12.0 | 5000 | 41.6 | 140.7 | 0.33 | 0.62 |
| Embodiment(I-146) | Compound(2-35) | 5.3 | 12.2 | 5000 | 40.9 | 144.8 | 0.33 | 0.61 |
| Embodiment(I-147) | Compound(2-36) | 5.1 | 12.0 | 5000 | 41.7 | 142.3 | 0.33 | 0.62 |
| Embodiment(I-148) | Compound(2-44) | 5.3 | 12.2 | 5000 | 41.1 | 137.4 | 0.33 | 0.62 |
| Embodiment(I-149) | Compound(2-45) | 5.2 | 11.8 | 5000 | 42.5 | 145.6 | 0.33 | 0.61 |
| Embodiment(I-150) | Compound(2-49) | 5.4 | 12.9 | 5000 | 38.9 | 132.7 | 0.33 | 0.62 |
| Embodiment(I-151) | Compound(2-50) | 5.3 | 12.6 | 5000 | 39.8 | 130.8 | 0.33 | 0.61 |
| Embodiment(I-152) | Compound(2-51) | 5.5 | 12.9 | 5000 | 38.7 | 128.2 | 0.33 | 0.61 |
| Embodiment(I-153) | Compound(2-52) | 5.2 | 12.8 | 5000 | 39.1 | 126.7 | 0.33 | 0.62 |
| Embodiment(I-154) | Compound(2-61) | 5.5 | 12.4 | 5000 | 40.4 | 130.0 | 0.33 | 0.61 |
| Embodiment(I-155) | Compound(2-65) | 5.1 | 12.1 | 5000 | 41.4 | 145.7 | 0.33 | 0.62 |
| Embodiment(I-156) | Compound(2-71) | 5.5 | 12.3 | 5000 | 40.6 | 140.2 | 0.33 | 0.61 |
| Embodiment(I-157) | Compound(2-77) | 5.3 | 12.2 | 5000 | 41.1 | 145.1 | 0.33 | 0.62 |
| Embodiment(I-110) | Compound(1-139) | 5.5 | 13.9 | 5000 | 35.9 | 114.9 | 0.33 | 0.61 |
| Embodiment(I-111) | Compound(1-140) | 5.3 | 14.3 | 5000 | 35.1 | 122.4 | 0.33 | 0.62 |
| Embodiment(I-112) | Compound(1-141) | 5.2 | 12.5 | 5000 | 40.0 | 126.8 | 0.33 | 0.61 |
| Embodiment(I-113) | Compound(1-142) | 5.4 | 13.2 | 5000 | 38.0 | 120.2 | 0.33 | 0.61 |
| Embodiment(I-114) | Compound(1-143) | 5.2 | 14.5 | 5000 | 34.6 | 119.9 | 0.33 | 0.62 |
| Embodiment(I-115) | Compound(1-144) | 5.5 | 14.4 | 5000 | 34.8 | 120.1 | 0.33 | 0.61 |
| Embodiment(I-116) | Compound(1-145) | 5.2 | 11.9 | 5000 | 42.2 | 141.5 | 0.33 | 0.61 |
| Embodiment(I-117) | Compound(1-146) | 5.2 | 11.7 | 5000 | 42.6 | 136.5 | 0.33 | 0.62 |
| Embodiment(I-118) | Compound(1-147) | 5.1 | 12.5 | 5000 | 40.0 | 132.4 | 0.33 | 0.62 |
| Embodiment(I-119) | Compound(1-149) | 5.2 | 12.9 | 5000 | 38.8 | 130.8 | 0.33 | 0.61 |
| Embodiment(I-120) | Compound(1-151) | 5.5 | 12.9 | 5000 | 38.9 | 133.1 | 0.33 | 0.62 |
| Embodiment(I-121) | Compound(1-153) | 5.3 | 12.1 | 5000 | 41.2 | 142.9 | 0.33 | 0.62 |
| Embodiment(I-122) | Compound(1-154) | 5.3 | 12.8 | 5000 | 39.1 | 130.5 | 0.33 | 0.62 |
| Embodiment(I-123) | Compound(1-155) | 5.5 | 12.5 | 5000 | 39.9 | 130.9 | 0.33 | 0.62 |
| Embodiment(I-124) | Compound(1-156) | 5.5 | 13.4 | 5000 | 37.2 | 132.0 | 0.33 | 0.62 |
| Embodiment(I-125) | Compound(1-157) | 5.3 | 12.4 | 5000 | 40.3 | 128.1 | 0.33 | 0.62 |
| Embodiment(I-126) | Compound(1-158) | 5.1 | 12.9 | 5000 | 38.9 | 134.4 | 0.33 | 0.61 |
| Embodiment(I-127) | Compound(1-159) | 5.2 | 13.3 | 5000 | 37.5 | 121.3 | 0.33 | 0.61 |

TABLE 4-continued

| | | | | | | | | |
|---|---|---|---|---|---|---|---|---|
| Embodiment(I-128) | Compound(1-160) | 5.4 | 12.8 | 5000 | 39.1 | 130.5 | 0.33 | 0.61 |
| Embodiment(I-129) | Compound(1-170) | 5.5 | 12.3 | 5000 | 40.7 | 145.4 | 0.33 | 0.62 |
| Embodiment(I-130) | Compound(1-173) | 5.4 | 12.3 | 5000 | 40.6 | 139.2 | 0.33 | 0.61 |
| Embodiment(I-131) | Compound(1-177) | 5.4 | 12.0 | 5000 | 41.8 | 143.3 | 0.33 | 0.62 |
| Embodiment(I-132) | Compound(2-1) | 5.2 | 11.5 | 5000 | 43.5 | 148.8 | 0.33 | 0.61 |
| Embodiment(I-133) | Compound(2-2) | 5.0 | 11.5 | 5000 | 43.4 | 146.3 | 0.33 | 0.61 |
| Embodiment(I-86) | Compound(1-112) | 5.2 | 13.8 | 5000 | 36.2 | 132.3 | 0.33 | 0.61 |
| Embodiment(I-87) | Compound(1-113) | 5.3 | 12.5 | 5000 | 40.1 | 130.2 | 0.33 | 0.61 |
| Embodiment(I-88) | Compound(1-115) | 5.1 | 11.6 | 5000 | 43.0 | 147.2 | 0.33 | 0.62 |
| Embodiment(I-89) | Compound(1-116) | 5.3 | 13.7 | 5000 | 36.4 | 125.6 | 0.33 | 0.61 |
| Embodiment(I-90) | Compound(1-117) | 5.3 | 11.9 | 5000 | 41.9 | 139.2 | 0.33 | 0.61 |
| Embodiment(I-91) | Compound(1-118) | 5.3 | 12.5 | 5000 | 39.9 | 133.0 | 0.33 | 0.61 |
| Embodiment(I-92) | Compound(1-119) | 5.1 | 11.6 | 5000 | 43.0 | 145.1 | 0.33 | 0.62 |
| Embodiment(I-93) | Compound(1-121) | 5.1 | 11.8 | 5000 | 42.4 | 141.1 | 0.33 | 0.62 |
| Embodiment(I-94) | Compound(1-122) | 5.4 | 12.6 | 5000 | 39.6 | 126.8 | 0.33 | 0.61 |
| Embodiment(I-95) | Compound(1-124) | 5.2 | 13.8 | 5000 | 36.1 | 131.0 | 0.33 | 0.61 |
| Embodiment(I-96) | Compound(1-125) | 5.3 | 11.9 | 5000 | 42.0 | 138.0 | 0.33 | 0.61 |
| Embodiment(I-97) | Compound(1-126) | 5.3 | 13.0 | 5000 | 38.4 | 126.3 | 0.33 | 0.61 |
| Embodiment(I-98) | Compound(1-127) | 5.5 | 13.4 | 5000 | 37.3 | 127.2 | 0.33 | 0.61 |
| Embodiment(I-99) | Compound(1-128) | 5.4 | 13.6 | 5000 | 36.8 | 132.9 | 0.33 | 0.62 |
| Embodiment(I-100) | Compound(1-129) | 5.1 | 12.5 | 5000 | 39.9 | 127.6 | 0.33 | 0.61 |
| Embodiment(I-101) | Compound(1-130) | 5.3 | 13.5 | 5000 | 37.1 | 118.7 | 0.33 | 0.62 |
| Embodiment(I-102) | Compound(1-131) | 5.1 | 12.1 | 5000 | 41.4 | 133.4 | 0.33 | 0.61 |
| Embodiment(I-103) | Compound(1-132) | 5.4 | 13.9 | 5000 | 36.0 | 121.7 | 0.33 | 0.62 |
| Embodiment(I-104) | Compound(1-133) | 5.1 | 12.4 | 5000 | 40.4 | 124.6 | 0.33 | 0.61 |
| Embodiment(I-105) | Compound(1-134) | 5.3 | 14.3 | 5000 | 34.9 | 121.2 | 0.33 | 0.62 |
| Embodiment(I-106) | Compound(1-135) | 5.4 | 14.3 | 5000 | 35.0 | 117.5 | 0.33 | 0.61 |
| Embodiment(I-107) | Compound(1-136) | 5.3 | 14.2 | 5000 | 35.2 | 116.2 | 0.33 | 0.61 |
| Embodiment(I-108) | Compound(1-137) | 5.3 | 12.5 | 5000 | 40.0 | 127.0 | 0.33 | 0.62 |
| Embodiment(I-109) | Compound(1-138) | 5.4 | 13.1 | 5000 | 38.0 | 114.2 | 0.33 | 0.62 |
| Embodiment(I-62) | Compound(1-77) | 5.3 | 12.1 | 5000 | 41.5 | 143.3 | 0.33 | 0.62 |
| Embodiment(I-63) | Compound(1-79) | 5.2 | 13.0 | 5000 | 38.5 | 134.1 | 0.33 | 0.61 |
| Embodiment(I-64) | Compound(1-81) | 5.2 | 12.2 | 5000 | 40.9 | 145.5 | 0.33 | 0.62 |
| Embodiment(I-65) | Compound(1-82) | 5.1 | 12.4 | 5000 | 40.3 | 126.3 | 0.33 | 0.61 |
| Embodiment(I-66) | Compound(1-83) | 5.3 | 12.2 | 5000 | 40.9 | 142.9 | 0.33 | 0.62 |
| Embodiment(I-67) | Compound(1-84) | 5.4 | 12.6 | 5000 | 39.6 | 132.4 | 0.33 | 0.62 |
| Embodiment(I-68) | Compound(1-85) | 5.5 | 11.8 | 5000 | 42.3 | 141.2 | 0.33 | 0.61 |
| Embodiment(I-69) | Compound(1-86) | 4.9 | 10.8 | 5000 | 46.2 | 154.5 | 0.33 | 0.62 |
| Embodiment(I-70) | Compound(1-87) | 5.2 | 12.3 | 5000 | 40.5 | 142.4 | 0.33 | 0.61 |
| Embodiment(I-71) | Compound(1-88) | 5.3 | 12.2 | 5000 | 40.8 | 138.4 | 0.33 | 0.62 |
| Embodiment(I-72) | Compound(1-90) | 5.5 | 13.2 | 5000 | 38.0 | 130.3 | 0.33 | 0.62 |
| Embodiment(I-73) | Compound(1-91) | 5.4 | 13.5 | 5000 | 36.9 | 133.1 | 0.33 | 0.61 |
| Embodiment(I-74) | Compound(1-92) | 5.3 | 13.2 | 5000 | 37.7 | 133.1 | 0.33 | 0.62 |
| Embodiment(I-75) | Compound(1-93) | 5.3 | 11.9 | 5000 | 42.1 | 143.3 | 0.33 | 0.61 |
| Embodiment(I-76) | Compound(1-97) | 5.4 | 11.9 | 5000 | 42.0 | 143.0 | 0.33 | 0.61 |
| Embodiment(I-77) | Compound(1-99) | 5.2 | 11.8 | 5000 | 42.3 | 143.2 | 0.33 | 0.62 |
| Embodiment(I-78) | Compound(1-100) | 5.5 | 11.8 | 5000 | 42.5 | 142.9 | 0.33 | 0.61 |
| Embodiment(I-79) | Compound(1-101) | 5.2 | 12.6 | 5000 | 39.8 | 135.4 | 0.33 | 0.62 |
| Embodiment(I-80) | Compound(1-102) | 5.2 | 11.9 | 5000 | 42.0 | 139.5 | 0.33 | 0.62 |
| Embodiment(I-81) | Compound(1-103) | 5.2 | 13.6 | 5000 | 36.7 | 125.0 | 0.33 | 0.61 |
| Embodiment(I-82) | Compound(1-106) | 5.2 | 12.3 | 5000 | 40.5 | 137.4 | 0.33 | 0.62 |
| Embodiment(I-83) | Compound(1-109) | 5.2 | 11.9 | 5000 | 42.1 | 135.1 | 0.33 | 0.62 |
| Embodiment(I-84) | Compound(1-110) | 5.4 | 12.7 | 5000 | 39.3 | 132.9 | 0.33 | 0.62 |
| Embodiment(I-85) | Compound(1-111) | 5.4 | 13.2 | 5000 | 37.8 | 131.8 | 0.33 | 0.62 |
| Embodiment(I-38) | Compound(1-49) | 5.0 | 11.2 | 5000 | 44.5 | 149.6 | 0.33 | 0.62 |
| Embodiment(I-39) | Compound(1-50) | 5.1 | 11.2 | 5000 | 44.8 | 152.1 | 0.33 | 0.61 |
| Embodiment(I-40) | Compound(1-51) | 5.4 | 12.1 | 5000 | 41.2 | 142.5 | 0.33 | 0.62 |
| Embodiment(I-41) | Compound(1-52) | 5.5 | 12.2 | 5000 | 41.1 | 144.9 | 0.33 | 0.62 |
| Embodiment(I-42) | Compound(1-53) | 5.1 | 12.4 | 5000 | 40.2 | 128.7 | 0.33 | 0.61 |
| Embodiment(I-43) | Compound(1-54) | 5.2 | 12.9 | 5000 | 38.6 | 132.8 | 0.33 | 0.62 |
| Embodiment(I-44) | Compound(1-55) | 5.3 | 12.5 | 5000 | 39.8 | 135.1 | 0.33 | 0.62 |
| Embodiment(I-45) | Compound(1-56) | 5.2 | 13.0 | 5000 | 38.5 | 134.4 | 0.33 | 0.61 |
| Embodiment(I-46) | Compound(1-57) | 5.2 | 12.7 | 5000 | 39.3 | 134.0 | 0.33 | 0.61 |
| Embodiment(I-47) | Compound(1-58) | 5.4 | 12.1 | 5000 | 41.4 | 142.8 | 0.33 | 0.61 |
| Embodiment(I-48) | Compound(1-59) | 5.4 | 12.3 | 5000 | 40.8 | 141.2 | 0.33 | 0.62 |
| Embodiment(I-49) | Compound(1-60) | 5.3 | 11.9 | 5000 | 42.2 | 139.8 | 0.33 | 0.61 |
| Embodiment(I-50) | Compound(1-61) | 5.5 | 12.0 | 5000 | 41.5 | 139.6 | 0.33 | 0.62 |
| Embodiment(I-51) | Compound(1-62) | 5.0 | 10.8 | 5000 | 46.1 | 156.0 | 0.33 | 0.61 |
| Embodiment(I-52) | Compound(1-63) | 5.3 | 12.1 | 5000 | 41.3 | 141.5 | 0.33 | 0.61 |
| Embodiment(I-53) | Compound(1-64) | 5.4 | 11.8 | 5000 | 42.3 | 139.8 | 0.33 | 0.62 |
| Embodiment(I-54) | Compound(1-66) | 5.3 | 12.7 | 5000 | 39.3 | 132.5 | 0.33 | 0.61 |
| Embodiment(I-55) | Compound(1-67) | 5.3 | 13.0 | 5000 | 38.6 | 133.4 | 0.33 | 0.62 |
| Embodiment(I-56) | Compound(1-69) | 5.5 | 12.7 | 5000 | 39.4 | 131.7 | 0.33 | 0.61 |
| Embodiment(I-57) | Compound(1-70) | 5.1 | 12.6 | 5000 | 39.7 | 131.4 | 0.33 | 0.62 |
| Embodiment(I-58) | Compound(1-71) | 5.5 | 12.7 | 5000 | 39.3 | 134.0 | 0.33 | 0.61 |
| Embodiment(I-59) | Compound(1-72) | 5.4 | 12.6 | 5000 | 39.8 | 132.7 | 0.33 | 0.62 |
| Embodiment(I-60) | Compound(1-73) | 5.1 | 11.3 | 5000 | 44.2 | 147.7 | 0.33 | 0.62 |
| Embodiment(I-61) | Compound(1-74) | 5.2 | 12.2 | 5000 | 41.0 | 139.5 | 0.33 | 0.61 |
| Embodiment(I-14) | Compound(1-18) | 5.3 | 12.8 | 5000 | 39.0 | 129.8 | 0.33 | 0.62 |
| Embodiment(I-15) | Compound(1-19) | 5.3 | 12.6 | 5000 | 39.7 | 131.2 | 0.33 | 0.62 |

TABLE 4-continued

| | | Voltage (V) | Current Density (mA/cm2) | Brightness (cd/m2) | Efficiency (cd/A) | Lifetime T(95) | CIE x | CIE y |
|---|---|---|---|---|---|---|---|---|
| Embodiment(I-16) | Compound(1-21) | 5.0 | 11.7 | 5000 | 42.7 | 149.2 | 0.33 | 0.62 |
| Embodiment(I-17) | Compound(1-22) | 5.1 | 11.1 | 5000 | 44.9 | 148.7 | 0.33 | 0.61 |
| Embodiment(I-18) | Compound(1-23) | 5.1 | 11.4 | 5000 | 44.0 | 151.5 | 0.33 | 0.61 |
| Embodiment(I-19) | Compound(1-24) | 5.1 | 11.4 | 5000 | 43.8 | 149.3 | 0.33 | 0.62 |
| Embodiment(I-20) | Compound(1-25) | 5.0 | 11.2 | 5000 | 44.7 | 152.8 | 0.33 | 0.61 |
| Embodiment(I-21) | Compound(1-26) | 5.2 | 11.6 | 5000 | 43.2 | 147.1 | 0.33 | 0.62 |
| Embodiment(I-22) | Compound(1-27) | 5.1 | 11.6 | 5000 | 43.2 | 146.1 | 0.33 | 0.62 |
| Embodiment(I-23) | Compound(1-29) | 5.1 | 12.6 | 5000 | 39.6 | 127.1 | 0.33 | 0.62 |
| Embodiment(I-24) | Compound(1-30) | 5.1 | 12.8 | 5000 | 39.1 | 128.1 | 0.33 | 0.61 |
| Embodiment(I-25) | Compound(1-33) | 5.1 | 12.6 | 5000 | 39.5 | 133.9 | 0.33 | 0.62 |
| Embodiment(I-26) | Compound(1-34) | 5.3 | 12.5 | 5000 | 39.9 | 135.8 | 0.33 | 0.61 |
| Embodiment(I-27) | Compound(1-36) | 5.4 | 12.9 | 5000 | 38.7 | 135.4 | 0.33 | 0.62 |
| Embodiment(I-28) | Compound(1-38) | 5.2 | 12.4 | 5000 | 40.3 | 133.9 | 0.33 | 0.62 |
| Embodiment(I-29) | Compound(1-39) | 5.4 | 13.0 | 5000 | 38.5 | 130.1 | 0.33 | 0.62 |
| Embodiment(I-30) | Compound(1-41) | 5.2 | 11.4 | 5000 | 44.0 | 148.2 | 0.33 | 0.62 |
| Embodiment(I-31) | Compound(1-42) | 5.1 | 11.5 | 5000 | 43.3 | 148.2 | 0.33 | 0.62 |
| Embodiment(I-32) | Compound(1-43) | 5.1 | 11.7 | 5000 | 42.7 | 146.6 | 0.33 | 0.61 |
| Embodiment(I-33) | Compound(1-44) | 5.2 | 12.8 | 5000 | 39.1 | 133.1 | 0.33 | 0.62 |
| Embodiment(I-34) | Compound(1-45) | 5.4 | 12.9 | 5000 | 38.8 | 131.5 | 0.33 | 0.61 |
| Embodiment(I-35) | Compound(1-46) | 5.3 | 12.7 | 5000 | 39.5 | 126.6 | 0.33 | 0.61 |
| Embodiment(I-36) | Compound(1-47) | 5.1 | 13.0 | 5000 | 38.5 | 127.7 | 0.33 | 0.62 |
| Embodiment(I-37) | Compound(1-48) | 5.4 | 12.7 | 5000 | 39.5 | 132.4 | 0.33 | 0.62 |
| Comparative Example (I-1) | Comparative Compound I-1 | 6.2 | 21.2 | 5000 | 23.6 | 69.1 | 0.33 | 0.61 |
| Comparative Example (I-2) | Comparative Compound I-2 | 5.7 | 16.6 | 5000 | 30.2 | 91.0 | 0.33 | 0.62 |
| Comparative Example(I-3) | Comparative Compound I-3 | 5.8 | 18.1 | 5000 | 27.6 | 84.7 | 0.33 | 0.62 |
| Comparative Example(I-4) | Comparative Compound I-4 | 5.8 | 17.8 | 5000 | 28.2 | 86.7 | 0.33 | 0.62 |
| Comparative Example(I-5) | Comparative Compound I-5 | 5.8 | 18.9 | 5000 | 26.5 | 77.9 | 0.33 | 0.62 |
| Comparative Example(I-6) | Comparative Compound I-6 | 5.6 | 16.5 | 5000 | 30.3 | 88.6 | 0.33 | 0.62 |
| Comparative Example(I-7) | Comparative Compound I-7 | 5.7 | 17.6 | 5000 | 28.4 | 83.4 | 0.33 | 0.62 |
| Comparative Example(I-8) | Comparative Compound I-8 | 5.8 | 17.6 | 5000 | 28.5 | 87.1 | 0.33 | 0.61 |
| Comparative Example(I-9) | Comparative Compound I-9 | 5.8 | 18.6 | 5000 | 26.8 | 75.1 | 0.33 | 0.61 |
| Embodiment(I-1) | Compound(1-1) | 5.1 | 11.5 | 5000 | 43.6 | 152.4 | 0.33 | 0.62 |
| Embodiment(I-2) | Compound(1-2) | 5.1 | 11.6 | 5000 | 42.9 | 148.3 | 0.33 | 0.62 |
| Embodiment(I-3) | Compound(1-3) | 5.0 | 11.3 | 5000 | 44.3 | 148.8 | 0.33 | 0.62 |
| Embodiment(I-4) | Compound(1-4) | 5.1 | 11.3 | 5000 | 44.4 | 148.3 | 0.33 | 0.62 |
| Embodiment(I-5) | Compound(1-5) | 5.0 | 11.7 | 5000 | 42.9 | 152.4 | 0.33 | 0.62 |
| Embodiment(I-6) | Compound(1-6) | 5.3 | 11.7 | 5000 | 42.6 | 139.9 | 0.33 | 0.62 |
| Embodiment(I-7) | Compound(1-7) | 5.2 | 11.6 | 5000 | 43.0 | 150.4 | 0.33 | 0.61 |
| Embodiment(I-8) | Compound(1-8) | 5.2 | 12.5 | 5000 | 40.1 | 127.2 | 0.33 | 0.62 |
| Embodiment(I-9) | Compound(1-9) | 5.3 | 12.4 | 5000 | 40.3 | 127.1 | 0.33 | 0.62 |
| Embodiment(I-10) | Compound(1-14) | 5.3 | 12.8 | 5000 | 39.1 | 133.1 | 0.33 | 0.61 |
| Embodiment(I-11) | Compound(1-15) | 5.4 | 12.7 | 5000 | 39.2 | 129.4 | 0.33 | 0.61 |
| Embodiment(I-12) | Compound(1-16) | 5.2 | 13.0 | 5000 | 38.5 | 130.3 | 0.33 | 0.61 |
| Embodiment(I-13) | Compound(1-17) | 5.5 | 12.6 | 5000 | 39.5 | 127.1 | 0.33 | 0.61 |
| Embodiment(I-158) | Compound(2-94) | 5.1 | 11.8 | 5000 | 42.5 | 138.8 | 0.33 | 0.61 |
| Embodiment(I-159) | Compound(2-103) | 5.2 | 11.3 | 5000 | 44.2 | 142.9 | 0.33 | 0.61 |
| Embodiment(I-160) | Compound(2-104) | 5.5 | 12.7 | 5000 | 39.4 | 133.5 | 0.33 | 0.61 |
| Embodiment(I-161) | Compound(2-105) | 5.3 | 12.5 | 5000 | 40.1 | 133.3 | 0.33 | 0.62 |
| Embodiment(I-162) | Compound(2-106) | 5.4 | 12.4 | 5000 | 40.3 | 133.9 | 0.33 | 0.62 |
| Embodiment(I-163) | Compound(2-107) | 5.1 | 12.4 | 5000 | 40.3 | 128.7 | 0.33 | 0.62 |
| Embodiment(I-164) | Compound(2-108) | 5.3 | 12.9 | 5000 | 38.8 | 130.6 | 0.33 | 0.61 |
| Embodiment(I-165) | Compound(2-109) | 5.5 | 13.2 | 5000 | 38.0 | 119.6 | 0.33 | 0.62 |
| Embodiment(I-166) | Compound(2-110) | 5.1 | 12.9 | 5000 | 38.6 | 126.0 | 0.33 | 0.62 |

As shown in Table 4 above, the organic electronic light emitting element, which was measured using the material for an organic electronic light emitting element of the present invention, exhibited a low driving voltage, a high efficiency, and a high lifespan, compared with comparative compound I-1, $Alq_3$, which has been broadly used as an existing material for an electron transport layer. The reason is determined to be that, while the $T_1$ value of $Alq_3$ used for an electron transport layer is significantly lower than the $T_1$ value of $Ir(ppy)_3$ used as a dopant in a light emitting layer, the compound according to an embodiment of the present invention exhibits a generally higher $T_1$ value than $Ir(ppy)_3$, leading to a relative increase in the possibility of exciton staying in a light emitting layer.

As for the results of the organic electronic light emitting elements of the compound according to an embodiment of the present invention and comparative compounds I-2 to I-9, it can be verified that the compound according to an embodiment of the present invention exhibits a low driving voltage and significantly high efficiency and high lifespan, compared with comparative compounds I-2 to I-9. The reason is determined to be that comparative compounds I-2 and I-9, which has no fused benzene ring, even while having a thienopyrimidine or furopyrimidine core similar to the compound according to an embodiment of the present invention, has a significantly lower LUMO value than the compound according to an embodiment of the present invention having a fused benzene ring, thereby relatively degrading the electron transport ability. Whereas, the fusion of a benzene ring onto a thienopyrimidine or furopyrimidine core, like in the compound according to an embodiment of the present invention, allows high thermal stability, a comparatively low driving voltage through the regulation of packing density between materials, and comparatively efficient electron transport due to an increase in the LUMO value compared with the comparative compounds, thereby attaining a charge balance of holes and electrons and forming the emission of light inside a light emitting layer but not an interface of an electron transport layer, and resultantly, it could be verified that the compound according to an embodiment of the present invention exhibits high efficiency and lifespan compared with comparative compounds I-1 to I-9.

Furthermore, the correlation between an electron transport layer and a light emitting layer (host) needs to be considered, and thus even a person skilled in the art would have great difficulty in deriving features of an electron transport layer employing the compound according to the present invention in spite of the use of similar cores.

[Embodiment II-1] Green Organic Electronic Light Emitting Element (Phosphorescent Host for Light Emitting Layer)

An organic electronic light emitting element was manufactured by an ordinary method using the compound according to an embodiment of the present invention as a phosphorescent material. First, 2-TNATA was vacuum-deposited with a thickness of 60 nm on an ITO layer (anode) formed on a galas substrate to form a hole injection layer, and then, NPD was vacuum-deposited with a thickness of 60 nm on the hole injection layer to form a hole injection layer. Subsequently, compound 1-1 as a host material and Ir(ppy)$_3$ as a dopant material were doped at a weight ratio of 95:5 to form a light emitting layer with a thickness of 30 nm on the hole transport layer. Then, BAlq was vacuum-deposited with a thickness of 10 nm to form a hole blocking layer on the light emitting layer, and tris(8-quinolinol)aluminum (hereinafter, abbreviated as "Alq$_3$") was vacuum-deposited with a thickness of 40 nm to form an electron transport layer on the hole blocking layer. Thereafter, LiF as a halogenated alkali metal was deposited with a thickness of 0.2 nm to form an electron injection layer on the hole transport layer, and then Al was deposited with a thickness of 150 nm to form a cathode. Thereby, an organic electronic light emitting element was manufactured.

[Embodiment II-2] to [Embodiment II-151] Green Organic Electronic Light Emitting Element (Phosphorescent Host for Light Emitting Layer)

Organic electronic light emitting elements were manufactured by the same method as in Embodiment II-1 except that compounds 1-5 to 2-108 according to an embodiment of the present invention, listed on table 5 below, instead of compound 1-1 according to an embodiment of the present invention, were used as a material for a host material for a light emitting layer.

Comparative Example II-1

An organic electronic light emitting element was manufactured by the same method as in Embodiment II-1 except that comparative compound II-1 below, instead of compound 1-1 according to an embodiment of the present invention, was used as a host material for a light emitting layer.

Comparative Example II-2

An organic electronic light emitting element was manufactured by the same method as in Embodiment II-1 except that comparative compound II-2 below, instead of compound 1-1 according to an embodiment of the present invention, was used as a host material for a light emitting layer.

Comparative Example II-3

An organic electronic light emitting element was manufactured by the same method as in Embodiment II-1 except that comparative compound II-3 below, instead of compound 1-1 according to an embodiment of the present invention, was used as a host material for a light emitting layer.

Comparative Example II-4

An organic electronic light emitting element was manufactured by the same method as in Embodiment II-1 except that comparative compound II-4 below, instead of compound 1-1 according to an embodiment of the present invention, was used as a host material for a light emitting layer.

Comparative Example II-5

An organic electronic light emitting element was manufactured by the same method as in Embodiment II-1 except that comparative compound II-5 below, instead of compound 1-1 according to an embodiment of the present invention, was used as a host material for a light emitting layer.

Comparative Example II-6

An organic electronic light emitting element was manufactured by the same method as in Embodiment II-1 except that comparative compound II-6 below, instead of compound 1-1 according to an embodiment of the present invention, was used as a host material for a light emitting layer.

Comparative Example II-7

An organic electronic light emitting element was manufactured by the same method as in Embodiment II-1 except that comparative compound II-7 below, instead of compound 1-1 according to an embodiment of the present invention, was used as a host material for a light emitting layer.

Comparative Example II-8

An organic electronic light emitting element was manufactured by the same method as in Embodiment II-1 except that comparative compound II-8 below, instead of compound 1-1 according to an embodiment of the present invention, was used as a host material for a light emitting layer.

Comparative Example II-9

An organic electronic light emitting element was manufactured by the same method as in Embodiment II-1 except that comparative compound II-9 below, instead of compound 1-1 according to an embodiment of the present invention, was used as a host material for a light emitting layer.

<Comparative Compound II-1>

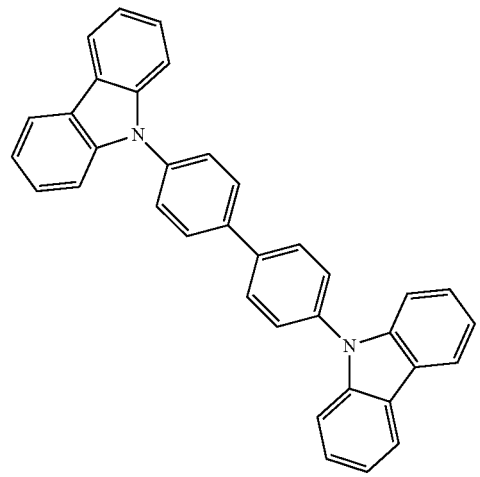

<Comparative Compound II-2>

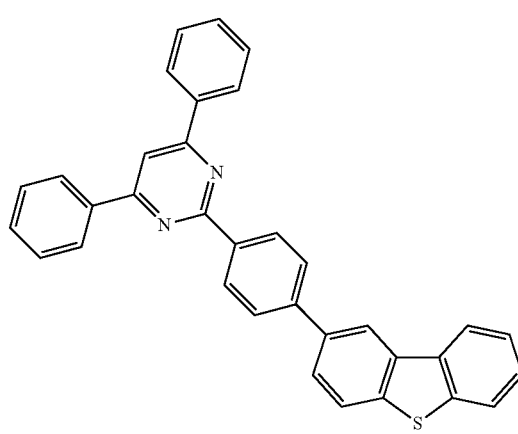

-continued

<Comparative Compound II-3>

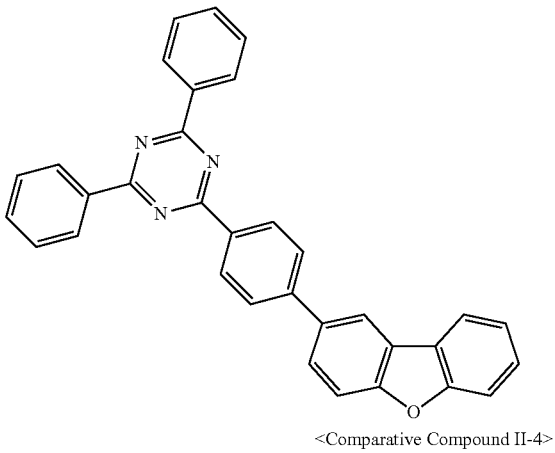

<Comparative Compound II-4>

<Comparative Compound II-5>

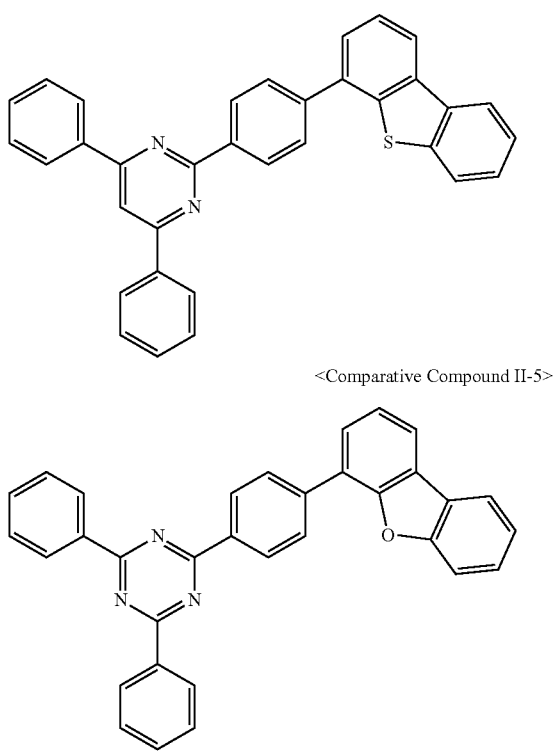

<Comparative Compound II-6>

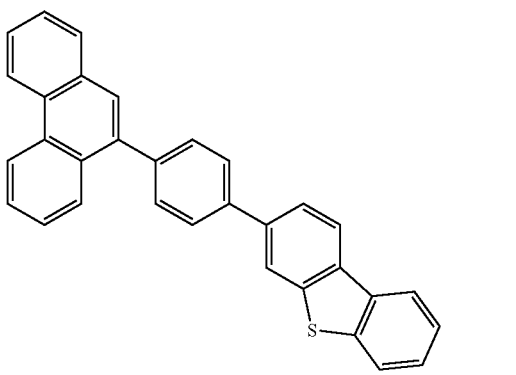

<Comparative Compound II-7>

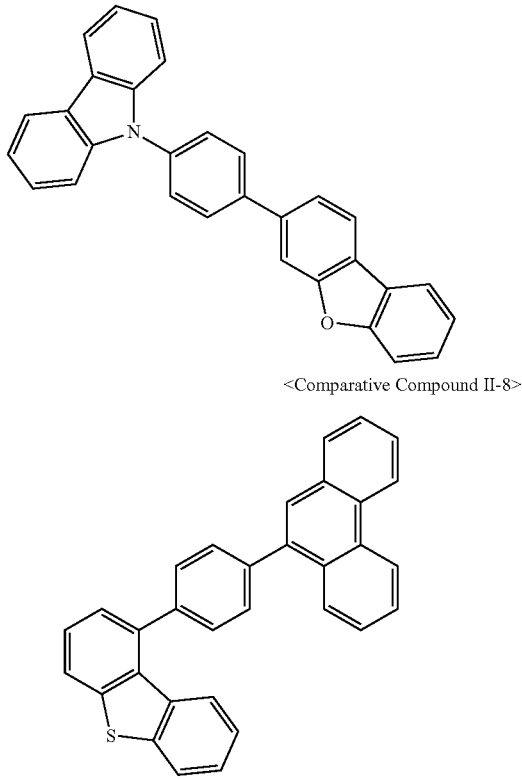

<Comparative Compound II-8>

<Comparative Compound II-9>

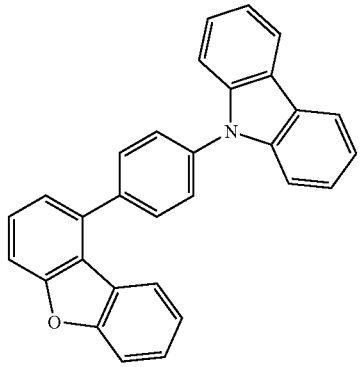

A forward bias DC voltage was applied to each of the organic electronic light emitting elements manufactured in Embodiments II-1 to II-151 and Comparative Examples II-1 to II-9 to measure electro-luminescence (EL) characteristics thereof by PR-650 (Photoresearch). Also, the T95 lifespan was measured by lifespan measuring equipment (Mc-science) at reference brightness of 5000 cd/m$^2$. The measurement results are shown in Table 5 below.

TABLE 5

| | | | | | | | | |
|---|---|---|---|---|---|---|---|---|
| Embodiment(II-86) | Compound(2-30) | 5.3 | 10.2 | 5000 | 48.9 | 159.4 | 0.33 | 0.62 |
| Embodiment(II-87) | Compound(2-31) | 5.2 | 10.5 | 5000 | 47.7 | 151.7 | 0.33 | 0.62 |
| Embodiment(II-88) | Compound(2-32) | 5.3 | 10.5 | 5000 | 47.8 | 154.9 | 0.33 | 0.62 |
| Embodiment(II-89) | Compound(2-33) | 5.0 | 9.9 | 5000 | 50.4 | 172.1 | 0.33 | 0.61 |
| Embodiment(II-90) | Compound(2-34) | 5.1 | 9.8 | 5000 | 51.0 | 167.3 | 0.33 | 0.62 |
| Embodiment(II-91) | Compound(2-35) | 5.1 | 10.0 | 5000 | 49.8 | 172.4 | 0.33 | 0.61 |
| Embodiment(II-92) | Compound(2-36) | 5.2 | 9.8 | 5000 | 51.1 | 166.9 | 0.33 | 0.61 |
| Embodiment(II-93) | Compound(2-37) | 5.3 | 11.0 | 5000 | 45.5 | 136.5 | 0.33 | 0.62 |
| Embodiment(II-94) | Compound(2-38) | 5.2 | 11.0 | 5000 | 45.4 | 145.3 | 0.33 | 0.61 |
| Embodiment(II-95) | Compound(2-39) | 5.3 | 11.0 | 5000 | 45.4 | 144.8 | 0.33 | 0.61 |
| Embodiment(II-96) | Compound(2-40) | 5.4 | 11.0 | 5000 | 45.7 | 140.6 | 0.33 | 0.62 |
| Embodiment(II-97) | Compound(2-41) | 5.4 | 11.0 | 5000 | 45.5 | 139.3 | 0.33 | 0.62 |
| Embodiment(II-98) | Compound(2-42) | 5.3 | 10.5 | 5000 | 47.7 | 154.5 | 0.33 | 0.61 |
| Embodiment(II-99) | Compound(2-43) | 5.1 | 10.5 | 5000 | 47.6 | 154.0 | 0.33 | 0.62 |
| Embodiment(II-100) | Compound(2-44) | 5.3 | 10.7 | 5000 | 46.7 | 149.0 | 0.33 | 0.61 |
| Embodiment(II-101) | Compound(2-45) | 5.3 | 10.9 | 5000 | 45.8 | 136.3 | 0.33 | 0.62 |
| Embodiment(II-102) | Compound(2-46) | 5.1 | 10.0 | 5000 | 50.2 | 170.9 | 0.33 | 0.62 |
| Embodiment(II-103) | Compound(2-47) | 5.2 | 9.9 | 5000 | 50.4 | 167.2 | 0.33 | 0.62 |
| Embodiment(II-104) | Compound(2-48) | 5.0 | 9.7 | 5000 | 51.4 | 169.5 | 0.33 | 0.61 |
| Embodiment(II-105) | Compound(2-49) | 5.2 | 10.6 | 5000 | 47.1 | 139.4 | 0.33 | 0.62 |
| Embodiment(II-106) | Compound(2-50) | 5.3 | 10.7 | 5000 | 46.6 | 154.5 | 0.33 | 0.62 |
| Embodiment(II-107) | Compound(2-51) | 5.3 | 11.1 | 5000 | 45.2 | 154.9 | 0.33 | 0.61 |
| Embodiment(II-108) | Compound(2-52) | 5.1 | 10.9 | 5000 | 45.7 | 138.5 | 0.33 | 0.61 |
| Embodiment(II-109) | Compound(2-53) | 5.1 | 10.5 | 5000 | 47.8 | 160.0 | 0.33 | 0.62 |
| Embodiment(II-62) | Compound(2-6) | 5.2 | 11.1 | 5000 | 45.0 | 135.8 | 0.33 | 0.62 |
| Embodiment(II-63) | Compound(2-7) | 5.4 | 10.7 | 5000 | 46.5 | 135.9 | 0.33 | 0.62 |
| Embodiment(II-64) | Compound(2-8) | 5.3 | 10.6 | 5000 | 47.0 | 146.2 | 0.33 | 0.62 |
| Embodiment(II-65) | Compound(2-9) | 5.2 | 11.0 | 5000 | 45.3 | 148.9 | 0.33 | 0.62 |
| Embodiment(II-66) | Compound(2-10) | 5.2 | 10.3 | 5000 | 48.5 | 161.7 | 0.33 | 0.61 |
| Embodiment(II-67) | Compound(2-11) | 5.2 | 10.5 | 5000 | 47.8 | 152.5 | 0.33 | 0.61 |
| Embodiment(II-68) | Compound(2-12) | 5.3 | 10.8 | 5000 | 46.3 | 145.6 | 0.33 | 0.61 |
| Embodiment(II-69) | Compound(2-13) | 5.4 | 11.0 | 5000 | 45.6 | 140.3 | 0.33 | 0.62 |
| Embodiment(II-70) | Compound(2-14) | 5.3 | 10.5 | 5000 | 47.7 | 165.0 | 0.33 | 0.62 |
| Embodiment(II-71) | Compound(2-15) | 5.3 | 10.3 | 5000 | 48.3 | 161.9 | 0.33 | 0.61 |
| Embodiment(II-72) | Compound(2-16) | 5.2 | 10.6 | 5000 | 47.3 | 149.6 | 0.33 | 0.62 |
| Embodiment(II-73) | Compound(2-17) | 5.3 | 10.6 | 5000 | 47.2 | 156.3 | 0.33 | 0.62 |
| Embodiment(II-74) | Compound(2-18) | 5.2 | 10.5 | 5000 | 47.7 | 148.1 | 0.33 | 0.62 |
| Embodiment(II-75) | Compound(2-19) | 5.1 | 10.6 | 5000 | 47.1 | 162.1 | 0.33 | 0.61 |

TABLE 5-continued

| | | | | | | | | |
|---|---|---|---|---|---|---|---|---|
| Embodiment(II-76) | Compound(2-20) | 5.1 | 10.6 | 5000 | 47.3 | 161.4 | 0.33 | 0.61 |
| Embodiment(II-77) | Compound(2-21) | 5.1 | 10.1 | 5000 | 49.3 | 168.1 | 0.33 | 0.61 |
| Embodiment(II-78) | Compound(2-22) | 5.3 | 11.0 | 5000 | 45.3 | 135.1 | 0.33 | 0.62 |
| Embodiment(II-79) | Compound(2-23) | 5.3 | 10.5 | 5000 | 47.5 | 151.1 | 0.33 | 0.61 |
| Embodiment(II-80) | Compound(2-24) | 5.3 | 10.8 | 5000 | 46.4 | 139.7 | 0.33 | 0.62 |
| Embodiment(II-81) | Compound(2-25) | 5.4 | 10.9 | 5000 | 45.7 | 137.0 | 0.33 | 0.62 |
| Embodiment(II-82) | Compound(2-26) | 5.2 | 10.2 | 5000 | 49.0 | 158.2 | 0.33 | 0.62 |
| Embodiment(II-83) | Compound(2-27) | 5.2 | 10.4 | 5000 | 48.2 | 149.4 | 0.33 | 0.62 |
| Embodiment(II-84) | Compound(2-28) | 5.3 | 10.6 | 5000 | 47.0 | 144.4 | 0.33 | 0.61 |
| Embodiment(II-85) | Compound(2-29) | 5.3 | 10.9 | 5000 | 46.0 | 145.0 | 0.33 | 0.62 |
| Embodiment(II-38) | Compound(1-176) | 5.3 | 10.3 | 5000 | 48.4 | 148.9 | 0.33 | 0.61 |
| Embodiment(II-39) | Compound(1-177) | 5.2 | 10.2 | 5000 | 48.8 | 163.9 | 0.33 | 0.62 |
| Embodiment(II-40) | Compound(1-179) | 5.2 | 10.6 | 5000 | 47.2 | 156.4 | 0.33 | 0.61 |
| Embodiment(II-41) | Compound(1-180) | 5.1 | 10.6 | 5000 | 47.2 | 147.1 | 0.33 | 0.62 |
| Embodiment(II-42) | Compound(1-182) | 5.2 | 10.6 | 5000 | 47.3 | 164.5 | 0.33 | 0.62 |
| Embodiment(II-43) | Compound(1-183) | 5.2 | 10.1 | 5000 | 49.3 | 151.0 | 0.33 | 0.62 |
| Embodiment(II-44) | Compound(1-185) | 5.3 | 10.2 | 5000 | 49.2 | 165.5 | 0.33 | 0.61 |
| Embodiment(II-45) | Compound(1-186) | 5.4 | 11.0 | 5000 | 45.5 | 144.2 | 0.33 | 0.62 |
| Embodiment(II-46) | Compound(1-188) | 5.2 | 10.2 | 5000 | 48.9 | 165.4 | 0.33 | 0.61 |
| Embodiment(II-47) | Compound(1-189) | 5.1 | 10.2 | 5000 | 49.2 | 147.8 | 0.33 | 0.62 |
| Embodiment(II-48) | Compound(1-190) | 5.2 | 10.4 | 5000 | 48.1 | 155.3 | 0.33 | 0.62 |
| Embodiment(II-49) | Compound(1-191) | 5.1 | 10.4 | 5000 | 48.2 | 164.9 | 0.33 | 0.61 |
| Embodiment(II-50) | Compound(1-192) | 5.3 | 10.9 | 5000 | 45.9 | 137.1 | 0.33 | 0.62 |
| Embodiment(II-51) | Compound(1-194) | 5.3 | 10.4 | 5000 | 48.3 | 164.4 | 0.33 | 0.61 |
| Embodiment(II-52) | Compound(1-195) | 5.1 | 10.3 | 5000 | 48.6 | 148.0 | 0.33 | 0.62 |
| Embodiment(II-53) | Compound(1-197) | 5.3 | 10.7 | 5000 | 46.9 | 148.0 | 0.33 | 0.62 |
| Embodiment(II-54) | Compound(1-198) | 5.3 | 11.1 | 5000 | 45.0 | 148.0 | 0.33 | 0.61 |
| Embodiment(II-55) | Compound(1-200) | 5.3 | 10.8 | 5000 | 46.2 | 137.7 | 0.33 | 0.61 |
| Embodiment(II-56) | Compound(1-201) | 5.2 | 10.2 | 5000 | 49.0 | 158.2 | 0.33 | 0.61 |
| Embodiment(II-57) | Compound(2-1) | 5.1 | 10.4 | 5000 | 48.2 | 149.5 | 0.33 | 0.62 |
| Embodiment(II-58) | Compound(2-2) | 5.1 | 10.6 | 5000 | 47.4 | 162.7 | 0.33 | 0.62 |
| Embodiment(II-59) | Compound(2-3) | 5.2 | 10.2 | 5000 | 49.0 | 152.1 | 0.33 | 0.62 |
| Embodiment(II-60) | Compound(2-4) | 5.1 | 10.5 | 5000 | 47.6 | 156.6 | 0.33 | 0.61 |
| Embodiment(II-61) | Compound(2-5) | 5.0 | 9.8 | 5000 | 51.2 | 168.1 | 0.33 | 0.61 |
| Embodiment(II-14) | Compound(1-118) | 5.3 | 11.7 | 5000 | 42.9 | 135.9 | 0.33 | 0.61 |
| Embodiment(II-15) | Compound(1-121) | 5.1 | 10.7 | 5000 | 46.7 | 148.0 | 0.33 | 0.61 |
| Embodiment(II-16) | Compound(1-122) | 5.3 | 11.2 | 5000 | 44.5 | 132.2 | 0.33 | 0.61 |
| Embodiment(II-17) | Compound(1-129) | 5.2 | 11.5 | 5000 | 43.6 | 132.2 | 0.33 | 0.61 |
| Embodiment(II-18) | Compound(1-130) | 5.4 | 11.8 | 5000 | 42.5 | 130.0 | 0.33 | 0.61 |
| Embodiment(II-19) | Compound(1-137) | 5.1 | 11.4 | 5000 | 43.9 | 138.8 | 0.33 | 0.62 |
| Embodiment(II-20) | Compound(1-138) | 5.5 | 12.3 | 5000 | 40.7 | 125.5 | 0.33 | 0.62 |
| Embodiment(II-21) | Compound(1-145) | 5.1 | 10.3 | 5000 | 48.4 | 163.4 | 0.33 | 0.62 |
| Embodiment(II-22) | Compound(1-146) | 5.2 | 10.9 | 5000 | 45.9 | 135.4 | 0.33 | 0.61 |
| Embodiment(II-23) | Compound(1-149) | 5.3 | 11.7 | 5000 | 42.8 | 135.0 | 0.33 | 0.62 |
| Embodiment(II-24) | Compound(1-151) | 5.3 | 11.2 | 5000 | 44.7 | 128.4 | 0.33 | 0.62 |
| Embodiment(II-25) | Compound(1-161) | 5.1 | 10.0 | 5000 | 49.9 | 171.4 | 0.33 | 0.61 |
| Embodiment(II-26) | Compound(1-162) | 5.0 | 10.0 | 5000 | 49.8 | 171.9 | 0.33 | 0.61 |
| Embodiment(II-27) | Compound(1-163) | 5.2 | 10.1 | 5000 | 49.8 | 171.3 | 0.33 | 0.61 |
| Embodiment(II-28) | Compound(1-164) | 5.3 | 10.3 | 5000 | 48.4 | 151.9 | 0.33 | 0.62 |
| Embodiment(II-29) | Compound(1-165) | 5.1 | 9.9 | 5000 | 50.6 | 170.3 | 0.33 | 0.61 |
| Embodiment(II-30) | Compound(1-166) | 5.2 | 10.4 | 5000 | 48.1 | 157.6 | 0.33 | 0.62 |
| Embodiment(II-31) | Compound(1-167) | 5.2 | 10.5 | 5000 | 47.7 | 148.1 | 0.33 | 0.62 |
| Embodiment(II-32) | Compound(1-168) | 5.2 | 10.3 | 5000 | 48.7 | 164.2 | 0.33 | 0.61 |
| Embodiment(II-33) | Compound(1-169) | 5.2 | 10.6 | 5000 | 47.3 | 160.9 | 0.33 | 0.62 |
| Embodiment(II-34) | Compound(1-170) | 5.2 | 10.6 | 5000 | 47.3 | 154.2 | 0.33 | 0.61 |
| Embodiment(II-35) | Compound(1-171) | 5.2 | 10.6 | 5000 | 47.3 | 148.8 | 0.33 | 0.62 |
| Embodiment(II-36) | Compound(1-173) | 5.3 | 10.4 | 5000 | 48.0 | 162.6 | 0.33 | 0.62 |
| Embodiment(II-37) | Compound(1-174) | 5.1 | 10.1 | 5000 | 49.3 | 150.7 | 0.33 | 0.61 |

| | | Voltage | Current Density | Brightness | Efficiency | Lifetime | CIE | |
|---|---|---|---|---|---|---|---|---|
| | Compound | (V) | (mA/cm2) | (cd/m2) | (cd/A) | T(95) | x | y |
| Comparative Example(II-1) | Comparative Compound II-1 | 6.2 | 21.2 | 5000 | 23.6 | 69.1 | 0.33 | 0.61 |
| Comparative Example(II-2) | Comparative Compound II-2 | 5.7 | 14.9 | 5000 | 33.5 | 79.0 | 0.33 | 0.61 |
| Comparative Example(II-3) | Comparative Compound II-3 | 5.7 | 14.9 | 5000 | 33.6 | 76.3 | 0.33 | 0.61 |
| Comparative Example(II-4) | Comparative Compound II-4 | 5.7 | 14.6 | 5000 | 34.2 | 78.5 | 0.33 | 0.61 |
| Comparative Example(II-5) | Comparative Compound II-5 | 5.8 | 14.7 | 5000 | 34.1 | 78.5 | 0.33 | 0.61 |
| Comparative Example(II-6) | Comparative Compound II-6 | 5.7 | 13.3 | 5000 | 37.7 | 86.6 | 0.33 | 0.62 |
| Comparative Example(II-7) | Comparative Compound II-7 | 5.7 | 14.9 | 5000 | 33.5 | 77.8 | 0.33 | 0.61 |
| Comparative Example(II-8) | Comparative Compound II-8 | 5.6 | 13.7 | 5000 | 36.6 | 90.1 | 0.33 | 0.61 |

TABLE 5-continued

| | | | | | | | | |
|---|---|---|---|---|---|---|---|---|
| Comparative Example(II-9) | Comparative Compound II-9 | 5.8 | 14.9 | 5000 | 33.6 | 81.6 | 0.33 | 0.61 |
| Embodiment(II-1) | Compound(1-1) | 5.1 | 10.3 | 5000 | 48.5 | 161.3 | 0.33 | 0.61 |
| Embodiment(II-2) | Compound(1-5) | 5.1 | 10.5 | 5000 | 47.6 | 151.4 | 0.33 | 0.61 |
| Embodiment(II-3) | Compound(1-7) | 5.2 | 10.3 | 5000 | 48.3 | 163.4 | 0.33 | 0.62 |
| Embodiment(II-4) | Compound(1-21) | 5.2 | 10.3 | 5000 | 48.8 | 149.7 | 0.33 | 0.61 |
| Embodiment(II-5) | Compound(1-24) | 5.3 | 10.4 | 5000 | 48.3 | 154.4 | 0.33 | 0.61 |
| Embodiment(II-6) | Compound(1-25) | 5.3 | 10.6 | 5000 | 47.2 | 159.3 | 0.33 | 0.62 |
| Embodiment(II-7) | Compound(1-77) | 5.3 | 11.0 | 5000 | 45.3 | 148.6 | 0.33 | 0.61 |
| Embodiment(II-8) | Compound(1-93) | 5.1 | 10.5 | 5000 | 47.4 | 165.2 | 0.33 | 0.62 |
| Embodiment(II-9) | Compound(1-97) | 5.4 | 11.0 | 5000 | 45.6 | 136.7 | 0.33 | 0.62 |
| Embodiment(II-10) | Compound(1-102) | 5.1 | 10.8 | 5000 | 46.5 | 154.9 | 0.33 | 0.62 |
| Embodiment(II-11) | Compound(1-106) | 5.2 | 11.1 | 5000 | 45.0 | 147.5 | 0.33 | 0.61 |
| Embodiment(II-12) | Compound(1-108) | 5.2 | 10.9 | 5000 | 45.8 | 154.3 | 0.33 | 0.61 |
| Embodiment(II-13) | Compound(1-117) | 5.3 | 10.7 | 5000 | 46.6 | 155.6 | 0.33 | 0.62 |
| Embodiment(II-134) | Compound(2-83) | 5.2 | 10.2 | 5000 | 49.1 | 152.0 | 0.33 | 0.62 |
| Embodiment(II-135) | Compound(2-84) | 5.4 | 11.0 | 5000 | 45.6 | 144.7 | 0.33 | 0.61 |
| Embodiment(II-136) | Compound(2-85) | 5.1 | 10.5 | 5000 | 47.8 | 162.0 | 0.33 | 0.62 |
| Embodiment(II-137) | Compound(2-87) | 5.2 | 10.3 | 5000 | 48.4 | 165.8 | 0.33 | 0.62 |
| Embodiment(II-138) | Compound(2-89) | 5.2 | 10.3 | 5000 | 48.6 | 149.7 | 0.33 | 0.62 |
| Embodiment(II-139) | Compound(2-90) | 5.1 | 10.4 | 5000 | 47.9 | 164.8 | 0.33 | 0.62 |
| Embodiment(II-140) | Compound(2-91) | 5.2 | 10.5 | 5000 | 47.8 | 163.8 | 0.33 | 0.61 |
| Embodiment(II-141) | Compound(2-93) | 5.1 | 10.6 | 5000 | 47.3 | 150.6 | 0.33 | 0.62 |
| Embodiment(II-142) | Compound(2-95) | 5.3 | 10.2 | 5000 | 49.0 | 151.0 | 0.33 | 0.61 |
| Embodiment(II-143) | Compound(2-96) | 5.2 | 10.2 | 5000 | 49.2 | 154.4 | 0.33 | 0.62 |
| Embodiment(II-144) | Compound(2-99) | 5.3 | 10.5 | 5000 | 47.6 | 153.9 | 0.33 | 0.61 |
| Embodiment(II-145) | Compound(2-101) | 5.0 | 10.5 | 5000 | 47.8 | 156.9 | 0.33 | 0.62 |
| Embodiment(II-146) | Compound(2-102) | 5.1 | 10.2 | 5000 | 49.1 | 161.4 | 0.33 | 0.61 |
| Embodiment(II-147) | Compound(2-104) | 5.3 | 11.0 | 5000 | 45.3 | 146.7 | 0.33 | 0.62 |
| Embodiment(II-148) | Compound(2-105) | 5.3 | 11.4 | 5000 | 43.7 | 126.4 | 0.33 | 0.61 |
| Embodiment(II-149) | Compound(2-106) | 5.1 | 10.5 | 5000 | 47.7 | 158.2 | 0.33 | 0.61 |
| Embodiment(II-150) | Compound(2-107) | 5.2 | 11.2 | 5000 | 44.8 | 143.5 | 0.33 | 0.61 |
| Embodiment(II-151) | Compound(2-108) | 5.3 | 11.6 | 5000 | 43.2 | 132.0 | 0.33 | 0.62 |
| Embodiment(II-110) | Compound(2-54) | 5.1 | 10.8 | 5000 | 46.4 | 140.6 | 0.33 | 0.62 |
| Embodiment(II-111) | Compound(2-56) | 5.4 | 11.6 | 5000 | 43.1 | 133.0 | 0.33 | 0.62 |
| Embodiment(II-112) | Compound(2-57) | 5.3 | 11.2 | 5000 | 44.5 | 129.6 | 0.33 | 0.61 |
| Embodiment(II-113) | Compound(2-58) | 5.2 | 11.1 | 5000 | 45.0 | 153.2 | 0.33 | 0.61 |
| Embodiment(II-114) | Compound(2-59) | 5.2 | 10.8 | 5000 | 46.5 | 150.2 | 0.33 | 0.62 |
| Embodiment(II-115) | Compound(2-60) | 5.4 | 11.6 | 5000 | 43.0 | 135.9 | 0.33 | 0.62 |
| Embodiment(II-116) | Compound(2-61) | 5.4 | 11.5 | 5000 | 43.5 | 134.0 | 0.33 | 0.62 |
| Embodiment(II-117) | Compound(2-62) | 5.1 | 11.1 | 5000 | 45.0 | 146.2 | 0.33 | 0.61 |
| Embodiment(II-118) | Compound(2-63) | 5.1 | 11.0 | 5000 | 45.3 | 143.6 | 0.33 | 0.61 |
| Embodiment(II-119) | Compound(2-64) | 5.3 | 11.1 | 5000 | 45.1 | 138.7 | 0.33 | 0.61 |
| Embodiment(II-120) | Compound(2-65) | 5.1 | 10.2 | 5000 | 49.2 | 158.4 | 0.33 | 0.62 |
| Embodiment(II-121) | Compound(2-66) | 5.1 | 10.5 | 5000 | 47.6 | 157.7 | 0.33 | 0.61 |
| Embodiment(II-122) | Compound(2-67) | 5.2 | 10.4 | 5000 | 48.1 | 153.9 | 0.33 | 0.62 |
| Embodiment(II-123) | Compound(2-68) | 5.2 | 10.6 | 5000 | 47.3 | 147.4 | 0.33 | 0.62 |
| Embodiment(II-124) | Compound(2-69) | 5.2 | 10.5 | 5000 | 47.5 | 161.3 | 0.33 | 0.62 |
| Embodiment(II-125) | Compound(2-70) | 5.2 | 10.4 | 5000 | 47.9 | 149.9 | 0.33 | 0.62 |
| Embodiment(II-126) | Compound(2-71) | 5.3 | 10.3 | 5000 | 48.6 | 152.9 | 0.33 | 0.61 |
| Embodiment(II-127) | Compound(2-72) | 5.1 | 10.3 | 5000 | 48.5 | 162.8 | 0.33 | 0.61 |
| Embodiment(II-128) | Compound(2-73) | 5.1 | 10.2 | 5000 | 48.9 | 148.3 | 0.33 | 0.62 |
| Embodiment(II-129) | Compound(2-75) | 5.2 | 10.2 | 5000 | 49.0 | 162.1 | 0.33 | 0.62 |
| Embodiment(II-130) | Compound(2-77) | 5.2 | 10.3 | 5000 | 48.6 | 160.0 | 0.33 | 0.61 |
| Embodiment(II-131) | Compound(2-78) | 5.1 | 10.1 | 5000 | 49.3 | 156.1 | 0.33 | 0.62 |
| Embodiment(II-132) | Compound(2-79) | 5.2 | 10.4 | 5000 | 48.2 | 164.8 | 0.33 | 0.62 |
| Embodiment(II-133) | Compound(2-81) | 5.3 | 10.2 | 5000 | 48.8 | 165.1 | 0.33 | 0.62 |

As can be seen from results on Table 5 above, Comparative Example (II-1), which employed CBP as an existing phosphorescent host material that has been widely used, exhibited tendencies of a high driving voltage, a low efficiency, and a low lifespan, and Comparative Examples (II-2) to (II-9), which employed the compounds having a thienopyrimidine or furopyrimidine core, exhibited gradually favorable results in both of efficiency and lifespan compared with Comparative Example (II-1). However, no excellent characteristics enough to have a great effect on elements were exhibited. Whereas, the compound according to an embodiment of the present invention, containing two nitrogen (N) atoms on a thienopyrimidine or furopyrimidine core, exhibited a lower driving voltage, higher efficiency, and higher lifespan than Comparative Examples (II-1) to (II-9). The reason is determined to be that the introduction of two nitrogen (N) atoms into a core (thienopyrimidine or furopyrimidine) having excellent hole characteristics allows an appropriate structure form to receive both holes and electrons, thereby easily attaining a charge balance of holes and electrons, leading to the efficient emission of light in a light emitting layer. In addition, it can be verified that the resistance to electrons becomes stronger, contributing to the improvement of the lifespan of elements.

In addition, the characteristics of elements have been described in view of an electron transport layer and a light emitting layer from the foregoing evaluation results of the manufacture of elements, but the materials used for an electron transport layer and a light emitting layer may be ordinarily used alone or in a mixture with other materials, for the foregoing organic material layer for an organic electronic element, such as an an electron injection layer, a hole injection layer, a hole transport layer, and an auxiliary light emitting layer. Therefore, for the foregoing reason, the compound of the present invention may be ordinarily used alone or in a mixture with other materials, for other organic material layer excluding an electron transport layer and a light emitting layer, for Embodiment, an electron injection layer, a hole injection layer, a hole transport layer, and an auxiliary light emitting layer.

Although exemplary embodiments of the present invention have been described for illustrative purposes, a person skilled in the art will appreciate that various modifications, additions, and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

EXPLANATION OF NUMERICAL REFERENCES

100: organic electronic element
110: substrate
120: first electrode
130: hole injection layer
140: hole transport layer
141: buffer layer
150: light emitting layer
151: auxiliary light emitting layer
160: electron transport layer
170: electron injection layer
180: second electrode

CROSS-REFERENCE TO RELATED APPLICATION

This patent application claims priority under 35 U.S.C. § 119(a) on Korean Patent Application No. 10-2014-0064696, filed on 28 May 2014, the disclosure of which are incorporated herein by reference. In addition, this patent application claims priorities in countries other than U.S., with the same reason based on the Korean Patent Application, the entire contents of which are incorporated herein by reference.

What is claimed is:

1. A compound represented by Formula 1:

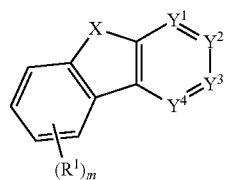

[Formula 1]

wherein in Formula 1:
m is an integer of 2 to 4;
$R^1$ is (i) selected from the group consisting of deuterium, halogen, a $C_6$-$C_{60}$ aryl group, a fluorenyl group, a $C_2$-$C_{60}$ heterocyclic group containing at least one heteroatom selected from O, N, S, Si, and P, a fused ring group of a $C_3$-$C_{60}$ aliphatic group and a $C_6$-$C_{60}$ aromatic group, $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, and (ii) a plurality of $R^1$ are identical to or different from each other and some or all of $R^1$ bind to each other to form at least one ring, wherein any $R^1$ that does not form a ring is defined as in (i) above;

X is O or S;
$Y^1$ and $Y^4$ are independently $CR^a$ or N;
$Y^2$ and $Y^3$ are independently $CR^b$ or N;
provided that one of $Y^1$ and $Y^4$ is N and one of $Y^2$ and $Y^3$ is N;
$R^a$ is selected from the group consisting of hydrogen, deuterium, and -$L^1$-$Ar^1$;
$R^b$ is selected from the group consisting of hydrogen, deuterium, and -$L^2$-$Ar^2$;
$Ar^1$ and $Ar^2$ each are independently selected from the group consisting of a $C_6$-$C_{60}$ aryl group, a fluorenyl group, a ring fused group of a $C_3$-$C_{60}$ aliphatic group and a $C_6$-$C_{60}$ aromatic group, a $C_2$-$C_{60}$ heterocyclic group containing at least one heteroatom selected from O, N, S, Si, and P, a $C_1$-$C_{50}$ alkyl group, a $C_2$-$C_{20}$ alkenyl group, a $C_2$-$C_{20}$ alkynyl group, $C_1$-$C_{30}$ alkoxy group, and a $C_6$-$C_{30}$ aryloxy group;
$L^1$ and $L^2$ each are independently selected from the group consisting of a single bond, a $C_6$-$C_{60}$ arylene group, a fluorenylene group, a $C_2$-$C_{60}$ bivalent heterocyclic group containing at least one heteroatom selected from O, N, S, Si, and P, a bivalent fused ring group of $C_3$-$C_{60}$ aliphatic group and $C_6$-$C_{60}$ aromatic group, and a bivalent aliphatic hydrocarbon group, wherein $L^1$ and $L^2$ (excluding a single bond) each may be substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group; and
the aryl group, fluorenyl group, heterocyclic group, fusion group, alkyl group, alkenyl group, alkoxy group, and aryloxy group of $R^1$, $Ar^1$, and $Ar^2$ each may be substituted with at least one substituent selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

2. The compound of claim 1, wherein the compound is one of the formulas below:

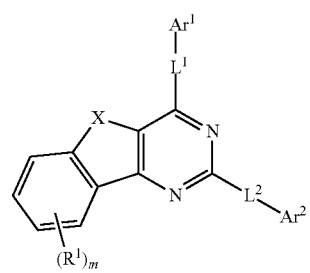

[Formula 2]

283
-continued

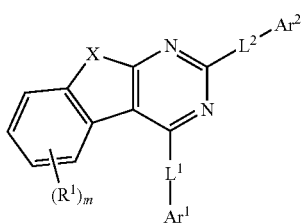

[Formula 3]

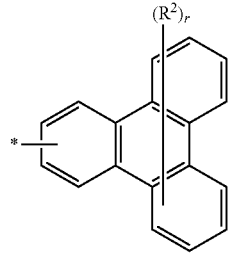

wherein in Formulas 2 and 3 above, X, $R^1$, $Ar^1$, $Ar^2$, $L^1$, $L^2$, and m are defined as in Formula 1.

3. The compound of claim 1, wherein $Ar^1$ and $Ar^2$ each are independently represented by one of Formulas A1 to A8 below:

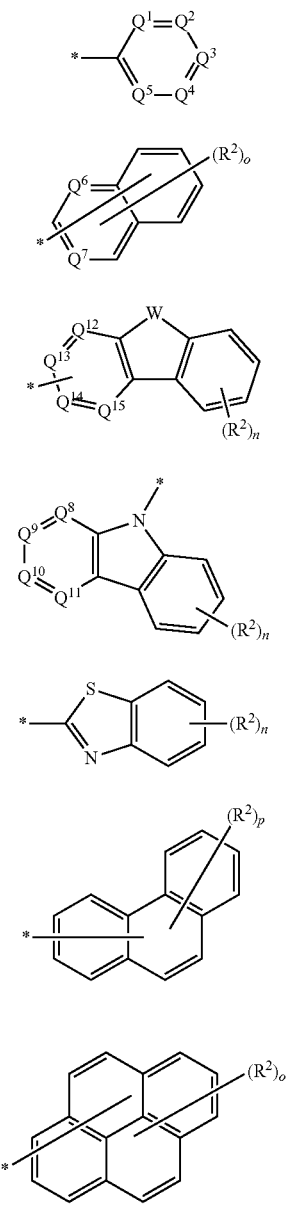

284
-continued wherein in Formulas A1 to A8:

n is an integer of 0-4; o is an integer of 0-5;

p is an integer of 0-6; and r is an integer of 0-8;

$Q^1$ to $Q^{11}$ each are independently $CR^c$ or N;

$Q^{12}$ to $Q^{15}$ each are independently C, $CR^d$, or N;

W is S, O, $NR^e$ or $CR^fR^g$;

$R^2$ is (i) selected from the group consisting of deuterium, halogen, a $C_6$-$C_{60}$ aryl group, a fluorenyl group, a $C_2$-$C_{60}$ heterocyclic group containing at least one heteroatom selected from O, N, S, Si, and P, a fused ring group of a $C_3$-$C_{60}$ aliphatic group and a $C_6$-$C_{60}$ aromatic group, $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group (when n, o, p, and r each are an integer of 2 or greater, a plurality of $R^2$ are identical to or different from each other, or (ii) when n, o, p, and r each are an integer of 2 or greater, a plurality of $R^2$ are identical to or different from each other and may bind to each other to form at least one ring (provided that $R^2$ not forming the ring is defined as in (i));

$R^c$ and $R^d$ each are independently selected from the group consisting of hydrogen, deuterium, a $C_6$-$C_{60}$ aryl group, a fluorenyl group, a fused ring group of a $C_3$-$C_{60}$ aliphatic group and a $C_6$-$C_{60}$ aromatic group, a $C_2$-$C_{60}$ heterocyclic group containing at least one heteroatom selected from O, N, S, Si, and P, a $C_1$-$C_{50}$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group; and $R^c$ and $R^d$ each may be substituted with at least one selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group;

$R^e$ to $R^g$ each are independently selected from the group consisting of a $C_6$-$C_{60}$ aryl group, a $C_2$-$C_{60}$ heterocyclic group containing at least one heteroatom selected from O, N, S, Si, and P, a $C_1$-$C_{50}$ alkyl group, a $C_2$-$C_{20}$ alkenyl group, a $C_1$-$C_{30}$ alkoxy group, and a fluorenyl group; and mark * represents a linkage with $L^1$ or $L^2$.

4. The compound of claim 1, wherein the compound is one of the compounds below:

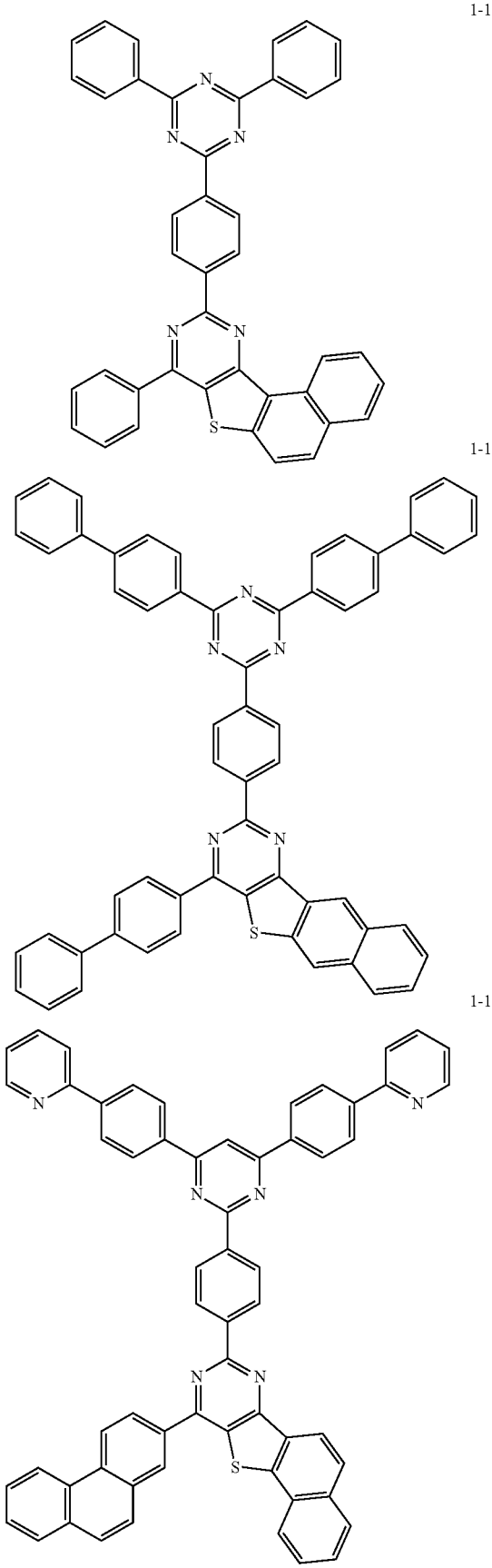
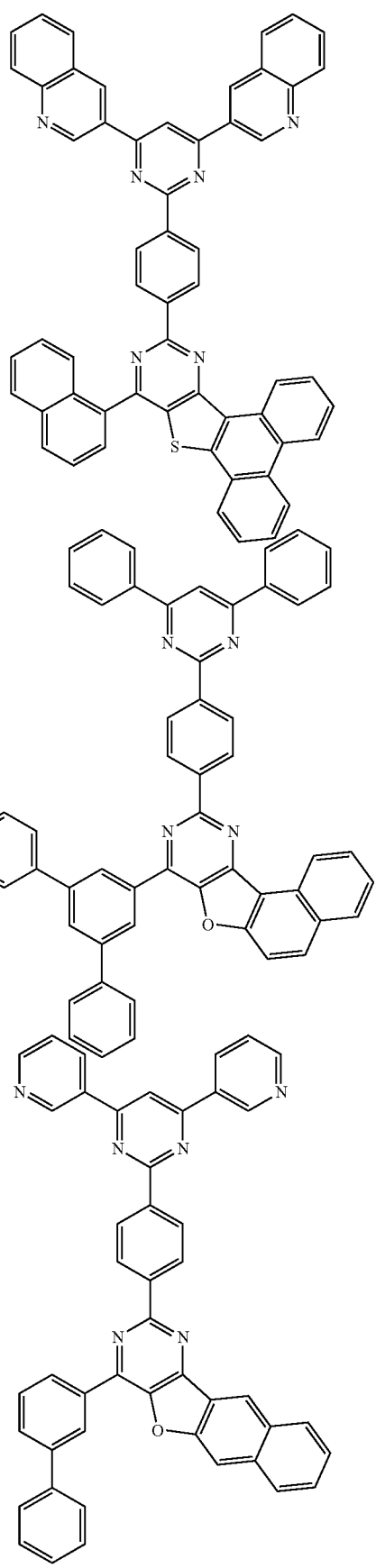

287
-continued
288
-continued
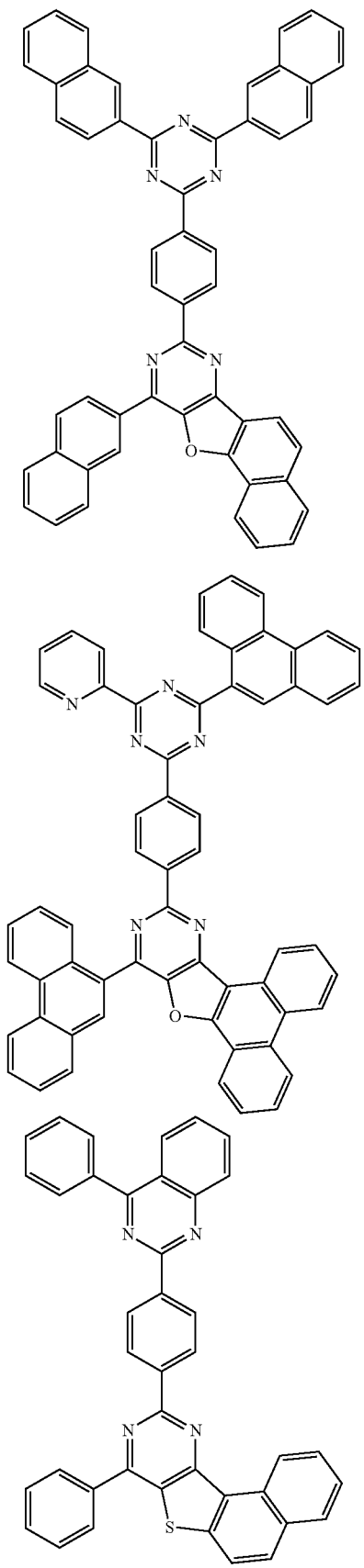
1-151
1-152
1-153
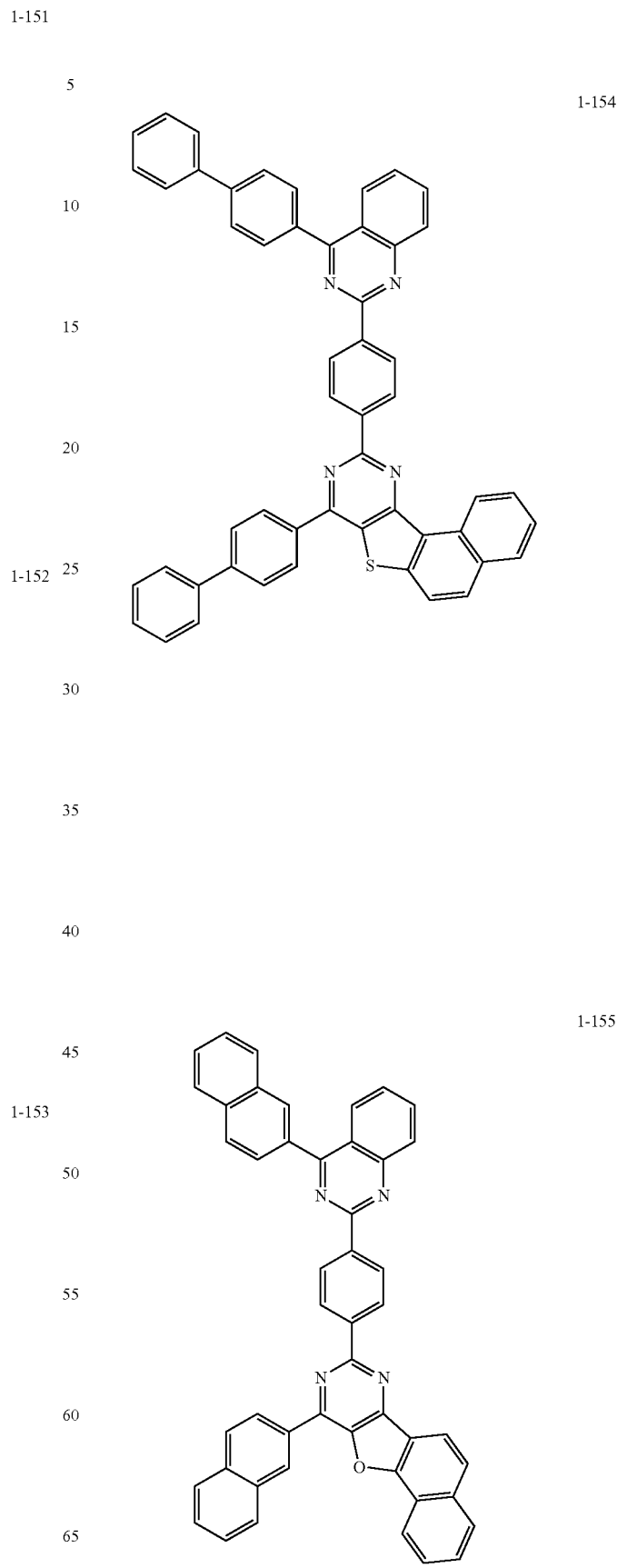
1-154
1-155

1-156

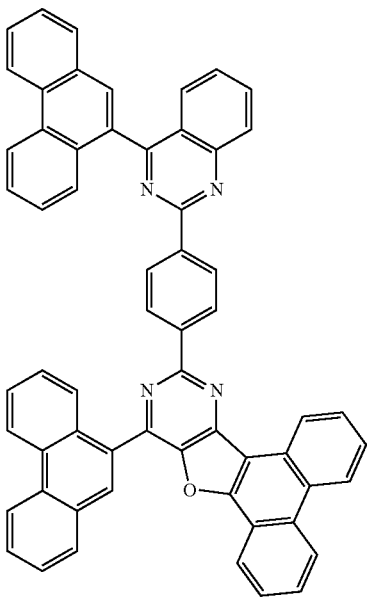

1-157

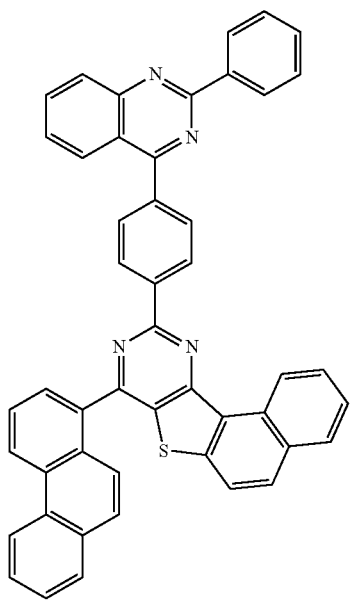

1-158

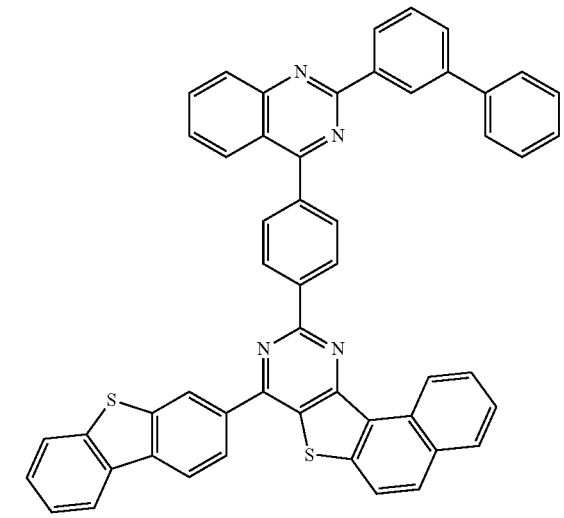

5. An organic electronic element, comprising:
   a first electrode;
   a second electrode; and
   an organic material layer disposed between the first electrode and the second electrode, wherein the organic material layer contains the compound of claim 1.

6. The organic electronic element of claim 5, wherein the organic material layer comprises a light emitting layer and an electron transport layer, the compound being contained alone or as a mixture in at least one of the light emitting layer and the electron transport layer.

7. The organic electronic element of claim 5, further comprising a light efficiency improving layer formed on at least one of one surface of the first electrode and one of the second electrode layers, which is opposite to the organic material layer.

8. The organic electronic element of claim 5, wherein the organic material layer is formed by a spin coating process, a nozzle printing process, an inkjet printing process, a slot coating process, a dip coating process, or a roll-to-roll process.

9. An electronic device, comprising:
   a display device comprising the organic electronic element of claim 5; and
   a controller for driving the display device.

10. The electronic device of claim 9, wherein the organic electronic element is one of an organic electronic light emitting element, an organic solar cell, an organic photo conductor, an organic transistor, and an element for a monochromatic or white illumination.

\* \* \* \* \*